United States Patent
Genovese et al.

(10) Patent No.: US 12,131,803 B2
(45) Date of Patent: Oct. 29, 2024

(54) METHODS AND SYSTEMS FOR DETECTION OF SOMATIC STRUCTURAL VARIANTS

(71) Applicants: THE BROAD INSTITUTE, INC., Cambridge, MA (US); PRESIDENT AND FELLOWS OF HARVARD COLLEGE, Cambridge, MA (US)

(72) Inventors: Giulio Genovese, Cambridge, MA (US); Po-Ru Loh, Cambridge, MA (US); Steven McCarroll, Cambridge, MA (US)

(73) Assignees: The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 1105 days.

(21) Appl. No.: 16/757,329

(22) PCT Filed: Oct. 17, 2018

(86) PCT No.: PCT/US2018/056342
§ 371 (c)(1),
(2) Date: Apr. 17, 2020

(87) PCT Pub. No.: WO2019/079493
PCT Pub. Date: Apr. 25, 2019

(65) Prior Publication Data
US 2020/0303036 A1 Sep. 24, 2020

Related U.S. Application Data

(60) Provisional application No. 62/573,642, filed on Oct. 17, 2017.

(51) Int. Cl.
*G16B 20/10* (2019.01)
*C12Q 1/6883* (2018.01)
(Continued)

(52) U.S. Cl.
CPC ............. *G16B 20/10* (2019.02); *G16B 5/00* (2019.02); *G16B 20/20* (2019.02); *G16H 10/40* (2018.01); *C12Q 1/6883* (2013.01); *C12Q 1/6886* (2013.01)

(58) Field of Classification Search
CPC .......... G16B 20/10; G16B 5/00; G16B 20/20; G16B 40/00; G16H 10/40; G16H 20/10;
(Continued)

(56) References Cited

U.S. PATENT DOCUMENTS

2009/0098547 A1* 4/2009 Ghosh ................. G16B 40/00
703/2
2010/0285478 A1 11/2010 Chen et al.
(Continued)

FOREIGN PATENT DOCUMENTS

WO 2019079493 A2 4/2019

OTHER PUBLICATIONS

Genovese, Giulio. On the importance of phase in improving detection of shared genomic segments. Dartmouth College, 2010. (Year: 2010).*

(Continued)

*Primary Examiner* — Jesse P Frumkin
(74) *Attorney, Agent, or Firm* — F. Brent Nix, Esq.; Johnson, Marcou, Isaacs & Nix, LLC; Drew P. Harding

(57) ABSTRACT

Embodiments disclosed herein provide methods, systems, and computer program products that utilize long-range phase information to detect subtle chromosome imbalances in genotype data. Clonal expansions result from mutation followed by selective proliferation, and the embodiments disclosed herein may be used to somatic structural variant events (SVs) predictive or diagnostic of cancer and other diseases.

31 Claims, 74 Drawing Sheets

(51) Int. Cl.
  *C12Q 1/6886* (2018.01)
  *G16B 5/00* (2019.01)
  *G16B 20/20* (2019.01)
  *G16H 10/40* (2018.01)

(58) Field of Classification Search
  CPC ........ G16H 20/40; G16H 20/70; G16H 50/20; C12Q 1/6883; C12Q 1/6886
  See application file for complete search history.

(56) References Cited

U.S. PATENT DOCUMENTS

| | | | |
|---|---|---|---|
| 2013/0085728 A1* | 4/2013 | Tang ...................... | G16B 40/00 703/2 |
| 2013/0311107 A1* | 11/2013 | Stuelpnagel ........... | G16B 20/20 702/19 |
| 2014/0364439 A1* | 12/2014 | Wu ......................... | A61P 35/02 514/254.1 |
| 2016/0244838 A1* | 8/2016 | Babiarz ................. | C12Q 1/6886 |
| 2016/0342733 A1* | 11/2016 | Reid ...................... | G16B 30/00 |
| 2020/0032349 A1* | 1/2020 | Espiritu ................. | G16H 50/30 |
| 2020/0087710 A1* | 3/2020 | McCullough .......... | G16B 20/10 |
| 2020/0303035 A1* | 9/2020 | Ball ........................ | G16B 5/20 |

OTHER PUBLICATIONS

Yu, Zhenhua, Ao Li, and Minghui Wang. "CloneCNA: detecting subclonal somatic copy number alterations in heterogeneous tumor samples from whole-exome sequencing data." BMC bioinformatics 17.1 (2016): 1-10. (Year: 2016).*
Yu, Zhenhua, Ao Li, and Minghui Wang. "CloneCNA: detecting subclonal somatic copy number alterations in heterogeneous tumor samples from whole-exome sequencing data." BMC bioinformatics 17.1 (2016): 1-10. Supplementary Table 3. (Year: 2016).*
Yu, Zhenhua, Ao Li, and Minghui Wang. "CLImAT-HET: detecting subclonal copy number alterations and loss of heterozygosity in heterogeneous tumor samples from whole-genome sequencing data." BMC medical genomics 10.1 (2017): 1-11. (Year: 2017).*
"International Preliminary Report on Patentability issued in International Patent Application No. PCT/US2018/056342 filed Oct. 17, 2018", mailed Apr. 30, 2020, 11 pages.
"International Search Report and Written Opinion issued in International Application No. PCT/US2018/056342", mailed Dec. 21, 2018, 13 pages.
Berndt, et al., "Genome-Wide Association Study Identifies Multiple Risk Loci for Chronic Lymphocytic Leukemia", Nature Genetics, vol. 45, No. 8, Aug. 2013, 25 pages.
Berndt, et al., "Meta-Analysis of Genome-Wide Association Studies Discovers Multiple Loci for Chronic Lymphocytic Leukemia", Nature Communications, vol. 7, No. 10933, Mar. 9, 2016, 9 pages.
Beroukhim, et al., "The Landscape of Somatic Copy-Number Alteration Across Human Cancers", Nature, vol. 463, No. 7283, Feb. 18, 2010, 17 pages.
Codd, et al., "Identification of Seven Loci Affecting Mean Telomere Length and their Association with Disease", Nature Genetics, vol. 45, No. 4, Apr. 2013, 17 pages.
Conde, et al., "Copy Number Variation Analysis on a Non-Hodgkin Lymphoma Case-Control Study Identifies an 11q25 Duplication Associated with Diffuse Large B-Cell Lymphoma", PLOS ONE, vol. 9, Issue 8, e105382, Aug. 2014, 5 pages.
Davoli, et al., "Cumulative Haploinsufficiency and Triplosensitivity Drive Aneuploidy Patterns and Shape the Cancer Genome", Cell, vol. 155, No. 4, Nov. 7, 2013, 25 pages.
Forsberg, et al., "Mosaicism in Health and Disease-Clones Picking up Speed", Nature Reviews Genetics, vol. 18, No. 2, Feb. 2017, 15 pages.
Gusev, et al., "Whole Population, Genome-Wide Mapping of Hidden Relatedness", Genome Research, vol. 19, No. 2, Feb. 2009, 318-326.
Jacobs, et al., "Detectable Clonal Mosaicism and Its Relationship to Aging and Cancer", Nature Genetics, vol. 44, No. 6, May 6, 2012, 20 pages.
Koren, et al., "Genetic Variation in Human DNA Replication Timing", Cell, vol. 159, No. 5, Nov. 20, 2014, 23 pages.
Lappalainen, et al., "Transcriptome and Genome Sequencing Uncovers Functional Variation in Humans", Nature, vol. 501, No. 7468, Sep. 26, 2013, 16 pages.
Laurie, et al., "Detectable Clonal Mosaicism from Birth to Old Age and it's Relationship to Cancer", Nature Genetics, vol. 44, Issue.6, May 6, 2012, 11 pages.
Lee, et al., "Estimating Missing Heritability for Disease from Genome-Wide Association Studies", American Journal of Human Genetics, vol. 88, No. 3, Mar. 11, 2011, 294-305.
Li, et al., "Allele-Specific Quantification of Structural Variations in Can Genomes", Cell Systems, vol. 3, No. 1, Jul. 27, 2016, 27 pages.
Loh, et al., "Contrasting Genetic Architectures of Schizophrenia and other Complex Diseases using Fast Variance Components Analysis", Nature Genetics, vol. 47, No. 12, Dec. 2015, 28 pages.
Loh, et al., "Efficient Bayesian Mixed Model Analysis Increases Association Power in Large Cohorts", Nature Genetics, vol. 47, No. 3, Mar. 2015, 24 pages.
Loh, et al., "Fast and Accurate Long-range Phasing in a UK Biobank Cohort", Nature Genetics, vol. 48, No. 7, Jul. 2016, 22 pages.
Loh, et al., "Reference-Based Phasing using the Haplotype Reference Consortiumpanel", Nature Genetics, vol. 48, No. 11, Nov. 2016, 20 pages.
Machiela, et al., "Characterization of Large Structural Genetic Mosaicism in Human Autosomes", American Journal of Human Genetics, vol. 96, No. 3, Mar. 5, 2015, 487-497.
Machiela, et al., "LDlink: a Web-Based application for Exploring Population-Specific Haplotype Structure and Linking Correlated Alleles of Possible Functional Variants", Bioinformatics, vol. 31, No. 21, Nov. 1, 2015, 3555-3557.
McKenna, et al., "The Genome Analysis Toolkit: A Mapreduce Framework for Analyzing Next-Generation DNA Sequencing Data", Genome Research, vol. 20, No. 9, Sep. 2010, 1297-1303.
O'Connell, et al., "Haplotype Estimation for Biobank-Scale Data Sets", Nature Genetics, vol. 48, No. 7, Jul. 2016, 13 pages.
Speedy, et al., "A Genome-Wide Association Study Identifies Multiple Susceptibility Loci for Chronic Lymphocytic Leukemia", Nature Genetics, vol. 46, No. 1, Jan. 2014, 7 pages.
Sudlow, et al., "UK Biobank: An Open Access Resource for Identifying the Causes of a Wide Range of Complex Diseases of Middle and Old Age", PLoS Medical, vol. 12, No. 3, Mar. 31, 2015, 10 pages.
Titsias, et al., "Statistical Inference in Hidden Markov Models using k-sigment Constraints", Journal of the American Statistical Association, vol. 111, No. 513, Nov. 6, 2013, 37 pages.
Traver, et al., "Cell-Free Nucleic Acids as Non-Invasive Biomarkers of Gynecological Cancers, Ovarian, Endometrial and Obstetric Disorders and Fetal Aneuploidy", Human Reproduction Update, vol. 20, No. 6, Nov.-Dec. 2014, 905-923.
Vattathil, et al., "Extensive Hidden Genomic Mosaicism Revealed in Normal Tissue", American Journal of Human Genetics, vol. 98, No. 3, 571-758., Mar. 3, 2016.
Wright, et al., "Genetic Variants Associated with Mosaic Y Chromosome Loss Highlight Cell Cycle Genes and Overlap with Cancer Susceptibility", Nature Genetics, vol. 49, No. 5, May 2017, 19 pages.
Xu, et al., "Detecting Very low Allele Fraction Variants using Targeted DNA Sequencing and a Novel Molecular Barcode-Aware Variant Caller", BMC Genomics, vol. 18, No. 1, Dec. 2017, 11 pages.
The Broad Institute, Inc., "Notice of Reasons for Rejection for JP Application No. 2020-521572", mailed on Jul. 5, 2022, 13 pages.
"European Search Report for European Patent Application No. 18868383.3", mailed Jun. 10, 2021, 12 pages.
Loh, et al., "Insights into clonal hematopoiesis from 8,342 mosaic chromosomal alterations", Nature, vol. 559, No. 7714, Jul. 11, 2018.
Vattathil, "Haplotype-based profiling of subtle allelic imbalance with SNP arrays", Genome Research, vol. 23, No. 1, Oct. 1, 2012, 8 pages.

(56) References Cited

OTHER PUBLICATIONS

The Broad Institute, Inc., "Notification of the First Office Action for Chinese Patent Application No. 2018800746526", mailed on Sep. 21, 2022, 17 pages.
The Broad Institute, Inc., "Notice of Reasons for Rejection for Japanese Patent Application No. 2023-023146", mailed on Oct. 24, 2023, 15 pages.
The Broad Institute, Inc., Office Action for Canadian Patent Application No. 3,079, 190, mailed Nov. 8, 2023, 11 pages.

* cited by examiner

*ETV6* del(16p11.2)

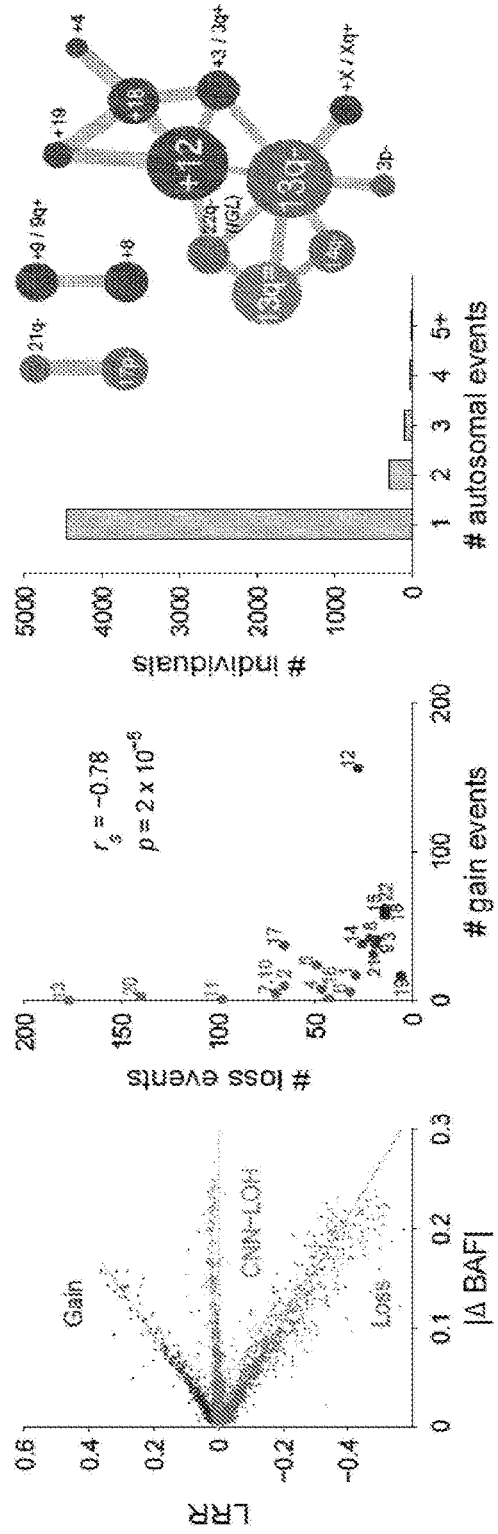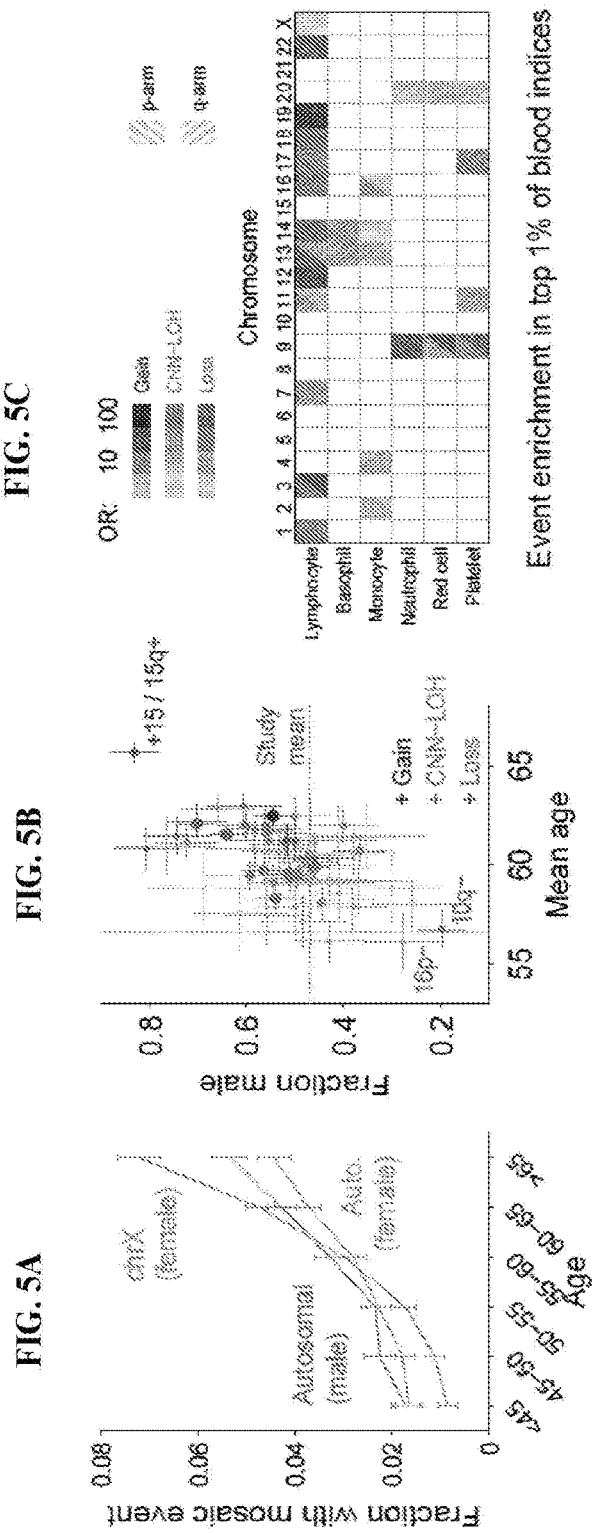
FIG. 5A  FIG. 5B  FIG. 5C
FIG. 5D  FIG. 5E  FIG. 5F

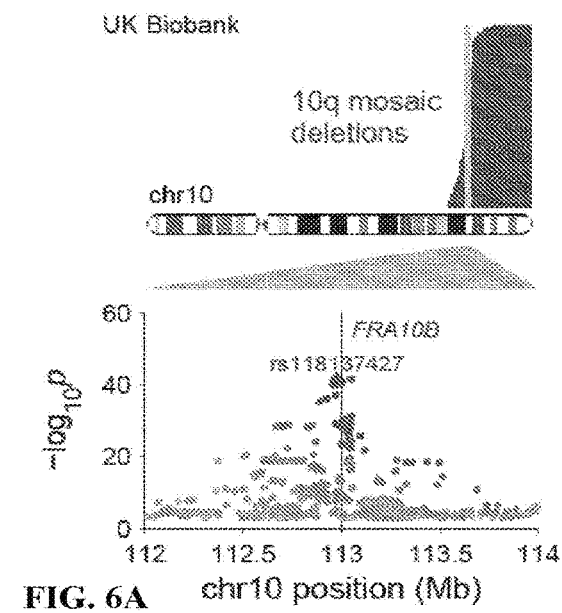
FIG. 6A
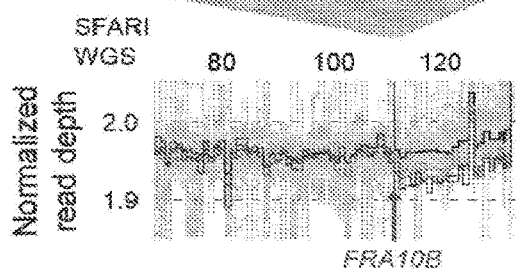
FIG. 6D
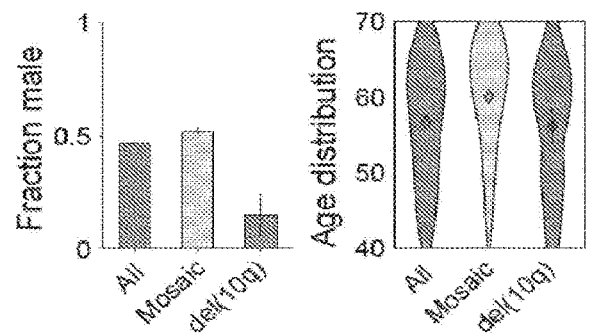
FIG. 6B
FIG. 6C
FIG. 6E

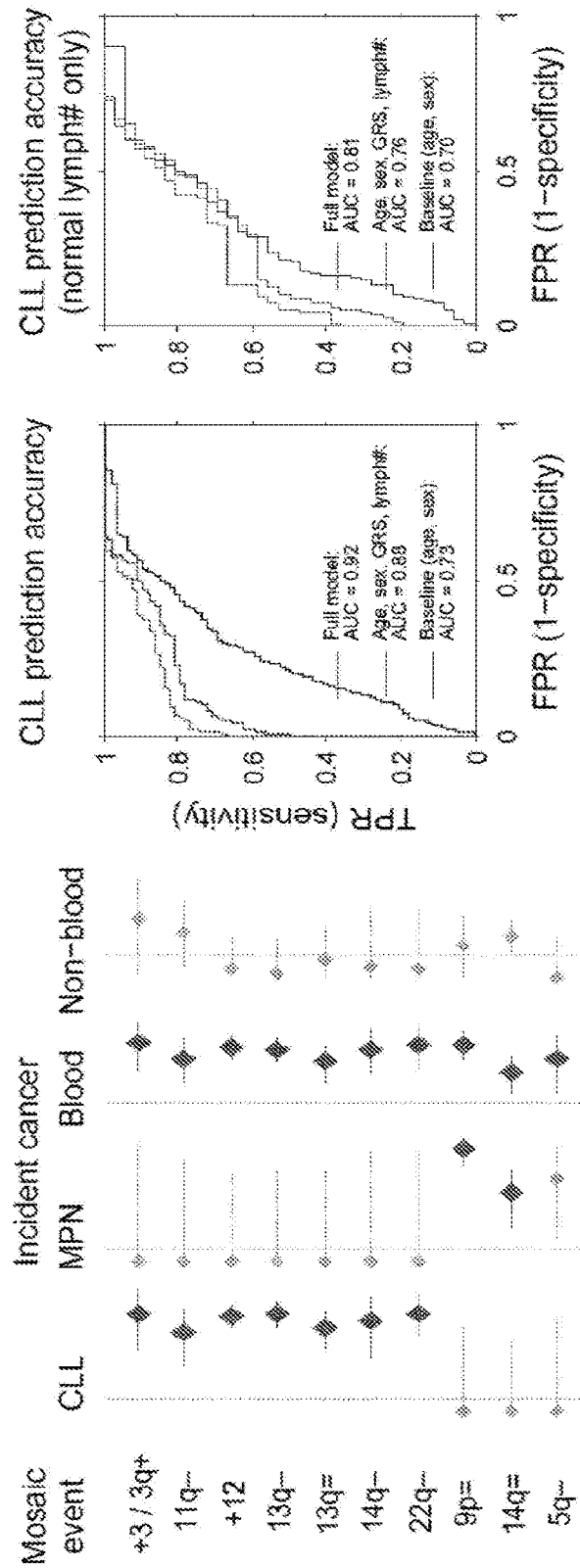
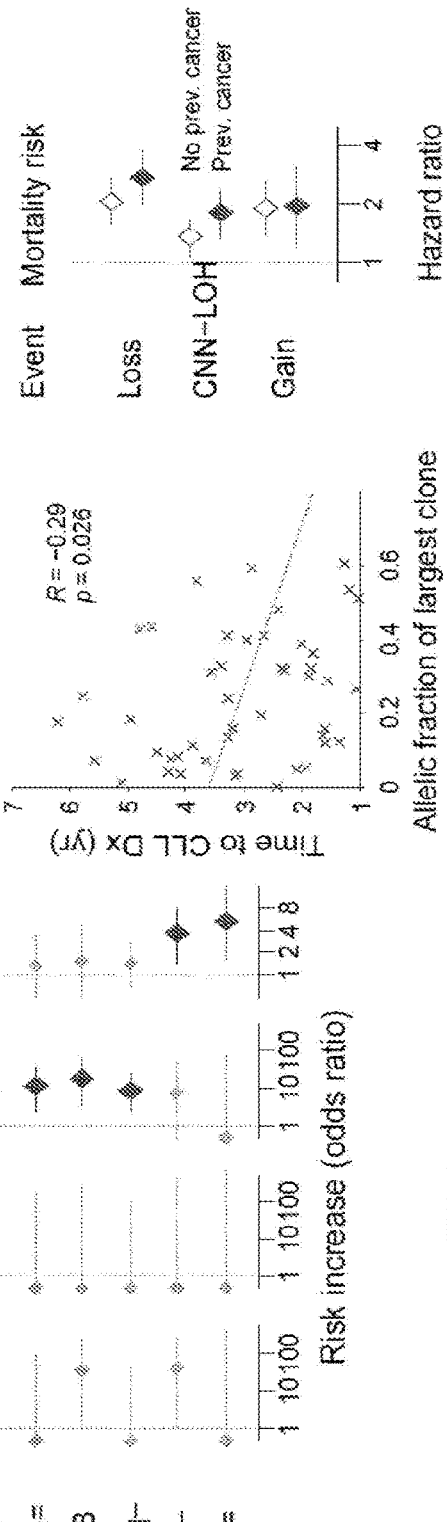
FIG. 8A
FIG. 8B
FIG. 8C
FIG. 8D
FIG. 8E

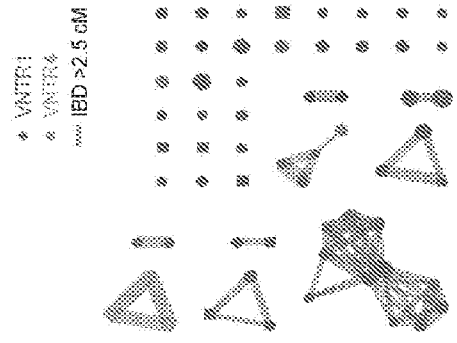
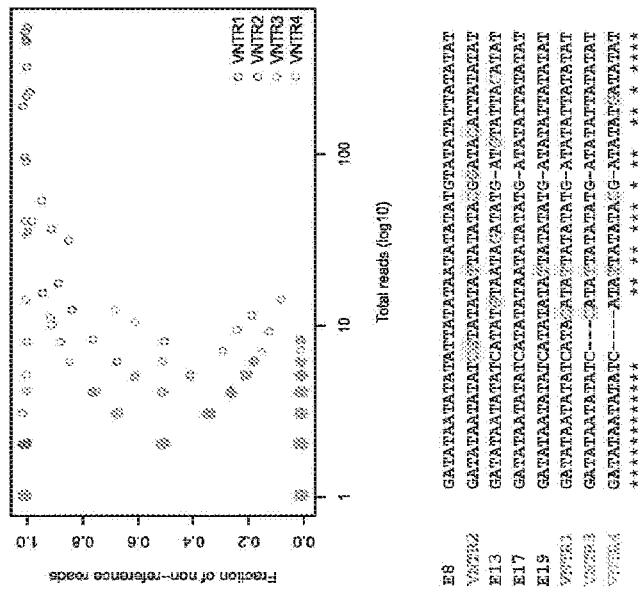
FIG. 42B
FIG. 42A

Edges = IBD>2.5cM (edge weights increase with IBD length)
Red nodes = carriers of rare MPL LoF SNP (rs369156948)
Green nodes = carriers of long rare haplotype (tag: rs144279569)
Blue nodes = carriers of long rare haplotype (tag: rs182971362)

- Hidden Markov model:
  - 1 parameter: $\theta = |\Delta BAF|$ in mosaic region
  - 3 states: $E[phase*\Delta BAF] = +\theta, 0, -\theta$

- Detection procedure:
  - Compute LRT statistic for testing $\theta \neq 0$
  - Calibrate empirically using permutation

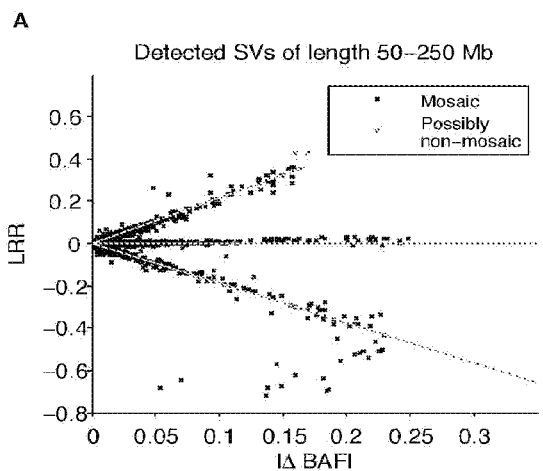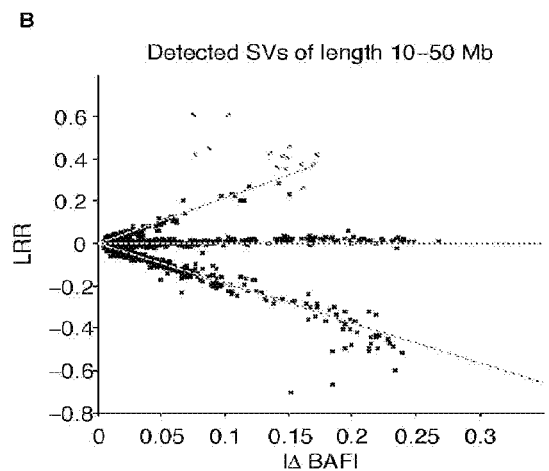
FIG. 52A          FIG. 52B
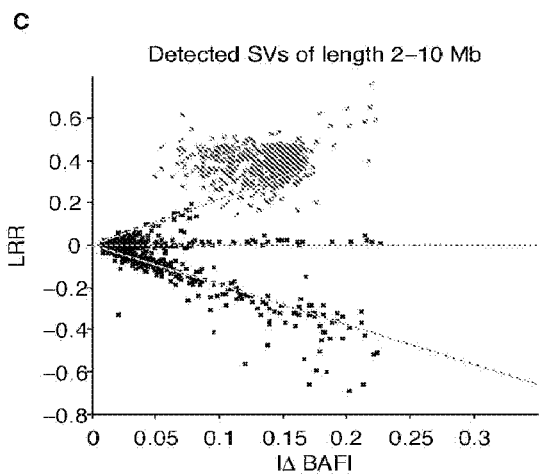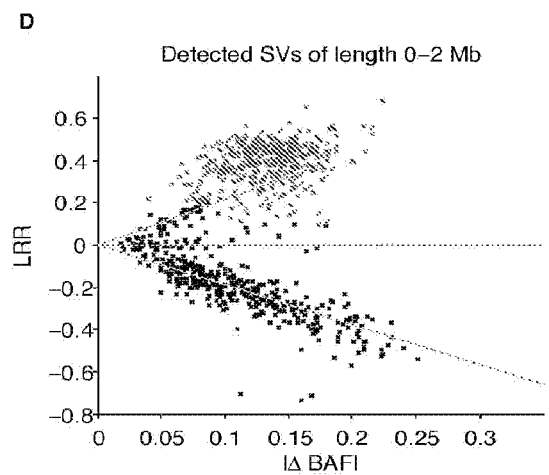
FIG. 52C          FIG. 52D

METHODS AND SYSTEMS FOR DETECTION OF SOMATIC STRUCTURAL VARIANTS

CROSS-REFERENCE TO RELATED APPLICATIONS

This application is a national stage application of International Patent Application No. PCT/US2018/056342 filed Oct. 17, 2018, and claims the benefit of U.S. Provisional Application No. 62/573,642, filed Oct. 17, 2017. The entire contents of the above-identified applications are hereby fully incorporated herein by reference.

STATEMENT REGARDING FEDERALLY SPONSORED RESEARCH

This invention was made with government support under grant numbers HG007805 awarded by the National Institutes of Health, HG006855 granted by the National Human Genome Research Institute, and W81XWH-16-1-0315 and W81XWH-16-1-0316 awarded by the Department of Defense. The government has certain rights in the invention.

TECHNICAL FIELD

The subject matter disclosed herein is generally directed to computer-based methods, products, and systems for detecting somatic structural variants from long range phasing data.

BACKGROUND

Clonal expansions of blood cells harboring somatic mutations are often observed in individuals not known to have cancer. The somatic mutations observed in clonal expansions cluster non-randomly across the genome and are enriched at genes commonly mutated in cancer; consistent with the idea that detectable clonal mosaicism is often a precancerous state, such mosaicism confers>10× increased risk of future hematological malignancy. Several results suggest potential contributions of inherited variation to the likelihood of clonal mosaicism. While previous studies have explored the health consequences of mosaicism in aggregate across the genome, the effects of specific somatic mutations on incident cancers have been challenging to quantify beyond the common loss of chromosome Y (mLOY) event.

The limiting factor in almost all studies of clonal mosaicism has been sample size, with earlier insights arising from up to ~1,000 mosaic events that were detectable genome-wide. Two key factors determine the number of detectable mosaic mutations: (i) the number of individuals analyzed, and (ii) the ability to detect clonal expansions present at low-to-modest cell fractions.

SUMMARY

In certain example embodiments, methods to identify somatic structural variants comprises determining total and relative allelic intensities for one or more samples, masking constitutional segmental duplications in each sample, identifying a putative set of somatic SV events for each sample, and defining a final set of somatic SV events for each sample based at least in part on application of a likelihood ratio test to the putative set of somatic SV events. Determining total and relative allelic frequencies may comprise converting genotype intensity data into log $R_2$ ratio (LRR) and B allele frequency (BAF) values. Segmental duplications may be masked based at least in part on modeling observed phased BAF deviations. In certain example embodiments, modeling observed BAF deviations comprises modeling across individual chromosomes using a 25-state hidden Markov model (HMM) with states corresponding to pBAF values. In certain example embodiments, selecting regions to mask comprises computing a Viterbi path through the HMM and examining continuous regions of non-zero states.

In certain example embodiments, identifying a putative set of SV events may comprise use of a 3-state HMM. The 3-state HMM may be parameterized by a single parameter representing mean |ΔBAF| within a given somatic SV event.

In certain example embodiments, the method may further comprise identifying a chromosomal location of each identified SV event. In certain other example embodiments, the method may further comprise identifying a copy number of each identified somatic SV event. In certain example embodiments, the method may further comprises detecting multiple sub-clonal events for each identified somatic SV event. In certain example embodiments, identifying the chromosomal location of each identified somatic SV event comprises taking 5 samples from the posterior of the 3-state HMM and determining the boundaries of each SV event based on a consensus of the 5 samples. In certain example embodiments, determining the copy number of each identified somatic SV event comprises determining a relative probability that the event was a loss, CNN-LOH, or gain based at least in part on the LRR and |ΔBAF| deviation. In certain example embodiments, detecting multiple sub-clonal events comprises re-analyzing each identified somatic SV using Viterbi decoding on a 51-state HMM with |ΔBAF| levels ranging from 0.01 to 0.25 in multiplicative increments.

In some embodiments, further comprising detecting a disease or susceptibility to a disease based on detection of the one or more somatic SV events. In some embodiments, the disease is cancer. In some embodiments, the cancer comprises a hematological cancer. In some embodiments, the hematological cancer is a leukemia. In some embodiments, the leukemia is chronic lymphocytic leukemia (CLL). In some embodiments, the detected one or more SV events comprise one or more SV events selected from Table 13.

In another aspect, the present disclosure includes computer program products, comprising: a non-transitory computer-executable storage device having computer-readable program instructions embodied thereon that when executed by a computer cause the computer to detect somatic structural variants (SVs) from genotyping data, the computer-executable program instructions comprising: computer-executable program instruction to determine total and relative allelic intensities for one or more samples; computer-executable program instructions to mask constitutional segmental duplications; computer-executable program instructions to identify a putative set of somatic SV events for each sample in the one or more samples; and computer-executable program instructions to define one or more somatic SV events for each sample of the one or more samples.

In some embodiments, the products further comprise computer-executable program instruction to locate a chromosomal location of each identified somatic SV event for each sample in the one or more samples. In some embodiments, the products further comprise computer-executable program instructions to determine a copy number of each identified somatic SV event. In some embodiments, the products further comprise computer-executable program instruction to detect multiple sub-clonal events for each identified somatic SV. In some embodiments, determining total and relative allelic frequencies comprises converting genotype intensity data into log $R_2$ ratio (LRR) and B allele frequency (BAF) values. In some embodiments, identifying the putative set of somatic SV events comprises use of a 3-state HMM. In some embodiments, the 3-state HMM is parameterized by a single parameter representing mean |ΔBAF| within a given somatic SV event.

In some embodiments, the products further comprise detecting a disease or susceptibility to a disease based on detection of the one or more somatic SV events. In some embodiments, the disease is cancer. In some embodiments, the cancer is a hematological cancer. In some embodiments, the hematological cancer is a leukemia. In some embodiments, the leukemia is chronic lymphocytic leukemia.

In another aspect, the present disclosure includes systems to detect one or somatic SV events, the system comprising: a storage device; and a processor communicatively coupled to the storage device, wherein the processor executes application code instructions that are stored in the storage device and that cause the system to: determine total and relative allelic intensities for one or more samples; mask constitutional segmental duplications; identify a putative set of somatic SV events for each sample in the one or more samples; and define one or more somatic SV events for each sample of the one or more samples.

In another aspect, the present disclosure includes kits comprising reagents for determining allelic frequencies and the computer program products or systems described herein.

In another aspect, the present disclosure includes methods for detecting presence or susceptibility of a condition in subject, the method comprising detecting one or more somatic structural variants using methods described herein in nucleic acids in a sample from the subject, wherein presence or absence of the one or more somatic structural variants indicates the presence or susceptibility of the condition.

In some embodiments, the nucleic acids are cell-free nucleic acids. In some embodiments, the sample is maternal blood and the cell-free nucleic acids are fetal cell-free nucleic acids. In some embodiments, the cell-free nucleic acids are circulating tumor DNA. In some embodiments, the condition is fetal aneuploidy. In some embodiments, the condition is cancer. In some embodiments, the methods further comprise performing a medical procedure based on the detected presence or susceptibility of the condition.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 5A-5F—Distributional properties of detected somatic SVs. (FIG. 5A) Log 2 R ratio (LRR), a measure of total allelic intensity, scales roughly linearly with B-allele frequency (BAF) deviation, a measure of relative allelic intensity, among events with each copy number [1, 2, 8]. (FIG. 5B) Autosomes with more gain events tend to have fewer loss events (excluding deletions involving V(D)J recombination on chromosomes 14 and 22). (FIG. 5C) Most individuals with a detected autosomal somatic SV have only one event, although a larger number than expected (441 vs. 100) have multiple events. Several pairs of SV types co-occur much more frequently than expected by chance; edge weights in the co-occurrence graph scale with enrichment. (FIG. 5D) Rates of detectable mosaicism increase as a function of age, especially for female loss of chromosome X. Error bars, 95% CI. (FIG. 5E) Carriers of different SV types have different age and sex distributions. Error bars, s.e.m. (FIG. 5F) Different SVs are significantly enriched (FDR 0.05) among individuals with anomalous blood counts in different blood lineages. Numeric data are provided in Tables 1-6.

FIGS. 6A-6E—Repeat expansions at fragile site FRA10B driving breakage at 10q25.2. The top panels (a-c) display UK Biobank analyses and the bottom panels (d,e) display SFARI analyses. (FIG. 6A) Germline variants at 10q25.2 associate strongly with terminal 10q mosaic deletion in UK Biobank. Note that the left boundaries of the deletions are called with error; the true breakpoints are probably near-identical. (FIG. 6B) UK Biobank carriers of terminal 10q deletion are predominantly female and have an age distribution similar to that of the overall study population. (FIG. 6C) All UK Biobank carriers of the deletion carry the rs118137427:G minor allele. (FIG. 6D) SFARI samples with terminal 10q deletion (two parent-child duos) carry inherited expanded repeats at FRA10B. (FIG. 6E) All SFARI carriers of expanded repeats at FRA10B carry the rs118137427:G minor allele.

In FIG. 7C, the differing arrow weights to CNN-LOH and loss events indicate that CNN-LOH is the more common scenario (both in the population and among carriers of the risk variant.

FIGS. 8A-8E—Associations between somatic SVs and incident cancers and mortality. (FIG. 8A) Multiple SV types confer increased risk of incident cancer diagnosed >1 year after DNA collection. (FIG. 8B, FIG. 8C) A logistic model including mosaic status (particularly for 13q deletion and trisomy 12) along with other risk factors achieves high out-of-sample prediction accuracy for incident CLL. (FIG. 8D) Time to malignancy tracks inversely with clonal cell fraction in individuals with detectable clonality (of any SV) and incident CLL. (FIG. 8E) Loss, gain, and CNN-LOH events (on any autosome) all confer increased mortality risk. Numeric data are provided in Tables 12 and 13.

FIG. 12-FIG. 34—each figure provides detected mosaic SV events on each chromosome in an example sample set. Specific chromosome being analyzed is indicated at top of each figure. Events are color-coded by copy-number: loss (vertical lines), CNN-LOH (descending diagonal lines), gain (ascending diagonal lines), unknown (grey). Darker coloring indicates higher allelic fraction. Multiple events within a single individual are plotted with the same y-coordinate (at the top of the plot). Note that events with unknown copy number also generally have greater uncertainty in their boundaries due to low allelic fraction.

FIG. 38—Genomic coverage by somatic loss and CNN-LOH events. The red and green curves indicate the total numbers of detected somatic losses (solid line) and CNN-LOHs (dashed line) covering each position in the genome.

(FIG. 39A) Roughly 30 samples (red) exhibit read dropout throughout the region, likely due to technical effects. (FIG. 39B) One sample has a candidate mosaic duplication from ~26.8-31.9 Mb.

FIGS. 42A-42B—Multiple expanded repeats at FRA10B drive breakage at 10q25.2. (FIG. 42A) Thirty individuals in SFARI with expanded repeats carry four distinct repeat motifs with varying degrees of expansion. Repeat motifs are AT-rich and are similar to previously reported FRA10B repeats [35]. (FIG. 42B) Carriers of the 10q terminal deletion in UK Biobank share long haplotypes at 10q25.2 identical-by-descent. Square nodes in the IBD graph correspond to males and circles to females. Node size is proportional to clonal cell fraction and edge weight increases with IBD length. Colored nodes indicate imputed carriers of variable number tandem repeats (VNTRs) at FRA10B; color intensity scales with imputed dosage.

(FIG. 45A) Read depth profile plot of SFARI samples in the terminal 700 kb of chr15q. Three individuals in one family carry a ~70 kb deletion at 15q26.3, and a fourth carries the same deletion along with a ~290 kb duplication (probably on the same haplotype based on population frequencies of these events; see FIG. 38). These four individuals (black line) segregate with the rs182643535 T allele in SFARI. None exhibited evidence of 15q mosaicism. (FIG. 45B) Zoomed-in read depth profile plot, with deletion-only individuals in black lines and the del+dup individual dark gray lines. Breakpoint analysis indicates that the ~70 kb deletion spans chr15:102151467-102222161 and contains a 1139 bp mid-segment (chr15:102164897-102166035) that is retained in inverted orientation. The ~290 kb duplication spans chr15: 102026997-102314016.

FIGS. 52A-52D—Exclusion of possible constitutional duplications. Events of length >10 Mb with LRR>0.35 or LRR>0.2 and |ΔBAF|>0.16 were filtered, and then events of length <10 Mb with LRR>0.2 or LRR>0.1 and |ΔBAF|>0.1 were further filtered. More stringent filtering was applied to shorter events because (i) most constitutional duplications are short and (ii) shorter events have noisier LRR and |ΔBAF| estimates.

Figure 1:
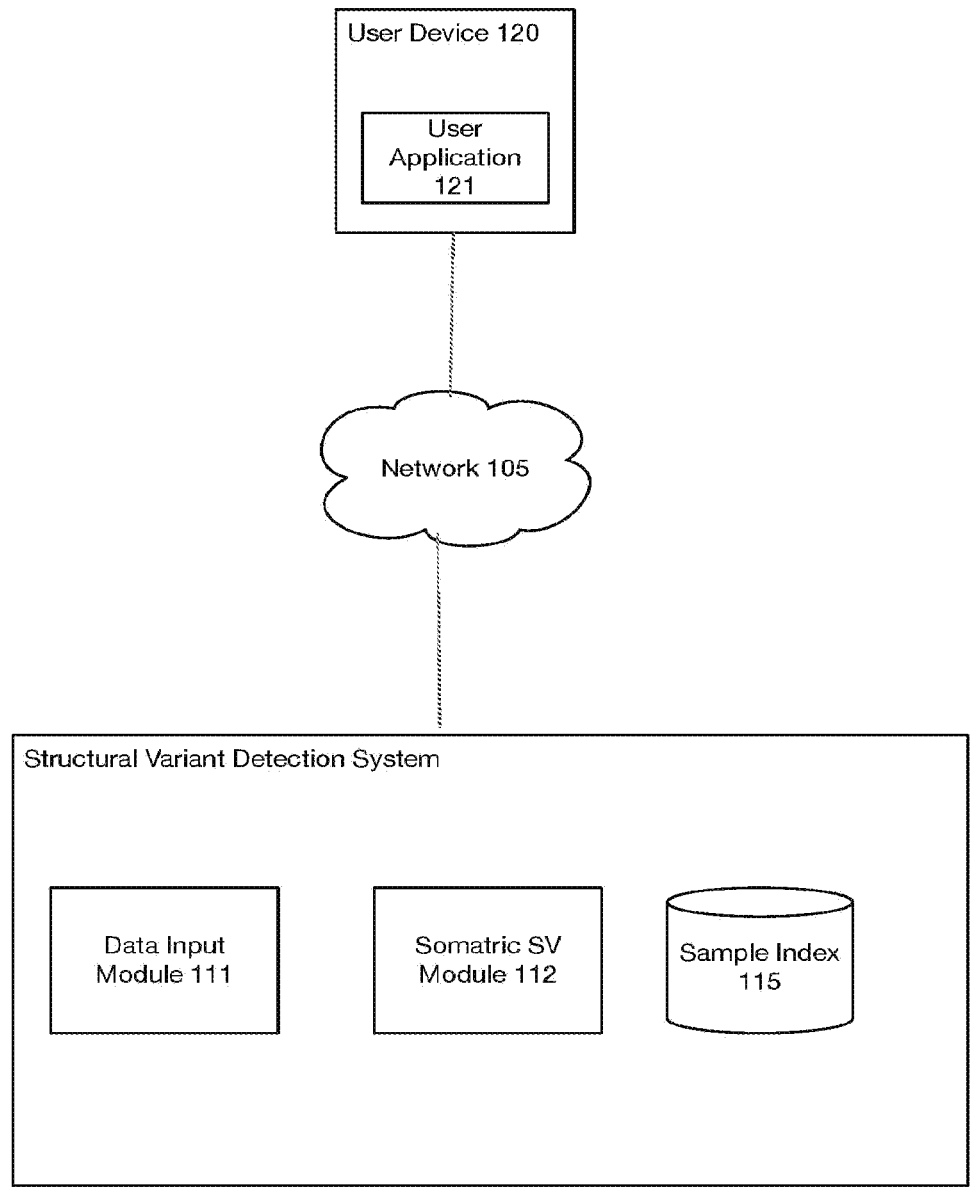
FIG. 1—is a block diagram depicting a system for detecting somatic structural variants, in accordance with certain example embodiments.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R.I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference. The enhanced sensitivity of the methods disclosed herein.

Overview

Embodiments disclosed herein provide methods, systems, and computer program products that utilize long-range phase information to detect subtle chromosome imbalances in genotype data. Clonal expansions result from mutation followed by selective proliferation, and the embodiments disclosed herein may be used to somatic structural variant events (SVs) predictive or diagnostic of cancer and other diseases. The enhanced sensitivity of the methods disclosed herein may be used to detect the presence of a disease or a susceptibility disease. Likewise the embodiments disclosed herein may be used to track disease progression and or therapeutic treatment to verify clearance of disease, for example elimination of clones comprising driver mutations of a particular disease state such as cancer.

The computer implemented methods disclosed herein may be further combined in kits are systems to provide useful diagnostics. For example, a software component may be packaged with reagents for sample genotyping, or incorporated into a genotyping system that processes samples to determine allelic frequencies including various sequencing and probe based approaches.

In some embodiments, the methods disclosed herein may be used for analyzing sample with a small amount of nucleic acid such as cell free nucleic acids or nucleic acids from a single or a small number of cells. For example, the methods may be used for analyzing fetal nucleic acid in the blood of a pregnant female, circulating tumor DNA, or nucleic acids from a single cell or multiple cells obtained from an embryo.

Example System Architectures

FIG. 1 is a block diagram depicting a system for detecting somatic structural variants from genotyping data, in accordance with certain example embodiments. As depicted in FIG. 1, the system 100 includes network devices 110 and 120 that are configured to communicate with one another via one or more networks 105. In some embodiments, a user associated with device 120 must install a user interface application 111 and/or make a feature selection to obtain the benefit of the techniques described herein.

Each network 105 includes a wired or wireless telecommunication means by which network devices (including devices 110 and 120) can exchange data. For example, each network 105 can include a local area network ("LAN"), a wide area network ("WAN"), an intranet, and Internet, a mobile telephone network, or any combination thereof. Throughout the discussion of example embodiments, it should be understood that the terms "data" and "information" are used interchangeably herein to refer to text, images, audio, video, or any other form of information that can exist in a computer-based environment.

Each network device 110 and 120 includes a device having a communication module capable of transmitting and receiving data over the network 105. For example, each network device 110 and 120 can include a server, desktop computer, laptop computer, tablet computer, smart phone, handheld computer, personal digital assistant ("PDA"), or any other wired or wireless, processor-driven device. In the example embodiment depicted in FIG. 1, the network devices 110 and 120 are operated by end-users and backend server operators/administrators (not depicted). A user can use the application 121, such as a web browser application or a stand-alone application to view, upload, download, or otherwise access files or web pages via a distributed network 105.

It will be appreciated that the network connections shown are example and other means of establishing a communication link between the computers and devices can be used. Moreover, those having ordinary skill in the art and having the benefit of the present disclosure will appreciate that the devices 110 and 120 illustrated in FIG. 1 can have any of several other suitable computer system configurations. For example, a user device 120 embodied as a mobile phone or handheld computer many not include all components described above.

In certain example embodiments, the network computing devices and any other computing machines associated with the embodiments presented herein may be any type of computing machine such as, but not limited to, those discussed in more detail with respect to FIG. 1. Furthermore, any components associated with any of these computing machines, such as components described herein or any other components (scripts, web content, software, firmware, or hardware) associated with the technology presented herein may be any of the components discussed in more detail with respect to FIG. 1. The computing machine discussed herein may communicate with one another as well as other computer machines or communication systems over one or more networks, such as network 105. The network 105 may include any type of data or communication network, including any of the network technology discussed with respect to FIG. 2.

Example Processes

Figure 2:
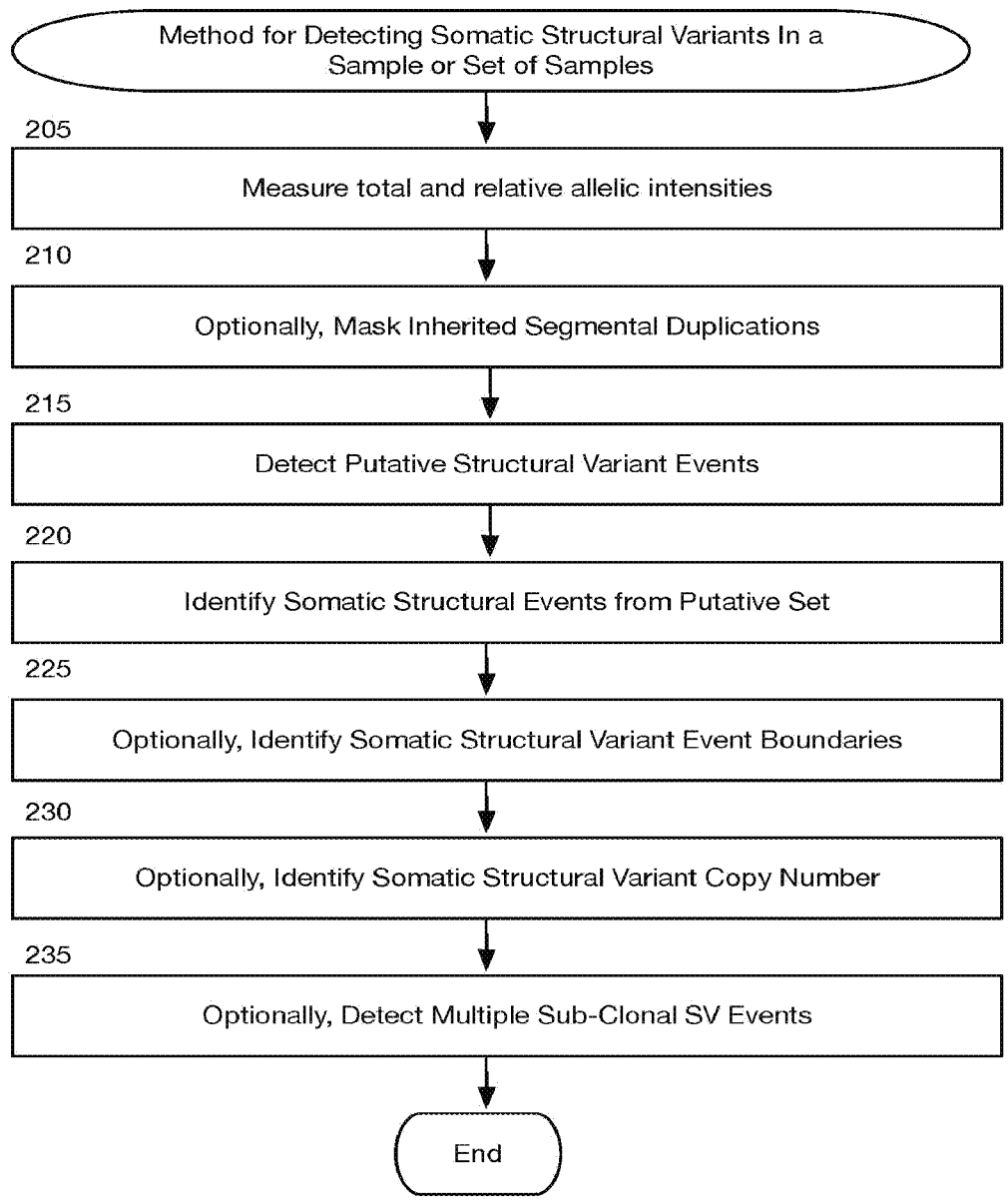
FIG. 2—is a block flow diagram depicting a method for detecting somatic structural variants in genotyping data, in accordance with certain example embodiments.

The example methods illustrated in FIG. 2 are described hereinafter with respect to the components of the example operating environment 100. The example method of FIG. 2 may also be performed with other systems and in other environments.

FIG. 2 is a block flow diagram depicting a method 200 to detect somatic structural variants (SVs), in accordance with certain example embodiments.

Method 200 begins at block 205, where the data input module 111 receives genotyping data from one or more samples for analysis. In certain example embodiments, the data input module 111 will determine a measure of total and relative allelic intensities from the input genotype data. Genotyping data may be acquired using standard techniques in the art, with genotyping data contained in the UK Biobank [23] being representative of a type of genotyping data that may be used with the embodiments disclosed herein. In certain example embodiments, determining total and relative allelic intensities from genotyping data will comprise converting genotype intensity data (e.g., A and B allele probe set intensities, $A_{int}$ and $B_{int}$.) In certain example embodiments, this may comprise converting the genotype intensity data into $\log_2 R$ ratio (LRR) and B allele frequency (BAF) values.

For certain example embodiments, the data input module 111 is configured to convert the genotype intensity data into LRR and BAF values comprises, for each genotyping batch, for each cluster of called genotypes (AA, AB, BB), computing a cluster median in (X, Y)=(contrast, size)-space [67]:

$$X = \log_2 A_{int} - \log_2 B_{int}$$

$$Y = (\log_2 A_{int} + \log_2 B_{int})/2.$$

Batch-level cluster centers are computed to account for possible batch effects. If a cluster contains fewer than 10 calls, the median intensity is set to missing. Next, for each individual, affine-normalized and GC-correct (X, Y) transformed intensities. This procedure corrects for systematic variation in probe intensities across SNPs for a particular individual (e.g. broadly elevated or reduced intensity levels), as well as for "GC-wave" artifacts [52]. In certain example embodiments a pair of multi-variate linear regressions $$X_{m,exp} = \alpha + X_m \beta_X + Y_m \beta_Y + \sum_{k=1}^{9} \sum_{p=1}^{2} \left[ (f_{m,k}^{GC})^p \cdot \beta_{k,p}^{GC} + (f_{m,k}^{CpG})^p \cdot \beta_{k,p}^{CpG} \right] \quad (3), (4)$$

$$Y_{m,exp} = \gamma + X_m \delta_X + Y_m \delta_Y + \sum_{k=1}^{9} \sum_{p=1}^{2} \left[ (f_{m,k}^{GC})^p \cdot \delta_{k,p}^{GC} + (f_{m,k}^{CpG})^p \cdot \delta_{k,p}^{CpG} \right],$$

wherein m indexes SNPs, $(X_m, Y_m)$ are intensity values in (contrast, size)-space for the current individual/sample at SNP m, $(X_{m, exp}, Y_{m, exp})$ is the cluster center (computed above) corresponding to the individual's called genotype at SNP m, and $\{f_{m,k}^{GC}, f_{m,k}^{CpG}\}_{k=1}^{9}$ are proportions of GC and CpG content in 9 windows of 50, 100, 500, 1 k, 10 k, 50 k, 100 k, and 250 k, and 1M bp centered around SNP m. The GC content may be determined using bedtools [68] on the human reference (hg19), and CpG content may be determined using the EpiGRAPH CpG annotation [69]. Equations (3) and (4) without the GC and CpG terms amount to an affine transformation of each individual's observed intensity values $(X_m, Y_m)$ to best match the "expected" intensity values $(X_{m,exp}, Y_{m,exp})$ based on each individual's called genotype. The GC and CpG terms constitute a polynomial (quadratic) model for artefactual variation due to effects of local GC and CpG content on measured probe intensities [52]. In certain example embodiments, a least-squares regression may be performed on equations (3) and (4) (ignoring SNPS at which the individual's genotype was uncalled or the relevant cluster center was set to missing) to obtain corrected (X, Y) values, defined as the regression predictions (i.e., $(X_{m,exp}, Y_{m,exp})$ minus the least-squares residuals).

Next, for each genotyping batch, for each cluster of called genotypes (AA, AB, BB), the data input module 111 determines means of corrected (X, Y) values. In this step cluster centers may be recomputed on the affine-normalized and GC-corrected (X, Y) values (taking means rather than medians but otherwise following the first step).

Then, for each genotype, the data input module 111 transforms corrected (X, Y) values to LRR and BAF values. The (X, Y) values may be transformed using a polar-like transformation followed by linear interpolation similar to that disclosed in [51]; Set $$\theta = \frac{2}{\pi} \cdot \arctan(2^{X_{AB} - X}) \quad (5)$$

$$\log_2 R = Y, \quad (6)$$

where in the first equation $X_{AB}$ denotes the mean corrected $X = \log_2 A_{int}/B_{int}$ value for genotypes called as hets at the current SNP. In certain example embodiments, SNPs for which $X_{AB}$ is missing may be filtered out. The cluster centers may then be transformed in the same manner to obtain $(\theta_{AA}, \log_2 R_{AA})$, $(\theta_{AB}, \log_2 R_{AB})$, and $(\theta_{BB}, \log_2 R_{BB})$. Linera interpolation between cluster centers may then be performed [51] in $(\theta, \log_2 R)$-space to estimate BAF and expected $\log_2 R$ for each genotype, from which LRR values may be obtained as $\log_2 R - \log_2 R_{exp}$. If a cluster center is missing, it may be set to the reflection of the opposite cluster center across the vertical line $\theta = \theta_{AB}$.

In certain example embodiments, the data input module 111 may determine a s.d. (BAF) for each sample within each autosome to filter out anomalous BAF and LRR values. In certain example embodiments chromosomes with mean LRR >3.0 (possible non-mosaic trisomy) or mean LRR <−0.5 (possible non-mosaic monosomy) may be filtered out.

In certain example embodiments, data input module 111 may be configured to mask certain genomic regions. For example, genotype measurements in the HLA region on chromosome 6 (28,477,797-33,338,354, build 37) and the X translocation region (XTR) on chromosome X (88,575,629-92,308,067) may be masked [2].

The method then proceeds to block 210, wherein the somatic SV module 112 identifies and masks inherited segmental duplications (i.e. constitutional duplications) in the genotyping data. Constitutional duplications can create false positive detections of mosaic SVs because they have the same effect on BAF and LRR as a somatic gain event at 100% cell fraction. Constitutional deletions also behave like somatic loss events at 100% cell fraction.

Figure 44:
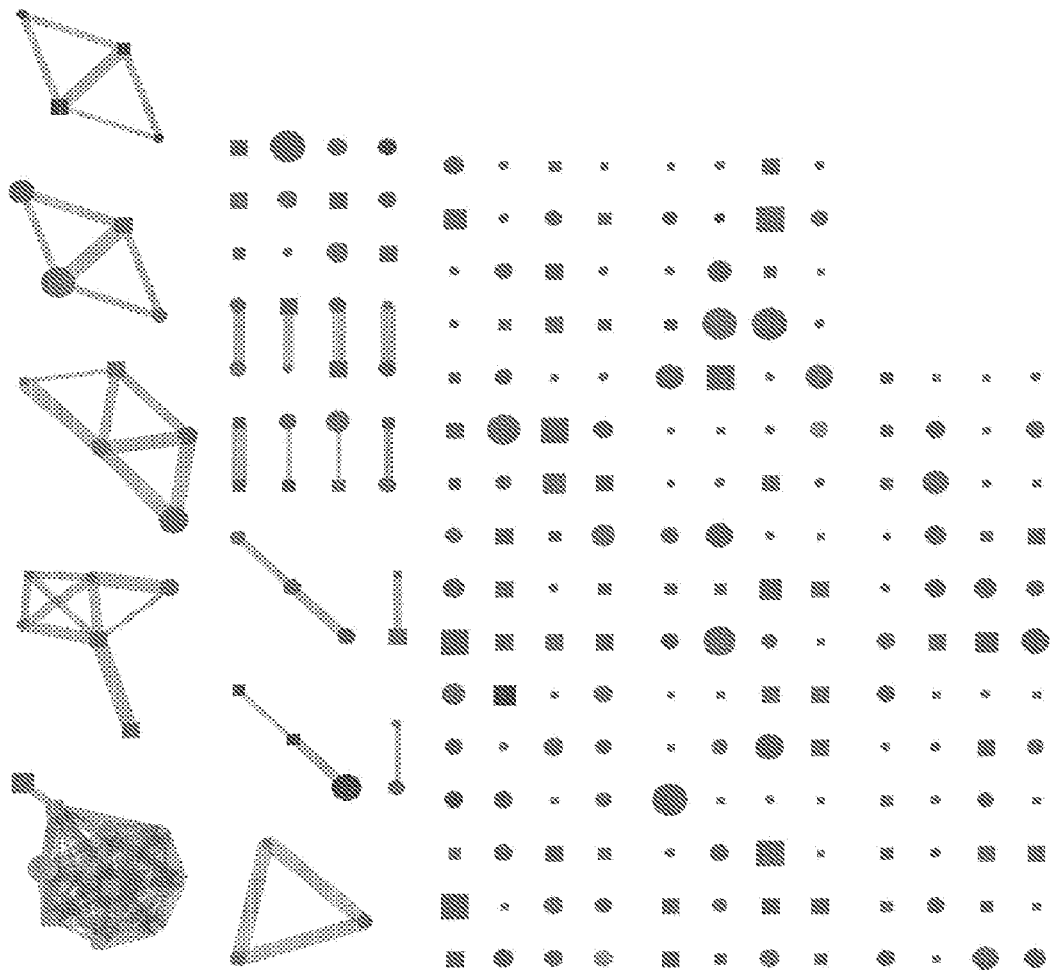
FIG. 44—Identity-by-descent graph at MPL locus (chr1: 43.8 Mb) on individuals with somatic SVs on chr1 extending to the p-telomere. Square nodes in the IBD graph correspond to males and circles to females. Node size is proportional to clonal cell fraction and edge weight increases with IBD length. Colored nodes indicate imputed carriers of SNPs associated with somatic chr1p CNN-LOH (FIG. 4); color intensity scales with imputed dosage.

Constitutional duplications are relatively easy to filter as they are characteristically short (typically <1 Mb) and produce extreme shifts in genotyping intensities; heterozygous sites have AAB or ABB genotypes with |ΔBAF|~0.17, and all sites have triploid total copy number with LRR~0.35 (FIG. 2 and FIG. 44). To call and mask such regions, the SV module 112 may model observed phased BAF deviations (pBAF) across a chromosome using a 25-state hidden Markov model (HMM). In certain example embodiments, the SV module 112 models observed phased BAF deviations with states corresponding to pBAF values in [−0.24, +0.24] at intervals of 0.02. Each state is assumed to have emitted a normally distributed observed pBAF with mean equal to the state value and standard deviation equal to the empirical s.d. (BAF) at each site (measured across all individuals within a genotyping batch), and z-scores may be capped at 4 to reduce outlier influence. The SV module 112 may be configured to allow transitions between the 0 state and each nonzero state with probability 0.003 (modeling event boundaries) and between each nonzero state and its negative with probability 0.001 (modeling phase switch errors). At the telomeres, a probability of 0.01 may be assigned to starting/ending in each nonzero state (to favor calls that end at the telomeres).

The SV module 112 may select regions to mask by computing the Viterbi (maximum likelihood) path through the above HMM and examining contiguous regions of nonzero states. In certain example embodiments, the SV module 11 may mask regions of <2 Mb with |ΔBAF|>0.1 and LRR>0.1, which are likely constitutional duplications, and further mask gaps (of <2 Mb) between nearby regions of this form (assuming that the 1 Mb flanks of the merged region had no apparent mosaicism, i.e., |ΔBAF|<0.05).

Figure 43:
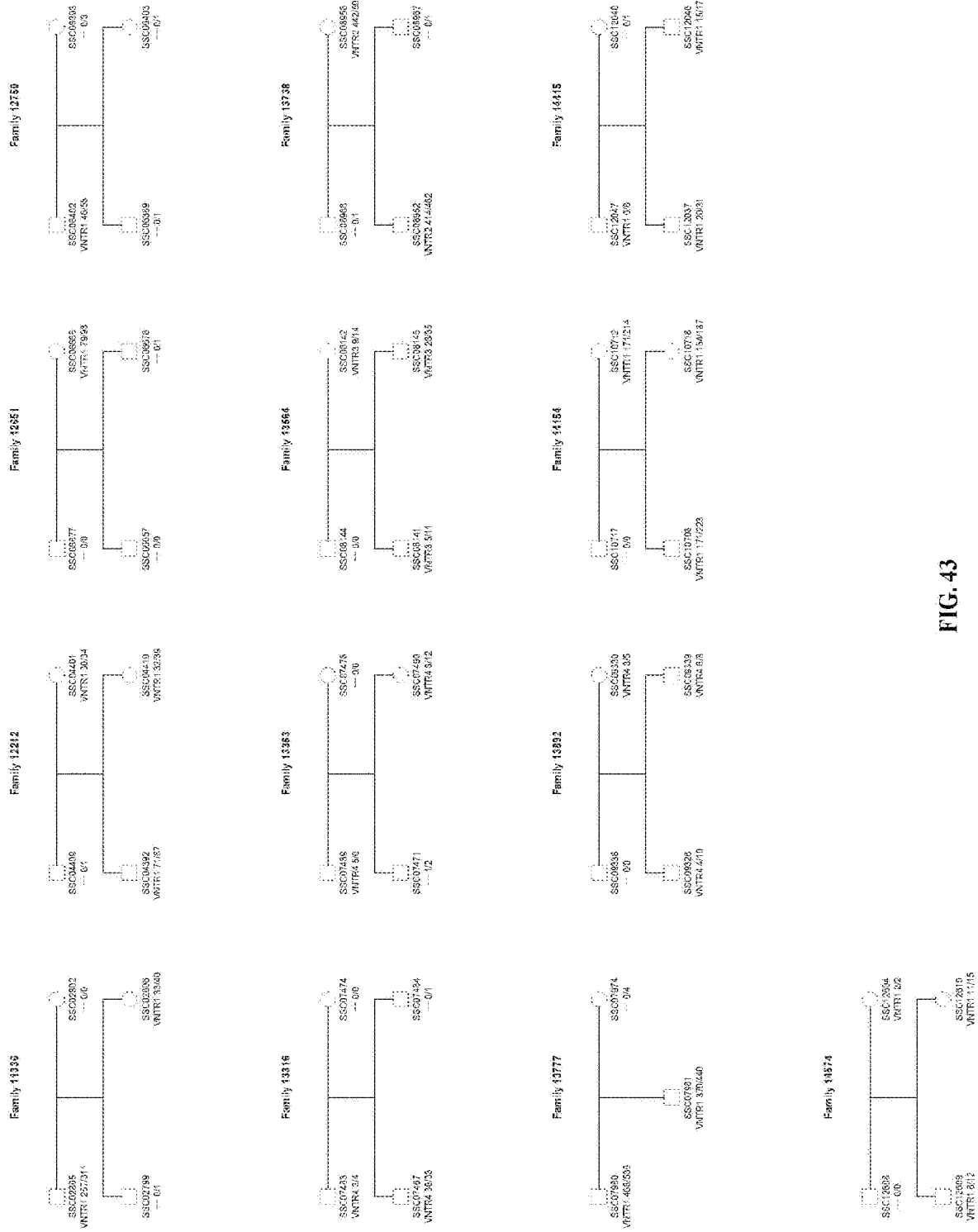
FIG. 43—SFARI pedigrees containing variable number tandem repeats at FRA10B. Read counts (non-reference/total) are reported for each individual, and autistic probands are indicated in orange.

The method then proceeds to block 215, where the SV module 112 detects putative somatic SV events. The above approach of performing Viterbi decoding on a many-state hidden Markov model works well for finding constitutional duplications, but to define a formal, well-calibrated statistical test sensitive to somatic SVs at low cell fractions, a different approach is required. The single 25-state HMM described above may be replaced with a family of 3-state HMMs parameterized by a single parameter θ representing mean |ΔBAF| within a mosaic event (i.e., the states of the HMM are {−θ, 0, +θ}; FIG. 43). The key advantages of this approach are that (i) it naturally produces a likelihood ratio test statistic for testing θ=? 0 (described in the following section); and (ii) the derived test statistic integrates over uncertainty in phase switches and SV boundaries (unlike maximum likelihood estimation).

Aside from the reduction in the number of states, the 3-state HMM used for event detection differs from the 25-state HMM described above only in values of a few constants. The ±θ→0 "stop" transition probability may be reduced to 3×10-4 in autosomes and 1×10-4 in chromosome X, reflecting the fact that most somatic events of interest span tens of megabases. The 0→±θ "start" transition probability may be reduced to 0.004 (resp. 0.08) times the stop probability in autosomes (resp. chromosome X). (The asymmetry in start vs. stop probabilities reflects the fact that the HMM should not expect to spend equal amounts of time in the mosaic vs. non-mosaic states; most portions of most chromosomes are expected to be non-mosaic.) The the −θ↔+θ switch error probability may be kept at 0.001, roughly reflecting our estimated rate of large-scale phase switches [24, 26]. A probabilistic penalty does not have to be assessed to starting/ending in nonzero states except in acrocentric chromosomes, for which the probability of starting in a nonzero state (at the centromere, given that we had no p-arm genotypes) was reduced by a factor of 0.2. As above, it is assumed each state emitted a normally distributed observed pBAF. In certain example embodiments, z-scores may be capped at 2 to further reduce outlier influence.

A potential criticism of this 3-state HMM is that it does not properly model chromosomes with multiple SVs of differing |ΔBAF|. However, the primary purpose of this model is event discovery (particularly for SVs at low cell fractions); after chromosomes containing SV events are identified, additional post-processing (described below) is performed on the putative set to pick up complex SVs. Additionally, |ΔBAF| may be re-estimated within SV boundaries after making event calls.

The method then proceed to block 220, where the SV module 112 detects a final set of somatic SV events. In certain example embodiments, the SV module 112 detects a final set of somatic SV events by applying a likelihood ratio test to values determined in detecting the putative SV events above. In certain example embodiments, for a given sequence of phased BAF deviations (denoted x) on a chromosome, the family of HMMs parameterized by θ gives rise to a likelihood ratio test statistic as follows. For a given θ, the likelihood L(θ|x) may be determined by the SV module 112 as the total probability of observing x under the HMM with nonzero states ±θ. (This computation can be performed efficiently using dynamic programming.) The likelihood ratio for $$\theta \stackrel{?}{=} 0$$

is then given by $$\Lambda(x) = \frac{L(0 \mid x)}{sup_\theta \{L(\theta \mid x)\}}, \quad (7)$$

where the numerator is the likelihood under the model in which all states collapse to 0 (i.e., no SV is present) and the denominator is the likelihood under the best choice of θ.

Producing a hypothesis test for $$\theta \stackrel{?}{=} 0$$

takes one more step. While asymptotic theory can often be invoked to assert that −2 log Λ is approximately χ2 distributed under the null hypothesis, there are two issues here. Most importantly, the hidden Markov model is imperfect, and in particular, different choices of probability constants within the model can substantially change the absolute magnitude of the test statistic. Second, our null hypothesis θ=0 is at the boundary of the parameter space.

For these reasons, the SV module 112 may be configured to estimate an empirical null distribution for the test statistic −2 log Λ rather than relying on theory. In certain example embodiments, null distribution is approximated simply by taking observed pBAF sequences and randomizing phase at each heterozygous site (keeping |ΔBAF| fixed). In one example embodiment, 5 independent randomizations were performed per individual sample, computed −2 log Λ for each replicate, and used the resulting distribution of null test statistics to determine the cutoff value that would achieve a false discovery rate of 0.05 in light of the test statistics observed on real data. This calibration may be performed independently for each autosome and chromosome X, yielding critical values from 1.41-3.87.

The method then proceeds to block 225, where the SV module 112 may identify somatic SV event chromosomal locations (i.e. boundaries). The method thus far can detect whether or not a somatic SV occurred somewhere on a chromosome in order to described the observed BAF deviations. However, if so (i.e., if the null hypothesis is rejected), the method above makes no indication of where on the chromosome the SV is located. To estimate SV boundaries, the SV module 112, may take 5 samples from the posterior of the HMM using the likelihood-maximizing choice of 8. The SV module 112 may then identify a boundary of an SV using the consensus of the 5 samples.

Figure 27:
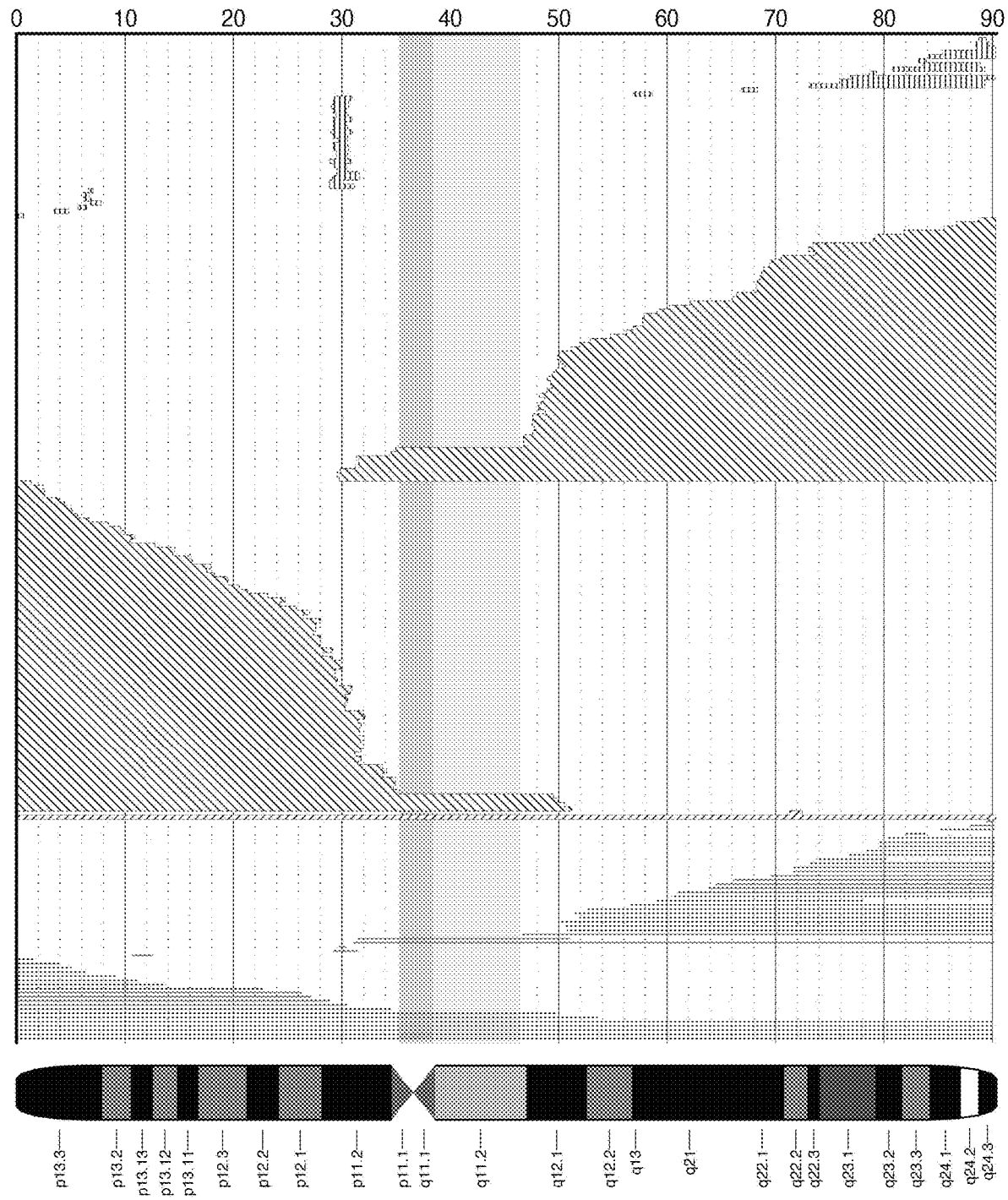
Figure 28:
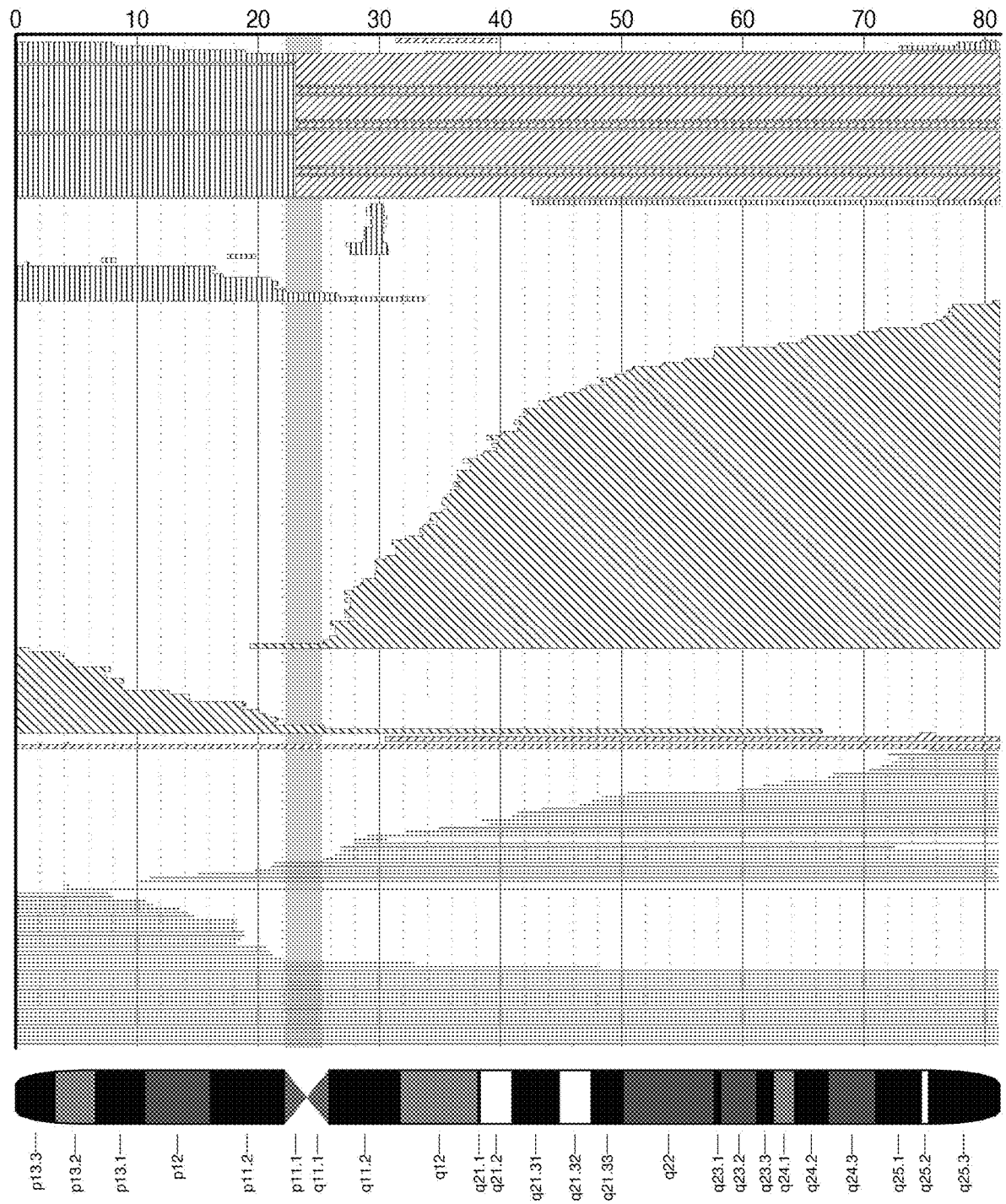
Figure 29:
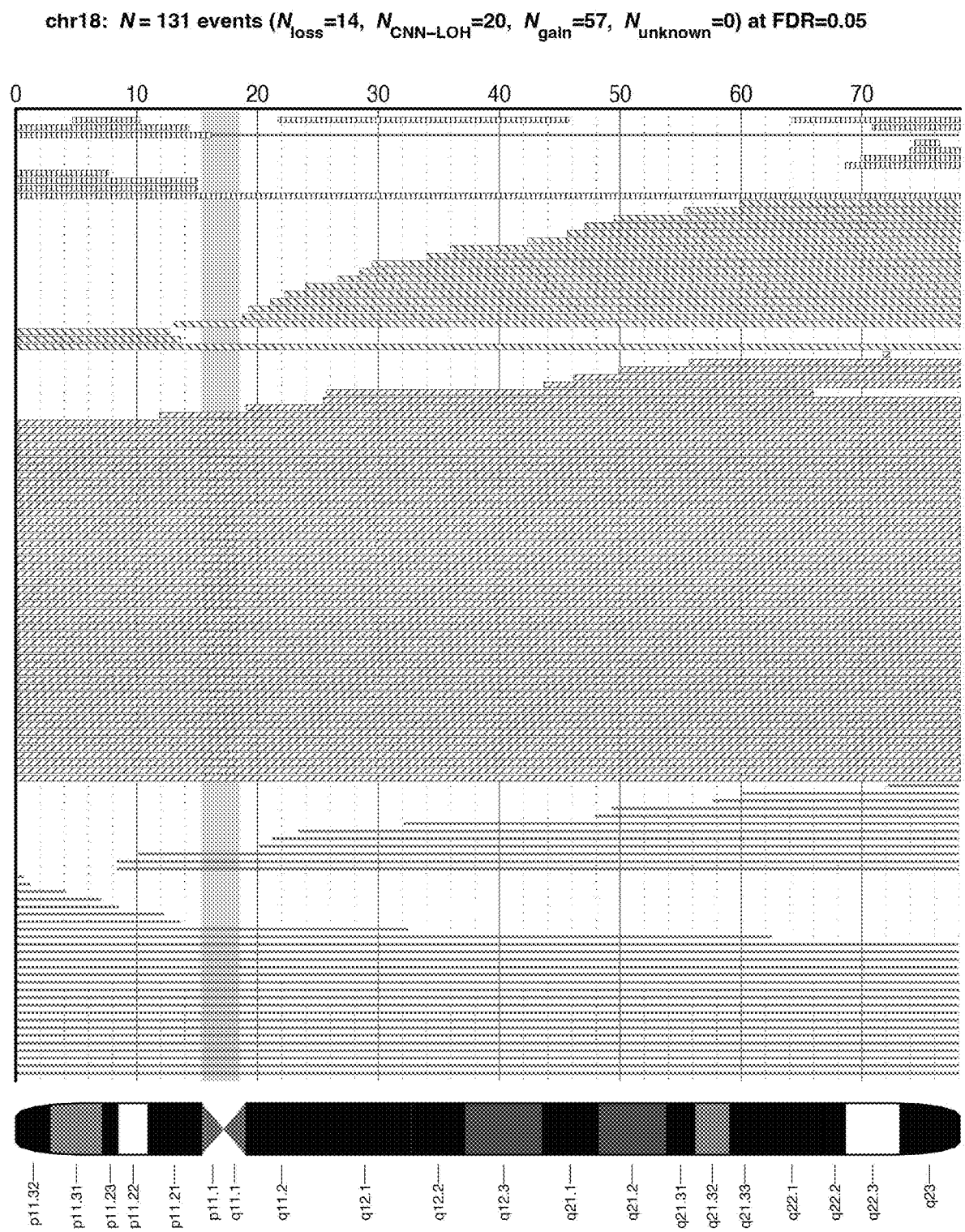
Figure 30:
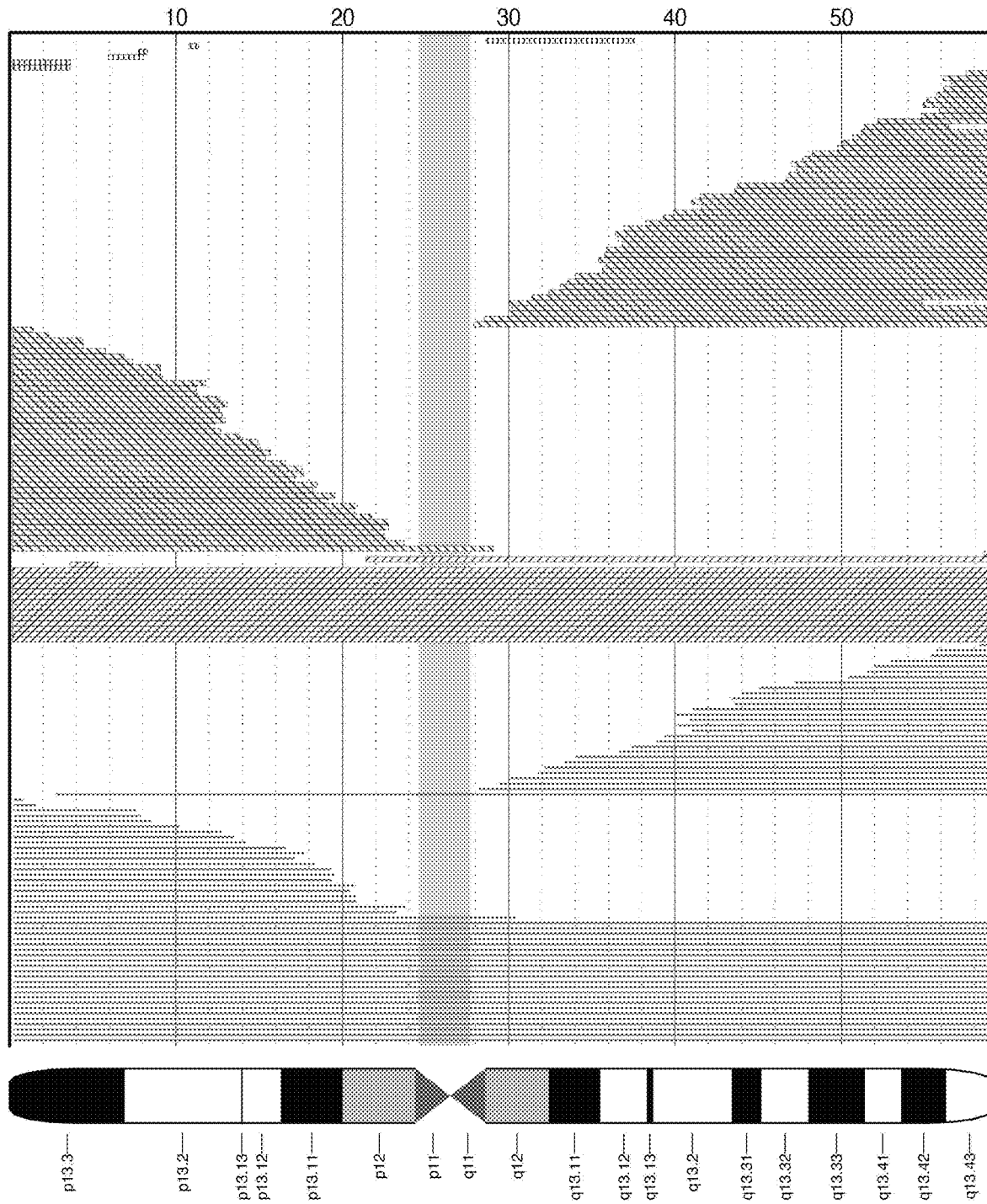
Figure 31:
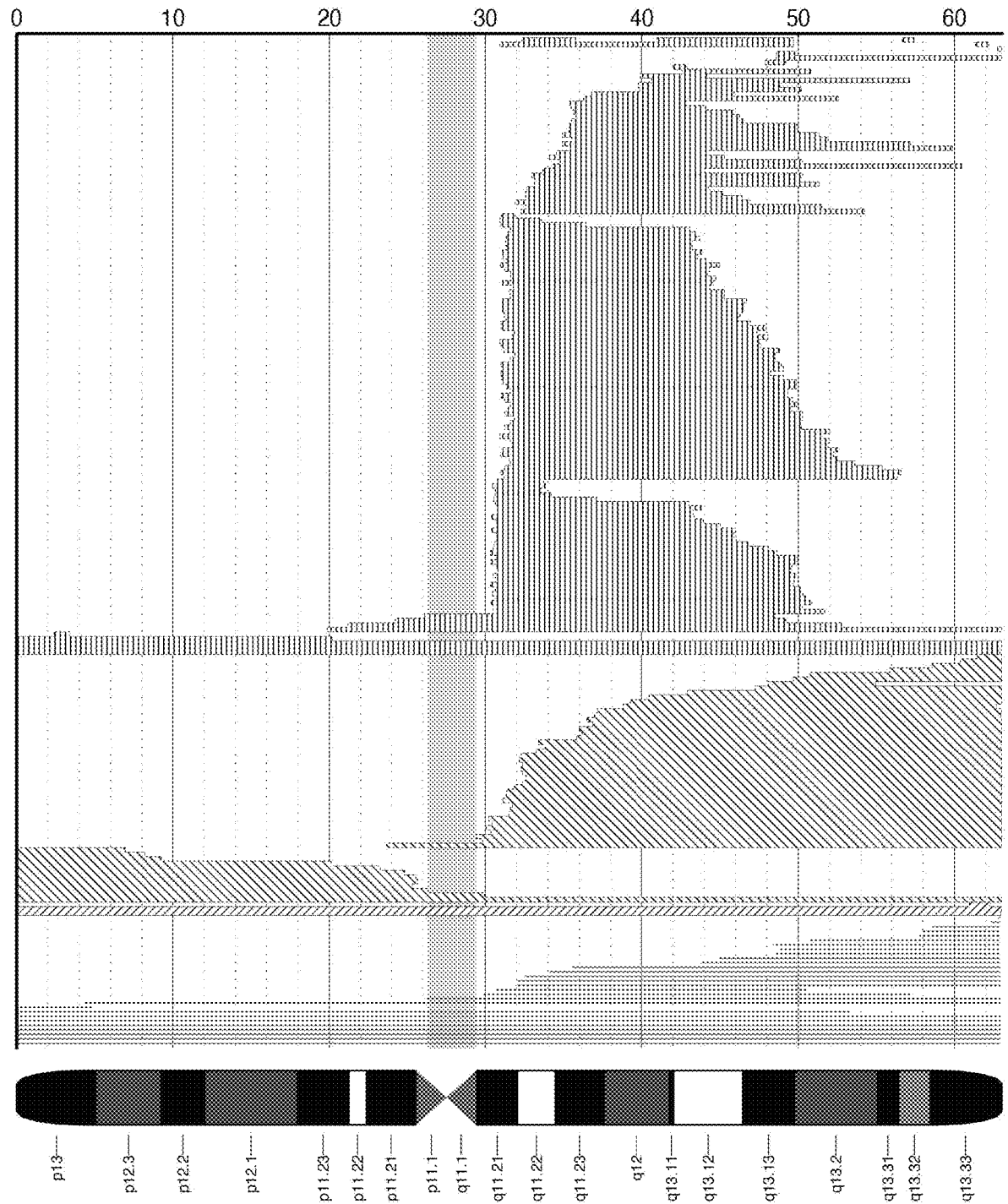
Figure 32:
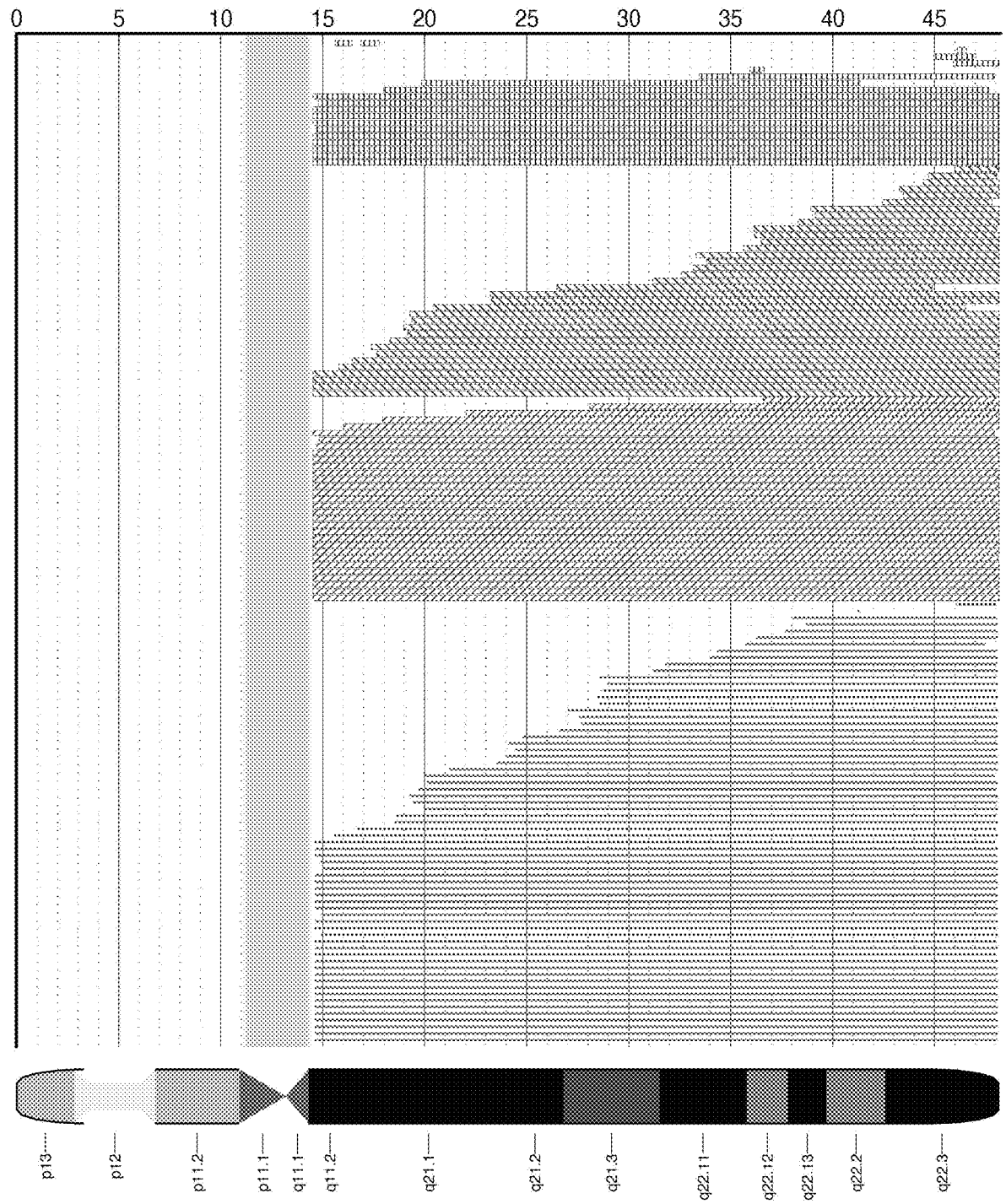
Figure 33:
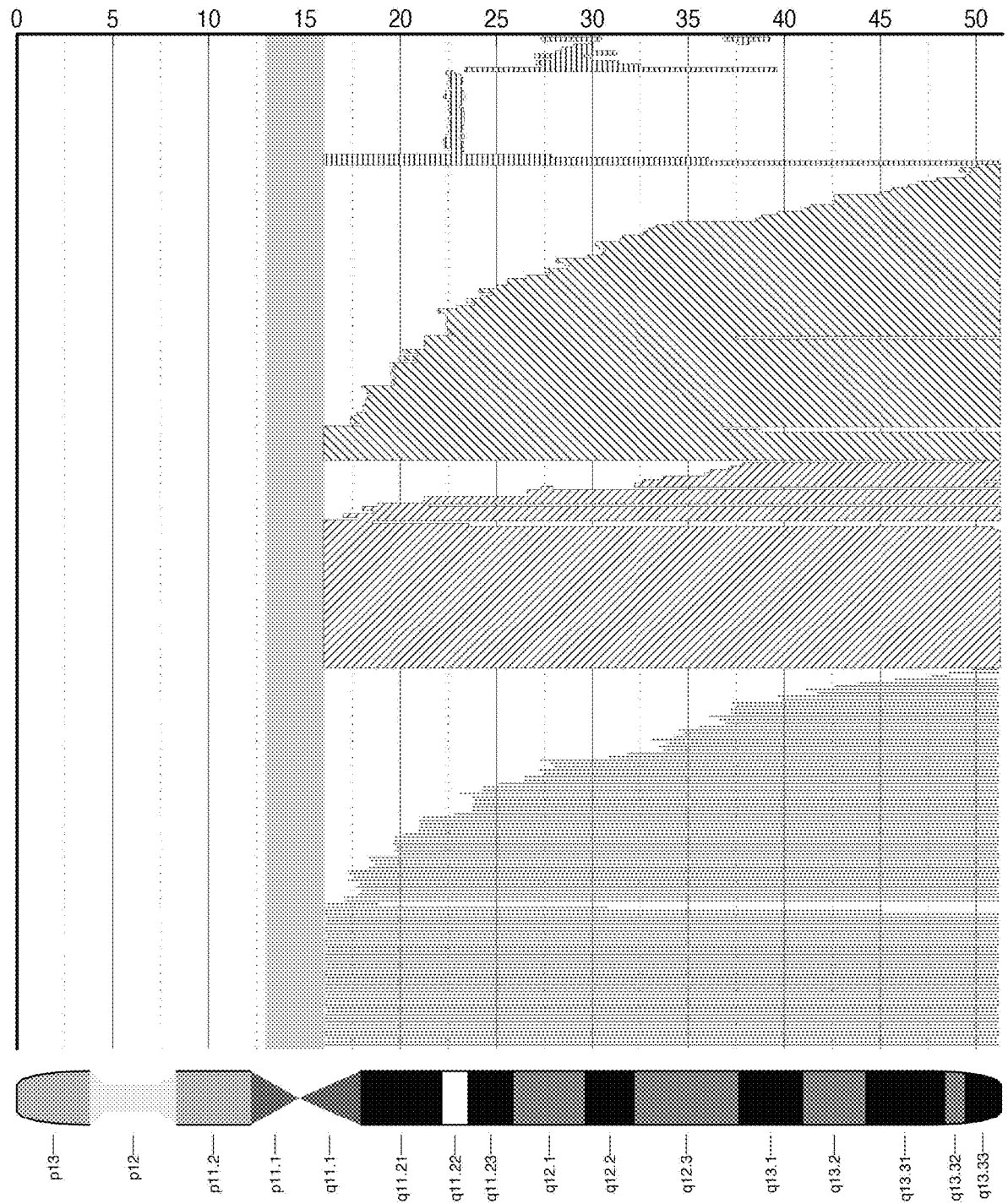

The method then proceeds to block 230, wherein the SV modules identifies somatic SV event copy number. LRR data may be incorporated to determine copy number. As previously described [1,2,8], the mean LRR in called SVs either increases or decreases linearly with estimated BAF deviation (for losses and gains) or was near zero (for CNN-LOHs) (FIG. 2 and FIG. 27). These trend lines allow the SV module 112 to estimate the expected LRR/|ΔBAF| slopes corresponding to gains and losses (approximately 2.16 and −1.89, respectively). For a particular event with estimate BAF deviation/|ΔBAF| and mean LRR $\hat{\mu}$, and standard error of LRR $\hat{\sigma}$, the SV module 112 can be configured to compute the relative probabilities that the event was a loss, CNN-LOH, or gain.

In certain example embodiments, the above approach may be improved by leveraging chromosome-specific frequencies of loss, CNN-LOH, and gain. Specifically, some chromosomes contained many of one type of event and very few of another (FIG. 1), and this information may be helpful for calling events with uncertain copy number (i.e., events with low |ΔBAF| and therefore little separation between the expected mean LRRs corresponding to loss, CNN-LOH, or gain). The SV module 112 may split the LRR vs. |ΔBAF| space into three zones bisecting the loss/CNN-LOH/gain trend lines: letting s=LRR/|ΔBAF|, requiring that events with s<−0.94 be called either as loss or unknown, events with −0.94≤s<1.08 be called either as CNN-LOH or unknown, and events with 1.08≤s be called either as gain or unknown. It may be further required that in order to call an event within one of these zones, its mean LRR $\hat{\mu}$ needed to be either (i) at least twice as close to its expectation according to the closest trend line vs. the next closest; or (ii) within two standard errors $\hat{\sigma}$ of its expectation. With these rules in place, the SV module 112 may be configured to set preliminary calls to each event, calling copy number for an event if the requirements above were satisfied and if the most likely call was at least 20 times more likely than the next-most likely (based on $\hat{\mu}$ and $\hat{\sigma}$ and the normal model described in the previous paragraph). The SV module 112 may then re-call all events by performing the same procedure but incorporating a prior on call probabilities: for a given event, for example by putting a prior on its copy number derived from the preliminary calls made for up to 20 events with similar boundaries (differing by <10 Mb and <10% of chromosome length), adding a pseudo-count of 0.5 to prevent copy numbers from being assigned zero probability.

Figure 20:
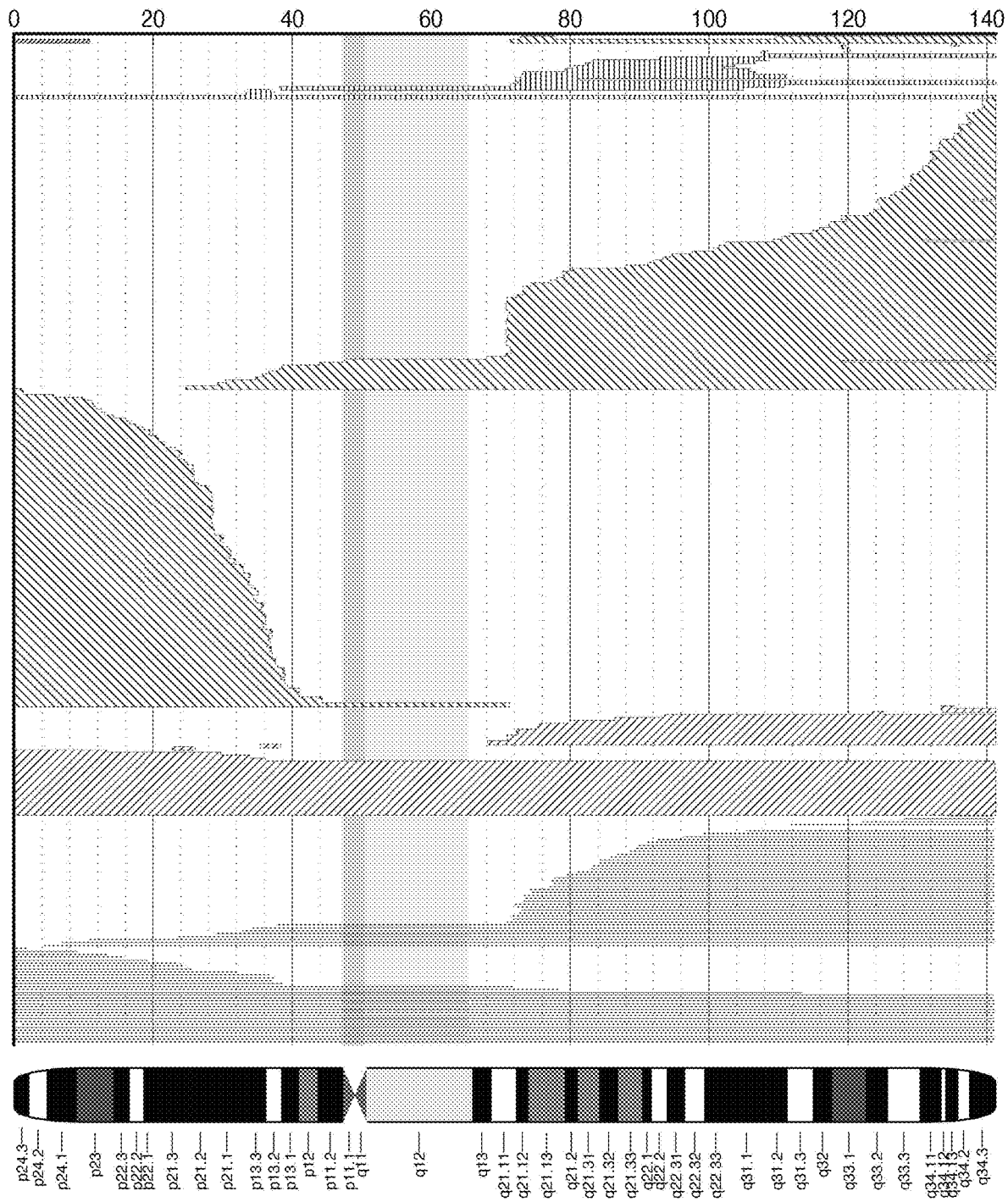
Figure 21:
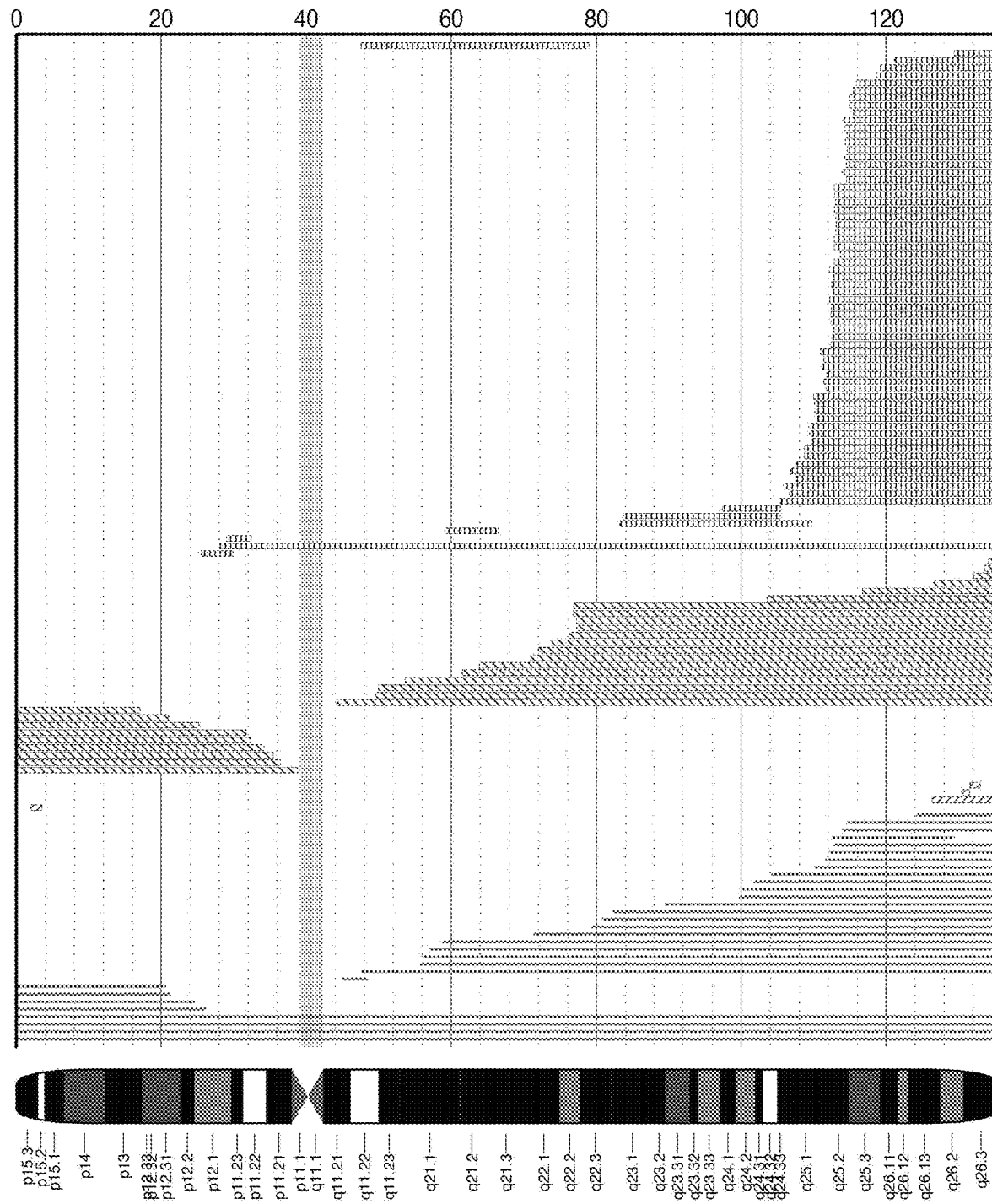

One special case may require separate handling: isochromosomes, which involve simultaneous loss of one chromosomal arm and gain of the other (most notably i(17q); FIG. 20). Therefore the SV module 112 may be configured to include a separate check for whole-chromosome events examining whether LRR was significantly different for the p vs. q arms, and if so, the SV module 112 may split the event at the centromere. The SV module 112 may also perform manual review more generally to search for events with multiple |ΔBAF| and/or LRR levels within a call, but did not find such events beyond subclonal CNN-LOHs (described below).

The method then proceeds to block 235, where the SV module 112 may detect multiple sub-clonal SV events. The framework described above is aimed at identifying and calling sporadic SVs arising in a population cohort for which most individuals with detectable clonality have a single simple event (a single clonal loss, CNN-LOH, or gain) at low-to-modest cell fraction. However, for a small subset of individuals (mostly with prevalent or incident cancer diagnoses), multiple events may be detected, giving rise to the possibility that some samples might carry overlapping or contiguous events that require more careful treatment.

Accordingly, the SV module 112 may execute a post-processing step in which detected events are re-analyzed using Viterbi decoding on a 51-state HMM with |ΔBAF| levels ranging from 0.01 to 0.25 in multiplicative increments. In this HMM, in addition to start/stop transitions between the 0 state and nonzero states (with probability 10-4) and switch error transitions between each state and its negative (with probability 0.001), the SV module 112 may also introduce |ΔBAF|-shift transitions between different nonzero states (with probability 10-7). At the telomeres, the SV module 112 may assign a probability of 0.01 to starting/ending in each nonzero state. All calls for which the posterior decoding resulted in more than one |ΔBAF| state were examined, and it was observed that in nearly all of these cases, the event in question had originally been called as a CNN-LOH but exhibited a step function of increasing BAF deviations toward the telomere (consistent with multiple subclonal CNN-LOH events covering varying segments of a chromosome arm). All such events are described in FIGS. 39A-39B.

The method then terminates.

Figure 53:
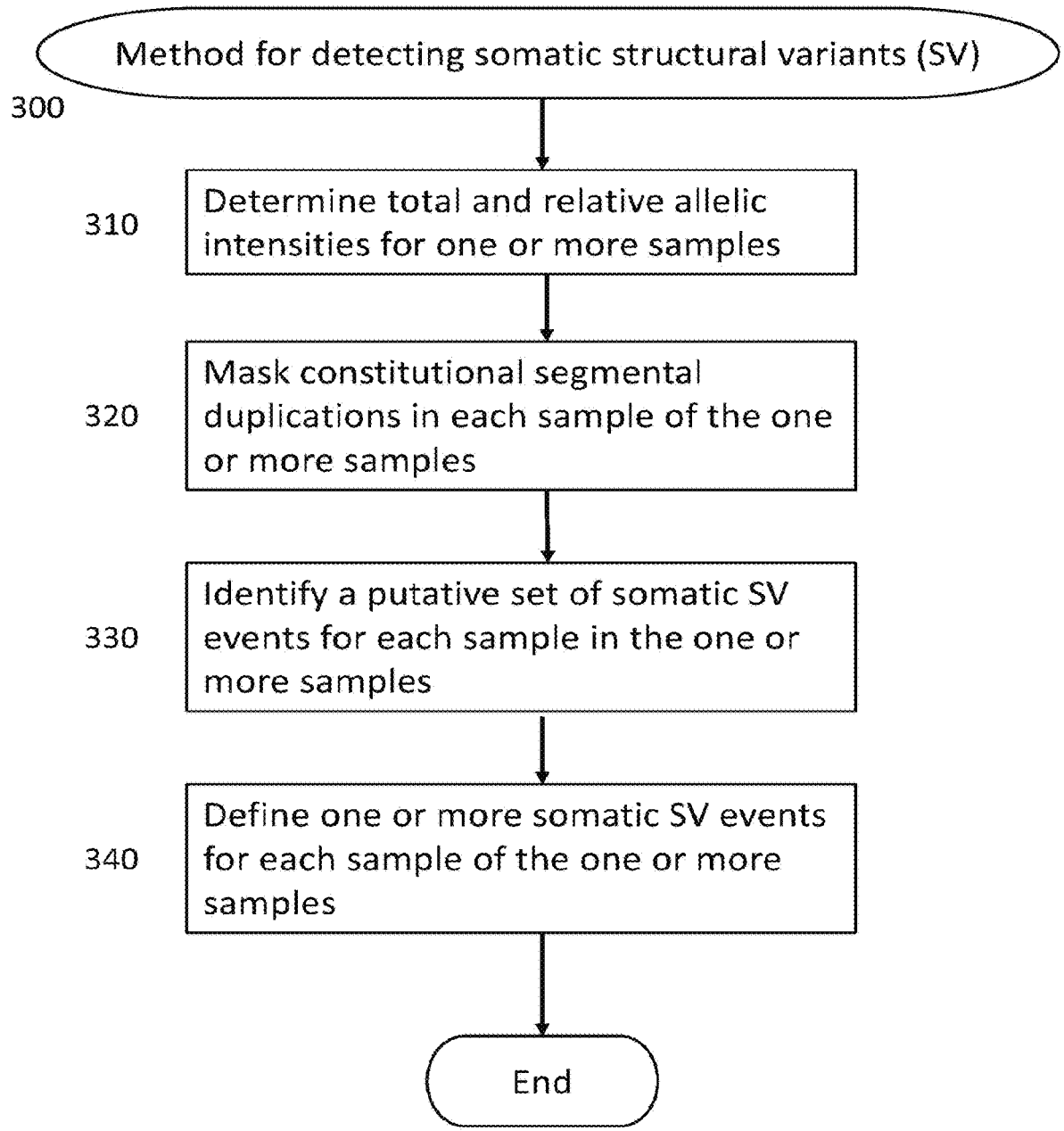
FIG. 53 shows an exemplary method (300) for detecting somatic structural variants (SV).

FIG. 53 shows an exemplary method (300) for detecting somatic structural variants (SV). Method 300 may be a computer-implemented method, e.g., can be performed using one or more computing devices. Step 310 may comprise determining the total and relative allelic intensities for one or more samples. The determination may comprise converting genotype intensity data into log $R_2$ ratio (LRR) and B allele frequency (BAF) values. Step 320 may comprise masking constitutional segmental duplications in each sample of the one or more samples. The masking may comprise modeling observed phased BAF deviations (pBAF). In certain examples, modeling the observed pBAFs may be performed by modeling across individual chromosomes using a 25-state hidden Markov model (HMM) with states corresponding to pBAF values. Step 330 may comprise identifying a putative set of somatic SV events for each sample in the one or more samples. In certain examples, the putative set of somatic SV events may be identified using a 3-state HMM. The 3-state HMM may be parameterized by a single parameter representing mean |ΔBAF| within a given somatic SV event. Step 340 may comprise defining one or more somatic SV events for each sample of the one or more samples. In some embodiments, steps 310-340 may be performed in any order, e.g., in the order shown by the arrows in FIG. 53. In some cases, steps 310-340 may be performed as a single step.

In some embodiments, method 300 may further comprise locating a chromosomal location of each identified somatic SV event for each sample in the one or more samples. The chromosomal location of each identified somatic SV event may be located by taking 5 samples from the posterior of the 3-state HMM and determining the boundaries of each SV event based on a consensus of the 5 samples.

In some embodiments, method 300 may further comprise determining a copy number of each identified somatic SV event for reach sample in the one or more samples. The copy number of each identified somatic SV event may be determined by determining a relative probability that the event was a loss, CNN-LOH, or gain based at least in part on the LRR and |ΔBAF| deviation.

In some embodiments, method 300 may further comprise detecting multiple sub-clonal events for each identified somatic SV event. The multiple sub-clonal events may be detected by re-analyzing each identified somatic SV using Viterbi decoding on a 51-state HMM with |ΔBAF| levels ranging from 0.01 to 0.25 in multiplicative increments.

In some embodiments, method 300 may further comprise selecting regions to mask, which comprises computing the Viterbi path through the HMM and examining contiguous regions of nonzero states. In certain embodiments, method 300 may further comprise detecting a disease or susceptibility to a disease disclosed herein, e.g., based on detection of the one or more somatic SV events.

Also disclosed herein includes a computer program product comprising a non-transitory computer-executable storage device having computer-readable program instructions embodied thereon that when executed by a computer cause the computer to for performing the methods disclosed herein. In some examples, the computer-executable program instructions may comprise computer-executable program instructions to perform one or more steps of method 300.

Further disclose herein includes a system to detect somatic SV events. In certain examples, the system may comprise a storage device and a processor communicatively coupled to the storage device, wherein the processor executes application code instructions that are stored in the storage device and that cause the system to perform one or more steps of method 300.

Disclosed herein also includes a kit for performing the methods herein. The kit may comprise reagents (e.g., for determining allelic frequencies), a computer program product, a system, or a combination thereof.

Other Example Embodiments

Figure 3:
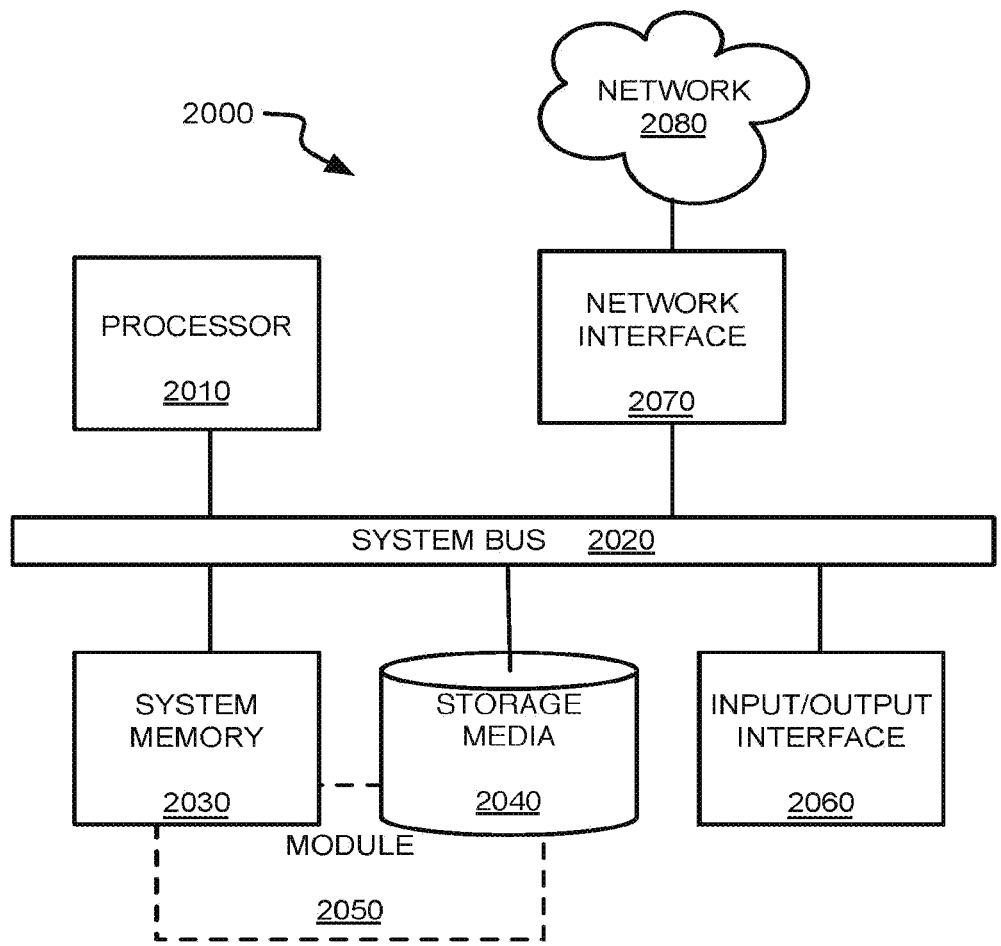
FIG. 3—is a block diagram depicting a computing machine and a module, in accordance with certain example embodiments.

FIG. 3 depicts a computing machine 2000 and a module 2050 in accordance with certain example embodiments. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a router or other network node, a vehicular information system, one more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain embodiments, the processor 2010 along with other components of the computing machine 2000 may be a virtualized computing machine executing within one or more other computing machines.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 may also include volatile memories such as random access memory ("RAM"), static random access memory ("SRAM"), dynamic random access memory ("DRAM"), and synchronous dynamic random access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, biometric readers, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks (WAN), local area networks (LAN), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or an analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to some embodiments, any of the processor 2010, the other elements of the computing machine 2000, or the various peripherals discussed herein may be integrated into a single device such as a system on chip ("SOC"), system on package ("SOP"), or ASIC device.

In situations in which the systems discussed here collect personal information about users, or may make use of personal information, the users may be provided with a opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement an embodiment of the disclosed embodiments based on the appended flow charts and associated description in the application text. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described herein. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments. Accordingly, such alternative embodiments are included in the invention claimed herein.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

Exemplary Applications

The methods herein may be used for analyzing one or more somatic structural variants associated with certain condition such as a disease, thereby detecting the presence or susceptibility of the condition. In some embodiments, disclosed herein include methods for detecting presence or susceptibility of a condition in subject, the method comprising detecting one or more somatic structural variants in nucleic acids in a sample from the subject. The presence or absence of the one or more somatic structural variants indicates the presence or susceptibility of the condition.

Samples

In some embodiments, the somatic structural variants are in nucleic acids in a sample, e.g., a sample containing a small amount of nucleic acids. In certain examples, the sample may be a biological sample that comprises nucleic acids of interest. In some cases, the sample may be a fluid, e.g., a biological fluid. Examples of biological fluids include blood, serum, plasma, sputum, lavage fluid, cerebrospinal fluid, urine, semen, sweat, tears, saliva, and the like. As used herein, the terms "blood," "plasma," and "serum" expressly encompass fractions or processed portions thereof. Similarly, where a sample is taken from a biopsy, swab, smear, etc., the "sample" expressly encompasses a processed fraction or portion derived from the biopsy, swab, smear, etc. In some examples, the sample may be blood. In some examples, the sample may be plasma. In some examples, the sample may be serum. In some examples, the sample may be a tissue or organ, or an embryo, or a portion thereof.

The nucleic acids in the sample may comprise cell-free nucleic acids. The terms "cell-free nucleic acids" and "circulating cell-free nucleic acids" are used herein interchangeably to refer to nucleic acids or fragments thereof existing outside of cells in vivo, for example, circulating in the blood of a subject (a pregnant subject or a patient). The terms can also be used to refer to the fragments of nucleic acids that have been obtained from the in vivo extracellular sources and separated, isolated or otherwise manipulated in vitro. Examples of cell-free nucleic acids include cell-free DNA, cell-free RNA, cell-free fetal DNA, cell-free fetal RNA, circulating tumor DNA, or circulating tumor RNA, or any combination thereof. In certain embodiments, the nucleic acids may be from a single cell or multiple cells from a tissue, organ, or embryo. In some cases, the nucleic acids may be from a single cell or multiple cells from an embryo, e.g., used for a preimplantation genetic screening.

Non-Invasive Prenatal Testing (NIPT)

In some embodiments, the methods herein may be used for performing non-invasive prenatal testing (NIPT). For example, the methods may comprise detecting and/or analyzing cell-free nucleic acids in fluid samples from pregnant subjects. Cell-free nucleic acid screening or NIPT may utilize bioinformatic tools and processes and next generation sequencing of fragments of DNA in maternal serum to determine the probability of certain chromosome conditions in a pregnancy. All individuals have their own cell-free DNA in their blood stream. During pregnancy, cell-free fetal DNA from the placenta (predominantly trophoblast cells) also enters the maternal blood stream and mixes with maternal cell-free DNA. The DNA of the trophoblast cells usually reflects the chromosomal make-up of the fetus.

The methods herein may comprise screening for a disorder or condition of the fetus such as aneuploidy (e.g., trisomy 21, trisomy 18, and trisomy 13), congenital adrenal hyperplasia, singe gene disorders (e.g., cystic fibrosis, beta thalassemia, sickle cell anemia, spinal muscular atrophy, and myotonic dystrophy), hemolytic diseases, or other conditions (e.g., fetal sex), using the cell-free nucleic acids from a maternal sample (e.g., maternal blood). In certain cases, the methods comprise screening chromosomal alteration(s), including, but not limited to, 22q11 duplication/deletions (e.g., as described in Schmid et al., Fetal Diagn Ther. 2017 Nov. 8. doi: 10.1159/000484317), 1q21 duplication/deletions, 16p11 duplication/deletions, 15q11 duplications/deletions, 15q13 duplication/deletions, or any combination thereof.

Abnormal results typically indicate an increased risk for the specified condition. In some cases, NIPT may be performed using methods described in Norton M E et al., Cell-free DNA Analysis for Noninvasive Examination of Trisomy, *N Engl J Med*, 2015; 372:1589-1597.

Cancer Diagnosis

The methods herein may be used for analyzing circulating nucleic acids to detect and analyze circulating tumor nucleic acids (e.g., circulating tumor DNA (ctDNA)). Circulating tumor nucleic acids may comprise nucleic acid molecules from tumor cells that are present in the blood or other biological tissue. Without being bound by theory, circulating tumor nucleic acids may be derived from dying tumor cells, including circulating tumor cells (CTCs), that release their contents into the blood as they deteriorate.

The methods may comprise detecting the presence of one or more somatic structural variants in circulating nucleic acids from a subject, thereby detecting whether circulating tumor nucleic acids are present. In the cases where the circulating tumor nucleic acids are present, the methods may further comprise analyzing the circulating tumor nucleic acids and detecting tumor-associated variants in the circulating tumor nucleic acids. Results of the analysis may be used for detecting the state of tumor, such as the stage of the cancer, remission, or relapse. In some cases, detecting somatic variants in circulating tumor DNA may be performed using methods described in Chen X et al., Manta: rapid detection of structural variants and indels for germline and cancer sequencing applications, Bioinformatics, Volume 32, Issue 8, 15 Apr. 2016, Pages 1220-1222.

The methods may comprise detecting a disease based on somatic structural variants, e.g., one or more somatic structural variant events or mosaic chromosomal alterations. The somatic structural variants may be associated with the disease. In some cases, the disease may be cancer. For example, the disease may be a hematological cancer. In certain examples, the hematological cancer may be a leukemia, e.g., chronic lymphocytic leukemia. In certain examples, the disease may be solid tumor. Examples of the diseases that can be detected by the methods herein include fibrosarcoma, myxo sarcoma, liposarcoma, chondrosarcoma, osteogenic sarcoma, chordoma, angiosarcoma, endotheliosarcoma, lymphangiosarcoma, lymphangioendothelioma sarcoma, synovioma, mesothelioma, Ewing's, leiomyosarcoma, rhabdomyo sarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof.

The method may further comprise treating a subject based on the analysis of the somatic structural variants. Treating a subject may comprise performing a medical procedure when the absence of somatic structural variant is determined for a sample. Alternatively or additionally, treating a subject may comprise performing a medical procedure when the presence of somatic structural variant is determined for a sample. The medical procedure may include health monitoring, retesting, further screening, follow-up examinations, administration of drugs or other types of therapy (e.g., such as chemotherapy, radiotherapy, gene therapy), surgery, lifestyle management, and any combinations thereof. In some cases, treating the subject may comprise altering one or more genes in the subject to correct the genomic defects associated with the somatic structural variants. For example, alteration of the one or more genes may be performed using a gene editing technology, such as CRISPR-Cas mediated gene editing.

Various additional embodiments are described in the following numbered paragraphs:

1. A computer-implemented method to detect somatic structural variants (SV), comprising; determining, using one or more computing devices, total and relative allelic intensities for one or more samples; masking, using the one or more computing devices, constitutional segmental duplications in each sample of the one or more samples; identifying, using the one or more computing devices, a putative set of somatic SV events for each sample in the one or more samples; and defining, using the one or more computing devices, one or more somatic SV events for each sample of the one or more samples, based at least in part on application of a likelihood ratio test to the putative set of somatic SV events.
2. The method of paragraph 1, further comprising locating, using the one or more computing devices, a chromosomal location of each identified somatic SV event for each sample in the one or more samples.
3. The method of paragraph 1 or 2, further comprising determining, using the one or more computing devices, a copy number of each identified somatic SV event for reach sample in the one or more samples.
4. The method of any one of paragraphs 1-3, further comprising detecting, using the one or more computing devices, multiple sub-clonal events for each identified somatic SV event.
5. The method of any one of paragraphs 1-4, wherein determining the total and relative allelic frequencies comprises converting genotype intensity data into log $R_2$ ratio (LRR) and B allele frequency (BAF) values.
6. The method of any one of paragraphs 1-5, wherein masking the constitutional segmental duplications comprises modeling, using the one or more computing devices, observed phased BAF deviations (pBAF).
7. The method of any one of paragraphs 1-6, wherein modeling the observed pBAFs is performed by modeling across individual chromosomes using a 25-state hidden Markov model (HMM) with states corresponding to pBAF values.
8. The method of any one of paragraphs 1-7, further comprising selecting regions to mask, which comprises computing the Viterbi path through the HMM and examining contiguous regions of nonzero states.
9. The method of any one of paragraphs 1-8, wherein identifying the putative set of somatic SV events comprises use of a 3-state HMM.
10. The method of any one of paragraphs 1-9, wherein the 3-state HMM is parameterized by a single parameter representing mean |ΔBAF| within a given somatic SV event.
11. The method of any one of paragraphs 1-10, wherein locating the chromosomal location of each identified somatic SV event comprises taking 5 samples from the posterior of the 3-state HMM and determining the boundaries of each SV event based on a consensus of the 5 samples.
12. The method of any one of paragraphs 1-11, wherein determining the copy number of each identified somatic SV event comprises determining a relative probability that the event was a loss, CNN-LOH, or gain based at least in part on the LRR and |ΔBAF| deviation.
13. The method of any one of paragraphs 1-12, wherein detecting multiple sub-clonal events comprises re-analyzing each identified somatic SV using Viterbi decoding on a 51-state HMM with |ΔBAF| levels ranging from 0.01 to 0.25 in multiplicative increments.
14. The method of any one of paragraphs 1-13, further comprising detecting a disease or susceptibility to a disease based on detection of the one or more somatic SV events.
15. The method of any one of paragraphs 1-14, wherein the disease is cancer.

16. The method of any one of paragraphs 1-15, wherein the cancer comprises a hematological cancer.
17. The method of any one of paragraphs 1-16, wherein the hematological cancer is a leukemia.
18. The method of any one of paragraphs 1-17, wherein the leukemia is chronic lymphocytic leukemia (CLL).
19. The method of any one of paragraphs 14 to 16, where the detected one or more SV events comprise one or more SV events selected from Table 13.
20. A computer program product, comprising: a non-transitory computer-executable storage device having computer-readable program instructions embodied thereon that when executed by a computer cause the computer to detect somatic structural variants (SVs) from genotyping data, the computer-executable program instructions comprising: computer-executable program instruction to determine total and relative allelic intensities for one or more samples; computer-executable program instructions to mask constitutional segmental duplications; computer-executable program instructions to identify a putative set of somatic SV events for each sample in the one or more samples; and computer-executable program instructions to define one or more somatic SV events for each sample of the one or more samples.
21. The computer program product of paragraph 20, further comprising computer-executable program instruction to locate a chromosomal location of each identified somatic SV event for each sample in the one or more samples.
22. The computer program product of paragraph 20 or 21, further comprising computer-executable program instructions to determine a copy number of each identified somatic SV event.
23. The computer program product of any one of paragraphs 20-22, further comprising computer-executable program instruction to detect multiple sub-clonal events for each identified somatic SV.
24. The computer program product of any one of paragraphs 20-23, wherein determining total and relative allelic frequencies comprises converting genotype intensity data into log $R_2$ ratio (LRR) and B allele frequency (BAF) values.
25. The computer program product of any one of paragraphs 20-24, wherein identifying the putative set of somatic SV events comprises use of a 3-state HMM.
26. The computer program product of any one of paragraphs 20-25, wherein the 3-state HMM is parameterized by a single parameter representing mean |ΔBAF| within a given somatic SV event.
27. The computer program product of any one of paragraphs 20-26, further comprising detecting a disease or susceptibility to a disease based on detection of the one or more somatic SV events.
28. The computer program product of any one of paragraphs 20-27, wherein the disease is cancer.
29. The computer program product of any one of paragraphs 20-28, wherein the cancer is a hematological cancer.
30. The computer program product of any one of paragraphs 20-29, wherein the hematological cancer is a leukemia.
31. The computer program product of any one of paragraphs 20-31, wherein the leukemia is chronic lymphocytic leukemia.
32. A system to detect one or somatic SV events, the system comprising: a storage device; and a processor communicatively coupled to the storage device, wherein the processor executes application code instructions that are stored in the storage device and that cause the system to: determine total and relative allelic intensities for one or more samples; mask constitutional segmental duplications; identify a putative set of somatic SV events for each sample in the one or more samples; and define one or more somatic SV events for each sample of the one or more samples.
33. A kit comprising reagents for determining allelic frequencies and the computer program product of anyone of paragraphs 20 to 31, or the system of paragraph 32.
34. A method for detecting presence or susceptibility of a condition in subject, the method comprising detecting one or more somatic structural variants according to any one of paragraphs 1-19 in nucleic acids in a sample from the subject, wherein presence or absence of the one or more somatic structural variants indicates the presence or susceptibility of the condition.
35. The method of paragraph 34, wherein the nucleic acids are cell-free nucleic acids.
36. The method of paragraph 34 or 35, wherein the sample is maternal blood and the cell-free nucleic acids are fetal cell-free nucleic acids.
37. The method of any one of paragraphs 34-36, wherein the cell-free nucleic acids are circulating tumor DNA.
38. The method of any one of paragraphs 34-37, wherein the condition is fetal aneuploidy.
39. The method of any one of paragraphs 34-38, wherein the condition is cancer.
40. The method of any one of paragraphs 34-39, further comprising performing a medical procedure based on the detected presence or susceptibility of the condition.

The invention is further described in the following examples, which do not limit the scope of the invention described in the claims.

EXAMPLES

Example 1—Atlas of 8,342 Mosaic Structural Variants Reveals Strong Inherited Drivers of Clonal Hematopoiesis Provided below are insights from an analysis of 8,342 somatic structural variants (SVs) which were ascertained in SNP-array data from 151,202 UK Biobank participants using a method in accordance example embodiment disclosed herein that utilizes long-range haplotype phase information. Health outcomes for UK Biobank participants during 5-10 years after DNA sampling were also utilized.

These data review new insights into clonal expansion, including mechanisms by which inherited variants at several loci act in cis to generate or propel mosaicism. Several somatic SVs that strongly predict future hematological malignancy (OR>100) were also identified.

Somatic SVs in UK Biobank

Allele-specific SNP-array intensity data from blood genotyping of 151,202 UK Biobank participants 40-70 years of age were analyzed; 607,525 genotyped variants remained after quality control (Methods). Applicant achieved sensitive detection of clonally expanded SVs at cell fractions as low as 1% by making use of long-range phase information uniquely available in UK Biobank [24-26]. The intuition behind this approach is that accurate phase information allows detection of subtle imbalances in the abundances of two haplotypes by combining allele-specific information across very many SNPs (FIGS. 9A-9C, 10A-10C, 11A-11C, and 12). To maximally leverage this information, Applicant developed a new statistical method for phase-based SV detection (Methods and Supplementary Note).

Figure 34:
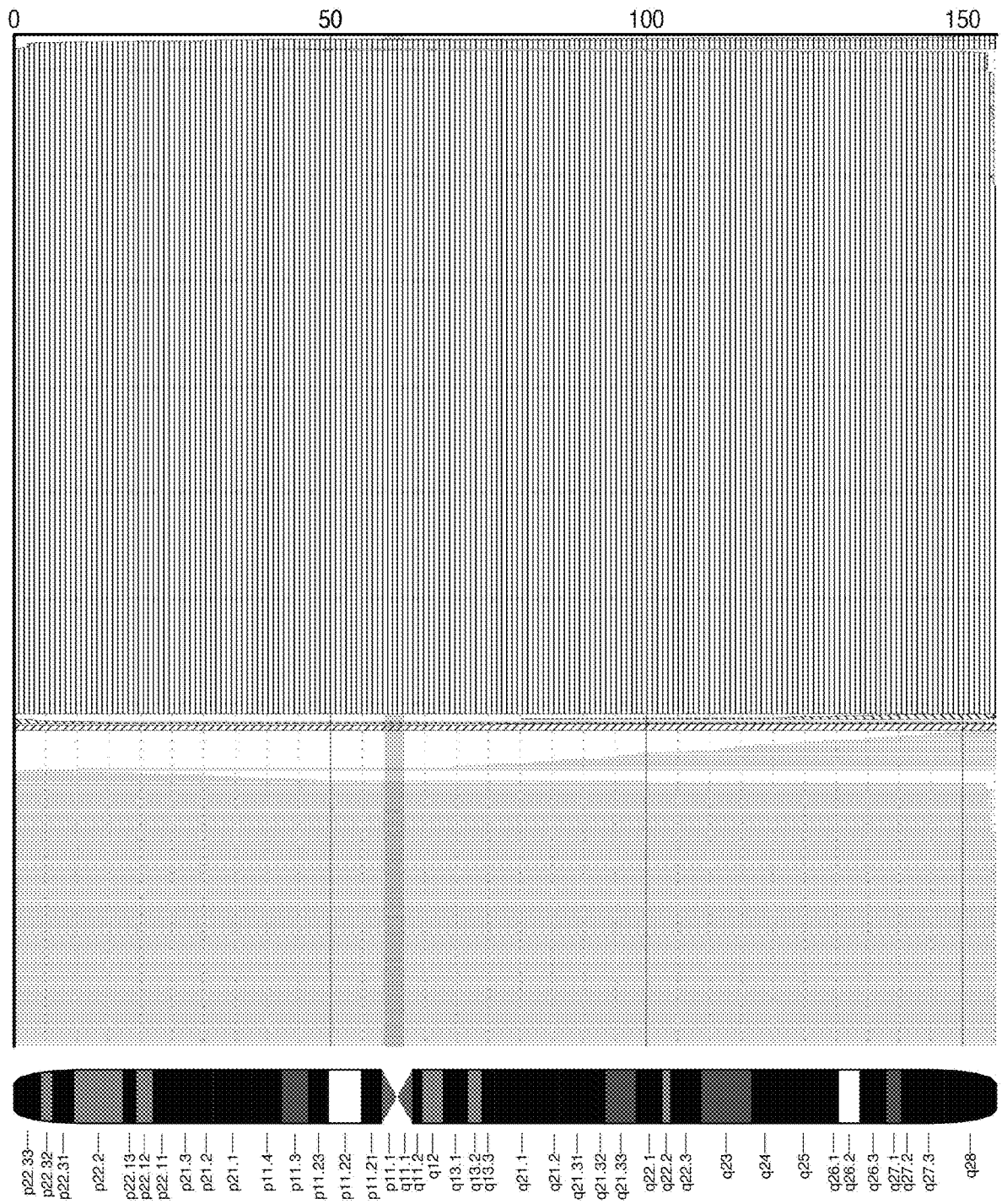
Figure 35:
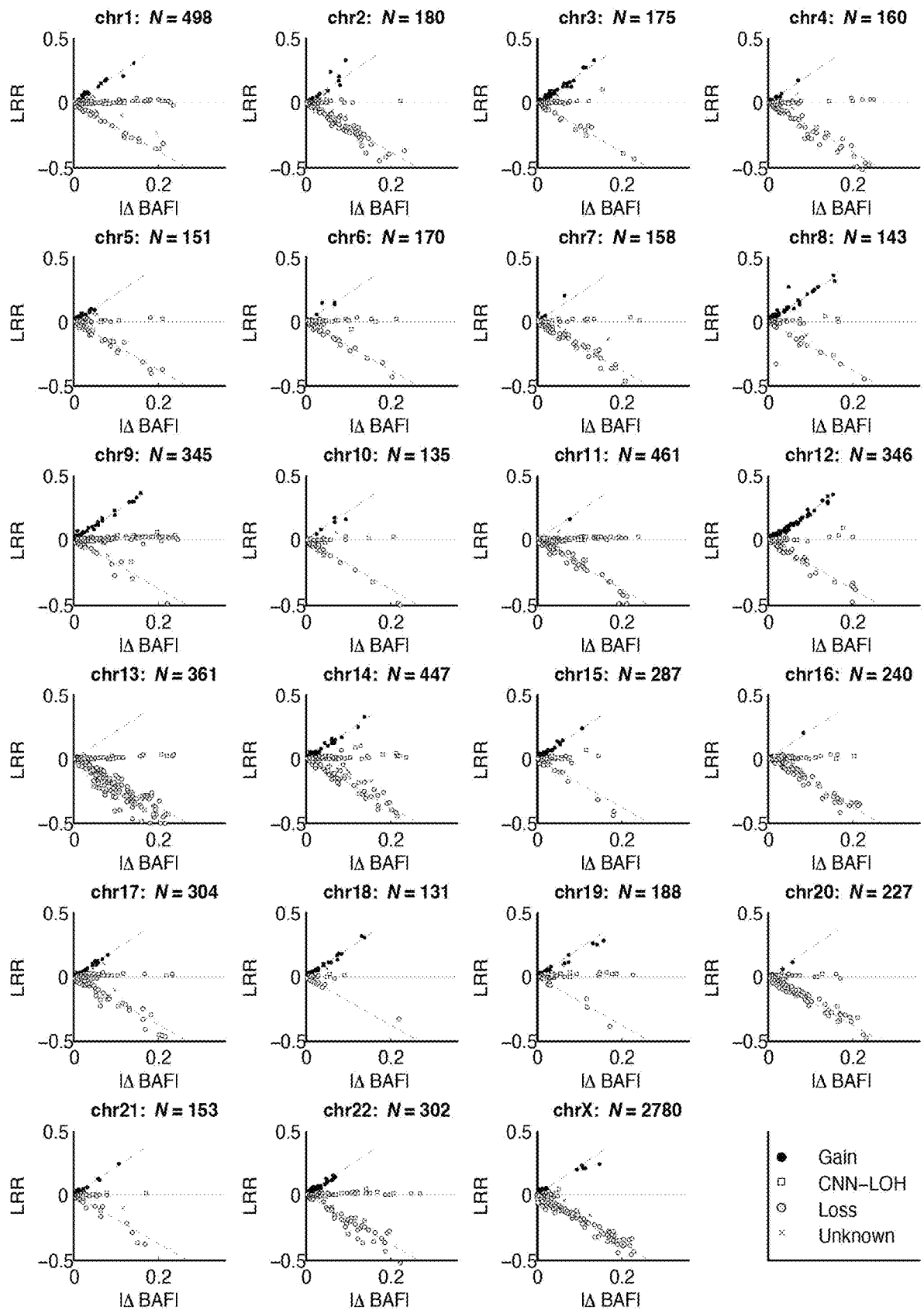
FIG. 35—total vs. relative allelic intensities of somatic SVs detected on each chromosome. Mean log 2 R ratio (LRR) of each detected SV is plotted against estimated change in B allele frequency at heterozygous sites ($|\Delta BAF|$).
Figure 36:
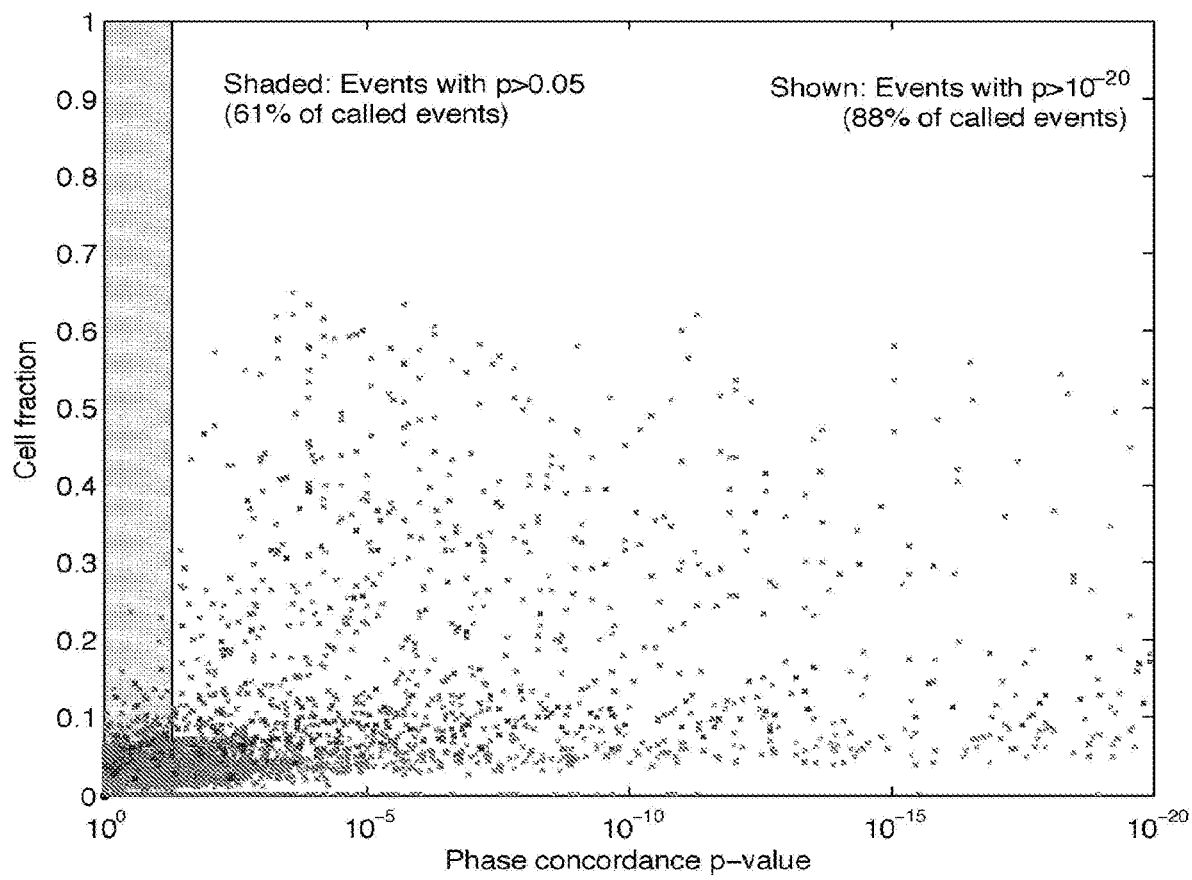
FIG. 36—Sensitivity of phase concordance-based statistical test for detecting somatic SVs. For each somatic SV called by our algorithm (red-loss, green-CNN-LOH, blue-gain, grey=unknown copy number), we computed a binomial P-value using the phase concordance test of ref. [54]. This test makes use of relative haplotype phase between successive heterozygous SNPs but does not take advantage of long-range phase information. We plotted the inferred cell fraction of each SV against its phase concordance P-value. (For events with uncertain copy number, we did not infer a cell fraction, so these events are plotted on the x-axis.) Applicants observed that the majority of events detectable by our analysis do not reach nominal significance using the phase concordance test, as expected for subtle allelic imbalances that must be aggregated in-phase over tens of megabases in order to be detectable.
Figure 37:
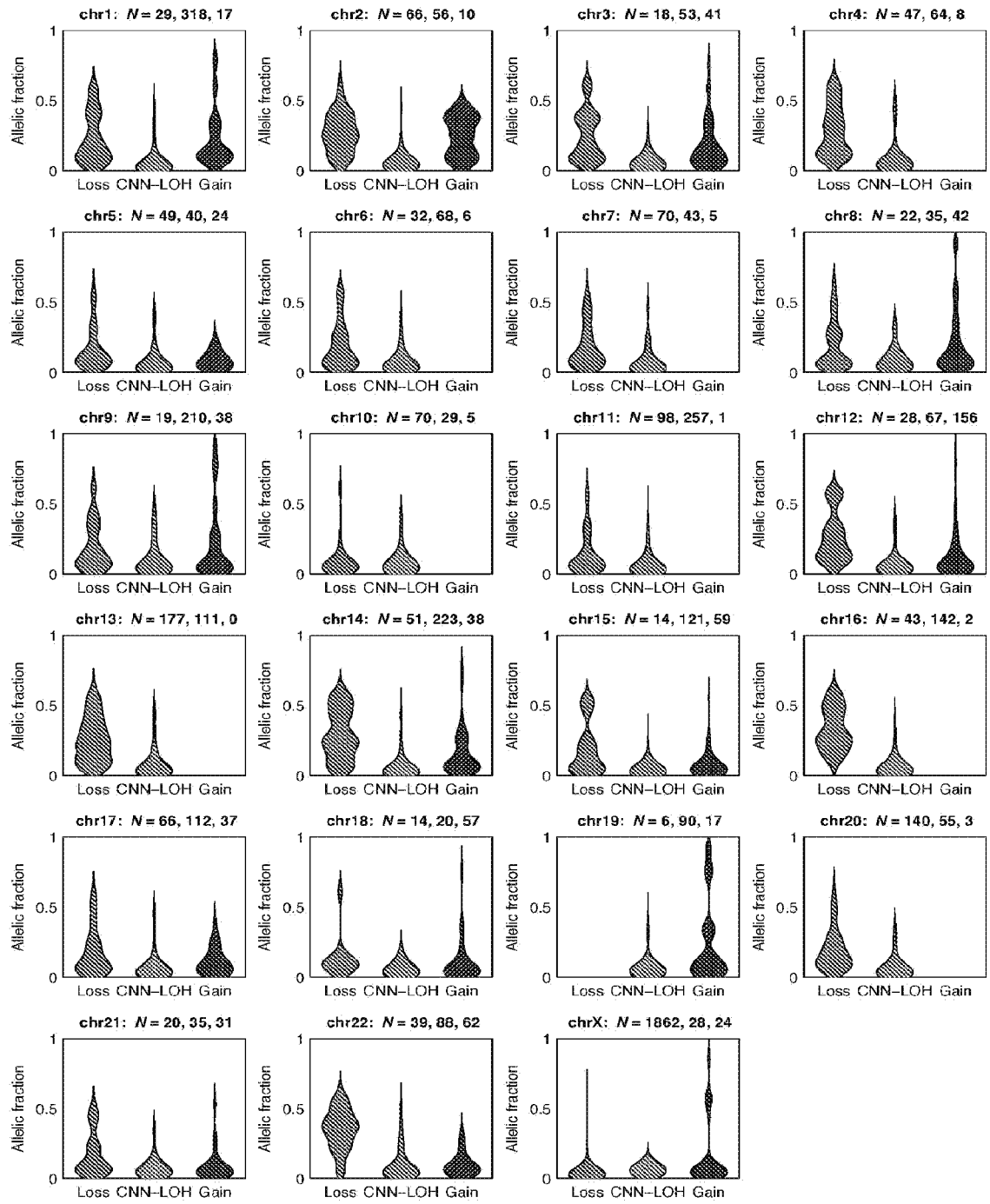
FIG. 37—Extent of clonal proliferation of somatic SVs detected on each chromosome. For each somatic SV called as a loss, CNN-LOH, or gain, we estimate its allelic fraction (i.e., fraction of blood cells with the SV) from LRR and $|\Delta BAF|$. The violin plots show allelic fraction distributions stratified by chromosome and copy number (whenever at least ten events were called).

Applicant detected 8,342 somatic SVs (in 7,484 of the 151,202 individuals analyzed) at a false discovery rate (FDR) of 0.05 (FIG. 4, FIGS. 12-34). Applicant confidently classified 71% of the detected SVs as either (i) loss, (ii) copy-number neutral loss of heterozygosity (CNN-LOH), or (iii) gain (FIG. 5A and FIG. 35). Most detected SVs had inferred clonal cell fractions less than 5% and would have been undetectable without long-range phasing (FIG. 36); the lowest inferred cell fractions were less than 1% (FIG. 37). The genomic distribution of detected SVs was broadly consistent with previous studies [1, 2, 7, 8]: most gains duplicated whole chromosomes or chromosome arms (a hallmark of mitotic missegregation); most CNN-LOHs affected partial chromosome arms (a hallmark of mitotic recombination); and most autosomal losses deleted much smaller focal regions (FIG. 4 and FIGS. 12-34).

Figure 4:
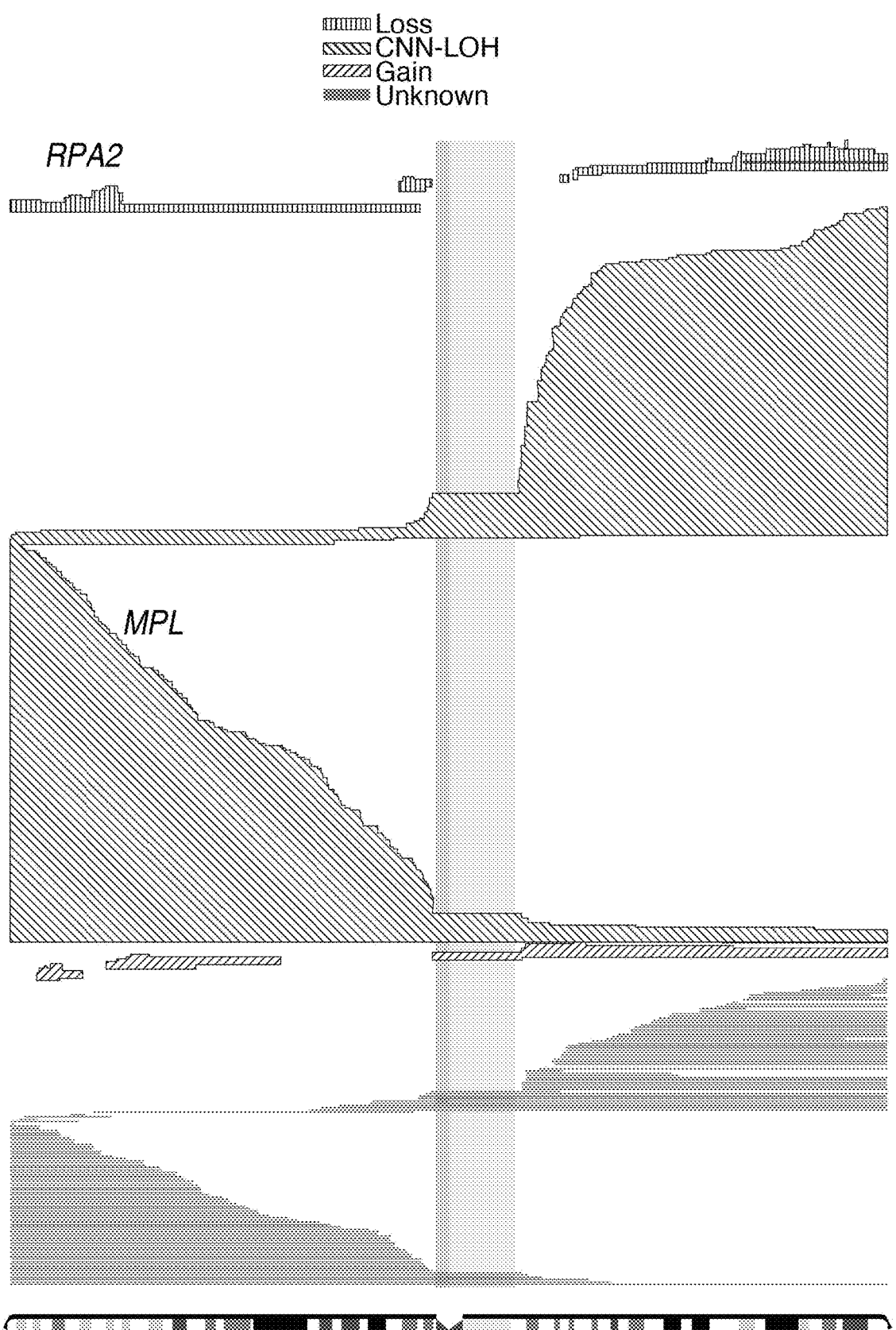
FIG. 4—Each horizontal line corresponds to a single somatic SV; a total of 5,562 autosomal events in 4,889 unique individuals are displayed. Applicant detected an additional, 2,780 chromosome X events in females (mostly whole-chromosome losses). Detected events are color coded by copy number (loss=vertical lines, copy-number neutral loss of heterozygosity (CNN-LOH)=descending diagonal lines, gain=ascending diagonal lines, unknown=gray). Focal deletions are labeled in red with names of putative target genes when possible. Loci influencing nearby somatic SVs are labeled in the color of the SV. Enlarged per-chromosome plots are provided in FIGS. 12-34.
Figure 4:
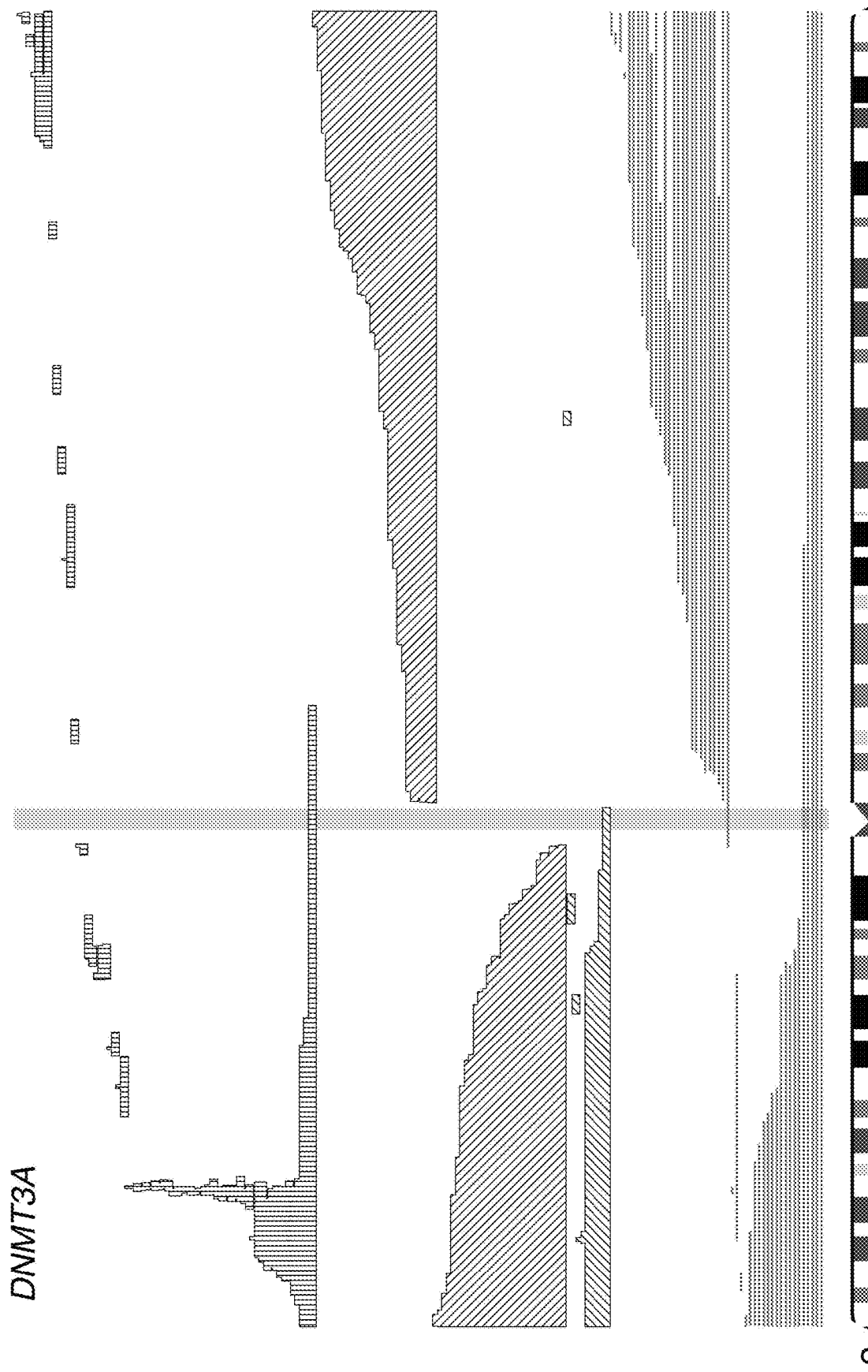
Figure 4:
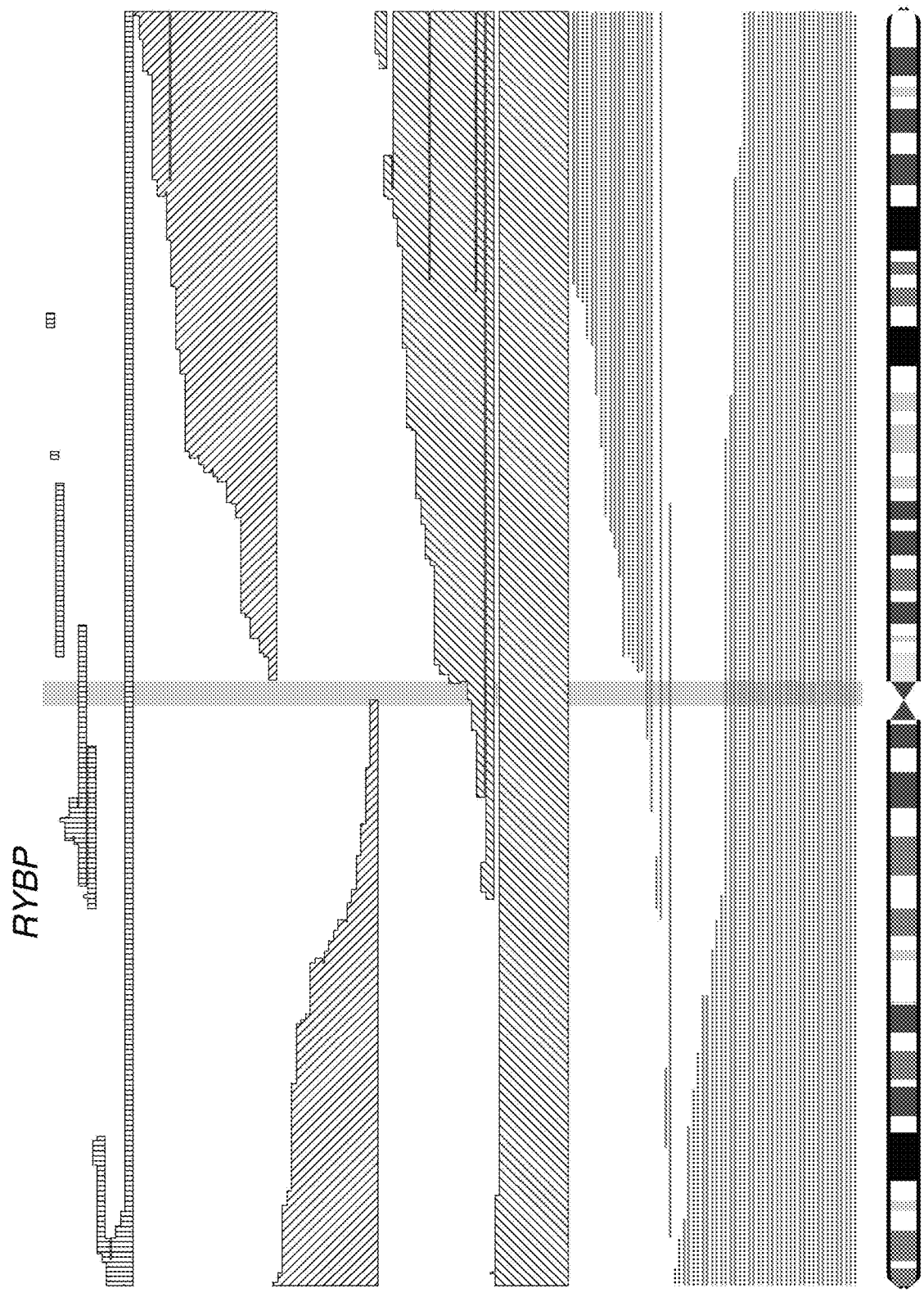
Figure 4:
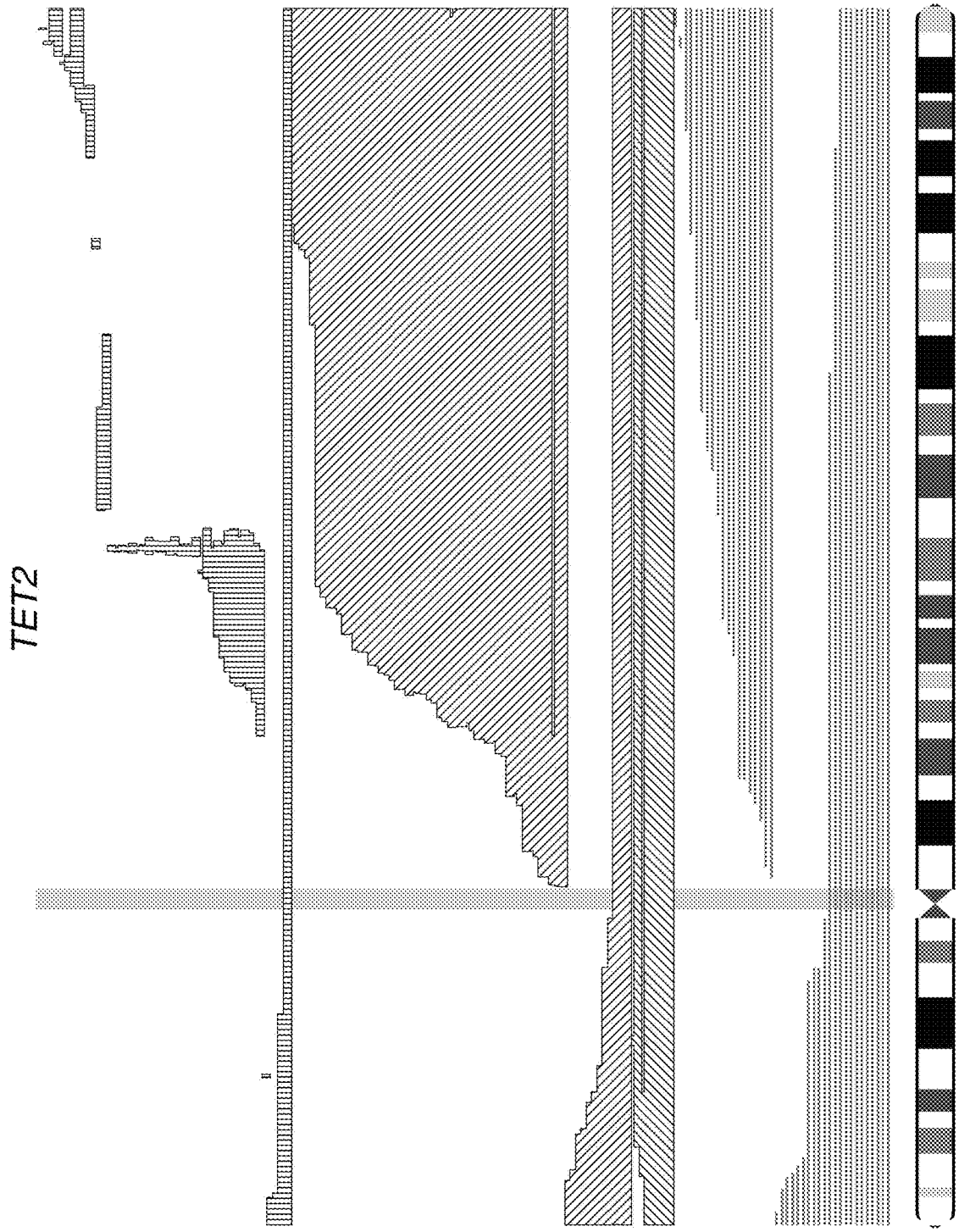
Figure 4:
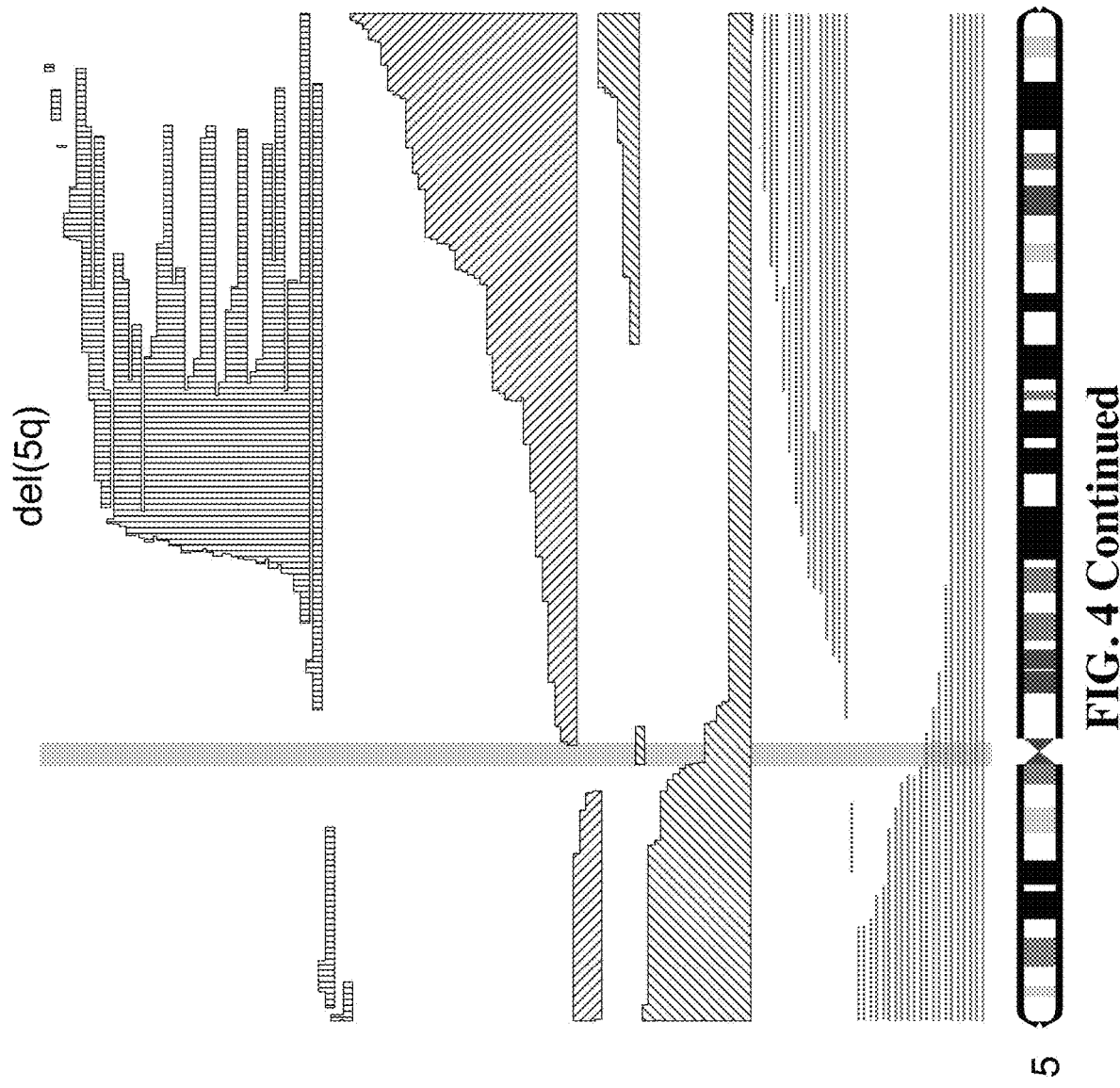
Figure 4:
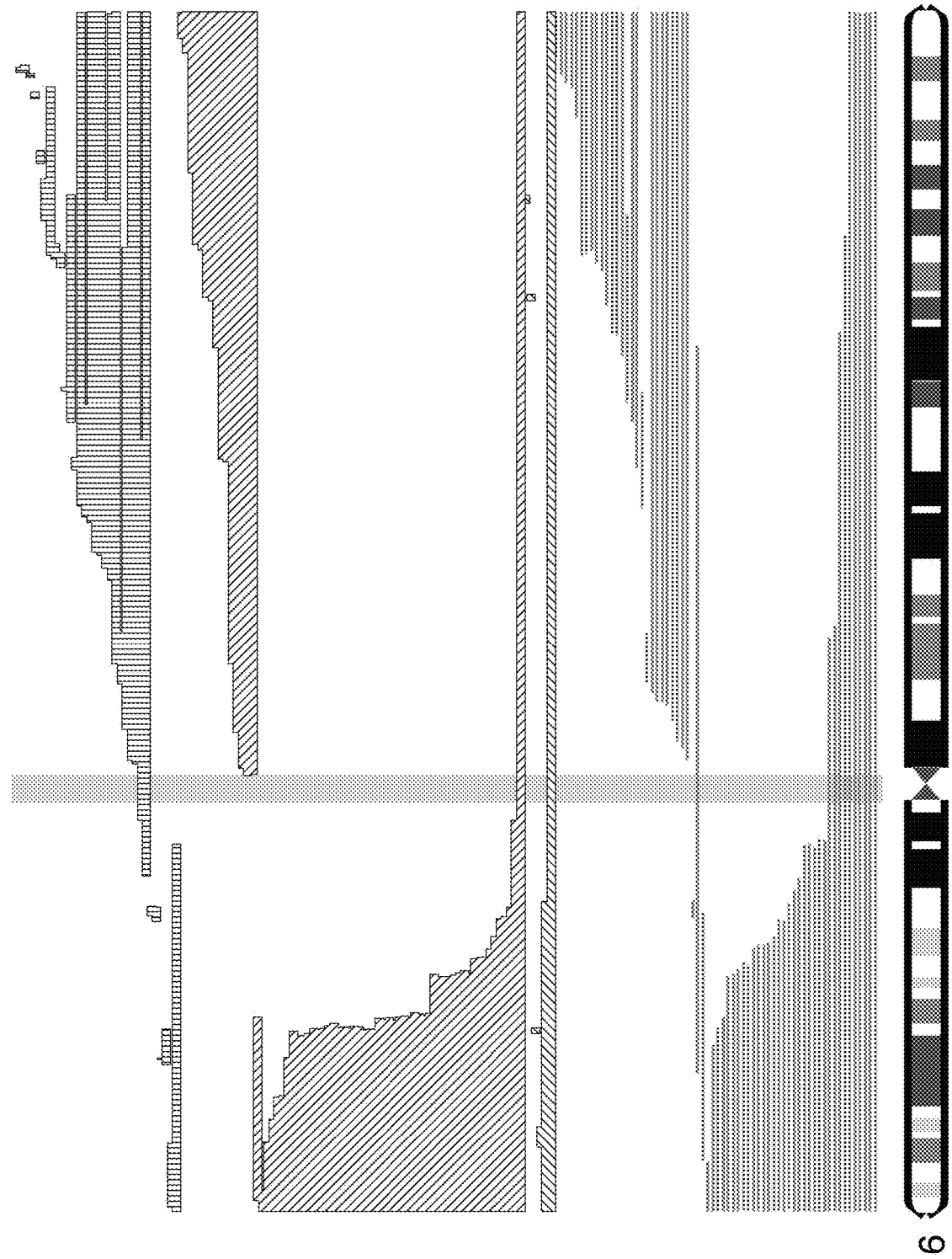
Figure 4:
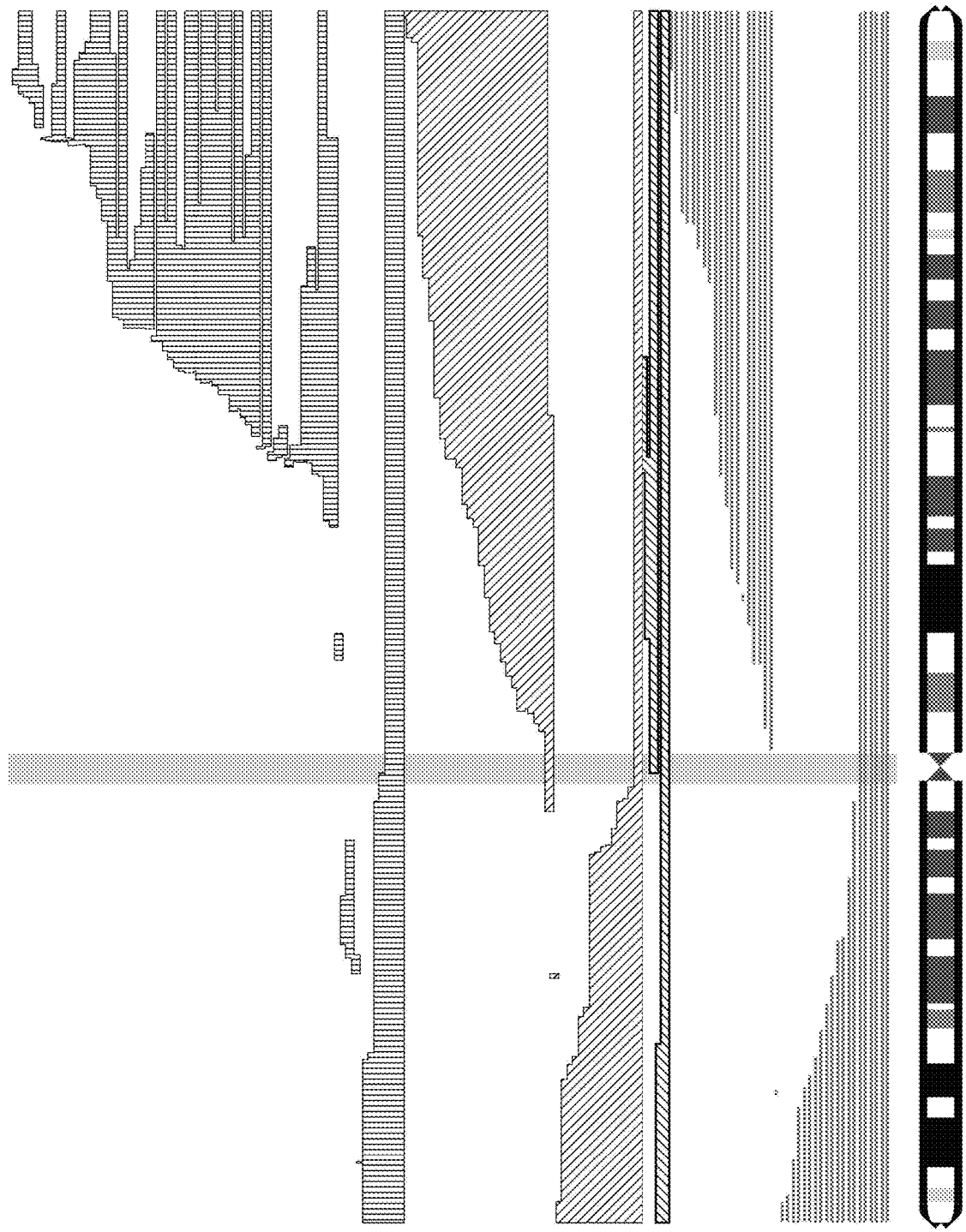
Figure 4:
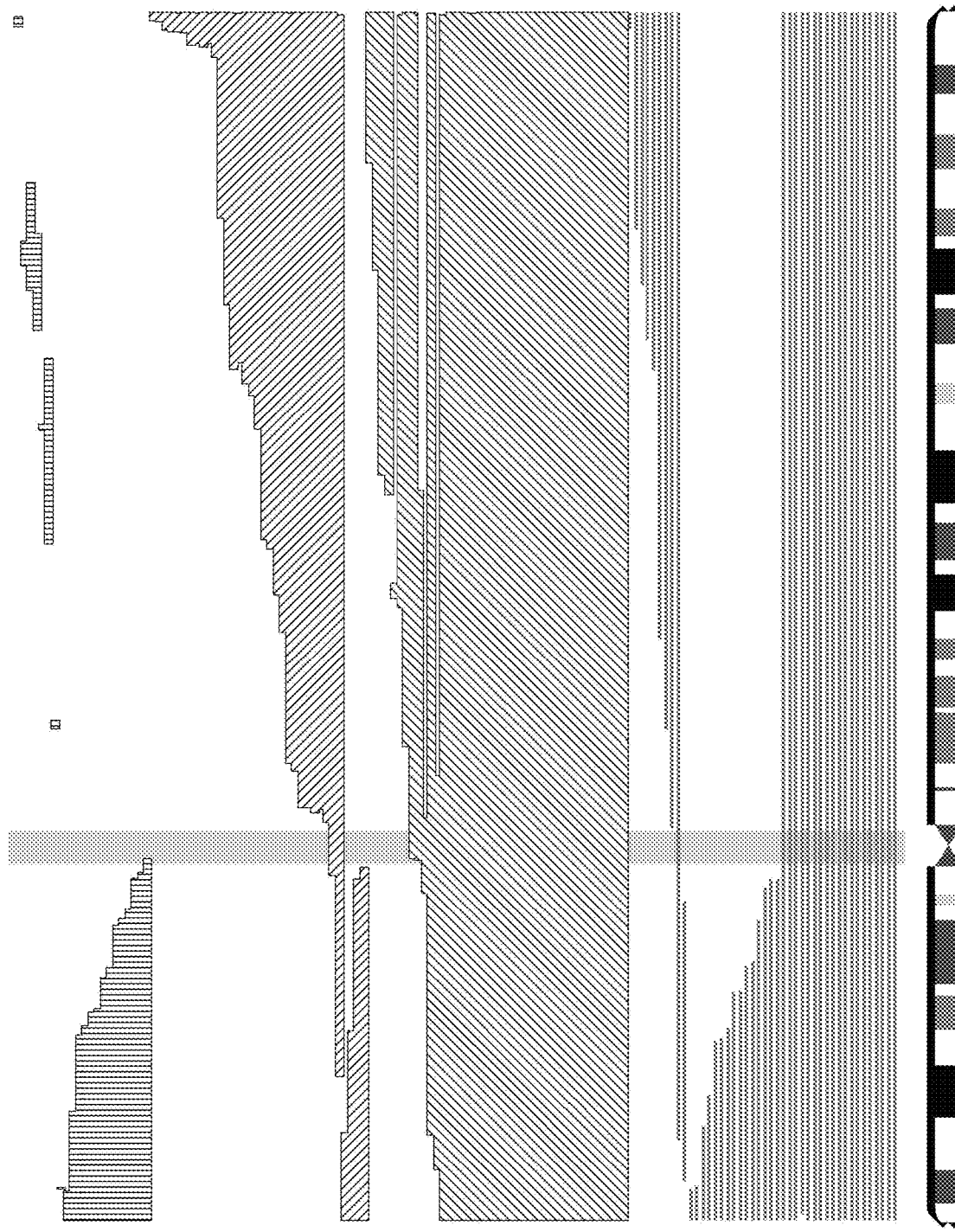
Figure 4:
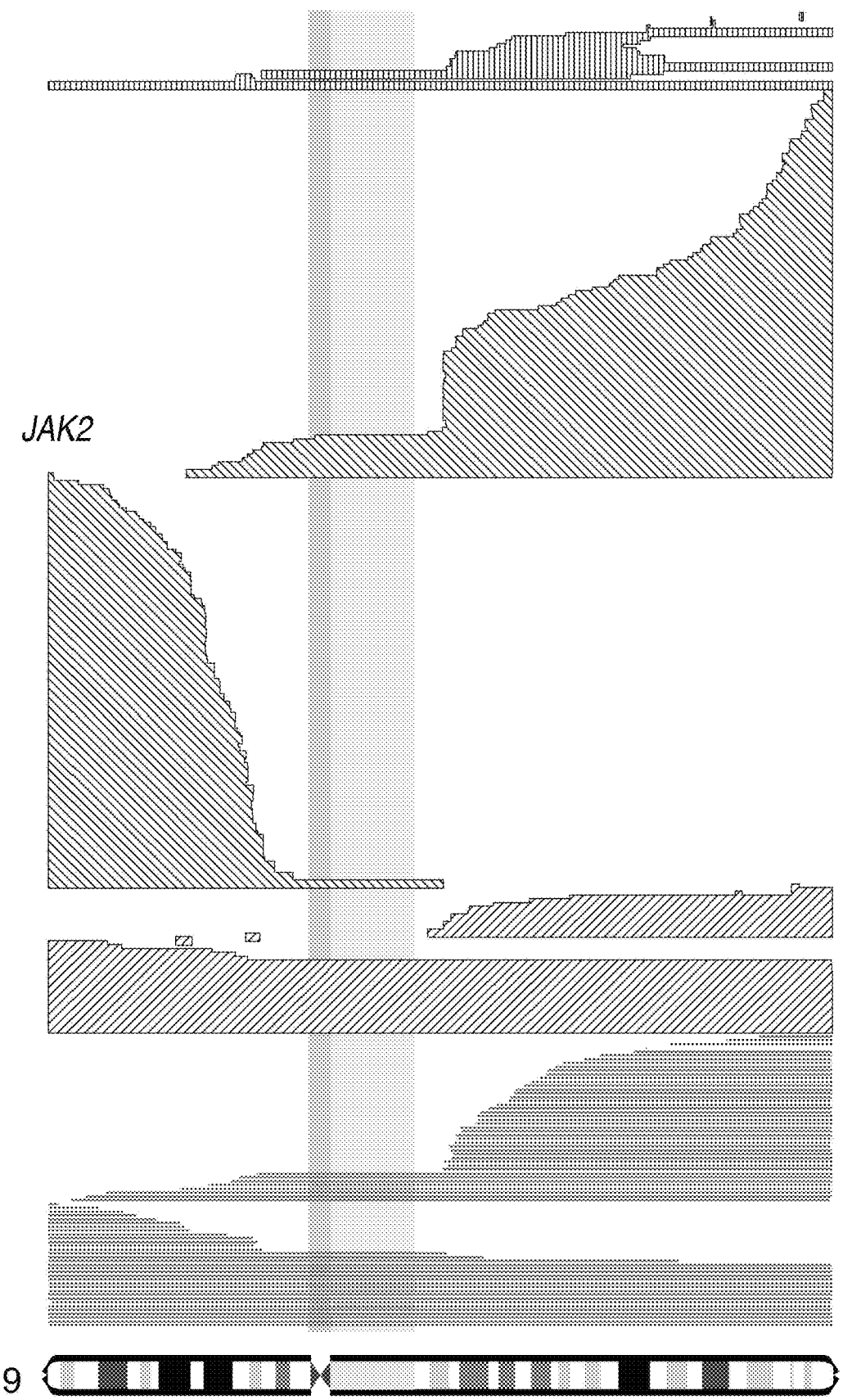
Figure 4:
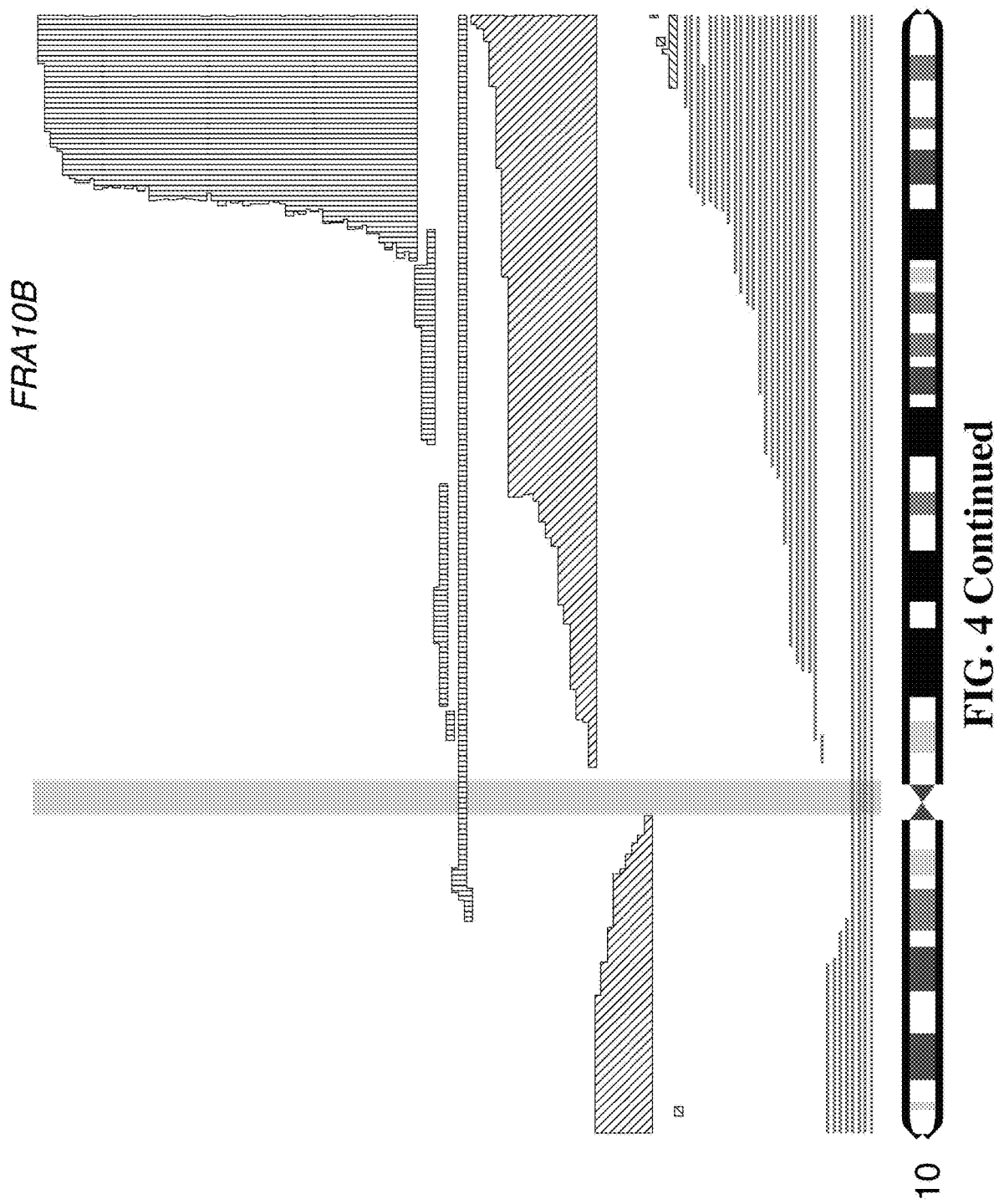
Figure 4:
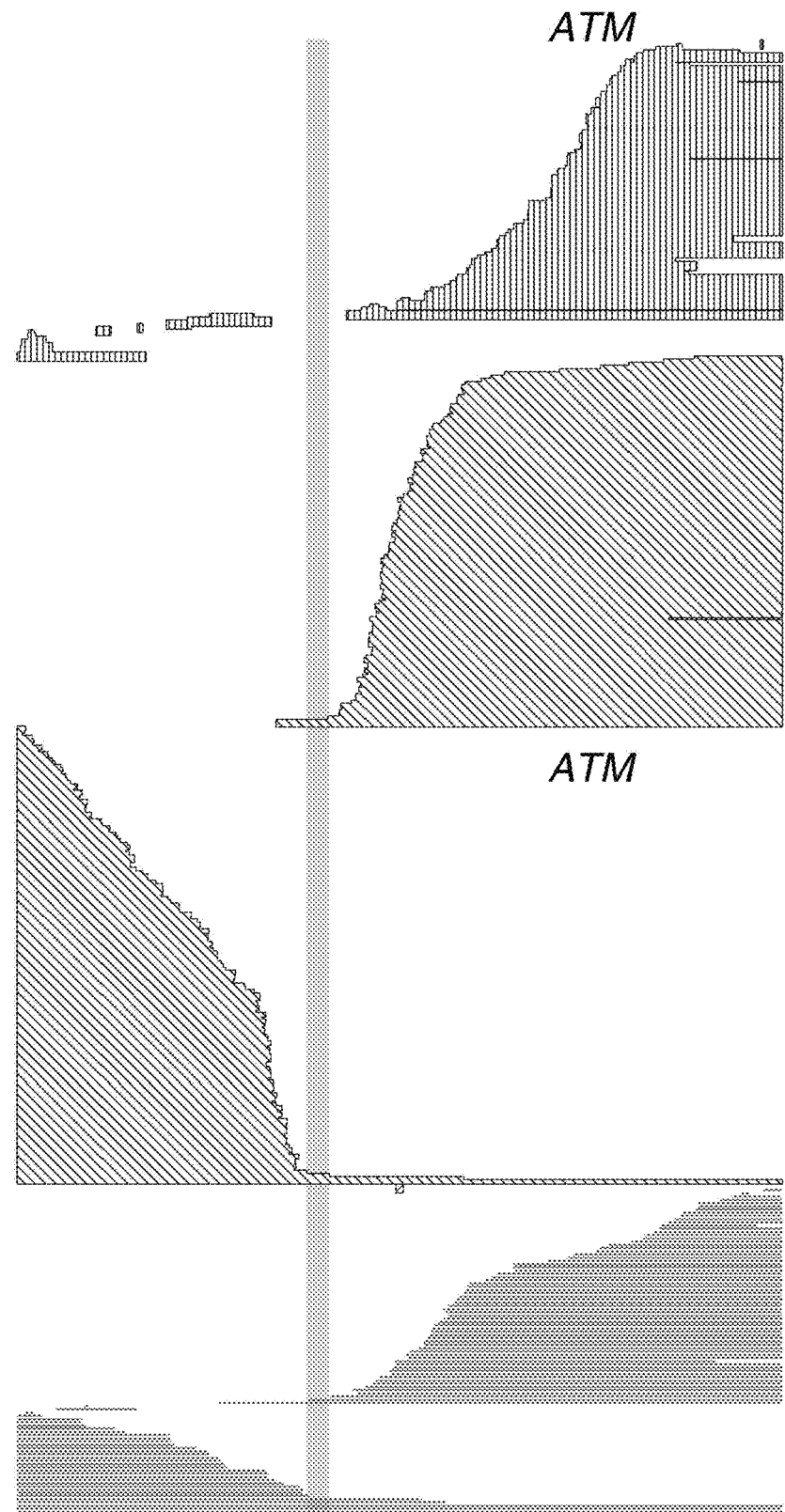
Figure 4:
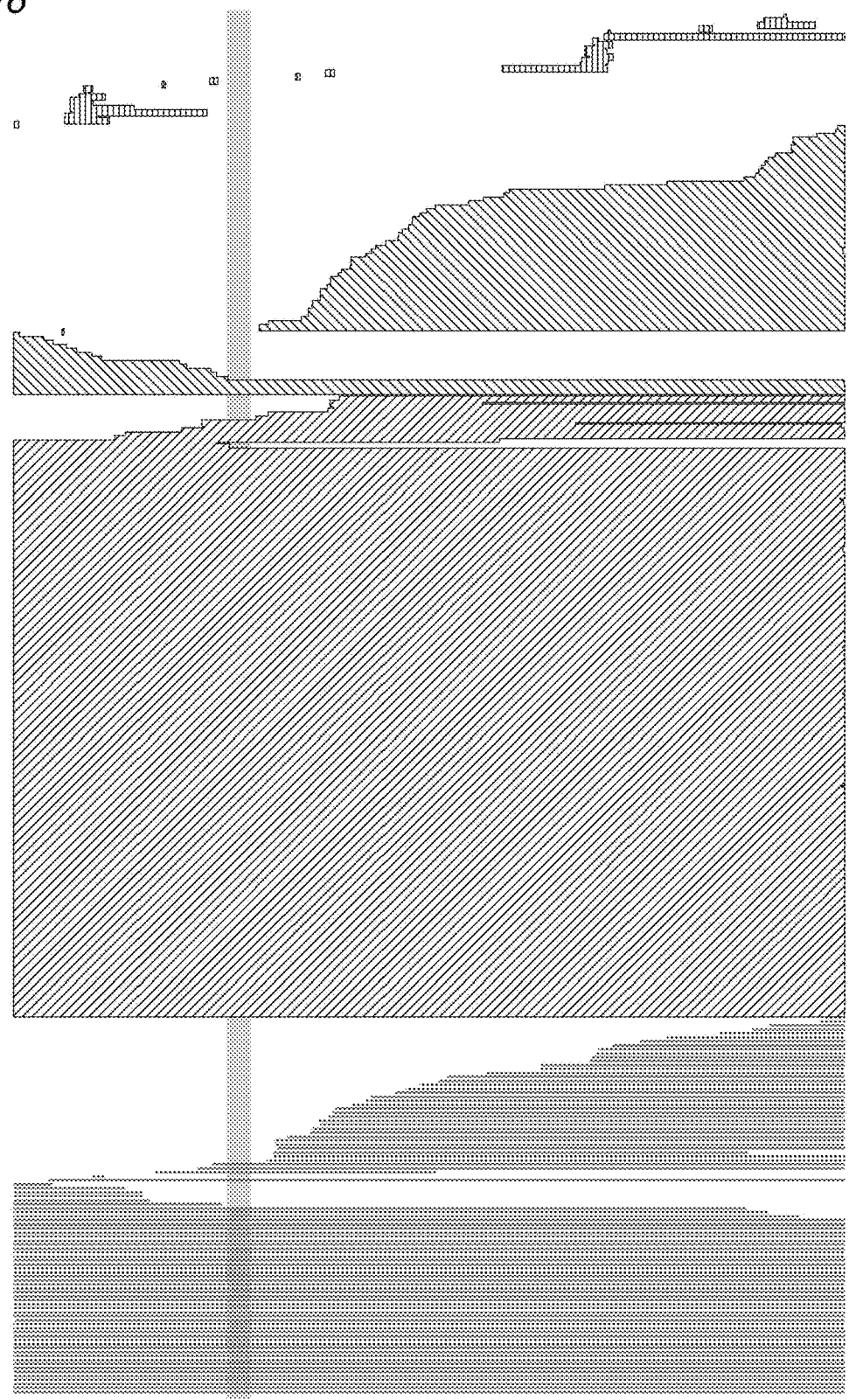
Figure 4:
Figure 4:
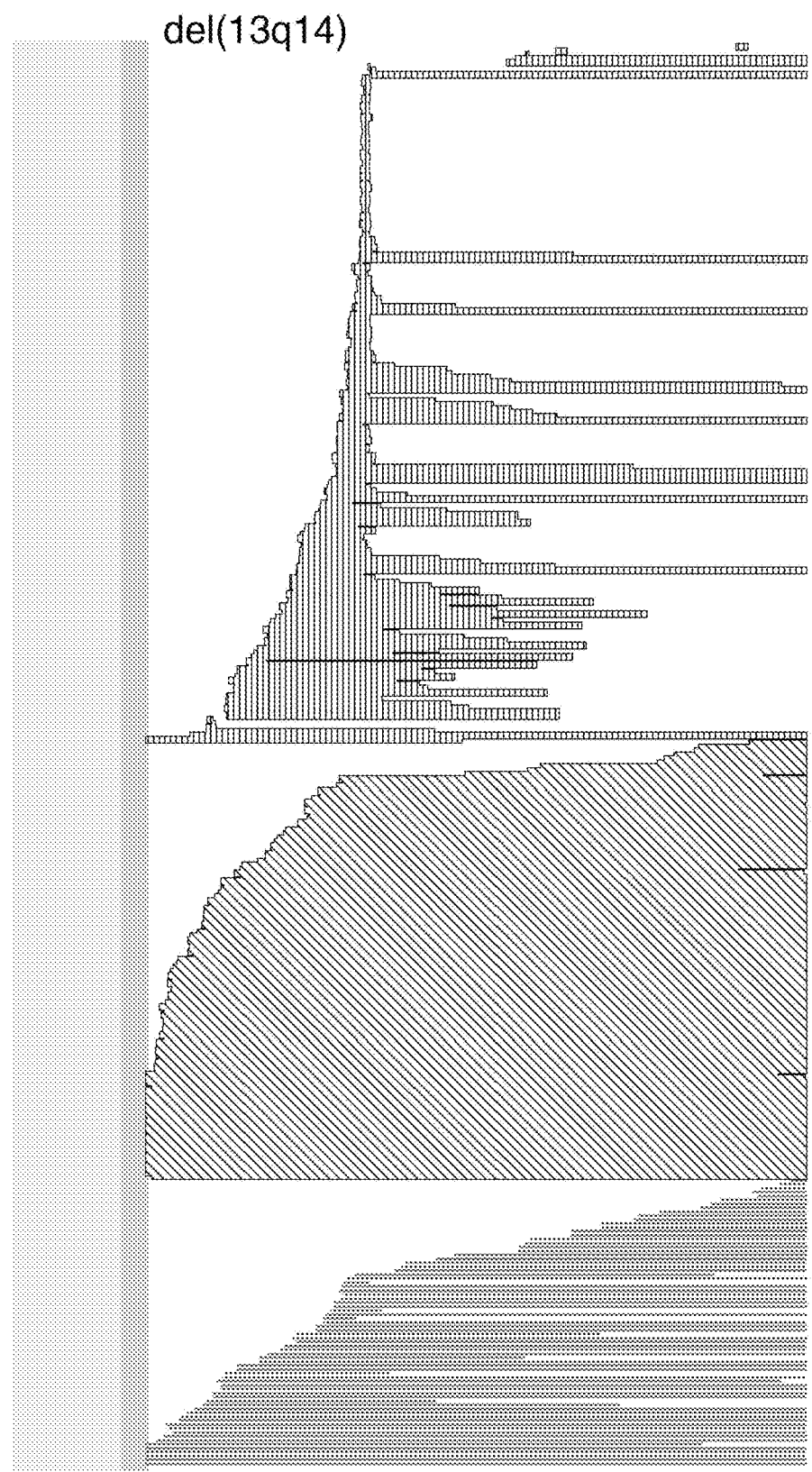
Figure 4:
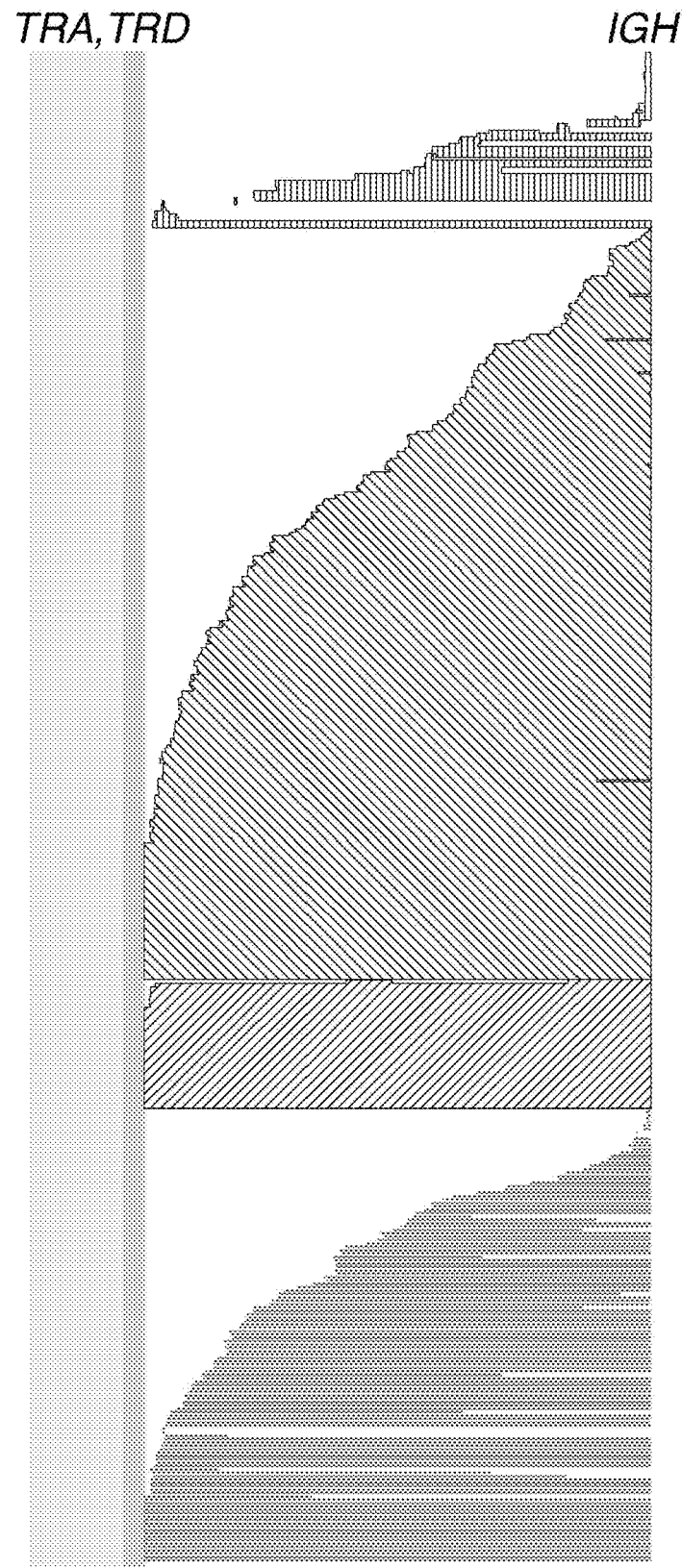
Figure 4:
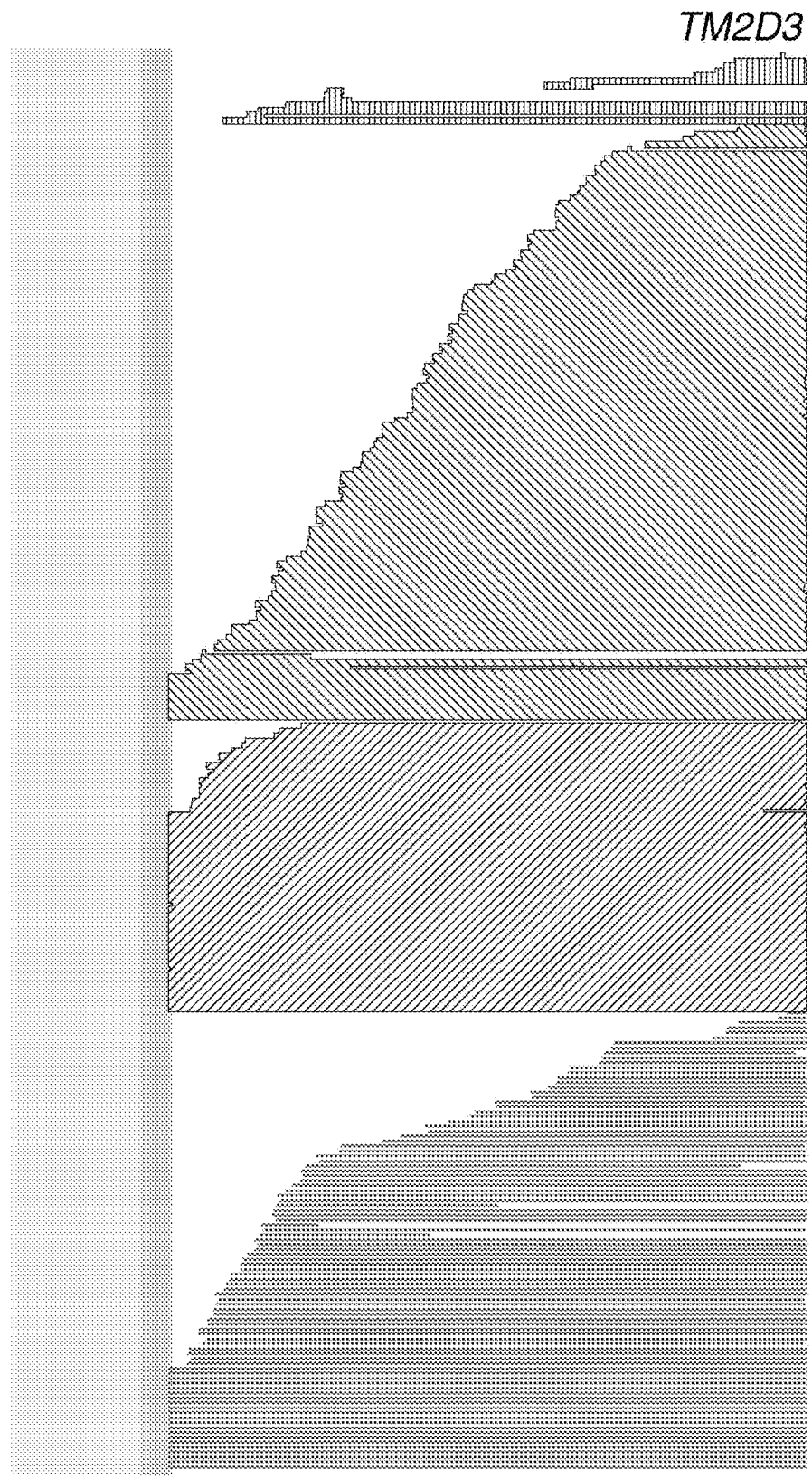
Figure 4:
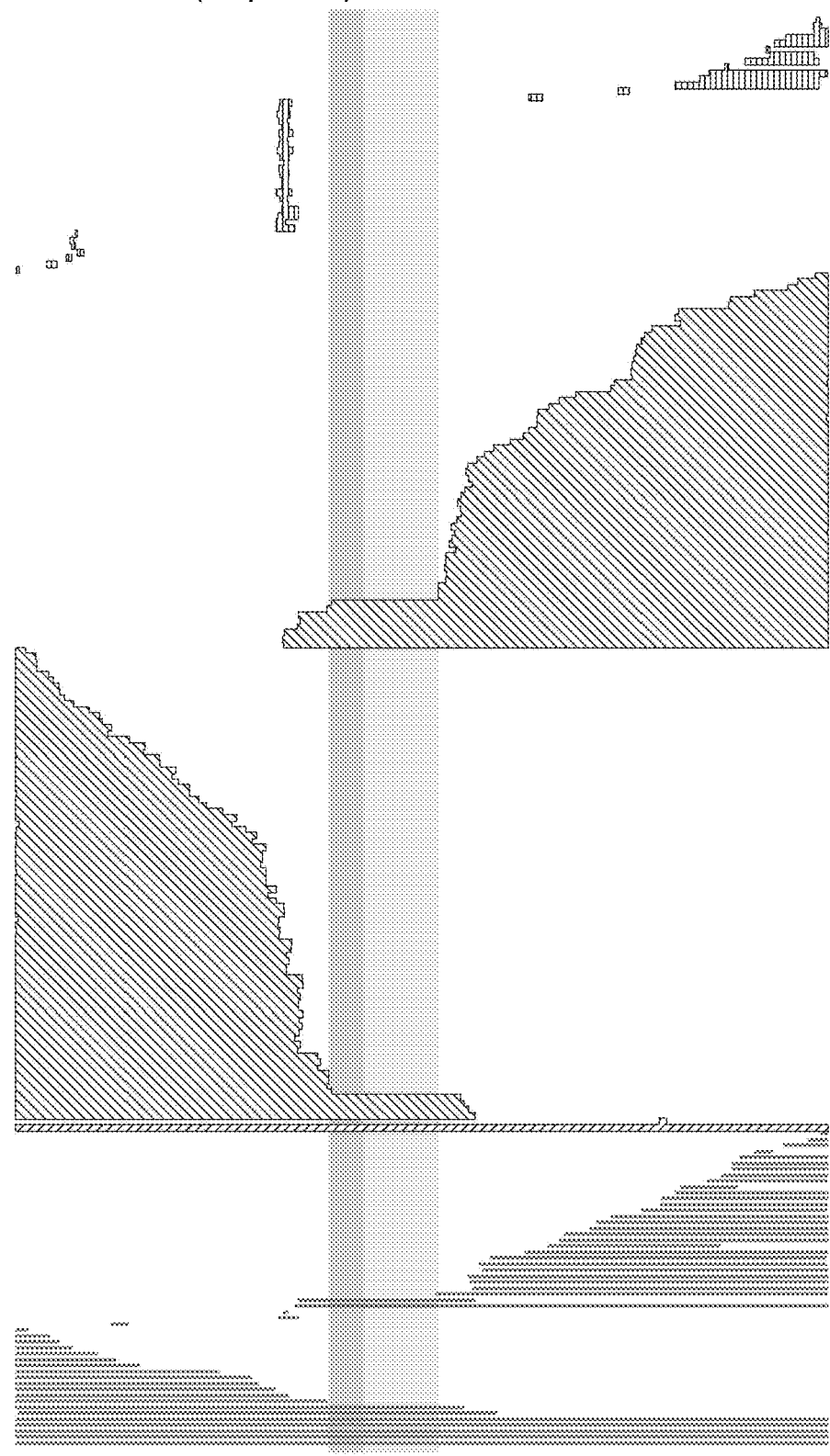
Figure 4:
Figure 4:
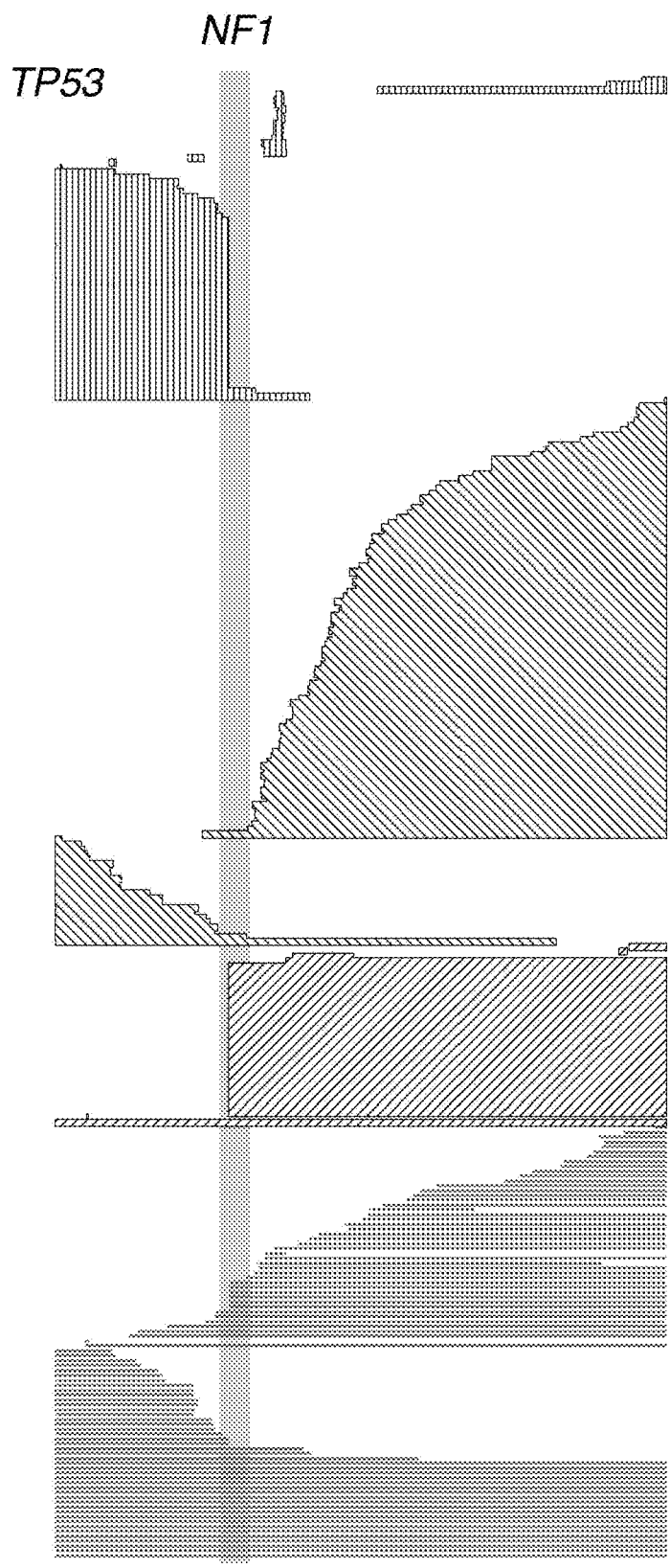
Figure 4:
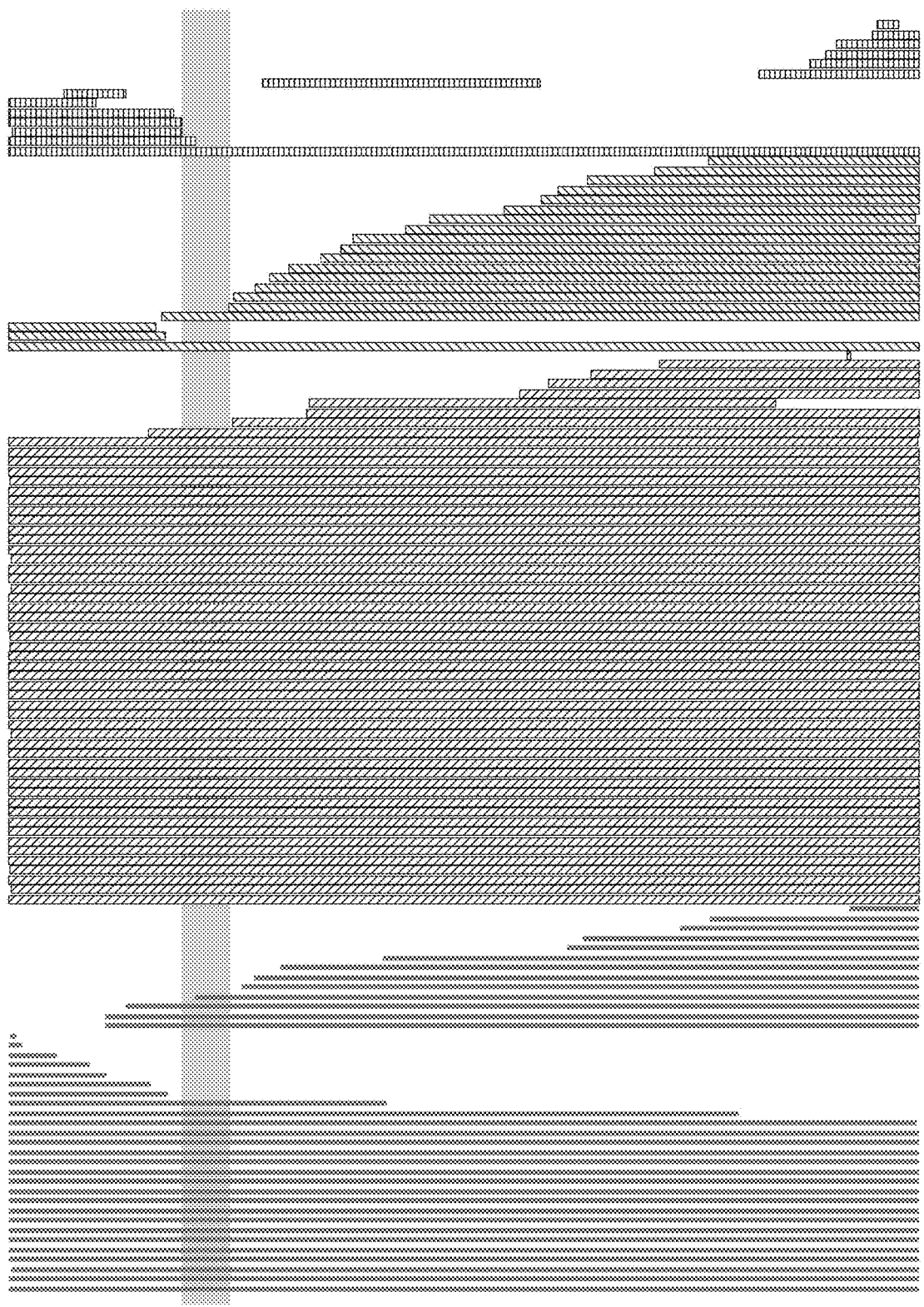
Figure 4:
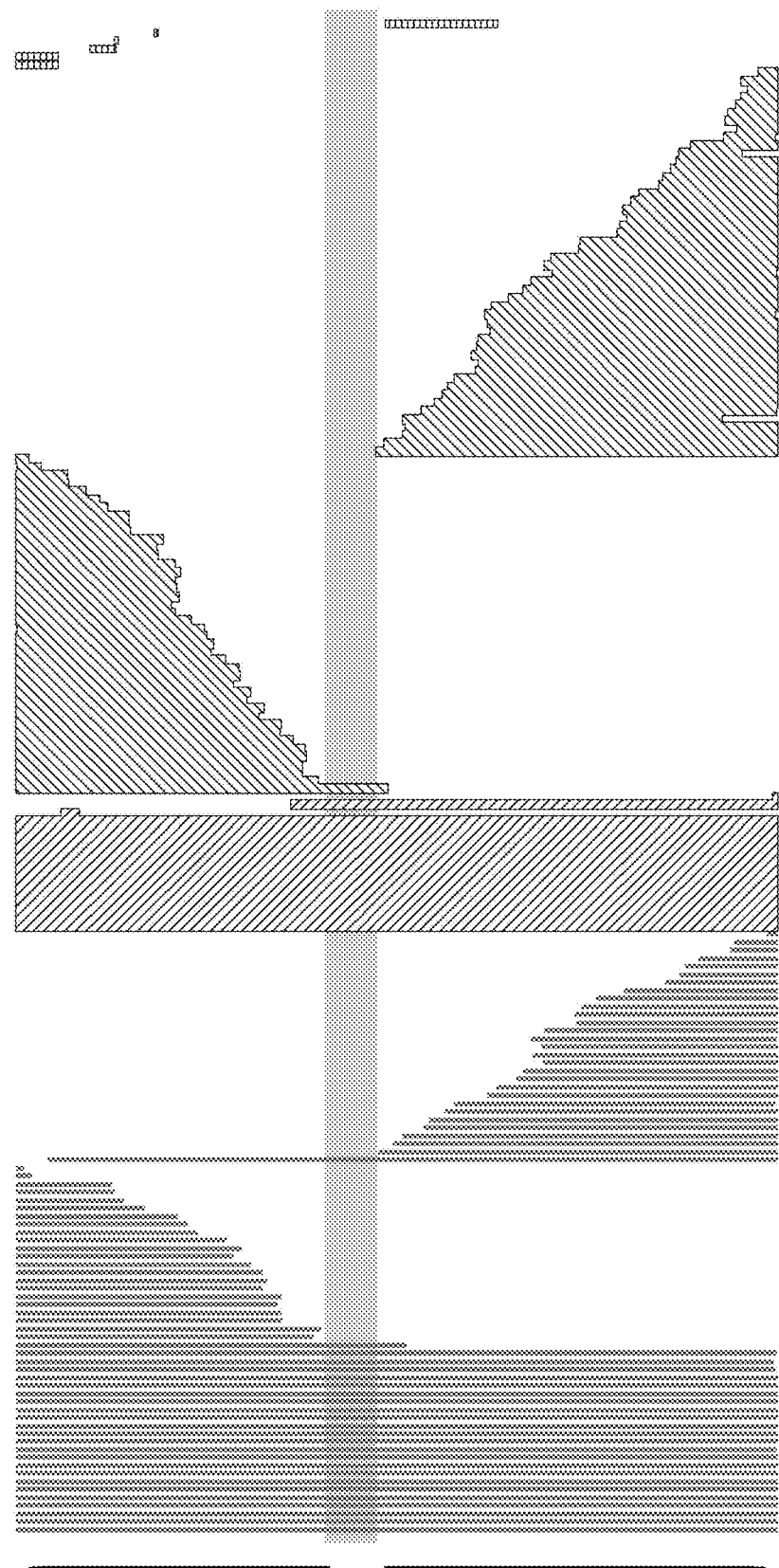
Figure 4:
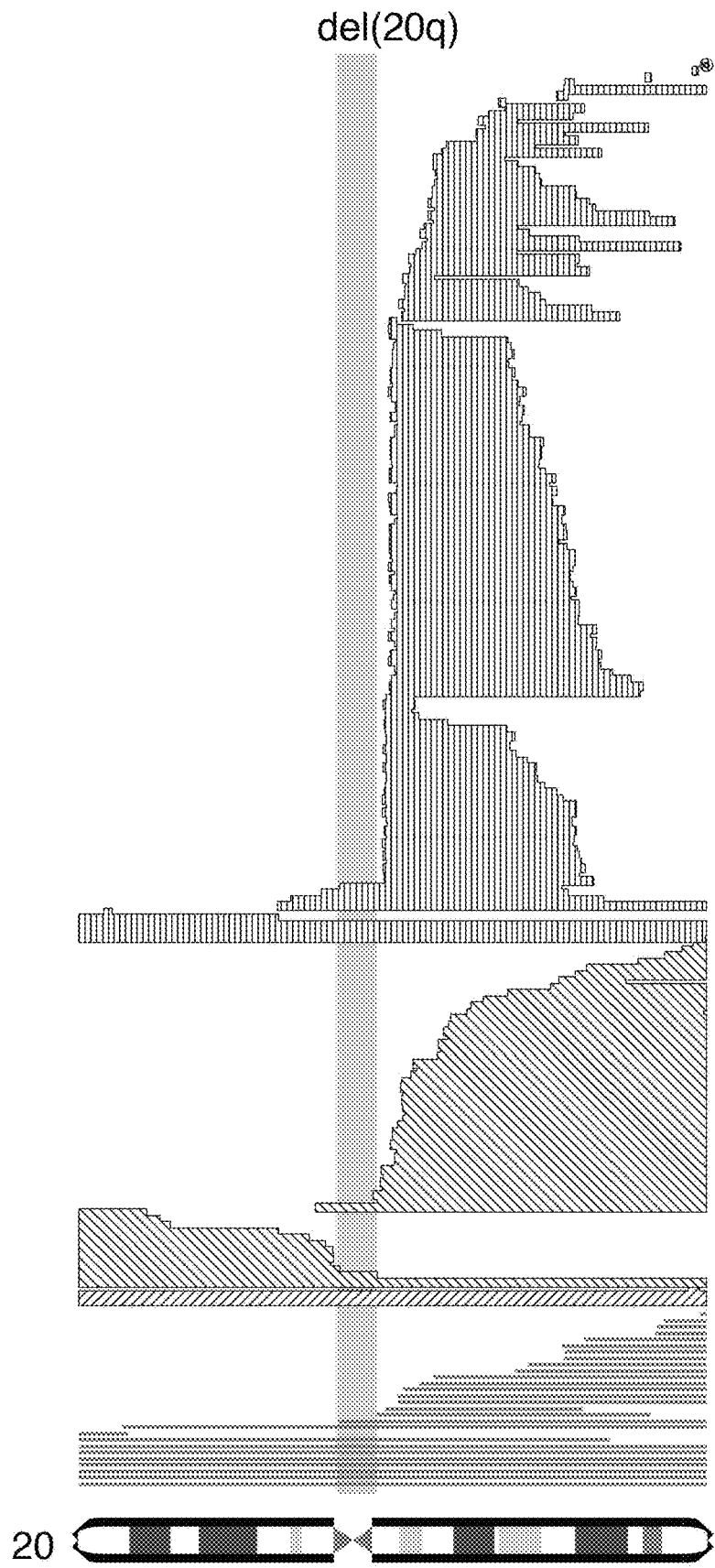
Figure 4:
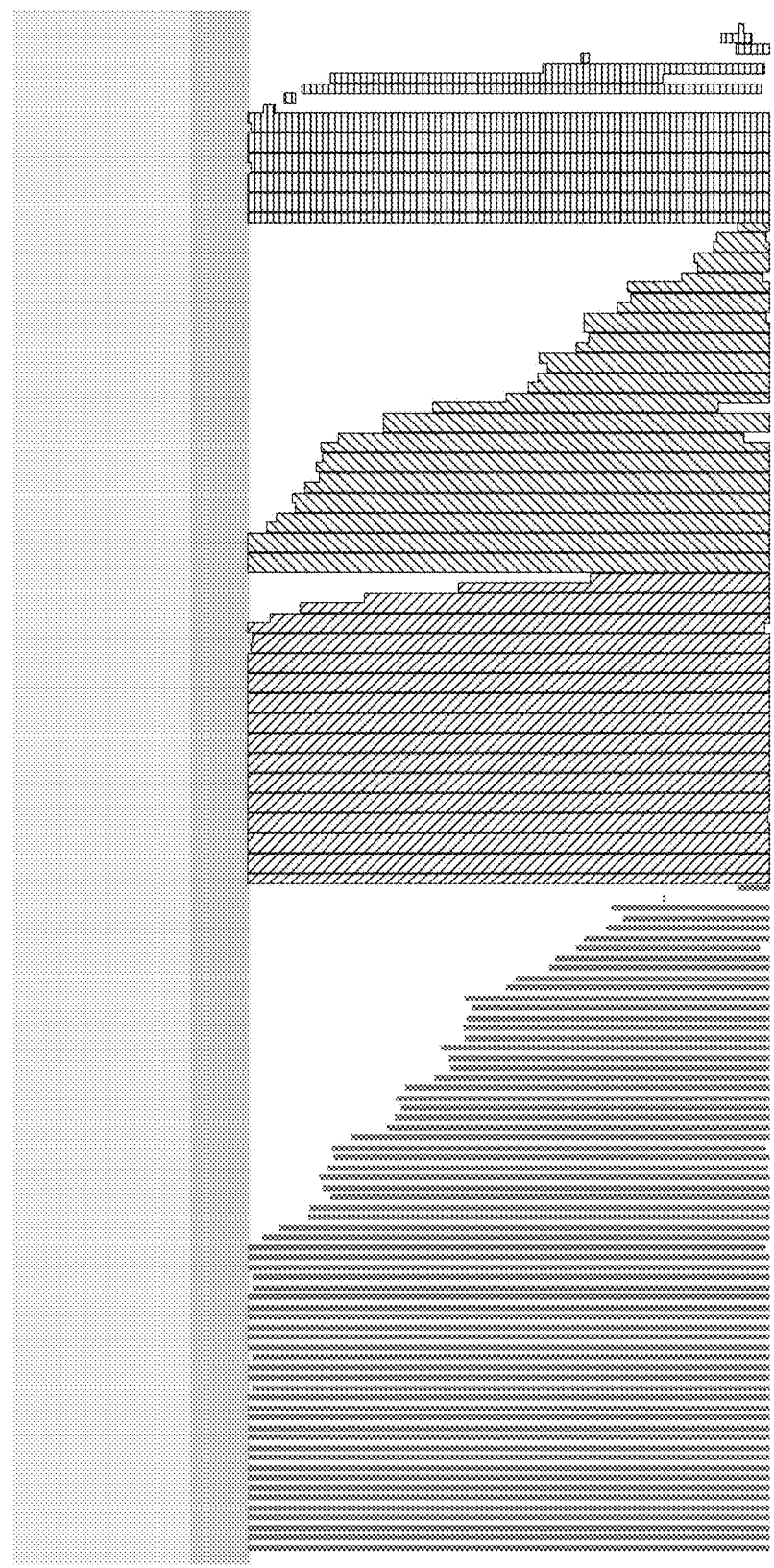
Figure 4:
Figure 4:
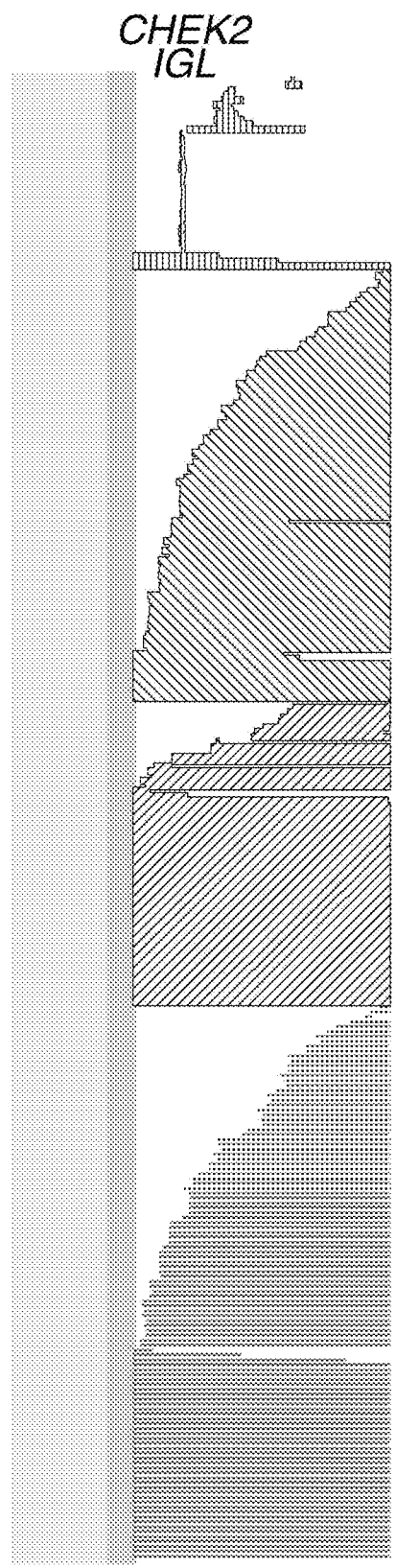
Figure 38:
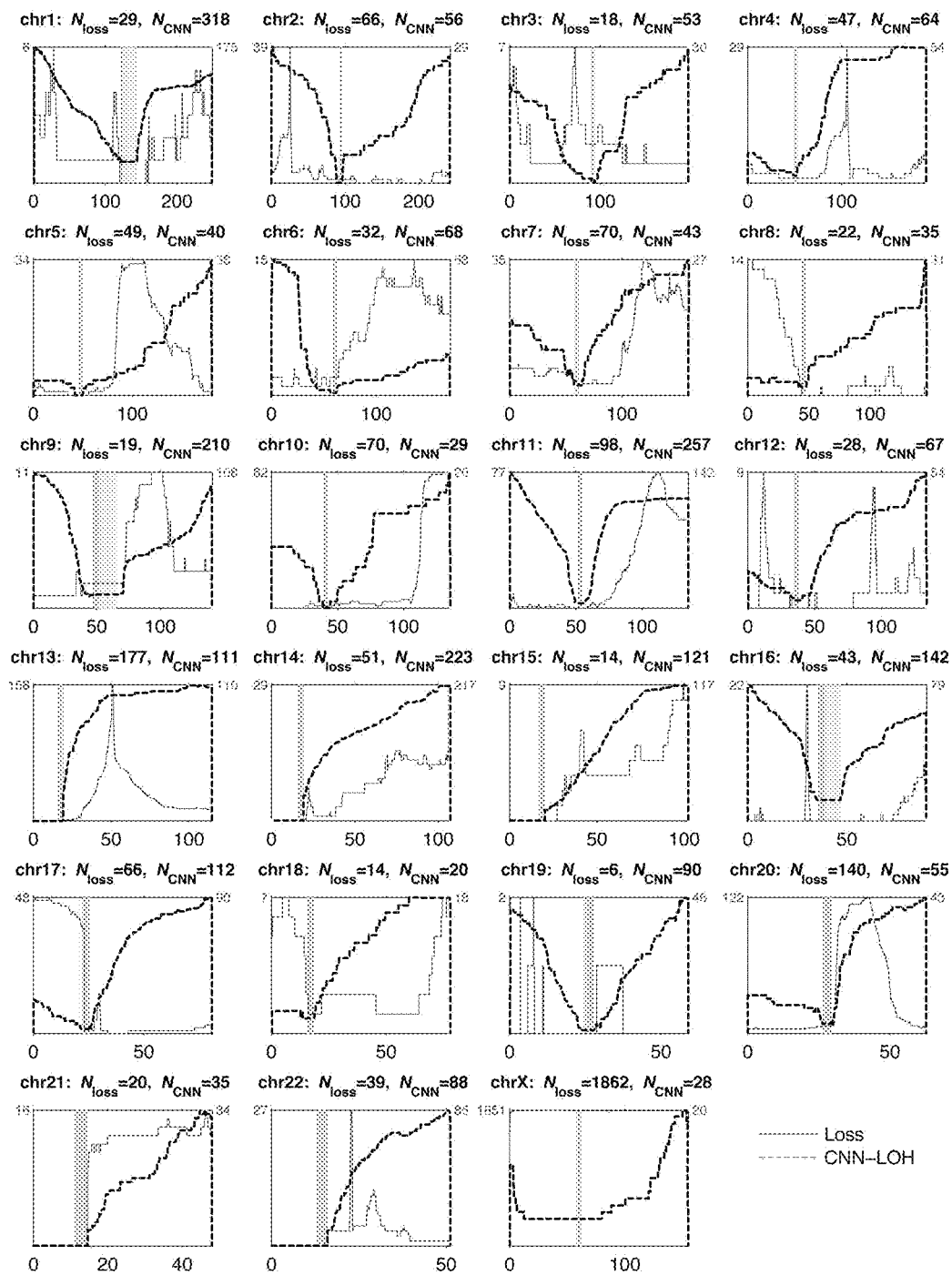
Figure 39A:
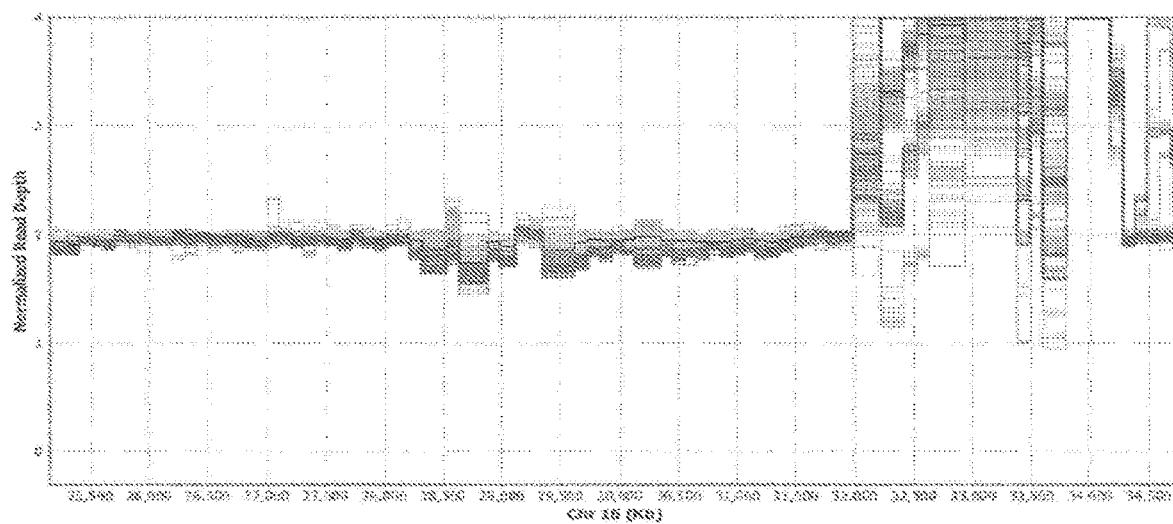
FIGS. 39A-39B—No evidence for mosaic 16p11.2 deletion in SFARI samples. Read depth profile plots in chr6:25-35 Mb (one line per SFARI individual) show no evidence of individuals carrying the 16p11.2 deletions we observed in UK Biobank (FIG. 27).
Figure 39B:
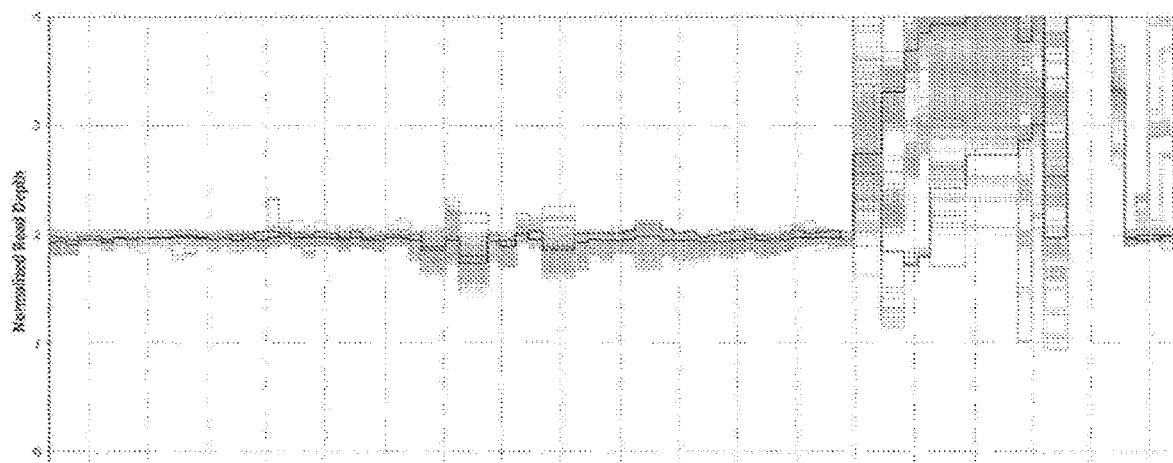

Commonly deleted regions (CDRs)<1 Mb in length are of particular interest as they may indicate haploid sufficient tumor-suppressor genes for which loss of one copy encourages excessive cell proliferation [2]. The three most frequent focal deletions targeted 13q14, DNMT3A, and TET2, loci identified in previous studies [2, 8]; Applicant further observed that most CNN-LOH events on 13q, 2p, and 4q spanned these same CDRs (FIG. 4 and FIG. 38). Applicant detected new CDRs at ETV6, NF1, and CHEK2, which are commonly mutated in cancers, and at RPA2 and RYBP (Supplementary Note). Applicant also observed a CDR at 16p11.2 overlapping a region whose deletion is a well-known inherited risk factor for autism; Applicant did not detect this mosaic event among 2,076 sequenced genomes from the Simons Simplex Collection in the Simons Foundation Autism Research Initiative (SFARI) (FIGS. 39A-39B).

Deletions tended to be concentrated on those chromosomes that are infrequently duplicated (FIG. 5F and Table 2), supporting the theory that cumulative haploinsufficiency and triplosensitivity shapes clonal evolution [28]. While a similar inverse relationship between propensity for somatic losses versus gains was previously observed in a pan-cancer analysis of somatic SVs [29], the sets of chromosomes with more losses versus gains are somewhat different in our analysis of blood-derived DNA, suggesting that some drivers of clonal evolution in blood are unique to the hematopoietic system.

Some kinds of somatic mutations could in principle have synergistic growth-promoting effects, a hypothesis suggested by the earlier observation that individuals tend to acquire multiple somatic SVs much more frequently than expected by chance [1,2,7,8] (FIG. 5C and Table 3). Our large set of detected mosaic SVs provided sufficient statistical resolution to identify three clusters of co-occurring SVs, one of which included events commonly observed together in chronic lymphocytic leukemia (CLL) [30, 31]: 13q LOH (including deletion and CNN-LOH), trisomy 12, and clonal V(D)J deletions on chromosomes 14 and 22 (FIG. 5C, Table 4). These co-occurrences of events could be explained by synergistic effects of proliferation, by shared genetic or environmental drivers, or by sequential progression from one event to the other.

Figure 40:
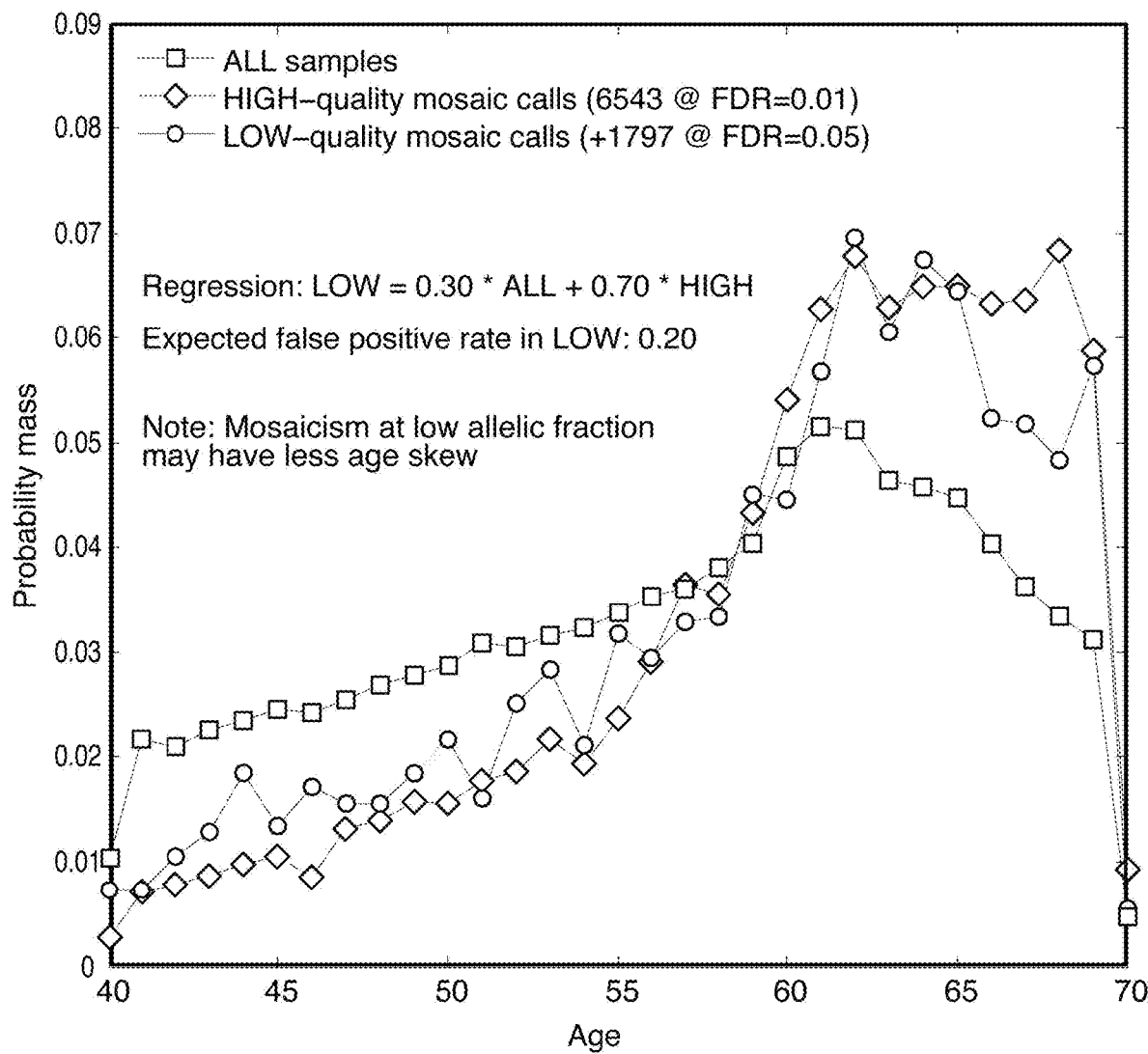
FIG. 40—Age distribution of individuals with high-confidence and lower-confidence somatic SV calls. Age distributions were generated for (i) "high-quality" detected events passing a stringent FDR threshold of 0.01 (diamond) and (ii) "low-quality" detected events below the FDR threshold of 0.01 but passing an FDR threshold of 0.05 (circle). These distributions were compared to the overall age distribution of UK Biobank participants (square), excluding a few individuals with ages outside the 40-70 range. Based on the numbers of events in each category, ≈20% of low-quality detected events are expected to be false positives. To sanity-check the FDR estimation procedure, the low-quality age distribution was regressed on the high-quality and overall age distributions, reasoning that the low-quality age distribution should be a mixture of (a) correctly called events with age distribution similar to that of the high-quality events and (b) spurious calls with age distribution similar to the overall sample. A regression weight of 0.30 was observed for the component corresponding to spurious calls, in good agreement with the estimated false positive rate.

Applicant found several interesting exceptions to a general pattern in which acquired mutations are most common in the elderly and in males [1, 2, 7, 8] (FIG. 5D and Table 5). Loss of chromosome X in females was by far the most common event Applicant detected (FIG. 34 and Table 2), with frequency increasing dramatically with advancing age (FIG. 5D and Table 5). (Applicant did not examine loss of chromosome Y, as our phase-based detection approach is not applicable and mLOY in UK Biobank has been studied elsewhere [19].) Stratifying autosomal SVs by location and copy number revealed a surprising relationship: although most gain events were (as expected) enriched in elderly individuals and in males, CNN-LOH events tended to affect both sexes equally and to be detectable in younger people (FIG. 5e and Table 6). Three SVs were clear outliers: gains on chromosome 15 were much more frequent in elderly males [33], while deletions on 10q and 16p were much more frequent in females and exhibited no enrichment in the elderly. (The overall age skew of somatic SV carriers also provided a convenient check of false discovery rate control; FIG. 40.)

Some acquired mutations could in principle arise or be selected within specific hematopoietic cell lineages. Applicant tested this hypothesis by focusing on individuals in the top 1% for indices of lymphocytes, basophils, monocytes, neutrophils, red blood cells, or platelets. Applicant identified many acquired SVs that were concentrated in one or more of these subsets of the cohort (FIG. 5F and Table 7). Consistent with the idea that these relationships might reflect clonal selection in specific blood-cell compartments, mutations commonly observed in CLL [30,31] were enriched among individuals with high lymphocyte counts, and JAK2-related 9p events (commonly observed in myeloproliferative neoplasms, MPNs) were most common among individuals with high myeloid indices. These results suggest that acquired SVs may produce subclinical blood-composition phenotypes in individuals with no known malignancy. Influences of Inherited Variants on Nearby Somatic SVs.

Figure 41:
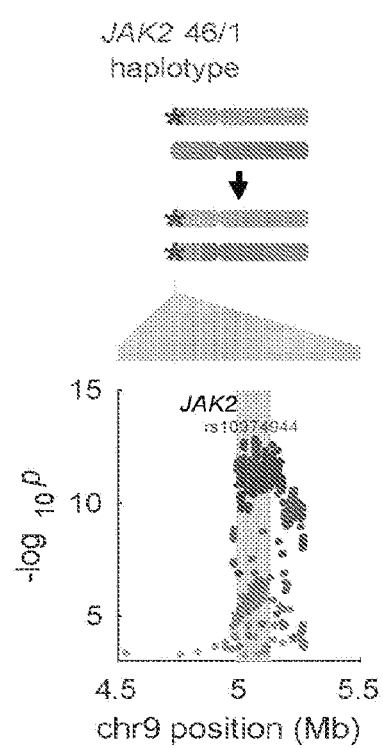
FIG. 41—Replication of previous association between JAK2 46/1 haplotype and 9p CNN-LOH in cis due to clonal selection. The common JAK2 46/1 haplotype has previously been shown to confer risk of somatic JAK2 V617F mutation such that subsequent 9p CNN-LOH produces a strong proliferative advantage [13-16, 18]. In the analysis, CNN-LOH on 9p is strongly associated with JAK2 46/1 (P=1.6× 10-13; OR=2.7 (2.1-3.5)) with the risk haplotype predominantly duplicated by CNN-LOH in hets (52/61 heterozygous cases; P=1.8×10-8). In this figure, the genomic modification is illustrated in the top panel and association signals are plotted in the bottom. The lead associated variant is labeled, and variants are colored according to linkage disequilibrium with the lead variant (scaled for readability).

To identify inherited influences on SV formation or selection, Applicant performed chromosome-wide scans for associations between recurring somatic SVs and germline variants on the same chromosome as each SV (Methods). This analysis revealed four loci that strongly associated with genomically nearby somatic SVs on 10q, 1p, 11q, and 15q, and two loci that associated with loss of chromosome X in females (Table 1, FIGS. 6A-6E, and FIGS. 7A-7C). (Applicant also replicated an earlier association of JAK2 46/1 with 9p CNN-LOH [13-16, 18]; FIG. 41.) To elucidate causal influences of inherited variation at these loci, Applicant fine-mapped these associations using whole-genome sequence data and studied the chromosomal phase of risk alleles relative to associated SV mutations.

Somatic terminal 10q deletions associated strongly with the common SNP rs118137427 near FRA10B, a known genomic fragile site [34, 35] at the estimated common breakpoint of the 10q deletions (Table 1 and FIG. 6A). All 60 individuals with these mosaic 10q deletions had inherited the rs118137427:G risk allele (RAF=5% in the population; FIG. 6C), which was always inherited on the same chromosome that subsequently acquired a terminal deletion (Table 1).

To identify a causal mutation potentially tagged by the rs118137427:G risk allele, Applicant searched for acquired 10q deletions in WGS data from 2,076 other individuals (SFARI cohort). Applicant identified two parent-child duos carrying the 10q terminal deletion (in mosaic form); all four individuals possessed expanded AT-rich repeats at FRA10B on the rs118137427:G haplotype background (FIGS. 6D and 6E and FIG. 34). Further evidence that the rs118137427:G risk allele tags an unstable version of the FRA10B locus [36] was provided by analysis of the variable number tandem repeat (VNTR) sequence at FRA10B in the WGS data (from all 2,076 SFARI participants). This analysis revealed four novel VNTR motifs, which were carried by 30 SFARI participants in 13 families; all four novel motifs were present on the rs118137427:G haplotype background, despite the low frequency of that haplotype in the population (5%) (FIG. 6E and FIGS. 42A-42B and 43). (The VNTRs did not associate with autism status.) Two of the four novel VNTR sequence motifs were sufficiently common in SFARI to impute into UK Biobank; although these two imputable VNTR motifs were estimated to be present in just 0.1-0.4% of the UKB cohort, they explained 24 of the 60 cases of 10q deletion (Table 8). Interestingly, 51 of 60 individuals with terminal 10q deletions were female, and the age distribution of cases matched the study population, a clear exception to the general pattern of male-biased, age-dependent acquisition among other mosaic SVs (FIG. 6B).

CNN-LOH events on chr1p strongly associated with three independent, rare risk haplotypes (risk allele frequency, RAF=0.01-0.05%) at the MPL proto-oncogene at 1p34.1 (encoding the thrombopoietin receptor); each of the three haplotypes conferred >50-fold increased risk for 1p CNN-LOH (Table 1). Identity-by-descent analysis at the MPL locus suggested that additional or recurrent very rare risk variants are also present at the locus (FIG. 44). Intriguingly, although gain-of function mutations in MPL are known to lead to myeloproliferative neo-plasms [37,38], the lead imputed SNP on one haplotype, rs369156948, is a loss-of-function (LOF) coding SNP in MPL; the other two lead SNPs tag long haplotypes that include MPL (FIG. 7A and Table 9).

Applicant were able to identify an intriguing likely mechanism for selection of the CNN-LOH events involving MPL. For all 16 events for which Applicant could confidently phase the rare risk allele relative to the somatic CNN-LOH, the risk allele was removed by the CNN-LOH (P=3×10-5; Table 1 and FIG. 7A). A plausible interpretation of these results is that among individuals with rare inherited variants that reduce MPL function, recovery of normal MPL gene activity via CNN-LOH provides a proliferative advantage. Despite the fact that clonal hematopoiesis is (at most loci) a strong risk factor for subsequent blood cancer, 0 of 36 imputed carriers of the rs369156948 LOF allele had prevalent or incident hematological cancer diagnoses, supporting the idea that this rare allele may actually be hypo-proliferative in its effects, and an object of negative selection.

Figures 7A, 7B, 7C:
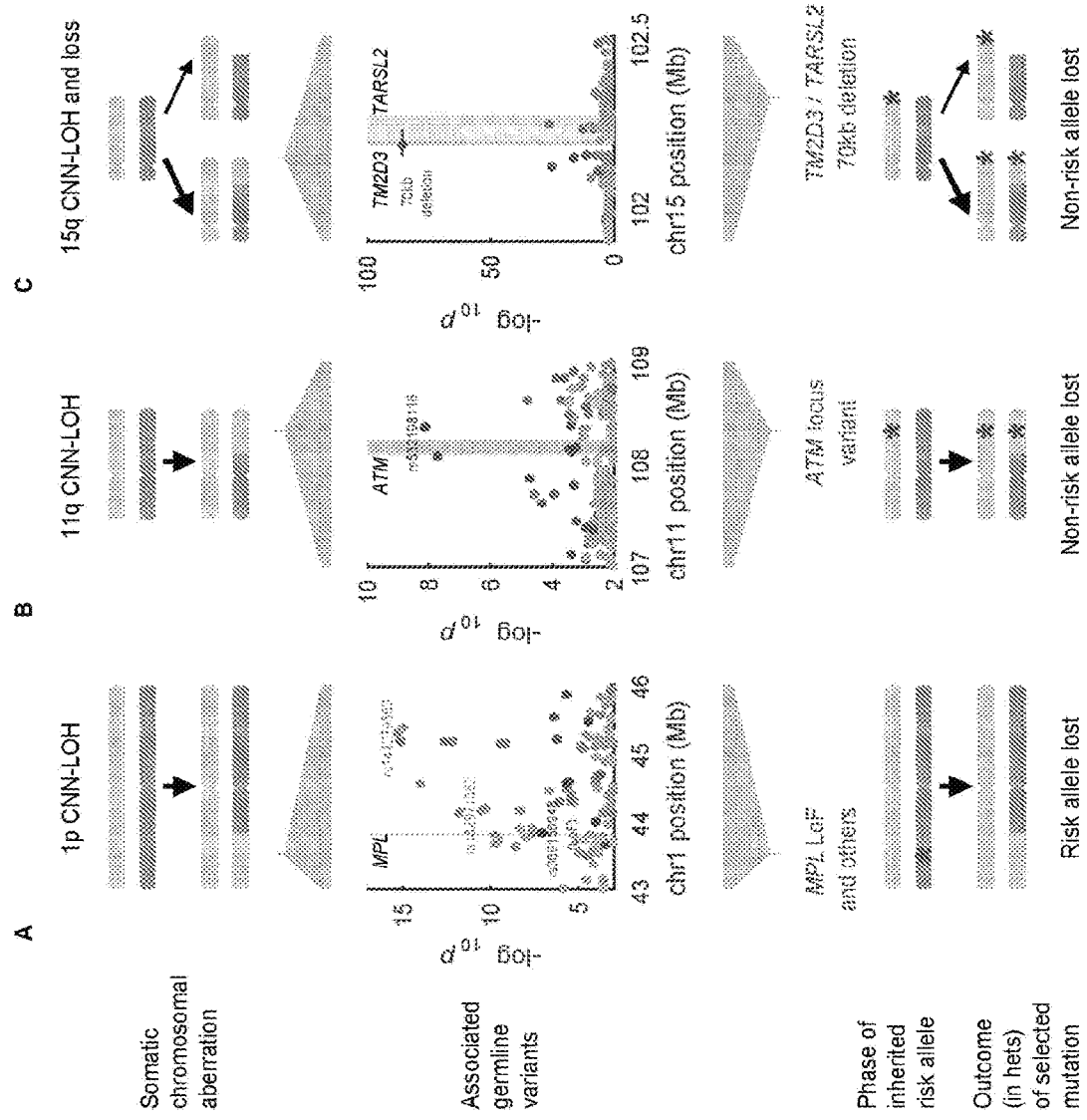
FIGS. 7A-7C—Novel loci associated with somatic SVs in cis due to clonal selection. In each locus, as shown in FIGS. 7A, 7B, and 7C, respectively, one or more inherited genetic variants causes chromosomal mutations to create a proliferative advantage. Genomic modifications are illustrated in the top part of each panel and association signals are plotted in the bottom. Independent lead associated variants are labeled, and variants are colored according to linkage disequilibrium with lead variants (scaled for readability).
Figure 9A:
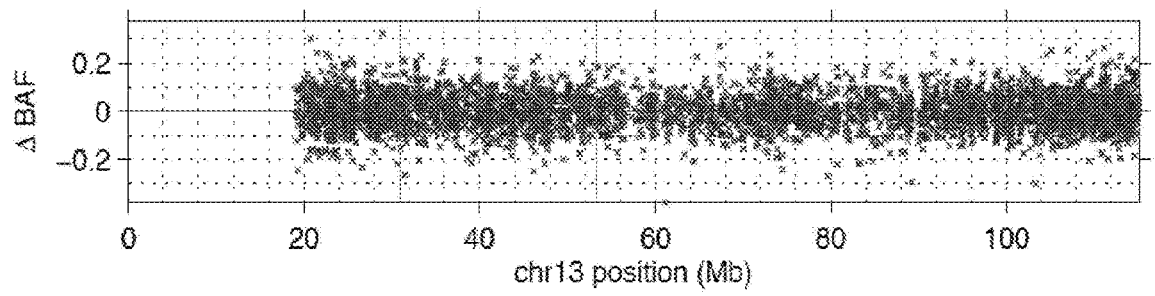
FIGS. 9A-9C—his UK Biobank sample (1282743) has a mosaic deletion of chr13 from roughly 31-53 Mb that cannot be confidently called from unphased B allele frequency (BAF) and log 2 R ratio (LRR) data alone (FIG. 9A, FIG. 9C). However, the existence of an event is evident in the phased BAF data (FIG. 9B), and the regional decrease in LRR indicates that this event is a deletion.
Figure 9B:
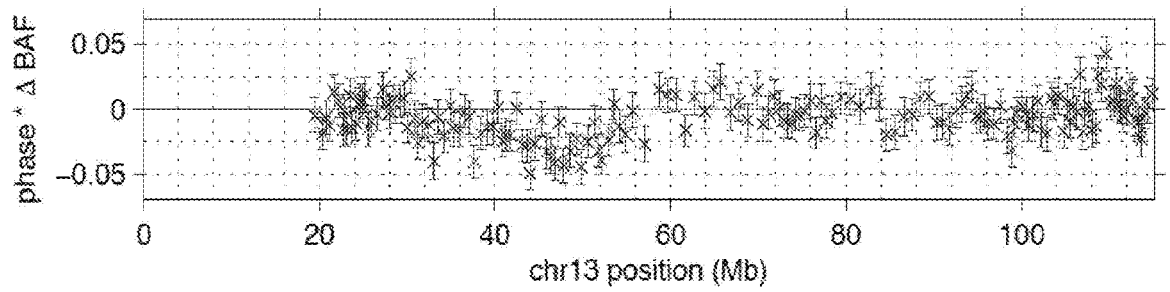
Figure 9C:
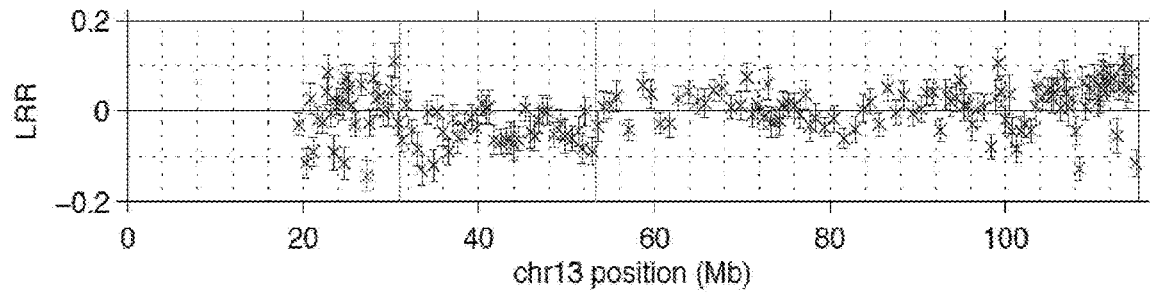
Figure 9C:
Figure 10A:
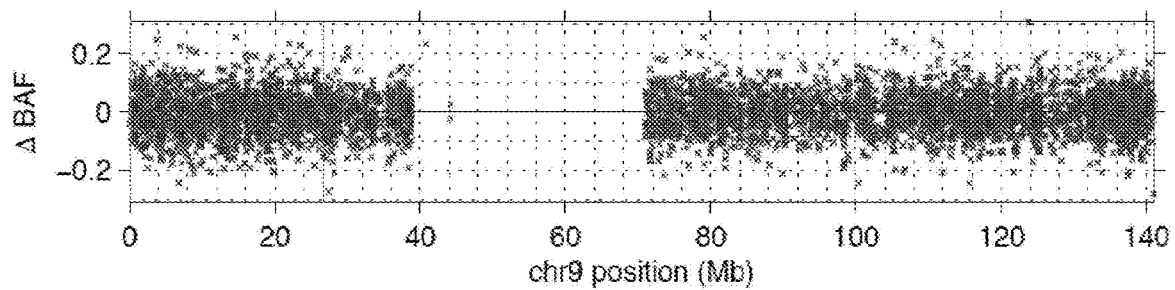
FIGS. 10A-10C—This UK Biobank sample (2480737) has a mosaic CNN-LOH on chr9p from the 9p telomere to roughly 27 Mb that cannot be confidently called from unphased B allele frequency (BAF) data (FIG. 10A) but is evident in phased BAF data (FIG. 10B). A phase switch error causes a sign flip in phased BAF at 20 Mb. The lack of a shift in log 2 R ratio (LRR) in the region (FIG. 10C) indicates that this event is a CNN-LOH.
Figure 10B:
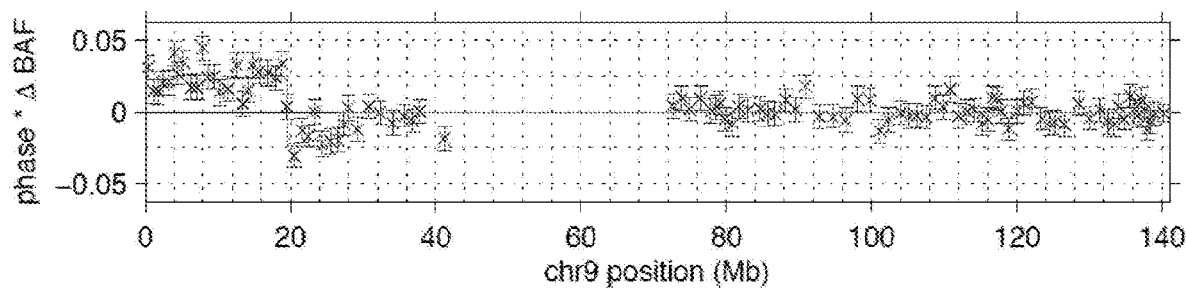
Figure 10C:
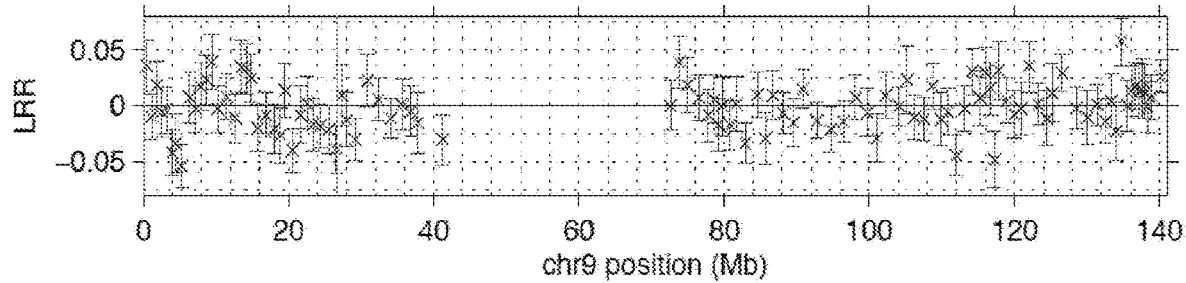
Figure 10C:
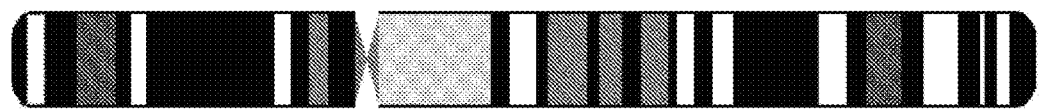
Figure 11A:
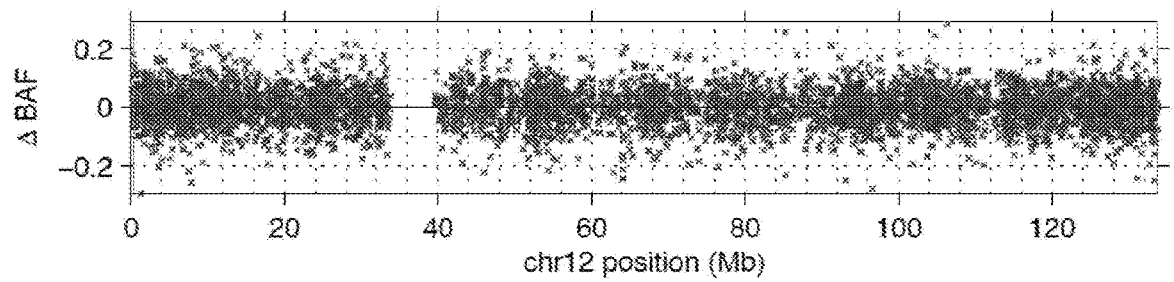
FIGS. 11A-11C—This UK Biobank sample (2961290) has a full-chromosome mosaic event on chr12 that cannot be confidently called from unphased B allele frequency (BAF) and log 2 R ratio (LRR) data alone (FIG. 11A, FIG. 11C) but is evident in phased BAF data (FIG. 11B). Several phase switch errors cause sign flips in phased BAF across chr12. The slight positive shift in mean LRR (FIG. 11C) indicates that this event is most likely a mosaic gain of chr12.
Figure 11B:
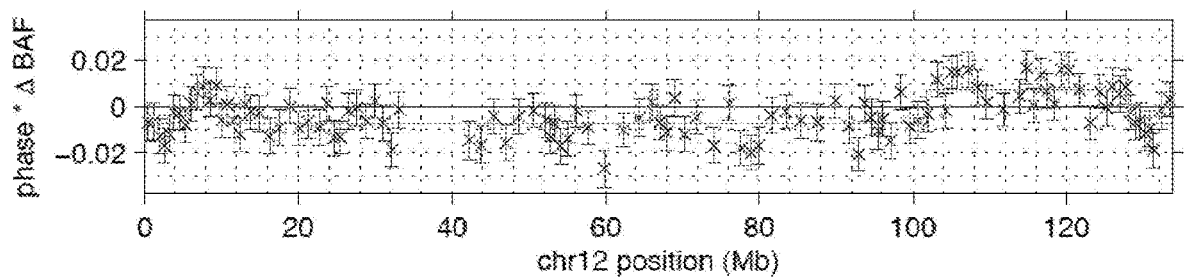
Figure 11C:
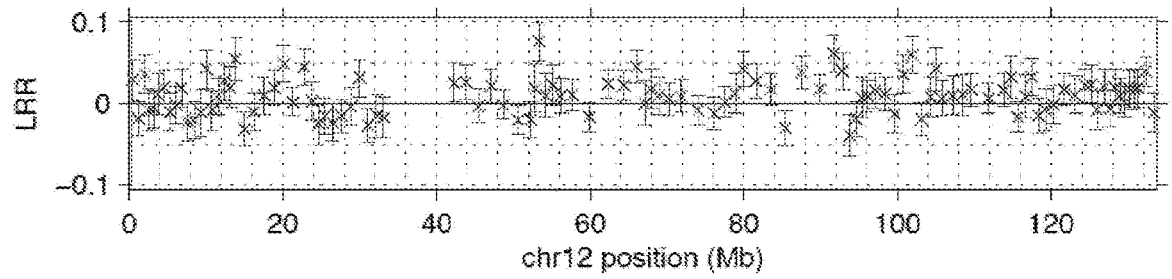
Figure 11C:
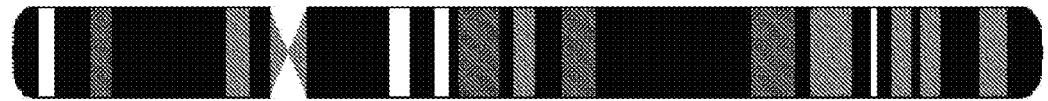
Figure 22:
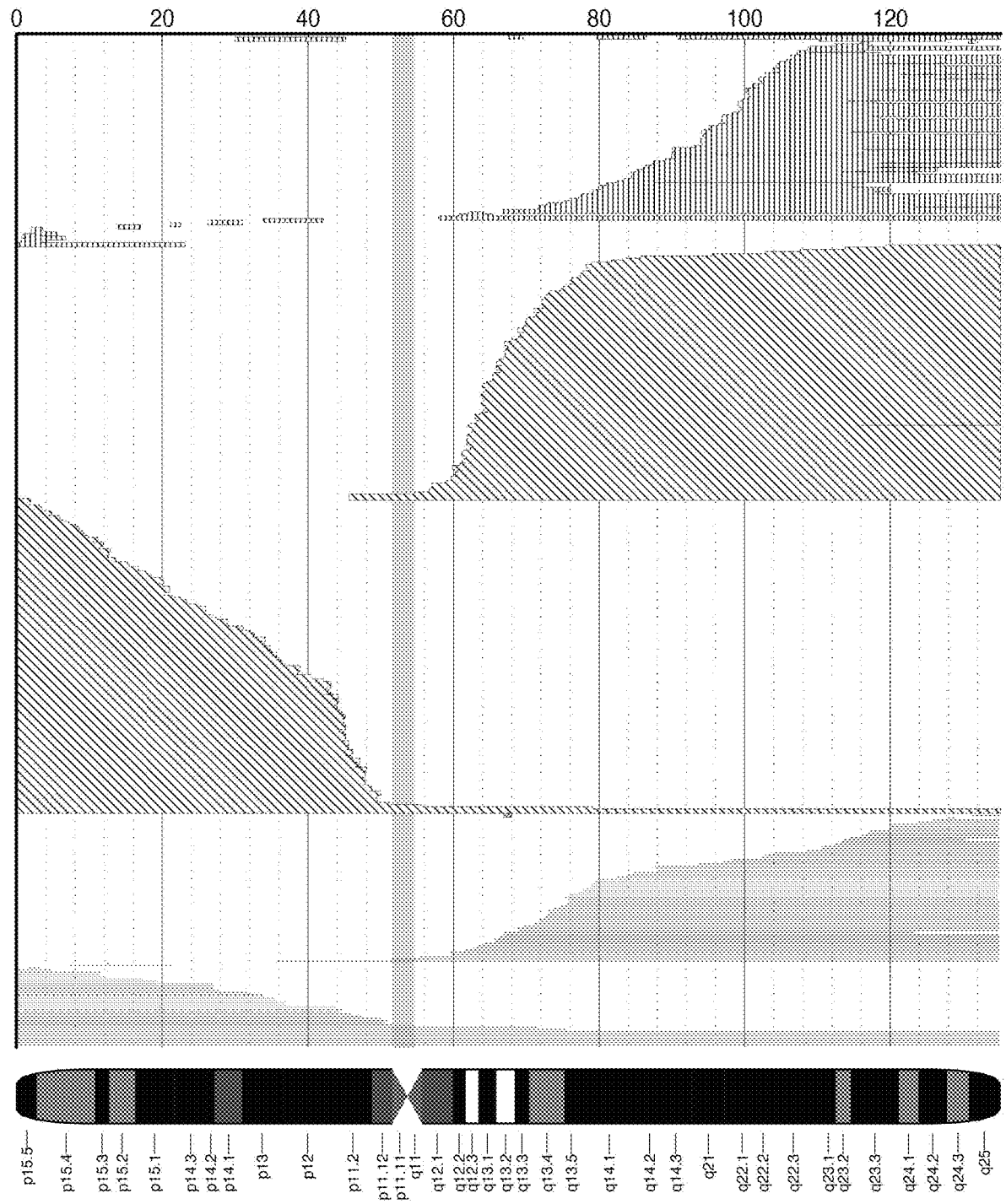
Figure 23:
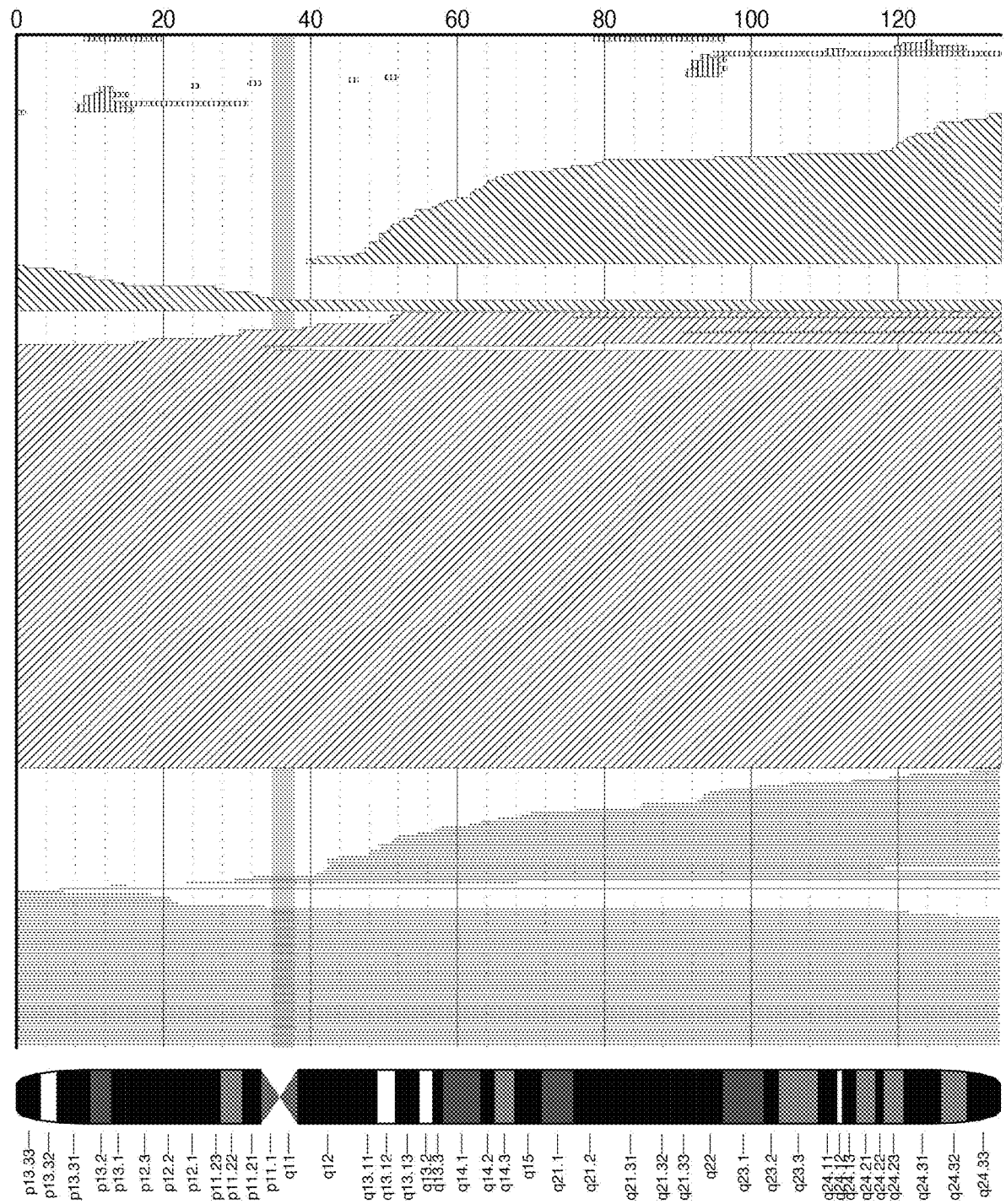
Figure 24:
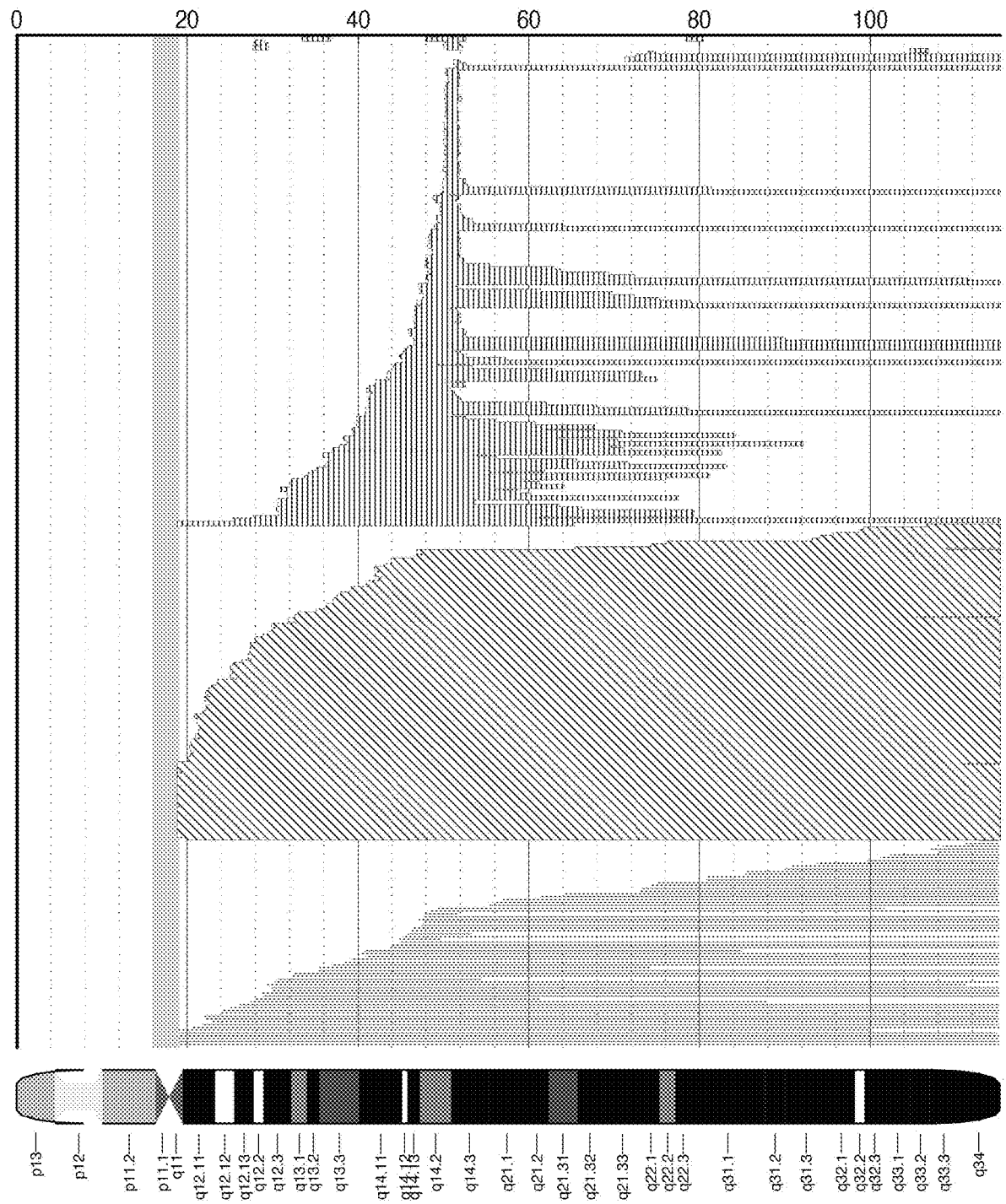

CNN-LOH events on chr11q associated strongly (>40-fold increased risk) with a rare risk haplotype (RAF=0.07%) surrounding the ATM gene at 11q22.3 (Table 1, FIG. 7B, and Table 9). For all 6 CNN-LOH events for which Applicant could confidently phase the risk allele relative to the somatic mutation, the LOH mutation had caused the rare risk allele to become homozygous (Table 1 and FIG. 7B). (This dynamic contrasts with the dynamic at MPL, at which the rare, inherited risk haplotypes were eliminated by LOH and clonal selection.) While more data will be required to identify a causal variant, ATM is a clear putative target: ATM plays a key role in cell cycle regulation, and LOF mutations and deletions of ATM are commonly observed in CLL [30, 31]. (In present analysis, acquired 11q deletions also appeared to target ATM; FIG. 4 and FIG. 22.)

Figure 45A:
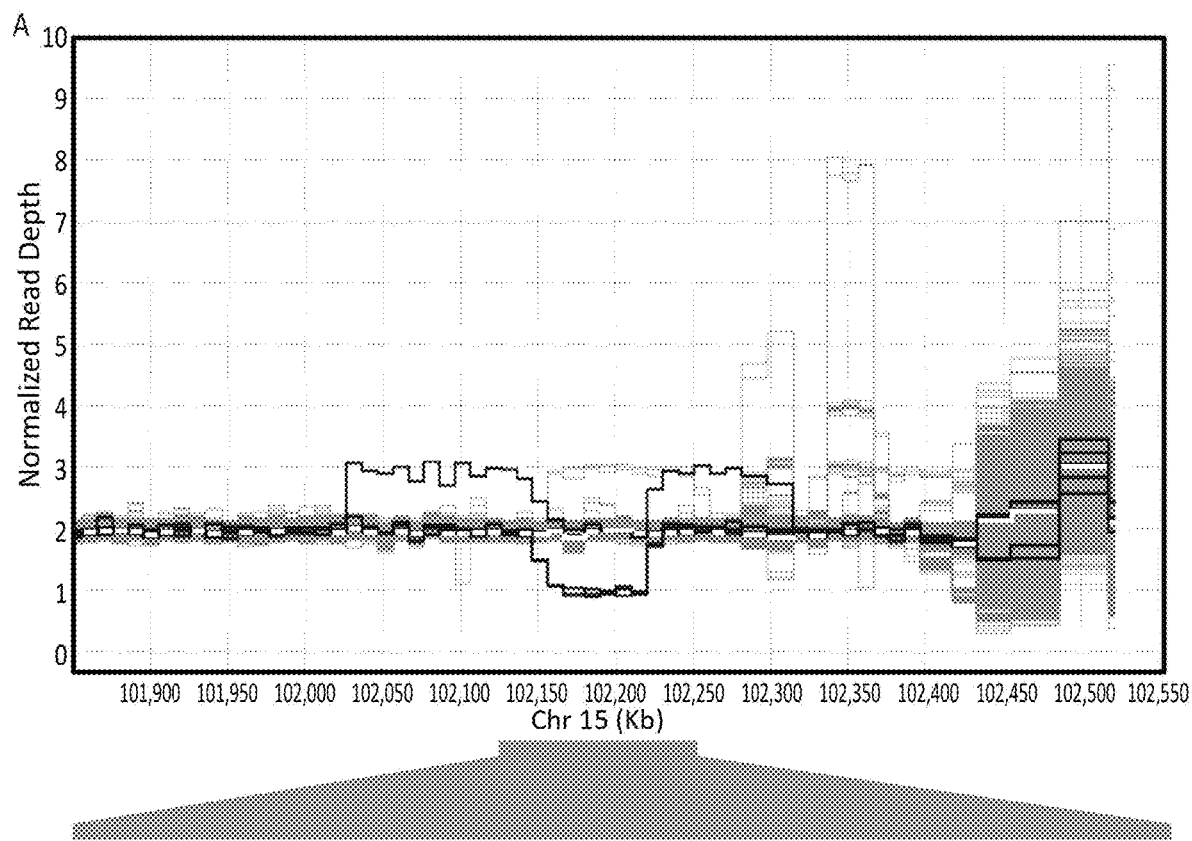
FIGS. 45A-45B—Germline CNVs at 15q26.3.
Figure 45B:
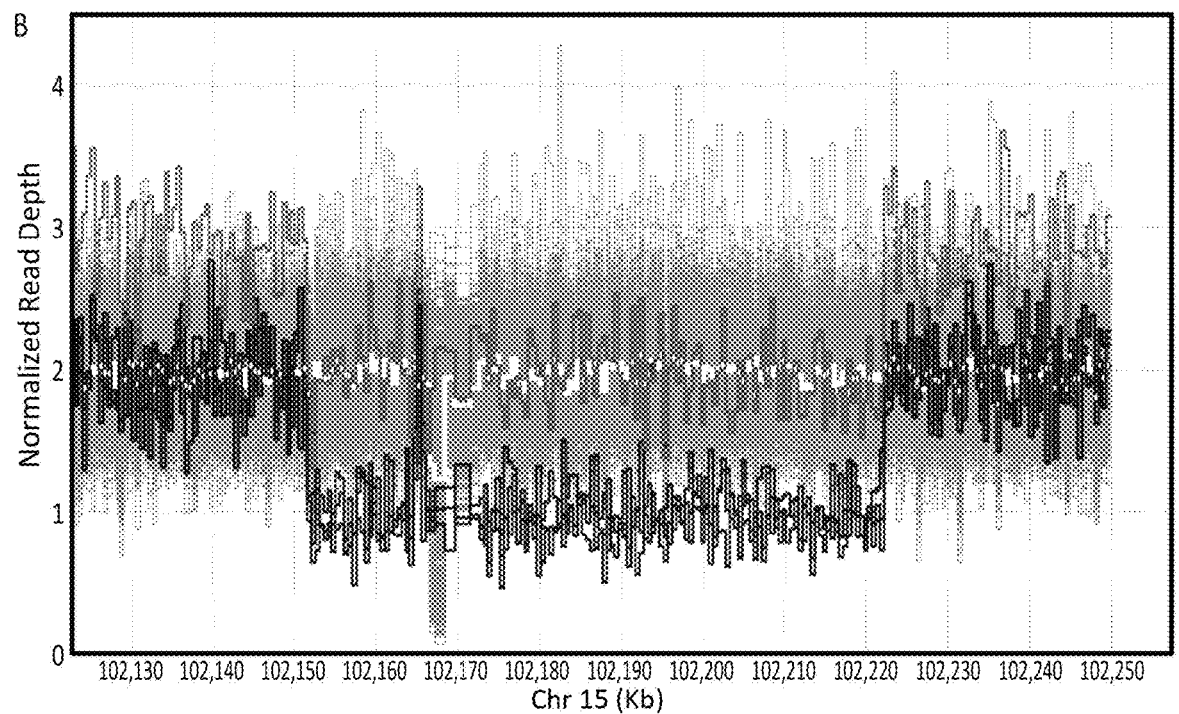
Figure 46:
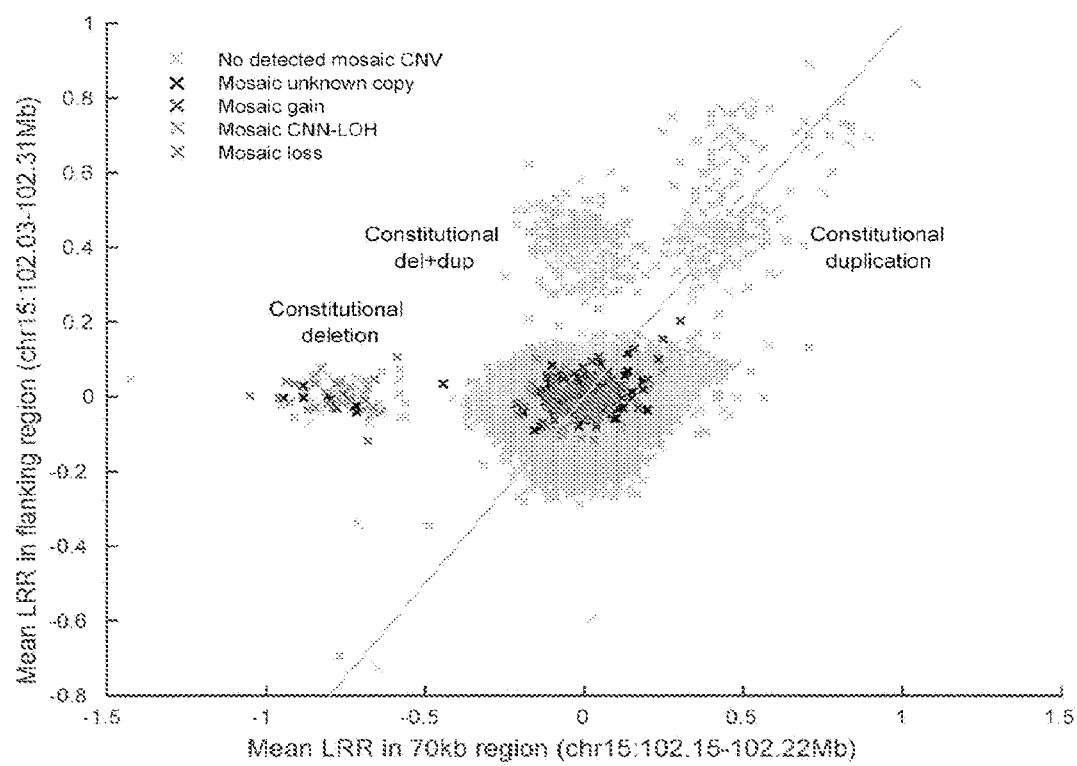
FIG. 46—Somatic SVs and germline CNVs at 15q26.3. Using identified breakpoints of the germline ~70 kb deletion and ~290 kb duplication (FIG. 37), we computed mean genotyping intensity (LRR) in UK Biobank samples within the ~70 kb deletion region (24 probes) and within the flanking ~220 kb region (97 probes). Individuals are plotted by flanking 220 kb mean LRR vs. 70 kb mean LRR and colored by mosaic status for somatic 15q SVs. UK Biobank samples carrying the 70 kb deletion, 290 kb duplication, and del+dup are all easily identifiable in distinct clusters. The plot also appears to contain clusters with higher copy number. The simple 70 kb deletion is the only constitutional CNV that predisposes to somatic SVs. Most somatic SVs are CNN-LOH events that make cells homozygous for the 70 kb deletion; two individuals have somatic loss of the homologous (normal) chromosome, making cells hemizygous for the 70 kb deletion.

CNN-LOH and loss events at chr15q associated with a rare, inherited 70 kb deletion that spanned all of TM2D3 and part of TARSL2 at 15q26.3. For 39 of 41 events with high-confidence phase calls, the CNN-LOH or loss was inferred to produce homozygosity or hemizygosity of the inherited deletion, removing the reference (non-deletion) allele from the genome (Table 1 and FIG. 8C). (This dynamic resembles the dynamic at ATM in suggesting clonal selection for the rare, inherited risk allele.) The 70 kb deletion was present at an allele frequency of 0.03% and conferred a ~700-fold increased risk of 15q mutation: 45 of 89 carriers exhibited detectable 15q events (32 CNN-LOH, 2 loss, 11 uncalled; FIG. 46). Interestingly, the 70 kb deletion was sometimes inherited on an allele that also had an independent 290 kb duplication of the locus (FIGS. 45A-45B); on this more-complex allele, TM2D3 and TARSL2 gene dosage were normal. Carriers of the more-complex allele did not exhibit the predisposition to somatic SVs (FIG. 46). Further study will be required to determine a proliferative mechanism involving TM2D3, TARSL2, or noncoding elements within the region.

Figure 47:
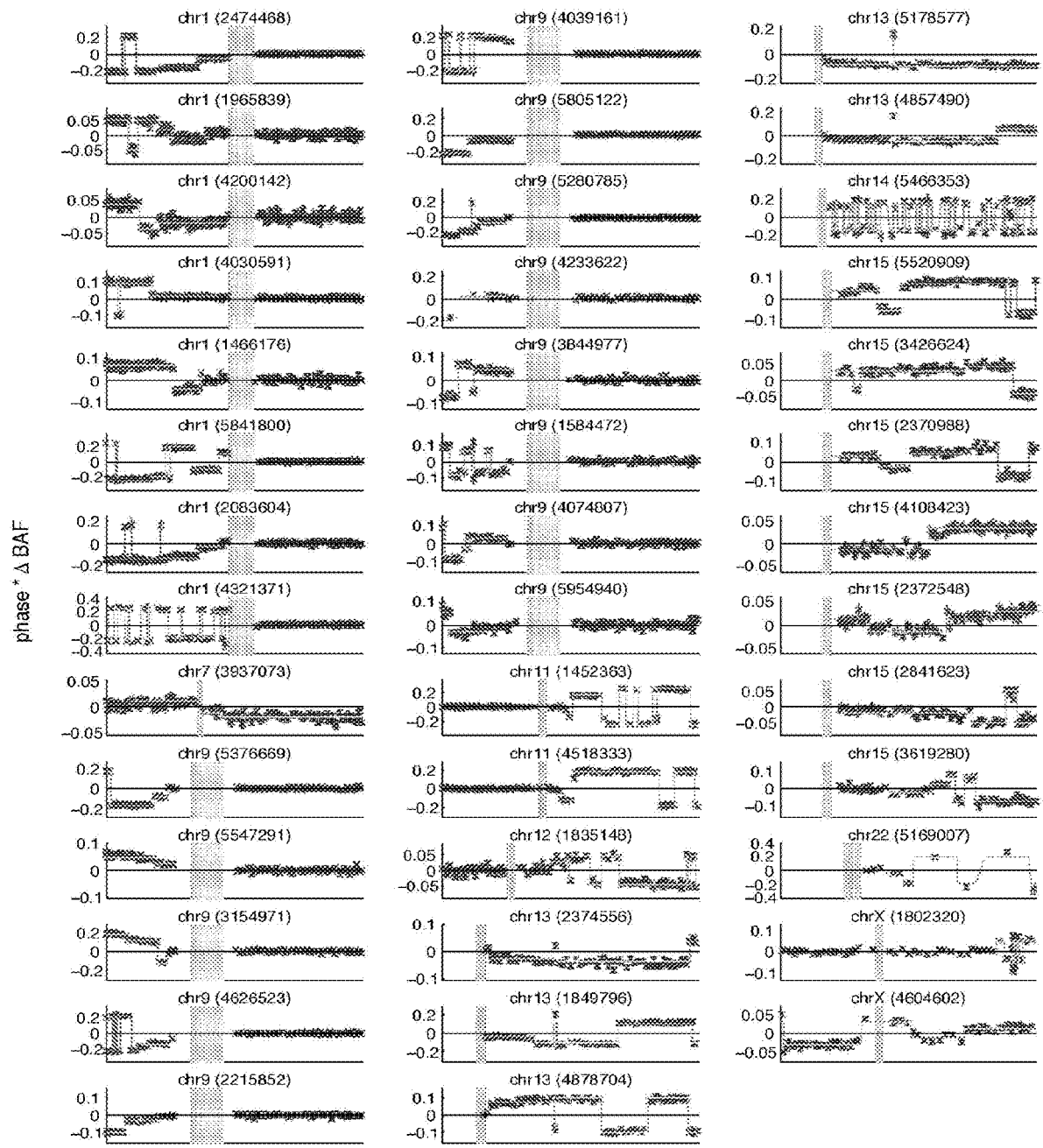
FIG. 47—Phased BAF plots of chromosomes with multiple CNN-LOH subclones. All of the above plots exhibit step functions of increasing |ΔBAF| toward a telomere, which is the hallmark of multiple clonal cell populations containing distinct CNN-LOH events that affect different spans of a chromosomal arm (all extending to the telomere). Distinct |ΔBAF| values (called using an HMM) are indicated with different colors. Flips in the sign of phased BAF correspond to phase switch errors, which are much more frequent in regions with very high |ΔBAF| (e.g., individual 5466353 with chr14q CNN-LOH events) because extreme shifts in genotyping intensities result in poor genotyping quality.
Figure 48:
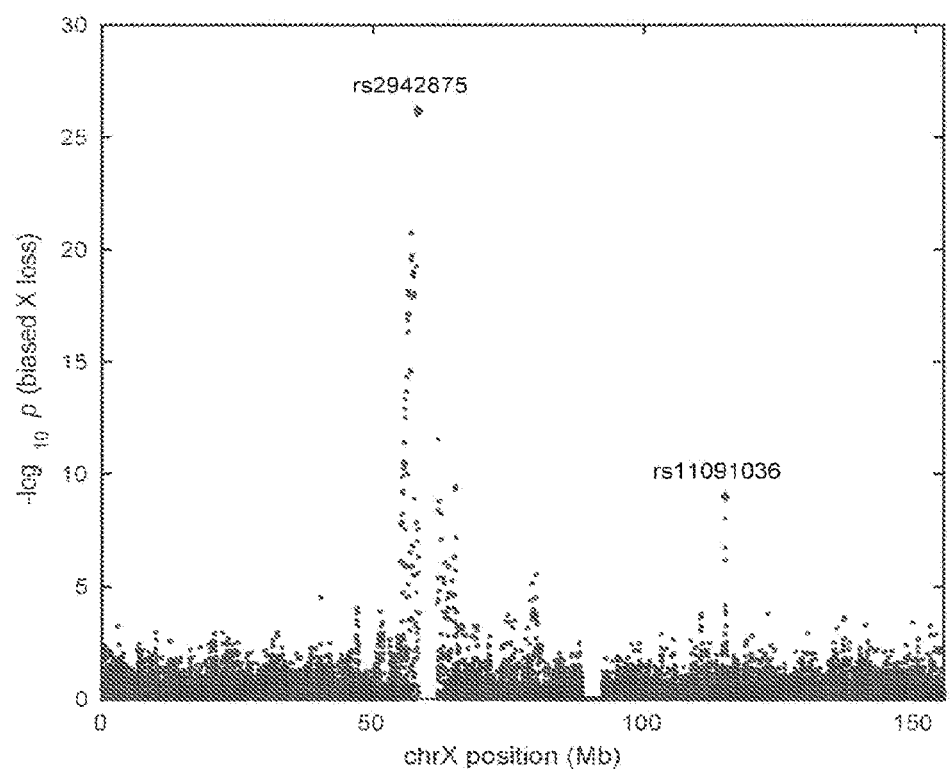
FIG. 48—Manhattan plot of cis associations with biased female chrX loss. The gaps in the plot correspond to the chrX centromere and X-transposed region (XTR); we masked the latter from our analyses, following Laurie et al. [2].

The high penetrances (of up to 50%) for the above cis associations led us to suspect that some risk-allele carriers might in fact harbor multiple subclonal cell populations with the associated somatic SVs. Applicant detected 41 individuals who had acquired two or more CNN-LOH mutations (with different breakpoints and allelic fractions) involving the same chromosome (FIG. 47). (In contrast, only 28 individuals carried multiple CNN-LOH mutations on distinct chromosomes.) For all 41 individuals with multiple same-chromosome CNN-LOH events, all events involved recurrent selection of the same haplotype (in different clones). Of the 41 haplotypes that were recurrently selected in the same individual, 16 carried one of the rare risk alleles identified by our association scans, 14 appeared to involve other (still-unmapped) allelic drivers at the same loci, and 11 involved other genomic loci (FIG. 47). This result indicates strong proliferative advantage conferred by CNN-LOH in these individuals and suggests that mitotic recombination is sufficiently common as to yield multiple opportunities for clonal selection in individuals carrying inherited haplotypes with different proclivities for expansion. In contrast to the results above describing rare alleles that strongly increase risk of acquiring nearby SVs, Applicant found two common variants on chromosome X that only weakly increase risk of X loss but strongly influence (in females heterozygous for the variant) which X chromosome is lost in the expanded clone. These involved a strong association (P=$6.6 \times 10^{-27}$, 1.9:1 bias in the lost haplotype) at Xp11.1 near DXZ1 and a weaker association (P=$1.0 \times 10^{-9}$, 1.5:1 bias in the lost haplotype) at Xq23 near DXZ4 (Table 1, FIG. 48, and Table 11). These associations do not appear to be explained by biased X chromosome inactivation [39] (Table 11) and hint at a mechanism very different from those Applicant have described above (Supplementary Note).

Trans Associations With Somatic SVs

Genetic variants near genes with roles in cell proliferation and cell cycle regulation predispose for male loss of Y [17,19], and female loss of X is also a heritable trait (h2-26% (17.4-36.2%) in sib-pair analysis) [19], but no associations for loss of X have previously been reported. Applicant confirmed the heritability of female X loss by performing BOLT-REML [40] analysis (Methods), obtaining a SNP-heritability estimate of hg2=10.6% (s.e. 3.6%). Genome-wide association analysis for trans variants influencing loss of X further revealed two novel genome-wide significant associations, at the SP140L and HLA loci (Table 1).

Germline variants that affect cancer risk or chromosome-maintenance phenotypes could in principle increase the risk of precancerous or benign clonal expansions. Applicant considered 86 variants implicated in previous GWAS on CLL, MPN, loss of Y, clonal hematopoiesis, and telomere length, and tested these variants for trans association with seven classes of somatic SVs, stratifying events by chromosome type (autosome versus X chromosome) and by copy number (Table 12). Four variants reached Bonferroni significance ($P<8.3\times10^{-5}$): two linked variants in TERT (an intronic deletion recently associated with clonal hematopoiesis [11], and a common SNP previously associated with MPN [41] and JAK2 V617F mutation [18]), a rare CHEK2 frameshift SNP (previously associated with JAK2 V617F mutation [18]), and a low-frequency 3' UTR SNP in TP53 (previously associated with cancers [42] and mLOY [19]) (Table 11). The TERT and CHEK2 variants associated with multiple types of autosomal events; in contrast, the TP53 SNP primarily associated with losses (both focal deletions on autosomes and whole-chromosome losses of X) (Table 12). Carriers of the CHEK2 frameshift SNP were especially prone to developing multiple clonal SVs: 8 of 33 carriers with detected autosomal SVs had two or more detectable events (compared to an expectation of 3; P=0.008), generally in multiple clones.

Somatic SVs and Cancer Onset

Cancer-free individuals with detectable mosaicism (at any locus) have >10× elevated risk of subsequent hematological cancer [1-4]. For chronic lymphocytic leukemia (CLL), a slowly progressing hematological cancer that is known to be preceded by clonal mosaicism years before progression [43, 44], mosaic aberrations observed in pre-CLL cases occur at the same loci as those observed in CLL [30, 31, 45, 46].

The large number of events detected in this work enabled us to evaluate the possibility that specific mosaic SVs might more strongly predict risk of specific cancers [47]. Applicant identified 17 somatic SV events that significantly associated (at FDR<0.05) with subsequent cancer diagnosis (>1 year after DNA collection) in analyses corrected for age and sex (FIG. 8A and Table 13). The odds ratios for a subset of these SVs were extremely high: several SVs commonly observed in blood cancers conferred >100-fold increased risk for incident CLL or MPN. DNMT3A deletion on 2p conferred 3.5-fold increased risk for incident non-blood cancer, though this weaker association might also be explained by other unobserved risk factors that increase risk for both non-blood cancer and clonal hematopoiesis.

Figure 49:
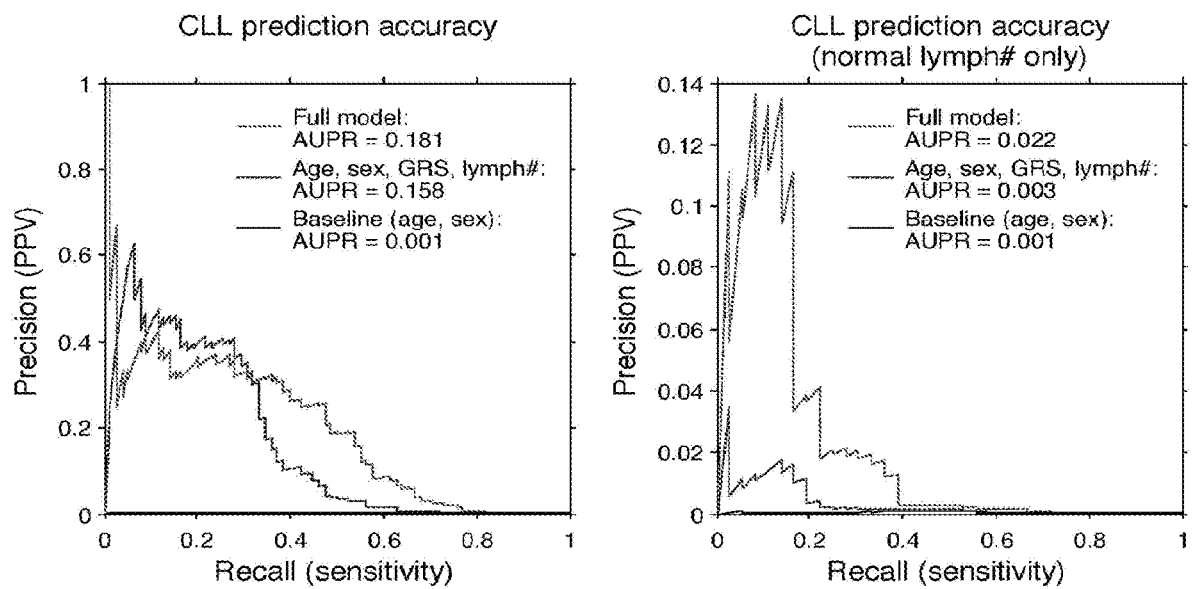
FIG. 49—CLL prediction accuracy: precision-recall curves. The precision-recall curves are for the same cross-validation benchmarks for which ROC curves were reported in FIG. 5b,c. The benchmark on the right includes only individuals with lymphocyte counts in the normal range (1×109/L to 3.5×109/L), whereas the benchmark on the left relaxes this restriction (and also uses additional mosaic event variables for prediction (11q-, 14q-, 22q-, and total number of autosomal events). In both benchmarks, individuals with previous cancer diagnoses or CLL diagnoses within 1 year of assessment are excluded; however, some individuals with very high lymphocyte counts pass this filter (and probably already had CLL at assessment despite being undiagnosed for >1 year), hence the difference in apparent prediction between the two benchmarks.
Figure 50:
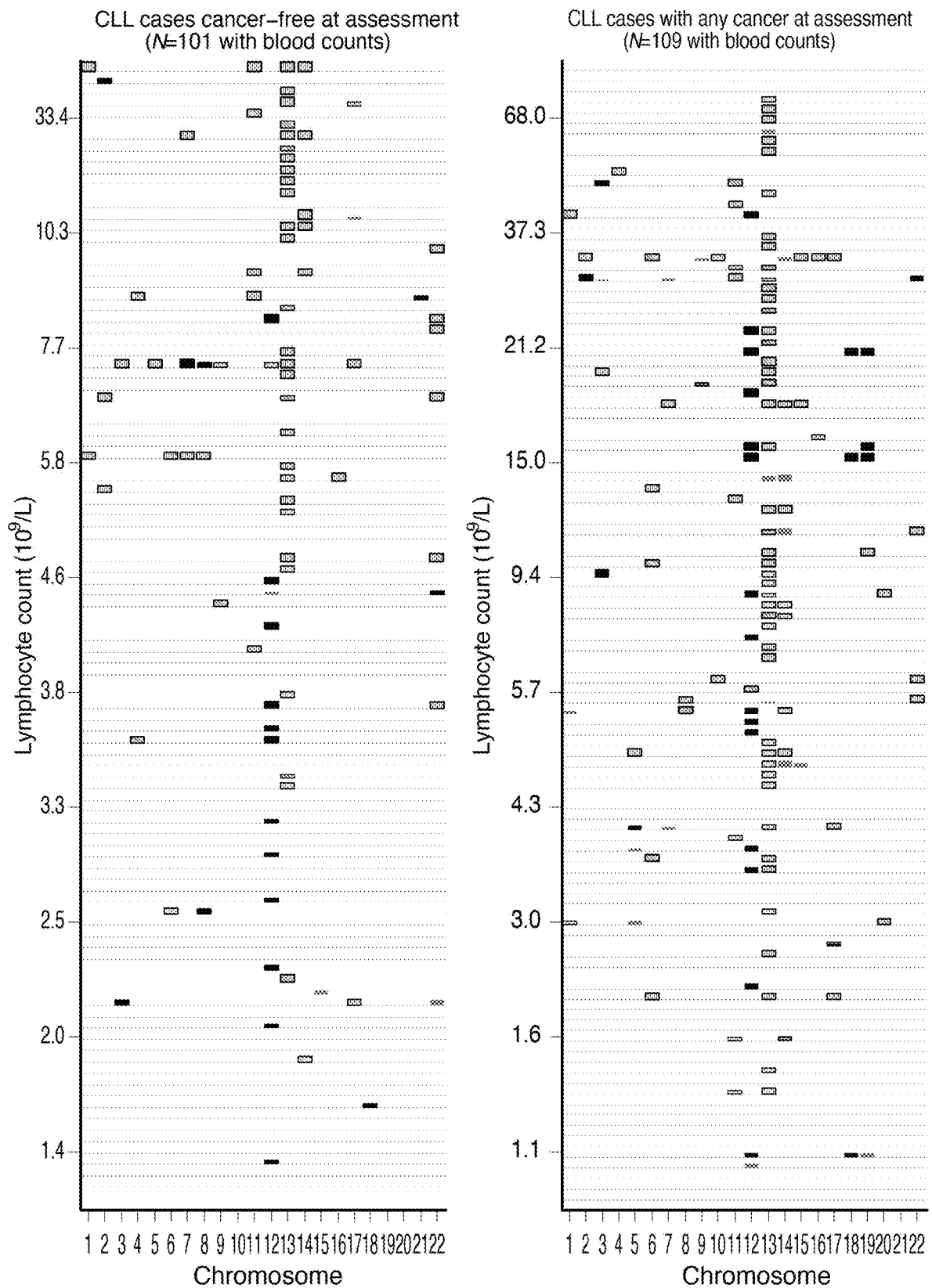
FIG. 50.—Somatic SVs detected in CLL cases sorted by lymphocyte count. Individuals are stratified by cancer status at DNA collection (no/any previous diagnosis), and SVs (loss=vertical lines, CNN-LOH=descending diagonal lines, gain=black, unknown=grey) are plotted per chromosome using colored rectangles (with height increasing with BAF deviation).

Based on the strength of association between aberrations commonly observed in CLL and incident CLL, Applicant reasoned that combining mosaic status for these events with other risk factors—age, sex, CLL genetic risk score (GRS) [48], and lymphocyte count—could improve prediction of incident CLL. A logistic model built from these predictors achieved high prediction accuracy (AUC=0.92) in 10-fold cross-validation, outperforming predictors built without information on mosaicism (FIG. 8B and FIG. 49). This result was robust to restricting the analysis to individuals with normal lymphocyte counts (1-3.5×109/L) at assessment (AUC=0.81; FIG. 8C). Early clones with trisomy 12, detectable at very low cell fractions, primarily drove this increase in prediction accuracy (FIG. 50). Individuals with incident CLL exhibited clonality up to 6 years before diagnosis, and clonal fraction was inversely related with time to malignancy (FIG. 8D). Applicant further observed that detectable mosaicism roughly doubled risk for all-cause.

Discussion

By using long-range phase information to detect subtle chromosomal imbalances in genotype data from 151,202 individuals, Applicant assembled an atlas of 8,342 somatic SVs—an order of magnitude more than previous analyses [1, 2, 7, 8]. Applicant used the statistical power afforded by these data to reveal the genomic distribution of mosaic SVs, identify many inherited drivers of clonal expansions, find likely mechanisms for these strong inherited influences, and investigate the effects of clonal expansions on health outcomes.

Clonal expansions result from mutation followed by selective proliferation [10], and the above results uncover diverse biological mechanisms driving this transformation. First, genomic modifications must occur. Our atlas of somatic SVs confirmed that mitotic recombination producing CNN-LOHs, missegregation producing chromosomal gains and losses, and replication errors producing interstitial deletions are the most common processes producing SVs [1, 2, 7, 8] while also highlighting breakage at the fragile site FRA10B as a specific source of mutation. Second, mutant cells harboring chromosomal aberrations must escape apoptosis and senescence. Applicant observed trans drivers of clonality in TP53, CHEK2, and TERT, corroborating recent results linking variation in cell cycle genes to mLOY [19]. Third, mutant cells must possess a proliferative advantage. Selective pressures are often clear for SVs that alter copy number (e.g., losses of tumor suppressor genes) [1, 2, 7, 8] but have been difficult to trace for CNN-LOHs aside from instances in which a CNN-LOH provides a second hit to a frequently mutated locus [49] or disrupts imprinting [50]. Here Applicant observed that CNN-LOHs can also achieve strong selective advantage by duplicating or removing inherited alleles.

The high penetrances (of up to 50%) for the inherited CNN-LOH risk variants challenge what is usually seen as a fundamental distinction between inherited alleles and (more-capricious) acquired mutations, because a large fraction of carriers of the inherited alleles subsequently acquire and then clonally amplify the mutations in question. The high penetrances imply that mitotic recombination is sufficiently common to predictably unleash latent, inherited opportunities for clonal selection of homozygous cells during the lifespan of an individual. Similarly, Applicant observed Mendelian inheritance patterns for 10q breakage at FRA10B despite this event involving an acquired (somatic) mutation (FIGS. 6A-6E).

Clonal expansions exhibit varying levels of proliferation and biological transformation and thus have a spectrum of effects on health [10]. Applicant found that many somatic SVs, including some of those driven by cis-acting genetic variation, had no discernible adverse effects. However, somatic SVs commonly seen in blood cancers strongly increased cancer risk and could potentially be used for early detection. As population-scale efforts to collect genotype data and health outcomes continue to expand-increasing both sample sizes and the power of population-based chromosomal phasing-Applicant anticipate ever-more-powerful analyses of clonal hematopoiesis and its clinical sequelae.

Methods

UK Biobank cohort and genotype intensity data. The UK Biobank is a very large prospective study of individuals aged 40-70 years at assessment [23]. Participants attended assessment centers between 2006-2010, where they contributed blood samples for genotyping and blood analysis and answered questionnaires about medical history and environmental exposures. In the years since assessment, health outcome data for these individuals (e.g., cancer diagnoses and deaths) have been accruing via UK national registries.

Applicant analyzed genetic data from the UK Biobank consisting of 152,729 samples typed on the Affymetrix UK BiLEVE and UK Biobank Axiom arrays with ~800K SNPs each and >95% over-lap. Applicant removed 480 individuals marked for exclusion from genomic analyses based on missingness and heterozygosity filters and 1 individual who had withdrawn consent, leaving 152,248 samples. Applicant restricted the variant set to biallelic variants with missingness≤10% and Applicant further excluded 111 variants found to have significantly different allele frequencies between the UK BiLEVE array and the UK Biobank array, leaving 725,664 variants on autosomes and the X chromosome. Finally, Applicant additionally excluded 118,139 variants for which fewer than 10 samples (or for chrX, fewer than 5 female samples) were called as homozygous for the minor allele; Applicant observed that genotype calls at these variants were susceptible to errors in which rare homozygotes were called as heterozygotes. Applicant phased the remaining 607,525 variants using Eagle2 [26] with —Kpbwt=40,000 and otherwise default parameters.

Applicant transformed genotype intensities to log 2 R ratio (LRR) and B-allele frequency (BAF) values [51] (which measure total and relative allelic intensities) after affine-normalization and GC wave-correction [52] in a manner similar to Jacobs et al. [1] (Supplementary Note). For each sample, Applicant then computed s.d. (BAF) among heterozygous sites within each autosome, and Applicant removed 320 samples with median s.d. (BAF)>0.11 indicating low genotype quality. Finally, Applicant removed an additional 725 samples with evidence of possible contamination [8] (based on apparent short interstitial CNN-LOH events in regions of long-range linkage disequilibrium; see Supplementary Note) and 1 sample without phenotype data, leaving 151,202 samples for analysis.

Detection of somatic SVs using long-range haplotype phase. Here Applicant outline the key ideas of our approach to somatic SV detection.

The core intuition is that Applicant wish to harness long-range phase information to search for local imbalances between maternal vs. paternal allelic fractions in a cell population (FIGS. 9A-9C, 10A-10C, and 11A-11C). The utility of haplotype phase for this purpose has previously been recognized [8, 53, 54], but previous approaches have needed to account for phase switch errors occurring roughly every megabase, a general challenge faced by haplotype-based analyses [55]. In UK Biobank, Applicant have phase information accurate at the scale of tens of megabases [24, 26], enabling a new modeling approach and further gains in detection sensitivity (FIG. 36).

Figure 51:
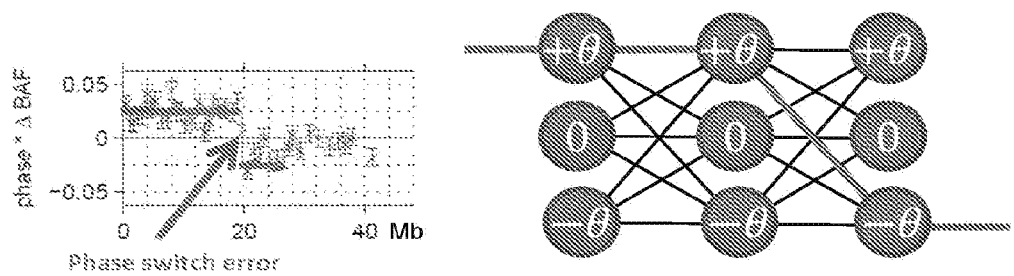
FIG. 51—Hidden Markov model for detecting somatic SVs. Somatic SVs, which alter the balance of maternal vs. paternal chromosome content in a cell population, cause deviations in allelic balance (|ΔBAF|) at heterozygous sites. In computationally phased genotyping intensity data, these deviations manifest as stretches of signed deviations with the same absolute value ($\theta$) but with sign flips at phase switch errors. A three-state Hidden Markov model with the single parameter $\theta$ captures this behavior and enables computation of a likelihood ratio test statistic.

The technique employs a three-state hidden Markov model (HMM) to capture SV-induced deviations in allelic balance ($|\Delta BAF|$) at heterozygous sites (FIG. 51). The model has a single parameter $\theta$ representing the expected absolute BAF deviation at germline hets within an SV. In computationally phased genotyping intensity data, multiplying phase calls with (signed) BAF deviations produces contiguous regions within the SV in which the expected phased BAF deviation is either $+\theta$ or $-\theta$ (with sign flips at phase switch errors); outside the SV, no BAF deviation is expected. The three states of our HMM encode these three possibilities, and emissions from the states represent noisy BAF measurements. Transitions between the $+\theta$ and $-\theta$ states represent switch errors, while transitions between $+\theta$ and the 0 state capture SV boundaries.

Modeling observed phased BAF deviations using a parameterized HMM has the key benefit of naturally producing a likelihood ratio test statistic for determining whether a chromosome contains a mosaic SV. Explicitly, for a given choice of $\theta$, Applicant can compute the total probability of the observed BAF data under the assumption that SV-induced BAF deviations have $E[|\Delta BAF|]=\theta$, using standard HMM dynamic programming computations to integrate over uncertainty in phase switches and SV boundaries. Taking the ratio of the maximum likelihood over all possible choices of $\theta$ to the likelihood for $\theta=0$ (i.e., no SV) yields a test statistic. If the HMM perfectly represented the data, this test statistic could be compared to an asymptotic distribution. However, Applicant know in practice that parameters within the HMM (e.g., transition probabilities) are imperfectly estimated, so Applicant instead calibrated our test statistic empirically: Applicant estimated its null distribution by computing test statistics on data with randomized phase, and Applicant used this empirical null to control FDR. Finally, for chromosomes passing the FDR threshold, Applicant called SV boundaries by sampling state paths from the HMM (using the maximum likelihood value of $\theta$).

The above detection procedure uses only BAF data and ignores LRR measurements by design (to be maximally robust to genotyping artifacts); however, after detecting events, Applicant incorporated LRR data to call detected SVs as loss, CNN-LOH, or gain. Mosaic SVs cause BAF (measuring relative allelic intensity) to deviate from 0.5 at heterozygous sites, and losses and gains cause LRR (measuring total intensity) to deviate from 0, with deviations increasing with clonal cell fraction; accordingly, Applicant observed that plotting detected events by LRR and BAF deviation produced three linear clusters (FIG. 5A and FIG. 27), consistent with previous work [1, 2, 8]. Applicant called copy number using chromosome-specific clusters to take advantage of the differing frequencies of event types on different chromosomes. Because the clusters converge as BAF deviation approaches zero, Applicant left copy number uncalled for detected SVs at low cell fraction with <95% confident copy number, comprising 29% of all detected SVs. Applicant then estimated clonal cell fractions as in ref. [1].

As a post-processing step to exclude possible constitutional duplications, Applicant filtered events of length >10 Mb with LRR>0.35 or LRR>0.2 and $|\Delta BAF|>0.16$, and Applicant filtered events of length <10 Mb with LRR>0.2 or LRR>0.1 and $|\Delta BAF|>0.1$ (FIG. 44). (Most constitutional duplications were already masked in a pre-processing step involving a separate HMM.

Enrichment of somatic SV types in blood lineages. Applicant analyzed 14 blood count indices (counts and percentages of lymphocytes, basophils, monocytes, neutrophils, red cells, and platelets, as well as distribution widths of red cells and platelets) from complete blood count data available for 97% of participants. Applicant restricted to individuals of self-reported European ancestry (96% of the cohort), leaving 140,250 individuals; Applicant then stratified by sex and quantile normalized each blood index after regressing out age, age squared, and smoking status.

To identify classes of somatic SVs linked to different blood cell types, Applicant first classified SVs based on chromosomal location and copy number. For each autosome, Applicant defined five disjoint categories of SVs that comprised the majority of detected events: loss on p-arm, loss on q-arm, CNN-LOH on p-arm, CNN-LOH on q-arm, and gain. Applicant subdivided loss and CNN-LOH events by arm but did not subdivide gain events because most gain events are whole-chromosome trisomies (FIG. 1). For chromosome X, Applicant replaced the two loss categories with a single whole-chromosome loss category. Altogether, this classification resulted in 114 SV types. Applicant restricted our blood cell enrichment analyses to 78 SV types with at least 10 occurrences, and Applicant further excluded the chr17 gain category (because nearly all of these events arise from i(17q) isochromosomes already counted as 17p− events; FIG. 20).

For each of the 77 remaining SV types, Applicant computed enrichment of SV detection among individuals with anomalous (top 1%) values of each normalized blood index using Fisher's exact test. Applicant reported significant enrichments passing an FDR threshold of 0.05 (FIG. 5F and Table 6).

Chromosome-wide association tests for cis associations with somatic SVs. To identify inherited variants influencing nearby somatic SVs, Applicant performed two types of association analyses. First, Applicant searched for variants that increased the probability of developing nearby somatic SVs. For each variant, Applicant performed a Fisher test for association between the variant and up to three variant-specific case-control phenotypes, defined by considering samples to be cases if they contained (i) loss, (ii)CNN-LOH, or (iii) gain events containing the variant or within 4 Mb (to allow for uncertainty in event boundaries). Applicant tested phenotypes with at least 25 cases. Applicant performed these tests on 51 million imputed variants with minor allele frequency (MAF)>$2 \times 10^{-5}$ (imputed by UK Biobank using a merge of the UK10K and 1000 Genomes Phase 3 reference panels [56]), excluding variants with non-European MAF greater than five times their European MAF, which tended to be poorly imputed. Applicant analyzed 120,664 individuals who remained after restricting to individuals of self-reported British or Irish ancestry, removing principal component outliers (>4 standard devi-ations), and imposing a related-ness cut off of 0.05 (using plinkrel-cutoff 0.05)[57].

Applicant also ran a second form of association analysis searching for variants for which somatic SVs tended to shift allelic balance (analogous to allele-specific expression). For a given class of SVs, for each variant, Applicant examined heterozygous SV carriers for which the SV overlapped the variant, and Applicant performed a binomial test to check whether the SV was more likely to delete or duplicate one allele versus the other. Applicant restricted the binomial test to individuals in which the variant was confidently phased relative to the SV (no disagreement in five random resamples; Supplementary Note).

Given that the two association tests described above are independent, Applicant applied a two-stage discovery and validation approach to identify genome-wide significant associations. Applicant used a P-value threshold of $10^{-8}$ for discovery in either test and checked for nominal P<0.05 significance for validation in the other test (reasoning that variants influencing somatic SVs would exhibit both types of associations). At all loci with P <$10^{-8}$ for either test, the most significant variant with P<$10^{-8}$ in one test validated in the other (Table 1). At identified loci, Applicant further searched for secondary independent associations reaching P<$10^{-6}$.

In a final analyses, Applicant refined somatic SV phenotypes to slightly increase power to map associations. For the loci associated with 1p, 9p, and 15q CNN-LOH, Applicant found that association strength improved by expanding case status to include all events reaching the telomere (because several detected telomeric events with uncertain copy number were probably CNN-LOH driven by the same germline variants). For the association signal at FRA10B, Applicant refined case status to only include terminal loss events extending from 10q25 to the telomere.

Identity-by-descent analysis at MPL and FRA10B. At loci for which Applicant found evidence of multiple causal rare variants, Applicant searched for long haplotypes shared identical-by-descent among SV carriers to further explore the possibility of additional or recurrent causal variants. Applicant called IBD tracts using GERMLINE with haplotype extension [58].

SFARI Simons Simplex Collection dataset. The Simons Simplex Collection (SSC) is a repository of genetic samples from autism simplex families collected by the Simons Foundation Autism Research Initiative (SFARI) [27]. Applicant analyzed 2,076 whole-genome sequences from the first phase of SSC sequencing (median coverage 37.8× [59]) to examine whether mosaic SVs Applicant detected contributed to genetic risk of autism. Approved researchers can obtain the SSC population dataset described in this study by applying at base.sfari.org.

Detection and calling of 70 kb deletion at 15q26.3. Applicant discovered the inherited 70 kb deletion associated with 15q CNN-LOH and loss by mapping the 15q26.3 association signal (specifically, the rs182643535 tag SNP) in WGS data (FIG. 7C and FIG. 37). Applicant then called this deletion in the UK Biobank SNP-array data using genotype intensities at 24 probes in the deleted region (FIG. 38).

Detection and imputation of VNTRs at FRA10B. For all SFARI samples with >10 reads at the FRA10B site, Applicant performed local assembly of the reads to attempt to generate a consensus VNTR sequence. Applicant identified four distinct sequences in 13 families (FIGS. 34 and 35). Applicant further examined individuals with high fractions of non-reference reads at FRA10B to find additional VNTR carriers. Applicant assembled a conservative list of 30 carriers with sufficient read evidence (requiring less evidence if another individual in the family was a carrier). Due to read dropout in some samples, it is possible these VNTR sequences are found in additional SFARI samples. Applicant imputed the VNTR sequences into UK Biobank using Minimac3 [60].

GWAS and heritability estimation for trans drivers of clonality. Applicant tested variants with MAF>0.1% for trans associations with six classes of SVs (any event, any loss, any CNN-LOH, any gain, any autosomal event, any autosomal loss) on 120,664 unrelated European-ancestry individuals (described above) using BOLT-LMM [61], including 10 principal components, age, and genotyping array as covariates. Applicant also tested association with female X loss using an expanded set of 3,462 likely X loss calls at an FDR of 0.1, restricting this analysis to 66,685 female individuals. In our targeted analysis of 86 variants implicated in previous GWAS, Applicant applied a Bonferroni significance threshold of $8.3 \times 10^{-5}$ based on 86 variants and 7 phenotypes. Applicant estimated SNP heritability of X loss using BOLT-REML [40], transforming estimates to the liability scale [62].

Analysis of X chromosome inactivation in GEUVADIS RNA-seq data. To test for possible mediation of preferential X haplotype loss by biased X chromosome inactivation (XCI), Applicant examined GEUVADIS RNA-seq data for evidence of biased XCI near the primary biased loss association at Xp11.1. Applicant identified three coding SNPs in FAAH2 within the pericentromeric linkage disequilibrium block containing the association signal. Applicant analyzed RNA-seq data for 61 European-ancestry individuals who were heterozygous for at least one SNP (60 of 61 were heterozygous for all three SNPs, and the remaining individual was heterozygous at two of the SNPs). Applicant used GATK [64] ASE Read Counter to identify allele-specific expression from RNA-seq BAM files. Most individuals displayed strong consistent allele-specific expression across the three SNPs, as expected for XCI in clonal lymphoblastoid cell lines [39]; however, Applicant observed no evidence of systematically biased XCI in favor of one allele or the other (Table 10).

UK Biobank cancer phenotypes. Applicant analyzed UK cancer registry data provided by UK Biobank for 23,901 individuals with one or more prevalent or incident cancer diagnoses. Cancer registry data included date of diagnosis and ICD-O-3 histology and behavior codes, which Applicant used to identify individuals with diagnoses of CLL, MPN, blood, and non-blood cancers [65, 66]. Because our focus was on prognostic power of somatic SVs for predicting diagnoses of incident cancers >1 year after DNA collection, Applicant excluded from analysis all individuals with cancers reported prior this time (either from cancer registry data or self-report of prevalent cancers). Applicant also restricted attention to the first diagnosis of cancer in each individual, and Applicant censored diagnoses after Sep. 30, 2014, as suggested by UK Biobank (resulting in a median follow-up time of 5.7 years, s.d. 0.8 years, range 4-9 years). Finally, Applicant restricted analyses to individuals who self-reported European ancestry. These exclusions reduced the total counts of incident cases to 78 CLL, 42 MPN, 441 blood, and 7,458 non-blood cancers, which Applicant analyzed with 119,330 controls.

Estimation of cancer risk conferred by clonal SVs. To identify classes of somatic SVs associated with incident cancer diagnoses, Applicant classified SVs based on chromosomal location and copy number into the 114 classes described above. Applicant then restricted attention to the 45 classes with at least 30 carriers. For each SV class, Applicant considered a sample to be a case if it contained only the SV or if the SV had highest cell fraction among all mosaic SVs detected in the sample (i.e., Applicant did not count carriers of subclonal events as cases). Applicant computed odds ratios and P-values for association between SV classes and incident cancers using Cochran-Mantel-Haenszel (CMH) tests to stratify by sex and by age (in six 5-year bins). Applicant used the CMH test to compute odds ratios (for incident cancer any time during follow-up) rather than using a Cox proportional hazards model to compute hazard ratios because both the SV phenotypes and the incident cancer phenotypes were rare, violating normal approximations underlying regression. Applicant reported significant associations passing an FDR threshold of 0.05 (FIG. 5A and Table 13).

Prediction of incident CLL. Applicant considered three nested logistic models for prediction of incident CLL. In the first model, a baseline, Applicant included only age and sex as explanatory variables.

In the second model, Applicant added log lymphocyte count and CLL genetic risk (computed using 14 high-confidence GWAS hits from ref. [48] that had both been previously published and reached $P<5\times10-8$); log lymphocyte count provided most of the improvement in accuracy. In the full model, Applicant added explanatory variables for 11q-, +12, 13q-, 13q CNN-LOH, 14q-, 22q-, and the total number of other autosomal events.

Applicant assessed the accuracy of each model on two benchmark sets of samples, one containing all samples (passing the exclusions above), and the other restricting to individuals with normal lymphocyte counts ($1-3.5\times10^9$/L) at assessment, i.e., exhibiting at most slight clonality. (In the second benchmark set, Applicant restricted the mosaic events in the full model to +12, 13q-, and 13q CNN-LOH.) Applicant performed 10-fold stratified cross-validation to compare model performance. Applicant assessed prediction accuracy by merging results from all cross-validation folds and computing area under the receiver operating characteristic curve (AUC) (FIGS. 8B and 8C), and Applicant also measured precision-recall performance (FIG. 41).

Estimation of mortality risk conferred by clonal SVs. Applicant analyzed UK death registry data provided by UK Biobank for 4,619 individuals reported to have died since assessment. Applicant censored deaths after Dec. 31, 2015, as suggested by UK Biobank, leaving 4,518 reported deaths over a median follow-up time of 6.9 years (range 5-10 years). Applicant examined the relationship be-tween somatic SVs and mortality, aiming to extend previous observations that mosaic point mutations increase mortality risk [3, 4, 11]. For this analysis, Applicant were insufficiently powered to stratify SVs by chromosome due to the weaker effects of SVs on mortality risk and the relatively small number of deaths reported during follow-up. Applicant therefore stratified SVs only by copy number and computed the hazard ratio conferred by each event class using a Cox proportional hazards model. Applicant restricted these analyses to individuals who self-reported European ancestry, and Applicant adjusted for age and sex as well as smoking status, which was previously associated with clonal hematopoiesis [3, 11, 21] and associates with mosaicism in UK Biobank (P=0.00017). Applicant ob-served that all classes of events conferred increased mortality among individuals with or without previous cancer diagnoses, with losses conferring the highest risk and CNN-LOHs conferring the lowest (FIG. 8D and Table 14).

Applicant found the approach that described herein to be quite robust, with the overall genomic distribution of detected events broadly consistent with previous work [1, 2, 7, 8]. However, in the initial analysis, Applicant did detect several hundred apparent short interstitial CNN-LOH events indicative of technical artifacts (given that CNN-LOHs are generally produced by mitotic recombination and stretch to a telomere). On inspection, Applicant discovered that the overwhelming majority of these artefactual events occurred at five specific regions of the genome: chr3: ~45 Mb (11 events), chr6: ~30 Mb (709 events), chr8: ~45 Mb (12 events), chr10: ~80 Mb (40 events), chr17: ~40 Mb (40 events). Applicant also noticed that multiple such detections often occurred in the same sample; the union of all carriers contained 717 samples, nearly all of which carried the chr6 artifact at HLA (which we did not mask from this initial analysis). The chr3, chr6, and chr8 regions have all been previously noted to harbor long-range LD [70], which suggested sample contamination [8] as the likely culprit: if a sample were contaminated with cells from another individual, then in regions of long-range LD (i.e., low haplotype diversity), allelic balance could shift in favor of one of the original sample's parental haplotypes (whichever one was a closer match to the foreign DNA). To be safe, Applicant therefore excluded all 717 of these samples from the analysis, and Applicant further excluded 6 individuals with three or more interstitial CNN-LOH calls and 2 individuals with three or more calls with high implied switch error rates, for a total of 725 exclusions.

Independent of the above issue, Applicant also observed a rarer technical artifact in which short interstitial CNN-LOH calls were made in runs of homozygosity (ROH) in which a small fraction of sites had been incorrectly called as hets and subsequently phased on the same haplotype, resulting in very strong phase-aligned BAF deviations. These calls were easy to filter; Applicant used a criterion of low heterozygosity (<⅓ the expected heterozygosity in the region) and LRR>−0.1 (guaranteeing that the region could not possibly be hemizygous due to a loss event). After applying these filters, Applicant were left with only 32 interstitial CNN-LOH calls among all samples with no obvious artifacts upon manual review.

Analysis of Focal Deletions

Figure 12:
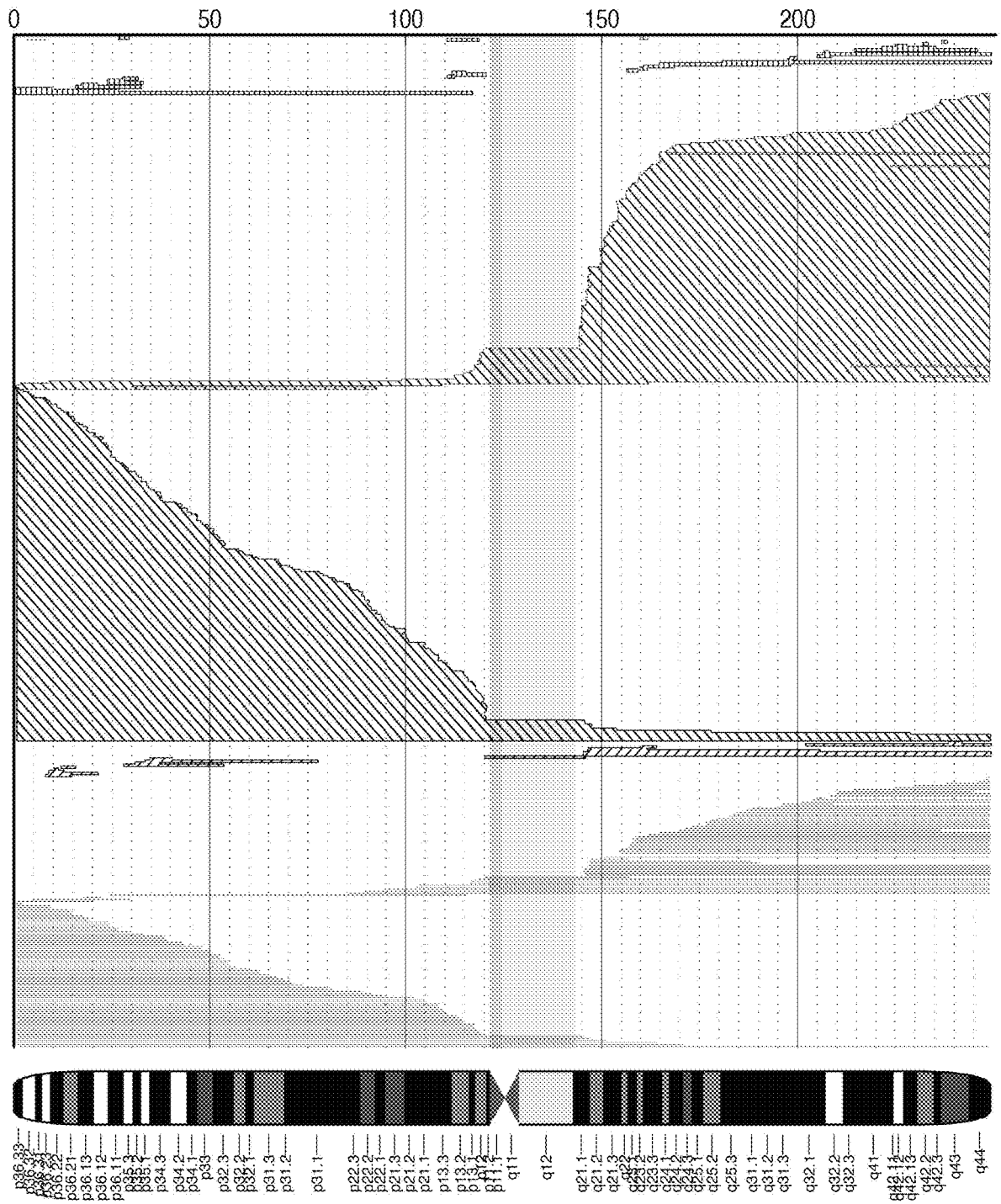
Figure 13:
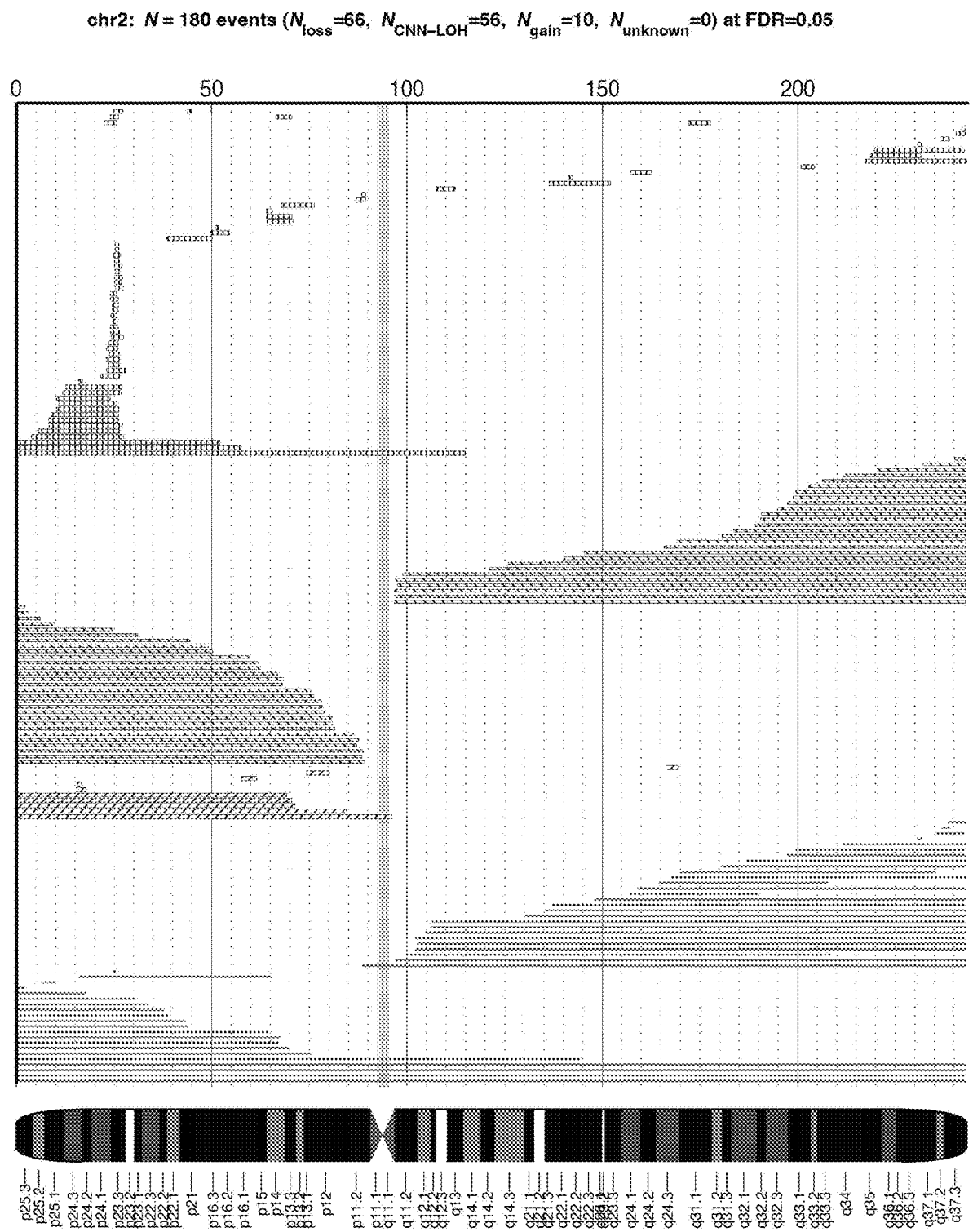
Figure 14:
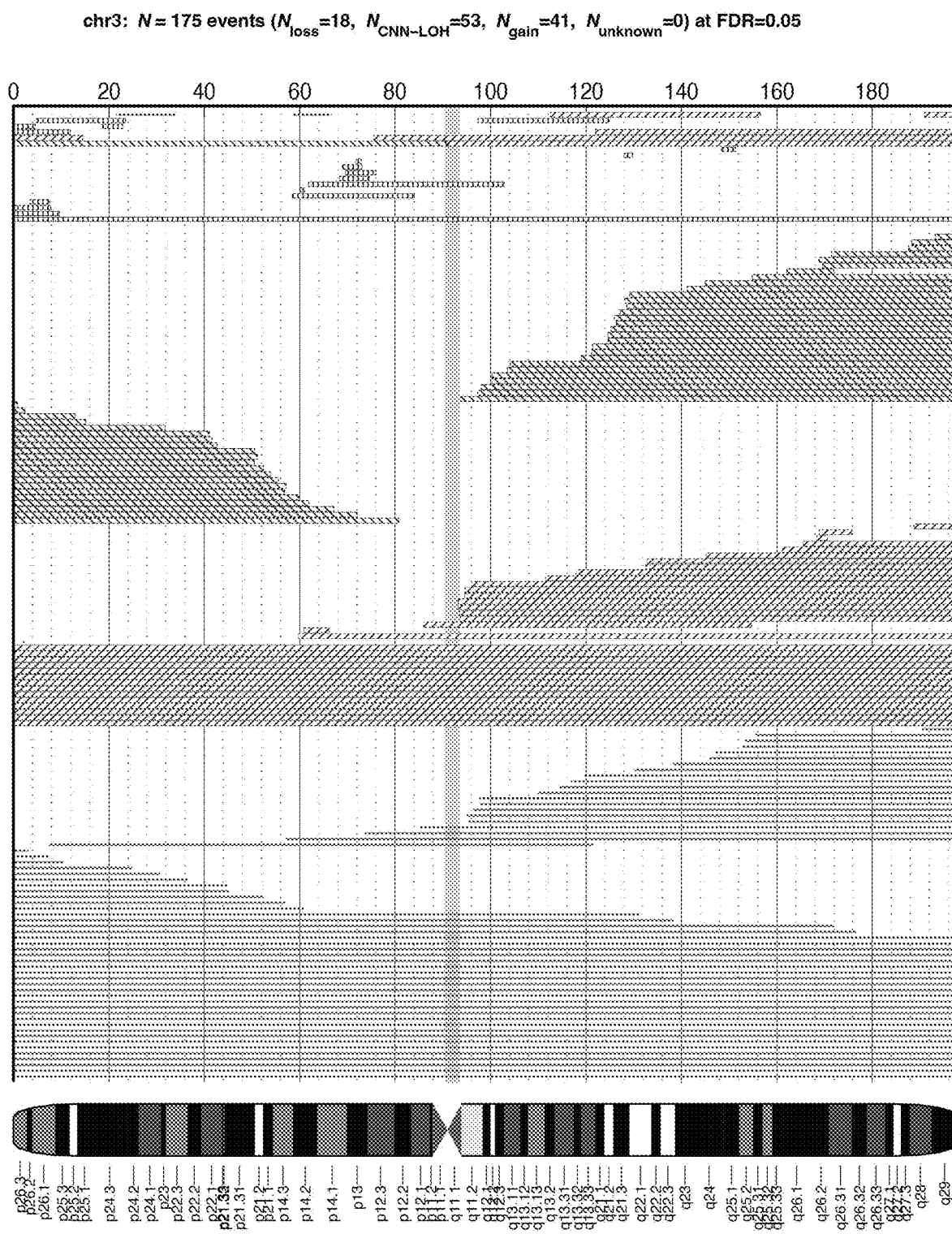
Figure 15:
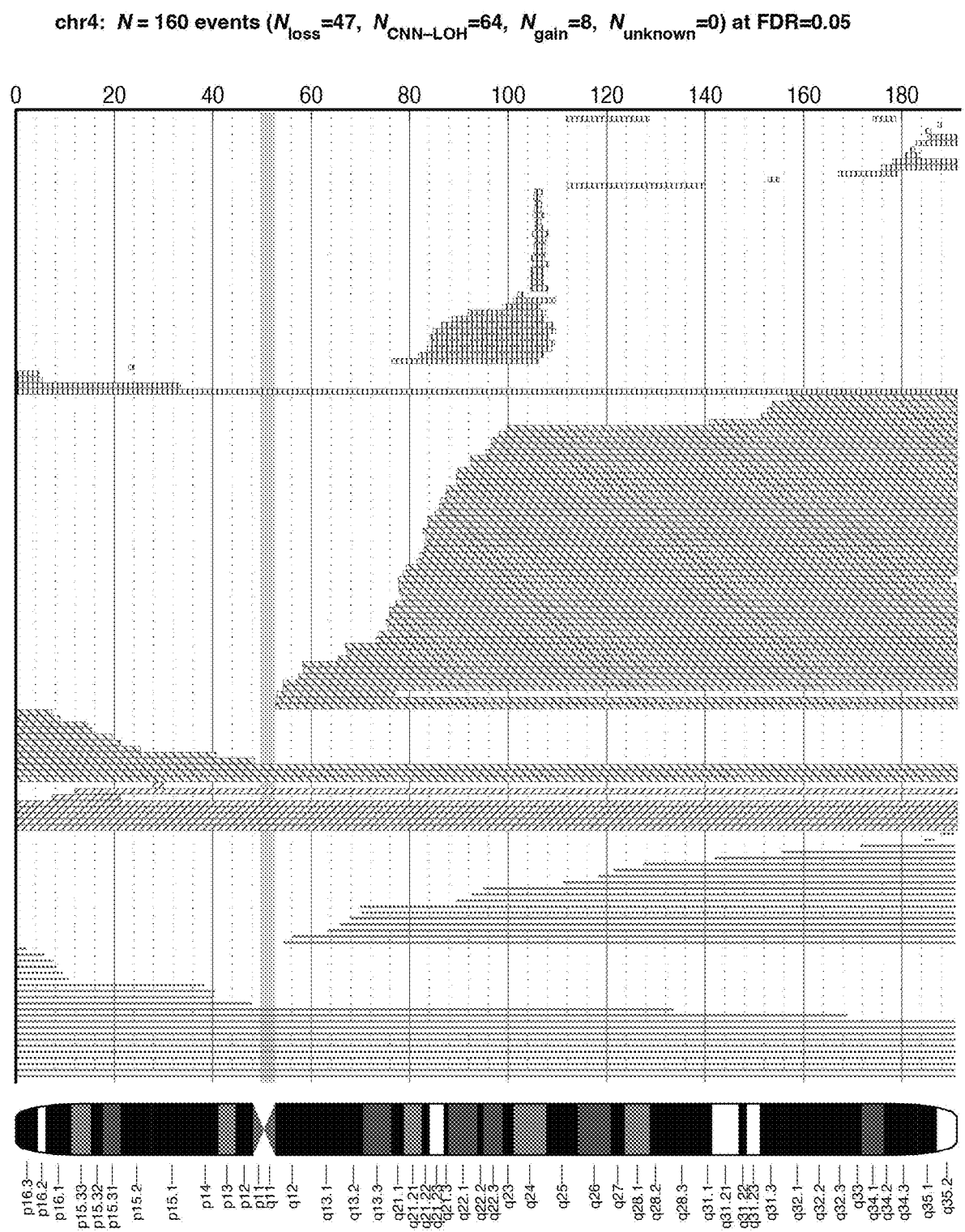
Figure 16:
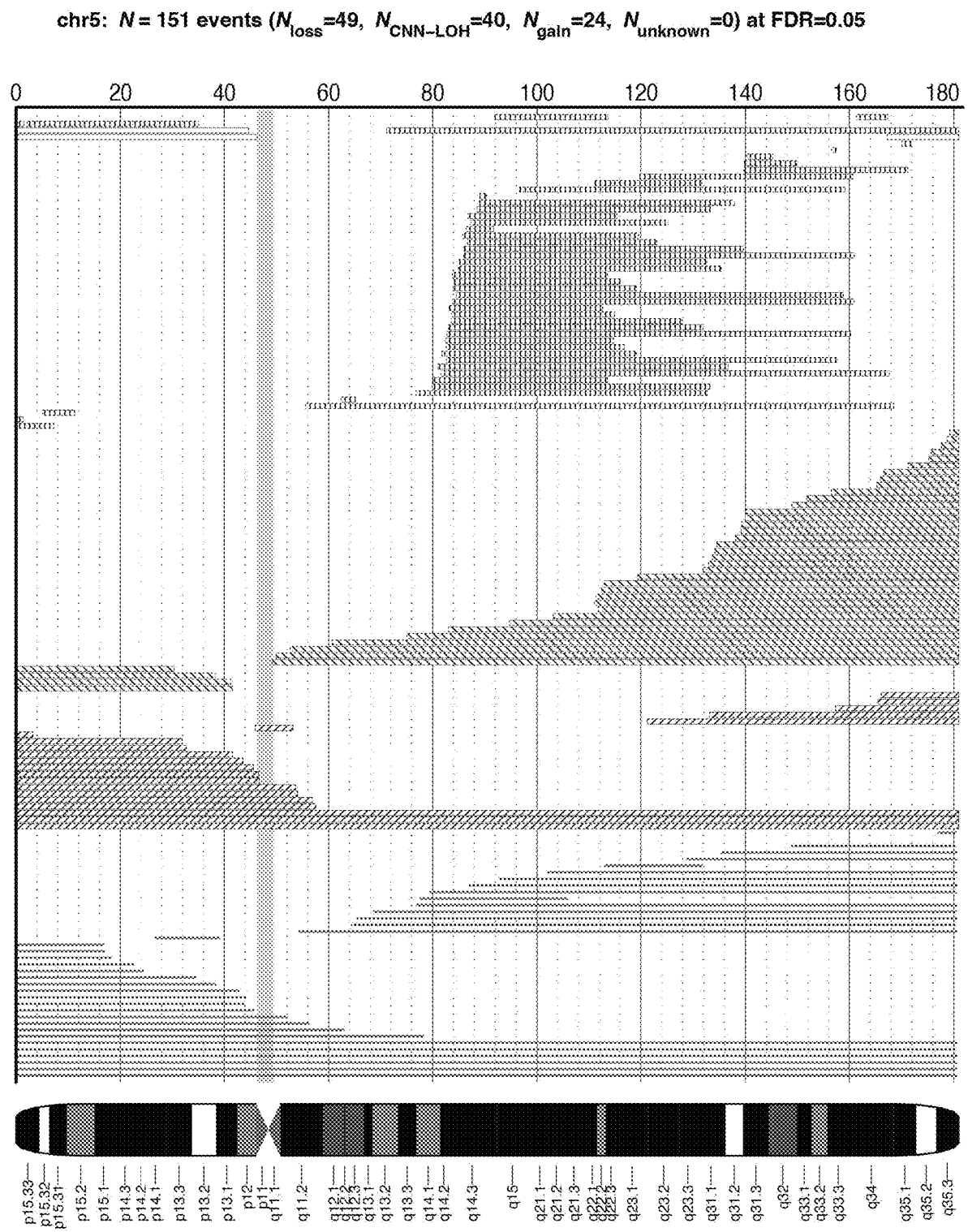
Figure 17:
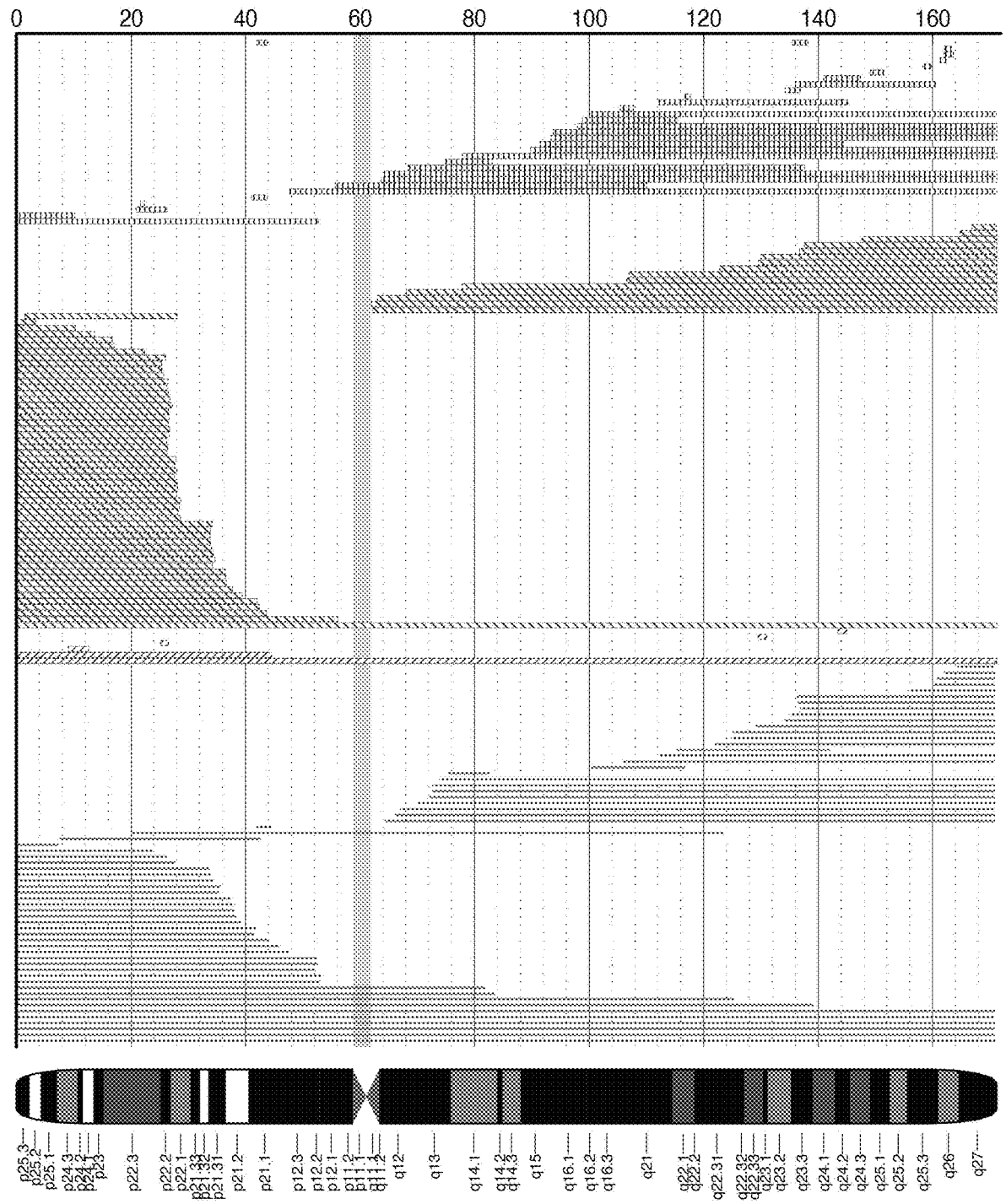
Figure 18:
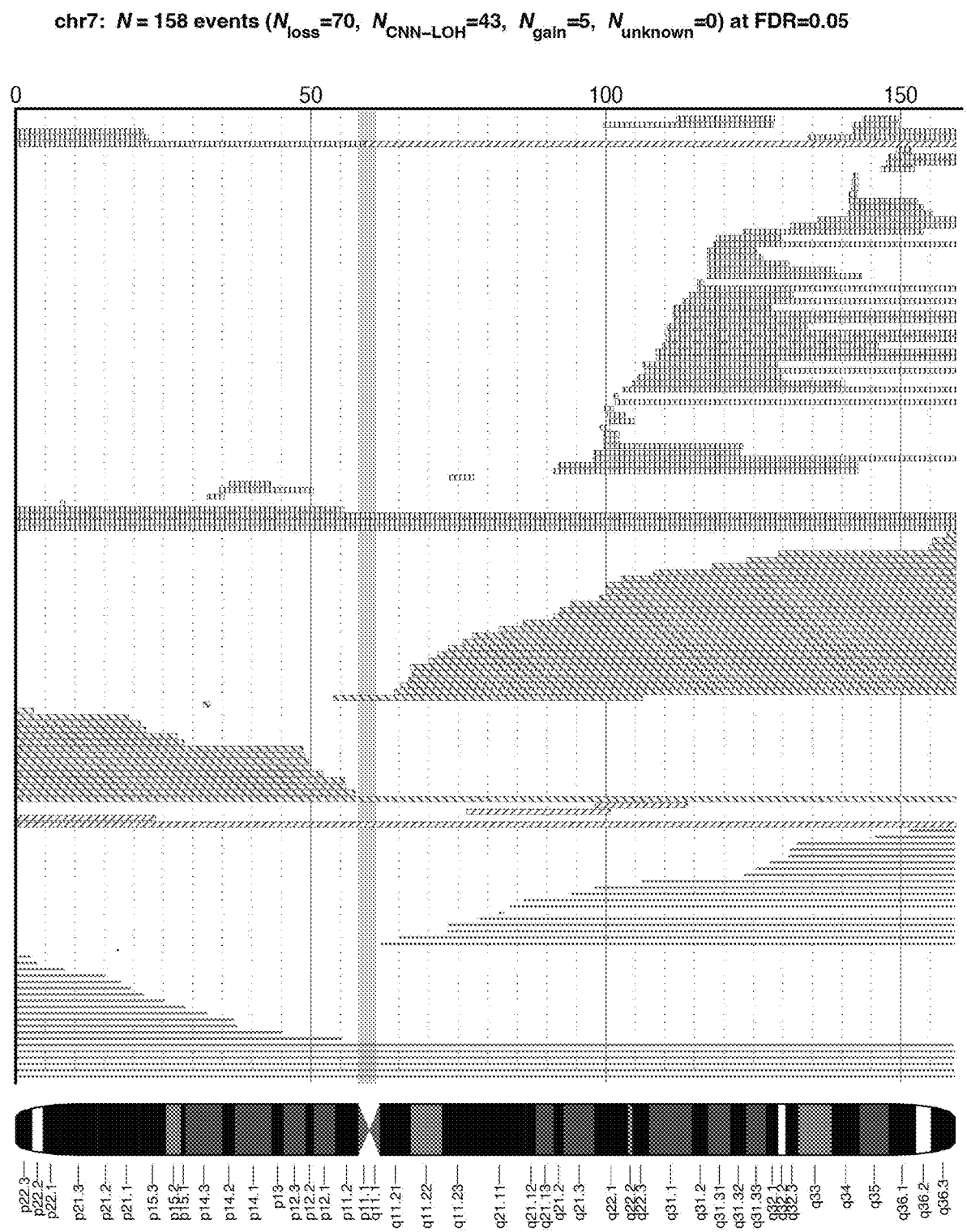
FIGS. 18 and 38).
Figure 19:
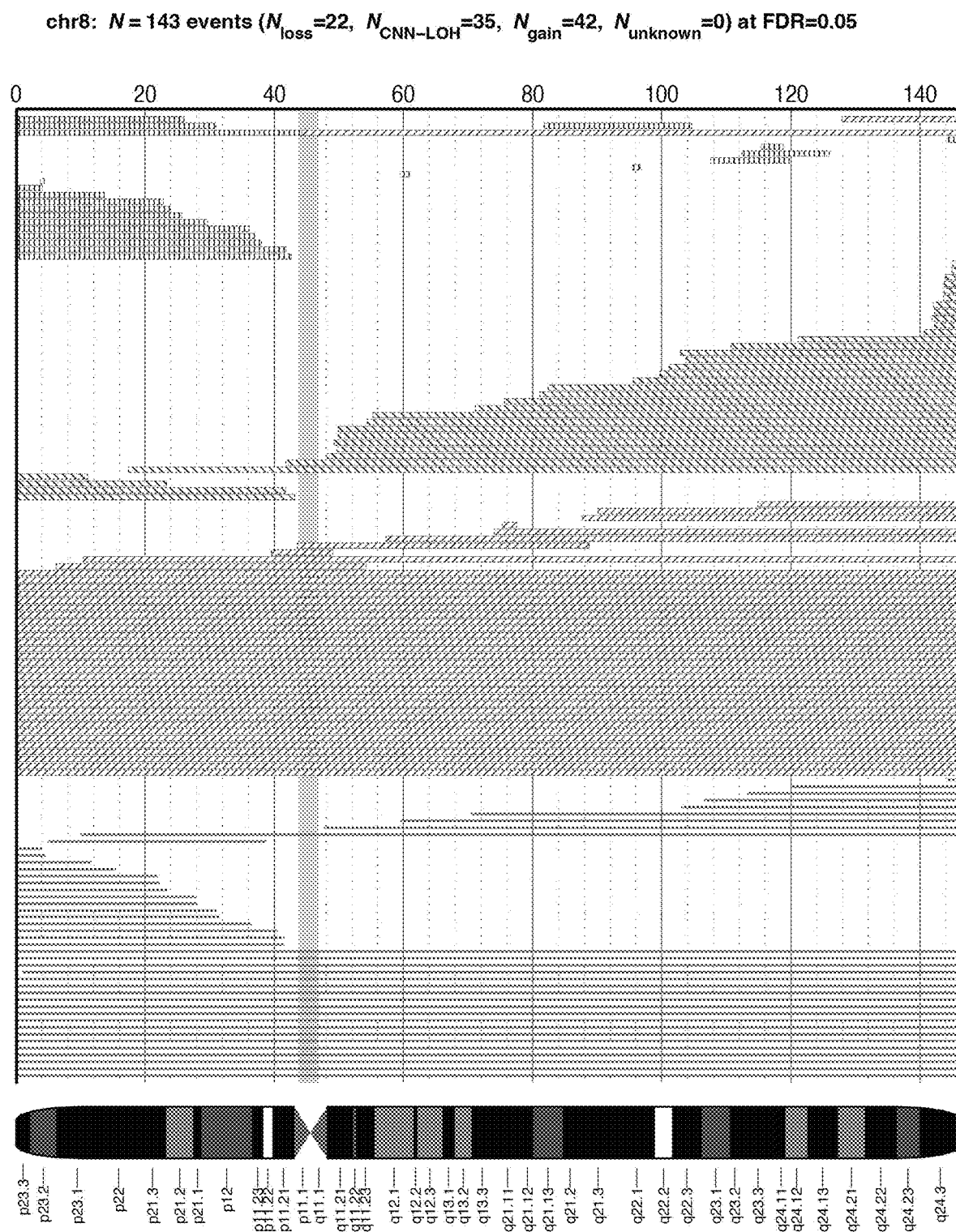
Figure 25:
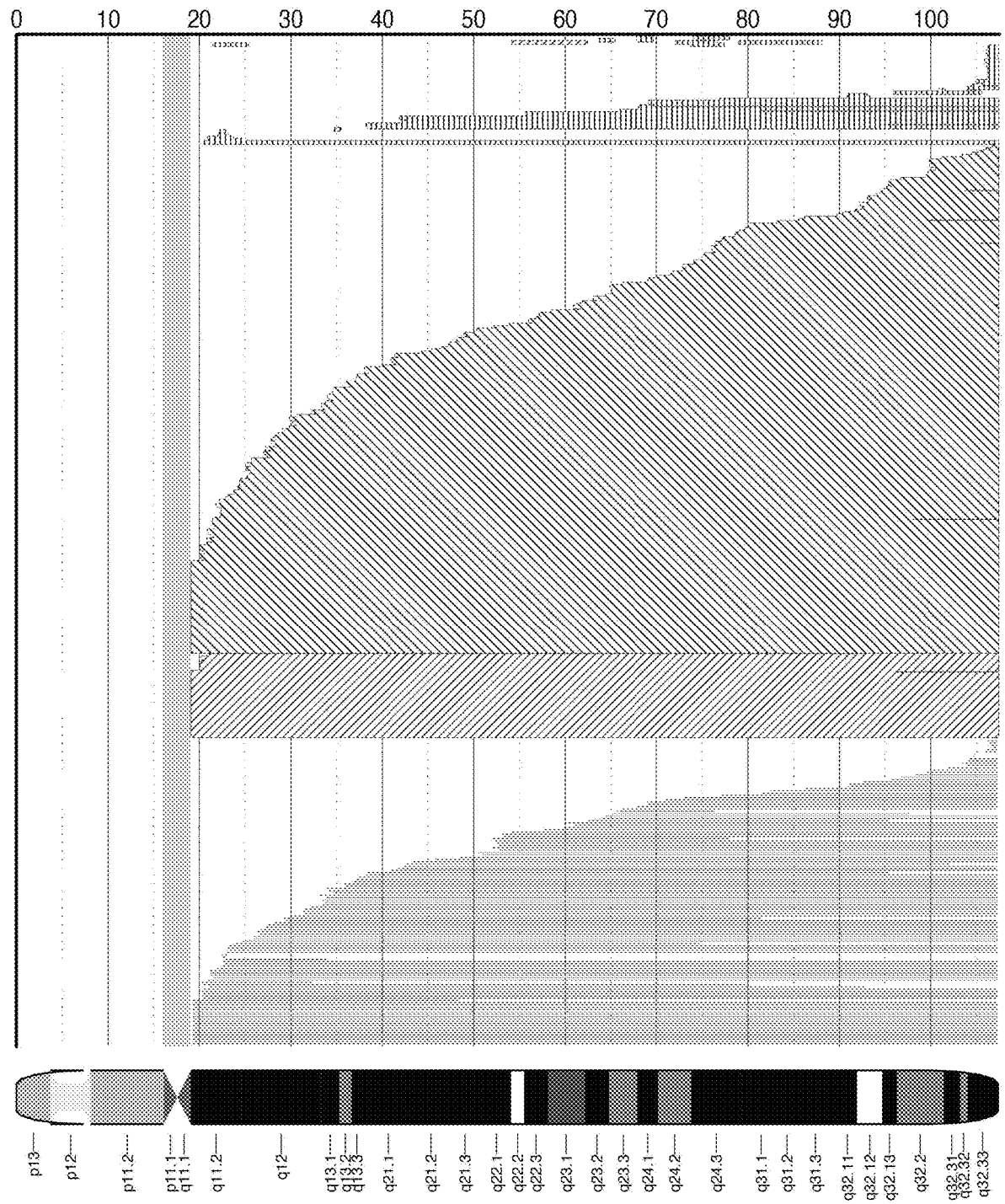
Figure 26:
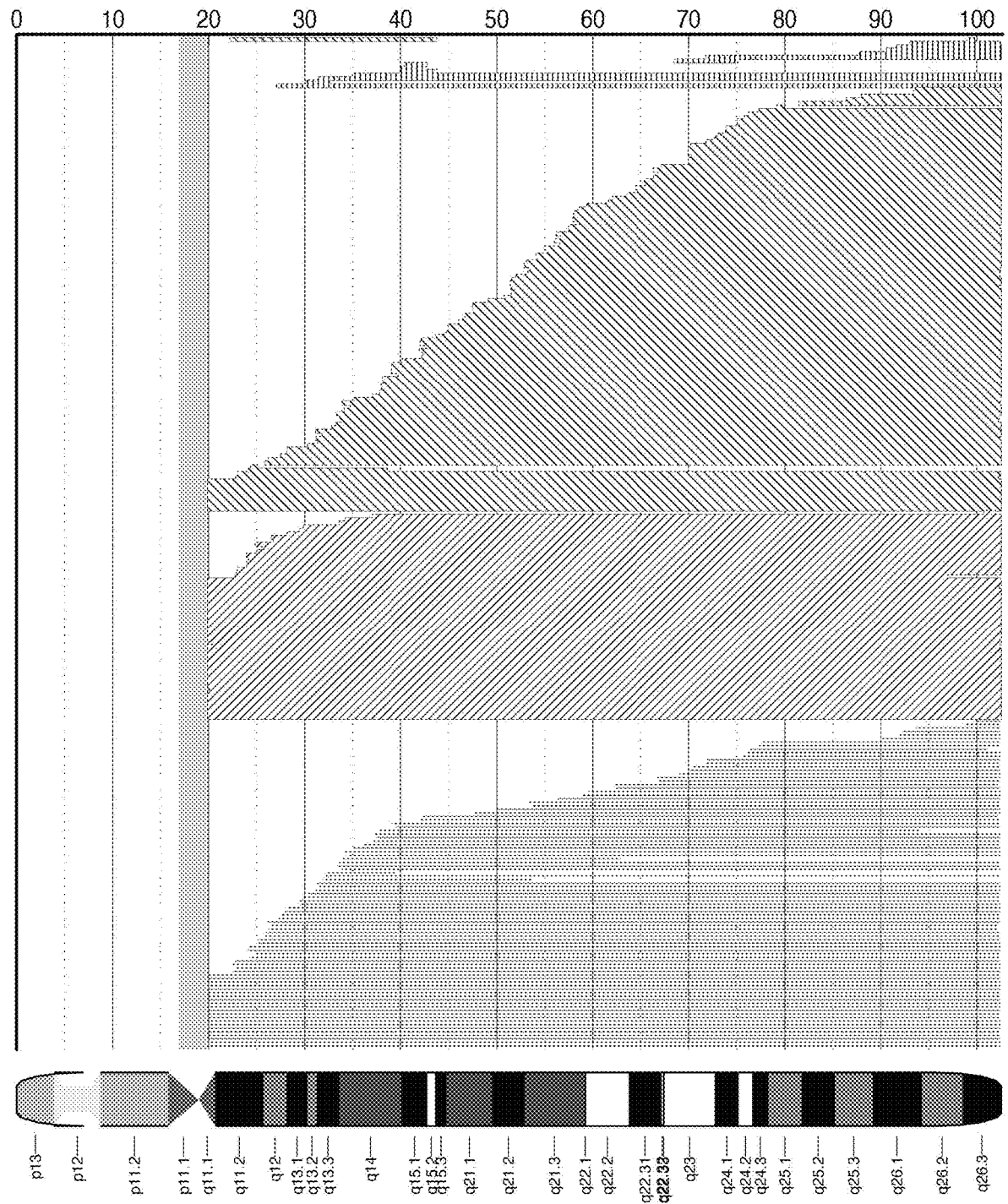

The genomic distribution of somatic SVs is highly non-random, and commonly deleted regions (CDRs)<1 Mb in length are of particular interest as they may indicate haplo insufficient genes for which loss of one copy leads to excessive cell proliferation [2]. Excluding V(D)J recombination regions in 14q11.2, 14q32.33, and 22q11.22, the three most commonly deleted regions targeted DNMT3A on 2p, TET2 on 4q, and DLEU2/DLEU7 on 13q, matching observations in previous studies [2, 8]; Applicant further observed that large majorities of CNN-LOH events on these chromosome arms included these genes, suggesting convergent patterns of selection (FIG. 4 and FIG. 38). (Applicant observed a similar pattern with longer deletions and CNN-LOH events spanning ATM on 11q.) Applicant also observed CDRs at three genes not previously noted in population studies of somatic SVs but commonly mutated in cancers: E716 on 12p (mutated in hematological malignancies), NF/on 17q (deleted in neurofibromatosis type 1), and CHEK2 on 22q (involved in the DNA damage response and mutated in many cancers) (FIGS. 15, 20, and 25). Additionally, Applicant observed two new CDRs for which literature search implicated putative target genes: RPA2, which is one of six genes in a 300 kb region of 1p36.11-1p35.3 contained in six deletions and is involved in DNA damage response [71], and RYBP, which is the only gene in a 620 kb region of 3p13 contained in seven deletions and has been reported to be a tumor suppressor gene [72] (FIGS. 12 and 14).

To detect CDRs, Applicant needed to identify short genomic regions covered by many loss events; however, Applicant also needed to require that the losses be somewhat specific to a focal region (e.g., a short deletion should carry much more weight than a deletion of an entire arm). To capture this intuition, Applicant gave each loss event a weight equal to 6 Mb/[event length], with a maximum weight of 1 (for events shorter than 6 Mb). Applicant then examined all regions with a total weight exceeding 4 and checked whether the pileup of losses at these regions was sufficiently focal to be deemed a CDR.

Analysis of Biased X Chromosome Loss

In addition to performing standard GWAS on mosaic status, Applicant also searched the detected SVs for a different type of association: shift in allelic balance in favor of one allele versus the other in heterozygous individuals (analogous to allele-specific expression). Applicant were well-powered to run this analysis on female chromosome X owing to the high frequency of X loss (FIG. 4), and to further increase association power, Applicant performed X loss association analyses using an expanded set of 3,462 likely X loss calls at an FDR of 0.1. Applicant observed a striking association ($P=6.6\times10^{-27}$, 1.9:1 bias in the lost haplotype) at Xp11.1 near DXZ1 and a weaker association ($P=1.0\times10^{-9}$, 1.5:1 bias in the lost haplotype) at Xq23 near DXZ4 (Table 1, FIG. 48, and Table 10). At both loci, Applicant also observed nominal associations ($P=1\times10^{-3}$) between allele count and X loss (Table 1). The Xp11.1 and Xq23 bias signals appear to be independent (2.7:1 bias when heterozygous risk haplotypes are in phase and 1.2:1 bias when out of phase). Applicant initially suspected that these observations could be explained by biased X chromosome inactivation (XCI) [39], especially given the role of Xp11.1 and Xp23 in XCI [73], but Applicant did not find any evidence of biased XCI in GEUVADIS RNA-seq data [63] (Table 11). Interestingly, Applicant observed weak evidence that the lead SNP rs2942875 at Xp11.1 appeared to have similar effects on gain of X (Table 10), suggesting a mechanism involving X missegregation, but larger sample sizes will be required to investigate this possibility; Applicant only called 29 likely X gains at FDR 0.1.

TABLE 1

Novel genome-wide significant associations of somatic SVs with inherited variants.

| SV type | Locus | Variant | Location | Alleles[a] | RAF[b] | GWAS | | Risk allelic shift in hets | | |
|---|---|---|---|---|---|---|---|---|---|---|
| | | | | | | P | OR (95% CI) | $N_{inc}$[c] | $N_{dac}$ | P |
| cis associations | | | | | | | | | | |
| 10q loss | FRA10B | rs118137427[d] | 10q25.2 | A/G | 0.05 | $6.1 \times 10^{-42}$ | 18 (12-26) | 0 | 43 | $2.3 \times 10^{-13}$ |
| 1p CNN-LOH | MPL | rs144279563 | 1p34.1 | C/T | 0.0005 | $6.2 \times 10^{-16}$ | 53 (28-99) | 0 | 9 | $3.9 \times 10^{-3}$ |
| | | rs182971382 | 1p34.1 | A/G | 0.0003 | $3.0 \times 10^{-11}$ | 63 (29-139) | 0 | 4 | $1.3 \times 10^{-1}$ |
| | | rs369156948[e] | 1p34.2 | C/T | 0.0001 | $7.3 \times 10^{-8}$ | 103 (35-300) | 0 | 3 | $2.5 \times 10^{-1}$ |
| 11q CNN-LOH | ATM | rs532198118 | 11q22.3 | A/G | 0.0007 | $7.4 \times 10^{-9}$ | 41 (18-94) | 6 | 0 | $3.1 \times 10^{-2}$ |
| 15q CNN-LOH and loss | TM2D3, TARSL2 | 70 kb deletion[f] | 15q26.3 | CN = 1/0 | 0.0003 | $1.3 \times 10^{-86}$ | 698 (442-1102) | 39 | 2 | $7.8 \times 10^{-10}$ |
| chrX loss | DXZ1 | rs2942875 | Xp11.1 | T/C | 0.55 | $9.7 \times 10^{-4}$ | 1.09 (1.04-1.15) | 423 | 796 | $6.6 \times 10^{-27}$ |
| | DXZ4 | rs11091036 | Xq23 | C/G | 0.73 | $1.1 \times 10^{-3}$ | 1.10 (1.04-1.17) | 369 | 555 | $1.0 \times 10^{-9}$ |
| trans associations | | | | | | | | | | |
| chrX loss | SP140L | rs725201 | 2q37.1 | G/T | 0.56 | $9.2 \times 10^{-10}$ | 1.17 (1.12-1.24) | | | |
| | HLA | rs141806003 | 6p21.33 | C/CAAAG | 0.34 | $6.1 \times 10^{-10}$ | 1.18 (1.12-1.25) | | | |

Results of two independent association tests are reported:

(i) a Fisher test treating individuals with a given SV type as cases; and (ii) (for cis associations) a binomial test for biased allelic imbalance in heterozygous cases (Methods). Loci with $P < 1 \times 10^{-8}$ in either test are reported; each cis association detected by one test reaches nominal (P <0.05) significance in the other test, providing validation. At significant loci, the lead associated variant as well as additional independent associations reaching $P < 1 \times 10^{-6}$ are reported.

[a]Risk lowering/risk increasing allele.

[b]Risk allele frequency (in UK Biobank European-ancestry individuals).

[c]Number of mosaic individuals heterozygous for the variant in which the somatic event shifted the allelic balance in favor of the risk allele (by duplication of its chromosomal segment and/or loss of the homologous segment).

[d]rs118137427 tags expanded repeats at FRAIOB (FIG. 3).

[e]rs369156948 is a nonsense mutation in MPL.

[f]This deletion spans chr15:102.15-102.22 Mb (hg19) and is tagged by rs182643535.

TABLE 2

Number of somatic SVs detected per chromosome

| Chromosome | $N_{loss}$ | $N_{CNN-LOH}$ | $N_{gain}$ | $N_{unknown}$ | $N_{total}$ |
|---|---|---|---|---|---|
| chr1 | 29 | 318 | 17 | 134 | 498 |
| chr2 | 66 | 56 | 10 | 48 | 180 |
| chr3 | 18 | 53 | 41 | 63 | 175 |
| chr4 | 47 | 64 | 8 | 41 | 160 |
| chr5 | 49 | 40 | 24 | 38 | 151 |
| chr6 | 32 | 68 | 6 | 64 | 170 |
| chr7 | 70 | 43 | 5 | 40 | 158 |
| chr8 | 22 | 35 | 42 | 44 | 143 |
| chr9 | 19 | 210 | 38 | 78 | 345 |
| chr10 | 70 | 29 | 5 | 31 | 135 |
| chr11 | 98 | 257 | 1 | 105 | 461 |
| chr12 | 28 | 67 | 156 | 95 | 346 |
| chr13 | 177 | 111 | 0 | 73 | 361 |
| chr14 | 51 /← | 223 | 38 | 135 | 447 |
| chr15 | 14 | 121 | 59 | 93 | 287 |
| chr16 | 43 | 142 | 2 | 53 | 240 |
| chr17 | 66 | 112 | 37 | 89 | 304 |
| chr18 | 14 | 20 | 57 | 40 | 131 |
| chr19 | 6 | 90 | 17 | 75 | 188 |
| chr20 | 140 | 55 | 3 | 29 | 227 |
| chr21 | 20 | 35 | 31 | 67 | 153 |
| chr22 | 39 /← | 88 | 62 | 113 | 302 |
| All autosomes | 1118 | 2237 | 659 | 1548 | 5562 |
| Female chrX | 1862 | 28 | 24 | 866 | 2780 |

/← Deletions on chr14 and chr22 include V(D)J recombination events (25 events on chr14 and 25 events on chr22).

TABLE 3

Distribution of the number of detected somatic autosomal SVs per individual.

| Somatic SV count | Frequency |
|---|---|
| 0 | 146313 |
| 1 | 4448 |
| 2 | 295 |
| 3 | 103 |
| 4 | 27 |
| 5 | 7 |
| 6 | 4 |
| 7 | 0 |
| 8 | 2 |
| 9 | 1 |
| 10 | 0 |
| 11 | 1 |
| 12 | 1 |

Most individuals with several detected somatic SVs have prevalent or incident cancers.

TABLE 4

Co-occurrence enrichment among somatic SVs

| SV1 | SV2 | P | OR (95% CI) |
|---|---|---|---|
| 3+ | 12+ | $3.1 \times 10^{-10}$ | 170 (65-144) |
| 3p− | 13q− | $1.4 \times 10^{-7}$ | 410 (105-1598) |
| 3+ | 13q− | $7.1 \times 10^{-8}$ | 120 (42-344) |
| 3+ | 18+ | $2.7 \times 10^{-18}$ | 829 (345-1991) |
| 4+ | 18+ | $1.3 \times 10^{-9}$ | 2361 (515-10832) |
| 8+ | 9+ | $1.1 \times 10^{-7}$ | 381 (112-1298) |
| 12+ | 13q− | $1.5 \times 10^{-8}$ | 41 (18-94) |
| 12+ | 18+ | $1.1 \times 10^{-33}$ | 473 (253-884) |
| 12+ | 19+ | $8.9 \times 10^{-34}$ | 3331 (1061-10457) |
| 12+ | 22q− | $4.5 \times 10^{-8}$ | 135 (47-388) |
| 13q− | 13q= | $4.1 \times 10^{-67}$ | 208 (137-313) |
| 13q− | 14q− | $3.7 \times 10^{-19}$ | 288 (135-616) |
| 13q= | 14q− | $3.2 \times 10^{-6}$ | 120 (36-396) |
| 13q− | 22q− | $6.3 \times 10^{-8}$ | 124 (43-356) |
| 13q= | 22q− | $2.1 \times 10^{-6}$ | 139 (42-160) |
| 13q− | X+ | $8.8 \times 10^{-10}$ | 403 (130-1255) |
| 17p− | 21q− | $2.7 \times 10^{-12}$ | 1919 (565-6522) |
| 18+ | 19+ | $3.7 \times 10^{-21}$ | 2671 (953-7489) |

We report pairs of somatic SV types (grouped by chromosome arm and copy number) with significant co-occurrence ($P < 8 \times 10^{-6}$ Bonferroni threshold and at least three individuals carrying both events). (We subdivided loss and CNN-LOH events by p-arm vs. q-arm, but we did not subdivide gain events by arm because most gain events are whole-chromosome trisomies; e.g., "3+" combines all gains-partial or complete-on chromosome 3.) We excluded individuals with >3 detected SVs in our calculations of co-occurrence enrichment to prevent individuals with large numbers of SVs (typically cancer cases) from dominating the results. Co-occurrence of 13− and 13= events (i.e., 13q14 deletion and 13q CNN-LOH, a frequent combination in chronic lymphocytic leukemia) was computed using a slightly different procedure than the rest of the table because these events affect both homologous copies of chr13, creating a special case not considered by our detection algorithm (which calls only 13q CNN-LOH in this circumstance). Specifically, we called 13q14 deletions based on mean total intensity (LRR) in 13q14 (50.6-51.6 Mb); we then computed co-occurrence with 13q CNN-LOH events.

TABLE 5

Fraction of individuals with detected somatic SVs as a function of age.

| Age range | % with autosomal event | % of females with chrX event |
|---|---|---|
| <45 | 1.7% (0.1%) | 0.9% (0.1%) |
| 45-50 | 2.0% (0.1%) | 1.1% (0.1%) |
| 50-55 | 2.3% (0.1%) | 1.7% (0.1%) |
| 55-60 | 3.0% (0.1%) | 3.0% (0.1%) |
| 60-65 | 4.0% (0.1%) | 4.7% (0.2%) |
| >65 | 4.9% (0.1%) | 7.2% (0.2%) |

This table provides numerical data plotted in FIG. 5D.

TABLE 6

Age and sex distribution of individuals with detected somatic SVs on each chromosome

| | Loss events | | | | CNN-LOH events | | | | Gain events | |
|---|---|---|---|---|---|---|---|---|---|---|
| | p-arm | | q-arm | | p-arm | | q-arm | | | |
| chr | Mean age | Frac. male | Mean age | Frac. male | Mean age | Frac. male | Mean age | Frac. male | Mean age | Frac. male |
| 1 | 61.0 (1.9) | 0.54 (0.14) | 58.8 (1.8) | 0.69 (0.12) | 59.5 (0.5) | 0.49 (0.04) | 59.5 (0.6) | 0.50 (0.04) | 61.4 (1.5) | 0.41 (0.12) |
| 2 | 62.0 (0.8) | 0.40 (0.07) | 61.0 (2.3) | 0.62 (0.14) | 60.6 (1.1) | 0.38 (0.09) | 58.0 (1.3) | 0.26 (0.09) | 54.7 (2.7) | 0.40 (0.16) |
| 3 | 57.1 (2.3) | 0.50 (0.15) | — | — | 59.8 (1.6) | 0.45 (0.11) | 59.1 (1.6) | 0.47 (0.09) | 61.5 (1.0) | 0.74 (0.07) |
| 4 | — | — | 61.8 (1.0) | 0.56 (0.08) | 53.3 (2.7) | 0.56 (0.18) | 62.4 (0.9) | 0.50 (0.07) | 63.2 (2.3) | 0.62 (0.18) |
| 5 | — | — | 60.3 (1.1) | 0.49 (0.08) | — | — | 57.9 (1.4) | 0.50 (0.08) | 61.5 (1.2) | 0.57 (0.11) |
| 6 | 64.4 (1.3) | 0.17 (0.17) | 60.8 (1.5) | 0.58 (0.10) | 56.2 (1.0) | 0.43 (0.07) | 58.3 (2.3) | 0.47 (0.13) | 57.7 (3.4) | 0.50 (0.22) |
| 7 | 61.4 (2.3) | 0.25 (0.16) | 62.0 (0.8) | 0.56 (0.07) | 61.4 (1.5) | 0.50 (0.14) | 57.6 (1.9) | 0.62 (0.10) | 59.1 (4.6) | 0.20 (0.20) |
| 8 | 61.2 (2.0) | 0.47 (0.13) | 63.5 (1.1) | 0.71 (0.18) | — | — | 57.2 (1.2) | 0.48 (0.09) | 61.2 (1.0) | 0.50 (0.08) |
| 9 | — | — | 59.1 (2.6) | 0.47 (0.13) | 59.7 (0.7) | 0.56 (0.05) | 59.3 (0.8) | 0.51 (0.04) | 61.2 (1.1) | 0.55 (0.08) |
| 10 | — | — | 56.8 (1.0) | 0.20 (0.05) | 61.2 (2.8) | 0.33 (0.17) | 58.8 (1.9) | 0.30 (0.11) | 60.6 (4.6) | 0.40 (0.24) |
| 11 | 57.5 (2.5) | 0.54 (0.14) | 62.0 (0.7) | 0.60 (0.05) | 58.3 (0.6) | 0.54 (0.04) | 61.7 (0.6) | 0.55 (0.05) | — | — |
| 12 | 62.0 (1.9) | 0.25 (0.13) | 60.0 (1.5) | 0.47 (0.13) | 58.2 (2.7) | 0.42 (0.15) | 60.5 (1.0) | 0.47 (0.07) | 62.4 (0.5) | 0.54 (0.04) |
| 13 | — | — | 61.5 (0.4) | 0.64 (0.04) | — | — | 59.8 (0.8) | 0.59 (0.05) | — | — |

TABLE 6-continued

Age and sex distribution of individuals with detected somatic SVs on each chromosome

| | Loss events | | | | CNN-LOH events | | | | Gain events | |
|---|---|---|---|---|---|---|---|---|---|---|
| | p-arm | | q-arm | | p-arm | | q-arm | | | |
| chr | Mean age | Frac. male | Mean age | Frac. male | Mean age | Frac. male | Mean age | Frac. male | Mean age | Frac. male |
| 14 | — | — | 61.1 (0.8) | 0.72 (0.07) | — | — | 59.9 (0.5) | 0.46 (0.03) | 62.9 (0.7) | 0.61 (0.08) |
| 15 | — | — | 62.5 (2.0) | 0.64 (0.13) | — | — | 59.5 (0.7) | 0.51 (0.05) | 65.7 (0.4) | 0.83 (0.05) |
| 16 | 56.1 (1.4) | 0.28 (0.08) | 63.2 (1.5) | 0.71 (0.13) | 59.1 (0.9) | 0.54 (0.06) | 60.1 (0.9) | 0.48 (0.06) | — | — |
| 17 | 61.1 (1.0) | 0.52 (0.07) | 59.5 (1.9) | 0.56 (0.13) | 58.5 (1.6) | 0.41 (0.11) | 58.1 (0.8) | 0.44 (0.05) | 60.3 (1.2) | 0.46 (0.08) |
| 18 | 55.5 (2.9) | 0.67 (0.21) | 61.2 (2.6) | 0.50 (0.22) | — | — | 61.5 (1.7) | 0.35 (0.12) | 62.2 (0.8) | 0.70 (0.06) |
| 19 | 60.8 (2.6) | 0.80 (0.20) | — | — | 59.2 (1.2) | 0.43 (0.08) | 60.6 (1.0) | 0.53 (0.07) | 60.9 (1.5) | 0.76 (0.11) |
| 20 | — | — | 62.1 (0.6) | 0.70 (0.04) | 59.1 (2.6) | 0.45 (0.16) | 57.9 (1.3) | 0.38 (0.08) | — | — |
| 21 | — | — | 59.2 (1.8) | 0.37 (0.11) | — | — | 57.4 (1.5) | 0.56 (0.09) | 60.8 (1.1) | 0.81 (0.07) |
| 22 | — | — | 62.8 (0.7) | 0.66 (0.08) | — | — | 60.7 (0.8) | 0.36 (0.05) | 61.2 (0.8) | 0.52 (0.06) |
| X | 60.3 (2.3) | — | 59.0 (2.5) | — | 61.4 (3.0) | — | 60.3 (1.1) | — | 56.8 (2.0) | — |

TABLE 7

Enrichment of somatic SVs in individuals with anomalous (top 1%) blood indices

| SV | Blood index | P-value | q-value | OR (95% CI) |
|---|---|---|---|---|
| 1p− | Lymphocyte # | 0.0027 | 0.047 | 33.1 (6.7-163.9) |
| 1p− | Lymphocyte % | 0.0027 | 0.047 | 33.1 (6.7-163.9) |
| 2p= | Monocyte # | 0.0027 | 0.047 | 11.9 (3.6-39.5) |
| 3p− | Lymphocyte # | 0.002 | 0.038 | 39.7 (7.7-204.6) |
| 3p− | Lymphocyte % | 0.002 | 0.038 | 39.7 (7.7-204.6) |
| 3+ | Lymphocyte # | 3.6e−6 | 0.00015 | 26.1 (9.7-70.1) |
| 3+ | Lymphocyte % | 3.6e−6 | 0.00015 | 26.1 (9.7-70.1) |
| 4q= | Monocyte % | 2.3e−7 | 1.2e−5 | 19.3 (8.6-43.5) |
| 7q− | Lymphocyte # | 3.3e−5 | 0.00097 | 15.5 (6.0-39.9) |
| 7q− | Lymphocyte % | 3.3e−5 | 0.00097 | 15.5 (6.0-39.9) |
| 9p= | Red # | 1.1e−13 | 7.6e−12 | 17.7 (10.2-30.6) |
| 9p= | Hematocrit | 3e−11 | 2e−9 | 14.9 (8.3-26.8) |
| 9p= | RBC dist. width | 2.8e−16 | 2.5e−14 | 20.5 (12.1-34.7) |
| 9p= | Platelet # | 1.9e−32 | 4.8e−30 | 39.3 (25.3-61.0) |
| 9p= | Platelet crit | 4.7e−34 | 1.6e−31 | 41.3 (26.7-63.8) |
| 9p= | Platelet dist. width | 7e−5 | 0.0019 | 7.5 (3.5-16.2) |
| 9+ | Neutrophil # | 1.1e−5 | 0.0004 | 19.9 (7.6-52.0) |
| 9+ | Neutrophil % | 0.00022 | 0.0054 | 15.3 (5.3-43.8) |
| 9+ | RBC dist. width | 1.1e−5 | 0.0004 | 19.9 (7.6-52.0) |
| 9+ | Platelet # | 0.00022 | 0.0054 | 15.3 (5.3-43.8) |
| 11q− | Lymphocyte # | 4.2e−8 | 2.3e−6 | 14.5 (7.2-29.2) |
| 11q− | Lymphocyte % | 8.1e−5 | 0.0021 | 9.2 (4.0-21.2) |
| 11q− | Platelet dist. width | 8.1e−5 | 0.0021 | 9.2 (4.0-21.2) |
| 11q= | Lymphocyte # | 0.0001 | 0.0026 | 7.0 (3.3-15.2) |
| 12+ | Lymphocyte # | 2.2e−20 | 3.2e−18 | 22.2 (13.8-35.7) |
| 12+ | Lymphocyte % | 3.7e−15 | 3e−13 | 17.2 (10.3-28.9) |
| 13q− | Lymphocyte # | 3.3e−117 | 3.3e−114 | 163.4 (113.3-235.7) |
| 13q− | Lymphocyte % | 8e−96 | 4e−93 | 116.3 (81.3-166.4) |
| 13q− | Basophil # | 4.2e−10 | 2.6e−8 | 11.8 (6.6-21.0) |
| 13q− | Basophil % | 0.0016 | 0.03 | 5.1 (2.2-11.6) |
| 13q− | Monocyte # | 3.7e−5 | 0.001 | 6.9 (3.4-14.2) |
| 13q= | Lymphocyte # | 5.2e−17 | 5.2e−15 | 23.0 (13.6-39.1) |
| 13q= | Lymphocyte % | 2.5e−14 | 1.9e−12 | 19.7 (11.3-34.4) |
| 14q− | Lymphocyte # | 6.4e−20 | 7.1e−18 | 73.7 (36.9-147.3) |
| 14q− | Lymphocyte % | 6.4e−20 | 7.1e−18 | 73.7 (36.9-147.3) |
| 14q= | Basophil # | 0.00032 | 0.0075 | 13.7 (4.8-39.0) |
| 14q= | Monocyte % | 0.00085 | 0.018 | 4.3 (2.1-8.7) |
| 16p− | Monocyte % | 0.0022 | 0.04 | 12.9 (3.9-43.2) |
| 16q− | Lymphocyte # | 4.6e−6 | 0.00018 | 49.7 (14.9-165.1) |
| 16q− | Lymphocyte % | 4.6e−6 | 0.00018 | 49.7 (14.9-165.1) |
| 16p= | Monocyte % | 0.0009 | 0.019 | 7.2 (2.9-17.9) |
| 17p− | Lymphocyte # | 4.6e−9 | 2.7e−7 | 25.7 (11.8-56.0) |
| 17p− | Lymphocyte % | 0.00062 | 0.013 | 11.3 (4.0-32.0) |
| 17q− | Platelet dist. width | 0.00033 | 0.0076 | 27.1 (7.5-97.1) |
| 18+ | Lymphocyte # | 0.00056 | 0.012 | 11.7 (4.1-33.0) |
| 19+ | Lymphocyte # | 6.6e−6 | 0.00024 | 44.1 (13.6-143.5) |
| 19+ | Lymphocyte % | 0.00026 | 0.0063 | 29.8 (8.2-108.3) |
| 20q− | Neutrophil % | 0.001 | 0.02 | 5.6 (2.4-12.7) |
| 20q− | RBC dist. width | 2e−5 | 0.00062 | 7.6 (3.7-15.6) |
| 20q− | Platelet dist. width | 0.001 | 0.02 | 5.6 (2.4-12.7) |
| 22q− | Lymphocyte # | 1.6e−31 | 3.2e−29 | 190.7 (88.5-410.9) |
| 22q− | Lymphocyte % | 5.5e−25 | 9.1e−23 | 123.3 (59.2-256.8) |
| 22+ | Lymphocyte # | 5e−8 | 2.6e−6 | 18.1 (8.5-38.5) |
| 22+ | Lymphocyte % | 1.4e−5 | 0.00044 | 13.0 (5.5-30.4) |
| −X | Lymphocyte # | 1.5e−6 | 7.1e−5 | 2.4 (1.8-3.4) |
| −X | Lymphocyte % | 3.7e−6 | 0.00015 | 2.4 (1.7-3.3) |

TABLE 8

Association of FRA10B variable number tandem repeats with breakage at 10q25.2

(a) Variable number tandem repeats identified in SFARI data and imputed into UK Biobank

| Variant | MAF | #del(10q) | P | Imputation $R^2$ |
|---|---|---|---|---|
| VNTR1 | 0.0044 | 21/60 | $3 \times 10^{-26}$ | 0.65 |
| VNTR2 | 0.0003 | 0/60 | 0.5 | 0.35 |
| VNTR3 | 0.0000 | 0/60 | 0.5 | 0.16 |
| VNTR4 | 0.0015 | 3/60 | $3 \times 10^{-4}$ | 0.52 |
| Any VNTR | 0.0062 | 24/60 | $5 \times 10^{-28}$ | 0.60 |

(a) Lead associated SNPs typed or imputed in UK Biobank

| Variant | MAF | #del(10q) | P | INFO |
|---|---|---|---|---|
| rs118137427 | 0.0527 | 60/60 | $6 \times 10^{-42}$ | 1.000 (typed) |
| rs758889647 | 0.0015 | 13/60 | $4 \times 10^{-21}$ | 0.695 |

TABLE 9

SNPs at MPL and ATM associated with cis somatic CNN-LOH at $P < 10^{-7}$

| SNP | hg19 coordinates | Alleles | RAF | P | OR (95% CI) |
|---|---|---|---|---|---|
| MPL locus: associations with chr1p CNN-LOH | | | | | |
| rs543652228 | 1:43640972 | A/G | 0.0003 | $2.4 \times 10^{-9}$ | 51 (22-118) |
| rs777132997 | 1:43669098 | A/G | 0.0002 | $2.0 \times 10^{-10}$ | 79 (34-187) |
| rs757080968 | 1:43720418 | C/G | 0.0002 | $2.6 \times 10^{-10}$ | 76 (32-178) |
| rs547321640 | 1:43752900 | T/C | 0.0002 | $1.0 \times 10^{-8}$ | 71 (28-180) |
| rs538358508 | 1:43753105 | T/G | 0.0002 | $1.0 \times 10^{-8}$ | 71 (28-180) |
| rs549761468 | 1:43788667 | C/T | 0.0002 | $2.1 \times 10^{-10}$ | 79 (34-187) |
| rsl43549194 | 1:43815673 | G/T | 0.0015 | $2.1 \times 10^{-8}$ | 14 (7-27) |
| rs369156948 | 1:43817942 | C/T | 0.0001 | $7.3 \times 10^{-8}$ | 103 (35-300) |
| rs576674585 | 1:43892277 | A/C | 0.0001 | $4.9 \times 10^{-9}$ | 83 (32-214) |
| rs558677971 | 1:43895592 | G/A | 0.0002 | $2.4 \times 10^{-8}$ | 59 (23-149) |
| rs566497062 | 1:43897662 | C/T | 0.0002 | $2.4 \times 10^{-8}$ | 59 (23-149) |
| rs143305686 | 1:44134295 | A/G | 0.0018 | $1.7 \times 10^{-12}$ | 17 (10-30) |
| rs773168056 | 1:44156366 | A/G | 0.0003 | $4.2 \times 10^{-9}$ | 46 (20-106) |
| rs182971382 | 1:44167774 | A/G | 0.0003 | $3.0 \times 10^{-11}$ | 63 (29-139) |
| rs554498272 | 1:44190215 | G/A | 0.0001 | $4.8 \times 10^{-11}$ | 103 (43-248) |
| rs765697775 | 1:44546545 | C/T | 0.0006 | $9.5 \times 10^{-15}$ | 41 (22-76) |
| rs540740393 | 1:45126775 | C/A | 0.0018 | $3.1 \times 10^{-10}$ | 15 (8-27) |
| rs553066968 | 1:45129752 | A/T | 0.0019 | $5.9 \times 10^{-10}$ | 14 (8-26) |
| rs572698005 | 1:45129772 | C/T | 0.0019 | $5.9 \times 10^{-10}$ | 14 (8-26) |
| rs565464974 | 1:45170759 | G/A | 0.0009 | $2.4 \times 10^{-13}$ | 30 (16-55) |
| rs748989559 | 1:45173569 | A/G | 0.0005 | $6.7 \times 10^{-16}$ | 53 (28-98) |
| rs548041003 | 1:45175146 | C/T | 0.0021 | $6.3 \times 10^{-13}$ | 16 (9-27) |
| rs144279563 | 1:45294379 | C/T | 0.0005 | $6.2 \times 10^{-16}$ | 53 (28-99) |
| rs572162077 | 1:45354774 | G/C | 0.0010 | $1.0 \times 10^{-15}$ | 31 (18-55) |
| ATM locus: associations with chr11q CNN-LOH | | | | | |
| rs535473237 | 11:108074178 | A/G | 0.0004 | $1.8 \times 10^{-8}$ | 61 (25-152) |
| rs532198118 | 11:108355523 | A/G | 0.0007 | $7.4 \times 10^{-9}$ | 41 (18-94) |

Alleles: risk lowering/risk increasing allele. RAF: risk allele frequency (in UK Biobank European-ancestry individuals).

TABLE 10 cis associations with biased loss of X ($P_{bias} < 10^{-6}$) and X gain data

| | | | | | Loss of female chrX | | | | Gain of female chrX | | | | |
|---|---|---|---|---|---|---|---|---|---|---|---|---|---|
| SNP | Location | A1/A2 | A2F | A2F$_{case}$ | P$_{GWAS}$ | N$_{A1+}$ | N$_{A2+}$ | P$_{bias}$ | A2F$_{case}$ | P$_{GWAS}$ | N$_{A1+}$ | N$_{A2+}$ | P$_{bias}$ |
| rs954958 | X:55129982 | C/T | 0.471 | 0.452 | $4.9 \times 10^{-3}$ | 540 | 716 | $7.6 \times 10^{-7}$ | 0.407 | 0.25 | 4 | 6 | 0.75 |
| rs10521478 | X:55208161 | A/G | 0.417 | 0.397 | $7.7 \times 10^{-4}$ | 515 | 713 | $1.8 \times 10^{-8}$ | 0.370 | 0.38 | 5 | 5 | 1.00 |
| rs1927307 | X:55337294 | G/A | 0.294 | 0.278 | $4.1 \times 10^{-3}$ | 436 | 621 | $1.4 \times 10^{-8}$ | 0.241 | 0.33 | 1 | 5 | 0.22 |
| rs5914315 | X:55354496 | T/C | 0.316 | 0.299 | $3.0 \times 10^{-3}$ | 447 | 639 | $6.2 \times 10^{-9}$ | 0.296 | 0.65 | 2 | 5 | 0.45 |
| rs12559108 | X:55422562 | T/C | 0.260 | 0.243 | $1.4 \times 10^{-3}$ | 374 | 572 | $1.3 \times 10^{-10}$ | 0.204 | 0.46 | 1 | 4 | 0.38 |
| rs7892090 | X:55432212 | T/C | 0.259 | 0.242 | $1.5 \times 10^{-3}$ | 379 | 569 | $7.3 \times 10^{-10}$ | 0.241 | 0.88 | 1 | 4 | 0.38 |
| rs57620007 | X:55476740 | T/C | 0.259 | 0.242 | $1.1 \times 10^{-3}$ | 377 | 568 | $5.6 \times 10^{-10}$ | 0.222 | 0.79 | 1 | 4 | 0.38 |
| rs3126241 | X:55601683 | T/C | 0.253 | 0.234 | $2.3 \times 10^{-4}$ | 360 | 562 | $3.0 \times 10^{-11}$ | 0.222 | 0.72 | 1 | 4 | 0.38 |
| rs149700928 | X:55684550 | G/C | 0.251 | 0.232 | $2.3 \times 10^{-4}$ | 357 | 555 | $5.8 \times 10^{-11}$ | 0.222 | 0.75 | 1 | 4 | 0.38 |
| rs5913856 | X:55747717 | A/G | 0.249 | 0.23 | $1.4 \times 10^{-4}$ | 349 | 558 | $4.0 \times 10^{-12}$ | 0.222 | 0.77 | 1 | 4 | 0.38 |
| rs1007153 | X:55778139 | C/T | 0.272 | 0.251 | $7.0 \times 10^{-5}$ | 363 | 592 | $1.2 \times 10^{-13}$ | 0.259 | 0.96 | 1 | 4 | 0.38 |
| rs5914476 | X:55852696 | T/G | 0.271 | 0.25 | $2.9 \times 10^{-5}$ | 358 | 590 | $4.7 \times 10^{-14}$ | 0.259 | 0.98 | 1 | 4 | 0.38 |
| rs6612385 | X:55853321 | A/G | 0.272 | 0.251 | $4.5 \times 10^{-5}$ | 364 | 589 | $3.1 \times 10^{-13}$ | 0.259 | 0.96 | 1 | 4 | 0.38 |
| rs10855058 | X:55936822 | G/A | 0.273 | 0.254 | $1.4 \times 10^{-4}$ | 385 | 592 | $3.7 \times 10^{-11}$ | 0.222 | 0.50 | 1 | 5 | 0.22 |
| rs6417935 | X:55960724 | C/T | 0.135 | 0.126 | $9.9 \times 10^{-3}$ | 219 | 352 | $2.9 \times 10^{-8}$ | 0.018 | 0.05 | 0 | 1 | 1.00 |
| rs6612472 | X:56152985 | A/G | 0.241 | 0.222 | $6.1 \times 10^{-4}$ | 322 | 547 | $2.2 \times 10^{-14}$ | 0.167 | 0.30 | 2 | 3 | 1.00 |
| rs4826461 | X:56226649 | A/G | 0.234 | 0.218 | $4.5 \times 10^{-4}$ | 311 | 539 | $4.8 \times 10^{-15}$ | 0.148 | 0.22 | 2 | 2 | 1.00 |
| rs6521388 | X:56345127 | A/G | 0.218 | 0.206 | $4.8 \times 10^{-3}$ | 289 | 533 | $1.4 \times 10^{-17}$ | 0.111 | 0.11 | 1 | 1 | 1.00 |
| rs5913935 | X:56428273 | T/C | 0.135 | 0.124 | $4.4 \times 10^{-3}$ | 203 | 356 | $9.9 \times 10^{-11}$ | 0.037 | 0.09 | 1 | 1 | 1.00 |
| rs5914638 | X:56456144 | T/C | 0.233 | 0.218 | $1.6 \times 10^{-3}$ | 305 | 557 | $7.3 \times 10^{-16}$ | 0.185 | 0.56 | 3 | 1 | 0.62 |
| rs1332731 | X:56495976 | T/C | 0.249 | 0.233 | $5.3 \times 10^{-4}$ | 327 | 579 | $4.7 \times 10^{-17}$ | 0.204 | 0.59 | 3 | 2 | 1.00 |
| rs721963 | X:56558810 | A/C | 0.225 | 0.211 | $4.7 \times 10^{-3}$ | 294 | 551 | $7.0 \times 10^{-19}$ | 0.130 | 0.17 | 2 | 1 | 1.00 |
| rs766912 | X:56630987 | A/G | 0.224 | 0.21 | $1.7 \times 10^{-3}$ | 293 | 548 | $1.1 \times 10^{-18}$ | 0.130 | 0.20 | 2 | 1 | 1.00 |
| rs74503599 | X:56640134 | C/T | 0.240 | 0.223 | $3.5 \times 10^{-4}$ | 312 | 566 | $8.1 \times 10^{-18}$ | 0.148 | 0.19 | 2 | 2 | 1.00 |
| rs5914806 | X:56847280 | A/G | 0.180 | 0.169 | $7.2 \times 10^{-3}$ | 249 | 459 | $2.5 \times 10^{-15}$ | 0.074 | 0.09 | 1 | 1 | 1.00 |
| rs5914815 | X:56870961 | T/C | 0.179 | 0.169 | $8.6 \times 10^{-3}$ | 250 | 460 | $2.8 \times 10^{-15}$ | 0.074 | 0.10 | 1 | 1 | 1.00 |
| rs5960832 | X:56894267 | C/T | 0.210 | 0.222 | $7.9 \times 10^{-3}$ | 501 | 351 | $3.1 \times 10^{-7}$ | 0.167 | 0.38 | 2 | 4 | 0.69 |
| rs5914035 | X:57008216 | T/C | 0.225 | 0.212 | $3.3 \times 10^{-3}$ | 292 | 560 | $2.9 \times 10^{-20}$ | 0.148 | 0.28 | 3 | 2 | 1.00 |
| rs912956 | X:57010138 | T/C | 0.207 | 0.195 | $5.1 \times 10^{-3}$ | 265 | 532 | $1.9 \times 10^{-21}$ | 0.093 | 0.08 | 1 | 1 | 1.00 |
| rs5914052 | X:57129959 | A/G | 0.225 | 0.213 | $3.6 \times 10^{-3}$ | 293 | 563 | $1.8 \times 10^{-20}$ | 0.148 | 0.27 | 3 | 2 | 1.00 |
| rs5960927 | X:57241324 | G/A | 0.209 | 0.222 | $6.7 \times 10^{-3}$ | 500 | 347 | $1.6 \times 10^{-7}$ | 0.185 | 0.69 | 2 | 4 | 0.69 |
| rs2516023 | X:57313357 | T/C | 0.226 | 0.212 | $2.3 \times 10^{-3}$ | 291 | 553 | $1.3 \times 10^{-19}$ | 0.148 | 0.28 | 3 | 2 | 1.00 |
| rs6611612 | X:57329089 | A/G | 0.227 | 0.213 | $1.3 \times 10^{-3}$ | 290 | 551 | $1.6 \times 10^{-19}$ | 0.148 | 0.26 | 3 | 2 | 1.00 |

TABLE 10-continued cis associations with biased loss of X ($P_{bias} < 10^{-6}$) and X gain data

| SNP | Location | A1/A2 | A2F | Loss of female chrX | | | | | Gain of female chrX | | | | |
|---|---|---|---|---|---|---|---|---|---|---|---|---|---|
| | | | | $A2F_{case}$ | $P_{GWAS}$ | $N_{A1+}$ | $N_{A2+}$ | $P_{bias}$ | $A2F_{case}$ | $P_{GWAS}$ | $N_{A1+}$ | $N_{A2+}$ | $P_{bias}$ |
| rs2060113 | X:57478582 | C/T | 0.221 | 0.209 | $6.8 \times 10^{-3}$ | 288 | 550 | $9.8 \times 10^{-20}$ | 0.130 | 0.18 | 3 | 1 | 0.62 |
| rs1594503 | X:57480930 | C/T | 0.244 | 0.231 | $8.6 \times 10^{-4}$ | 318 | 581 | $1.4 \times 10^{-18}$ | 0.167 | 0.29 | 3 | 2 | 1.00 |
| rs1997715 | X:57622607 | G/A | 0.225 | 0.213 | $3.7 \times 10^{-3}$ | 294 | 550 | $9.1 \times 10^{-19}$ | 0.148 | 0.28 | 3 | 2 | 1.00 |
| rs112877950 | X:57624653 | C/T | 0.028 | 0.027 | $7.9 \times 10^{-1}$ | 30 | 98 | $1.3 \times 10^{-9}$ | 0.018 | 0.67 | 0 | 0 | 1.00 |
| rs73226048 | X:57979353 | T/C | 0.221 | 0.209 | $5.7 \times 10^{-3}$ | 283 | 545 | $5.8 \times 10^{-20}$ | 0.111 | 0.10 | 2 | 1 | 1.00 |
| rs55950555 | X:57985647 | A/G | 0.302 | 0.313 | $5.6 \times 10^{-2}$ | 618 | 434 | $1.5 \times 10^{-8}$ | 0.333 | 0.50 | 1 | 4 | 0.38 |
| rs113699645 | X:58121440 | A/G | 0.026 | 0.025 | $6.9 \times 10^{-1}$ | 29 | 86 | $9.8 \times 10^{-8}$ | 0.018 | 0.72 | 0 | 0 | 1.00 |
| rs4625204 | X:58216902 | A/G | 0.202 | 0.215 | $4.2 \times 10^{-3}$ | 499 | 338 | $2.9 \times 10^{-8}$ | 0.222 | 0.77 | 1 | 5 | 0.22 |
| rs111318471 | X:58328362 | C/A | 0.026 | 0.026 | $6.8 \times 10^{-1}$ | 29 | 82 | $4.9 \times 10^{-7}$ | 0.018 | 0.76 | 0 | 0 | 1.00 |
| rs2942875 | X:58339545 | C/T | 0.447 | 0.429 | $9.7 \times 10^{-4}$ | 423 | 796 | $6.6 \times 10^{-27}$ | 0.315 | 0.07 | 6 | 1 | 0.12 |
| rs112064215 | X:61994151 | C/T | 0.053 | 0.05 | $9.4 \times 10^{-1}$ | 70 | 159 | $3.9 \times 10^{-9}$ | 0.056 | 0.96 | 1 | 0 | 1.00 |
| rs60576970 | X:61999396 | A/C | 0.493 | 0.513 | $9.4 \times 10^{-4}$ | 753 | 505 | $2.8 \times 10^{-12}$ | 0.500 | 0.88 | 1 | 5 | 0.22 |
| rs62597976 | X:62261609 | G/T | 0.300 | 0.322 | $1.1 \times 10^{-4}$ | 646 | 446 | $1.6 \times 10^{-9}$ | 0.259 | 0.44 | 1 | 6 | 0.12 |
| rs56329621 | X:62520485 | G/A | 0.032 | 0.029 | $3.4 \times 10^{-1}$ | 35 | 103 | $5.8 \times 10^{-9}$ | 0.037 | 0.33 | 1 | 0 | 1.00 |
| rs1221064 | X:62529141 | A/G | 0.085 | 0.078 | $6.2 \times 10^{-2}$ | 126 | 227 | $8.4 \times 10^{-8}$ | 0.074 | 0.87 | 1 | 0 | 1.00 |
| rs112933767 | X:63195237 | A/G | 0.042 | 0.041 | $9.2 \times 10^{-1}$ | 63 | 132 | $8.7 \times 10^{-7}$ | 0.056 | 0.25 | 1 | 1 | 1.00 |
| rs73213355 | X:64965828 | C/T | 0.060 | 0.061 | $6.0 \times 10^{-1}$ | 196 | 108 | $5.1 \times 10^{-7}$ | 0.074 | 0.76 | 1 | 1 | 1.00 |
| rs3848896 | X:65182724 | G/A | 0.096 | 0.096 | $7.0 \times 10^{-1}$ | 287 | 156 | $4.9 \times 10^{-10}$ | 0.111 | 0.79 | 3 | 1 | 0.62 |
| rs7056244 | X:65206855 | G/A | 0.070 | 0.074 | $1.9 \times 10^{-1}$ | 240 | 121 | $3.7 \times 10^{-10}$ | 0.111 | 0.32 | 3 | 1 | 0.62 |
| rs5918586 | X:65328292 | A/G | 0.136 | 0.136 | $6.8 \times 10^{-1}$ | 358 | 227 | $6.8 \times 10^{-8}$ | 0.130 | 0.78 | 4 | 1 | 0.38 |
| rs12836051 | X:114924811 | A/G | 0.160 | 0.148 | $5.5 \times 10^{-3}$ | 257 | 405 | $9.7 \times 10^{-9}$ | 0.125 | 0.50 | 2 | 4 | 0.69 |
| rs73224841 | X:114931929 | T/G | 0.022 | 0.022 | $7.6 \times 10^{-1}$ | 32 | 86 | $6.9 \times 10^{-7}$ | 0.018 | 0.81 | 1 | 0 | 1.00 |
| rs73224844 | X:114945104 | G/A | 0.022 | 0.022 | $5.3 \times 10^{-1}$ | 30 | 86 | $1.9 \times 10^{-7}$ | 0.018 | 0.83 | 1 | 0 | 1.00 |
| rs11091036 | X:115023111 | G/C | 0.266 | 0.249 | $1.1 \times 10^{-3}$ | 369 | 555 | $1.0 \times 10^{-9}$ | 0.304 | 0.50 | 6 | 6 | 1.00 |

A1, A2: major/minor allele.
A2F: minor allele frequency.
$A2F_{case}$: A2 frequency in individuals with loss (resp. gain) of X.
$P_{GWAS}$: association with increased risk of X event.
$N_{A1+}$: number of heterozygous individuals with X loss (resp. gain) in which the A1/A2 allelic balance shifts toward the A1 allele (and analogously for $N_{A2+}$).
$P_{bias}$: P-value for biased shift.

TABLE 11

No evidence for rs2942875-biased X inactivation in GEUVADIS RNA-seq data

| | Read counts | | | Read counts | | | | Read counts | | | | Read counts | |
|---|---|---|---|---|---|---|---|---|---|---|---|---|---|
| HG00122 | | | | HG00130 | | | | HG00353 | | | | HG00362 | |
| rs2516023 T/C | 2 | 1 | | rs2516023 T/C | 8 | 0 | | rs2516023 T/C | 0 | 0 | | rs2516023 T/C | 0 | 2 |
| rs1367830 C/T | 3 | 2 | | rs1367830 C/T | 9 | 0 | | rs1367830 C/T | 0 | 12 | | rs1367830 C/T | 3 | 5 |
| rs2060113 C/T | 1 | 1 | | rs2060113 C/T | 1 | 0 | | rs2060113 C/T | 1 | 4 | | rs2060113 C/T | 2 | 1 |
| Total maj/min | 6 | 4 | 0.60 | Total maj/min | 18 | 0 | 1.00 | Total maj/min | 1 | 16 | 0.06 | Total maj/min | 5 | 8 | 0.38 |
| HG00231 | | | | HG00232 | | | | HG01790 | | | | NA06985 | |
| rs2516023 T/C | 0 | 5 | | rs2516023 T/C | 0 | 1 | | rs2516023 T/C | 0 | 0 | | rs2516023 T/C | 2 | 0 |
| rs 1367830 C/T | 0 | 8 | | rs1367830 C/T | 0 | 6 | | rs1367830 C/T | 3 | 2 | | rs1367830 C/T | 4 | 0 |
| rs2060113 C/T | 0 | 4 | | rs2060113 C/T | 0 | 4 | | rs2060113 C/T | 0 | 2 | | rs2060113 C/T | 6 | 0 |
| Total maj/min | 0 | 17 | 0.00 | Total maj/min | 0 | 11 | 0.00 | Total maj/min | 3 | 4 | 0.43 | Total maj/min | 12 | 0 | 1.00 |
| HG00266 | | | | HG00276 | | | | NA11830 | | | | NA11832 | |
| rs2516023 T/C | 2 | 0 | | rs2516023 T/C | 0 | 2 | | rs2516023 T/C | 1 | 2 | | rs2516023 T/C | 0 | 6 |
| rs1367830 C/T | 10 | 0 | | rs1367830 C/T | 1 | 10 | | rs 1367830 C/T | 3 | 6 | | rs1367830 C/T | 0 | 9 |
| rs2060113 C/T | 9 | 0 | | rs2060113 C/T | 0 | 3 | | rs2060113 C/T | 1 | 3 | | rs2060113 C/T | 0 | 1 |
| Total maj/min | 21 | 0 | 1.00 | Total maj/min | 1 | 15 | 0.06 | Total maj/min | 5 | 11 | 0.31 | Total maj/min | 0 | 16 | 0.00 |
| HG00327 | | | | HG00332 | | | | NA12058 | | | | NA12156 | |
| rs2516023 T/C | 0 | 4 | | rs2516023 T/C | 0 | 8 | | rs2516023 T/C | 0 | 10 | | rs2516023 T/C | 1 | 4 |
| rs1367830 C/T | 0 | 4 | | rs1367830 C/T | 1 | 6 | | rs1367830 C/T | 0 | 11 | | rs1367830 C/T | 4 | 5 |
| rs2060113 C/T | 0 | 2 | | rs2060113 C/T | 1 | 3 | | rs2060113 C/T | 0 | 3 | | rs2060113 C/T | 0 | 1 |
| Total maj/min | 0 | 10 | 0.00 | Total maj/min | 2 | 17 | 0.11 | Total maj/min | 0 | 24 | 0.00 | Total maj/min | 5 | 10 | 0.33 |

TABLE 11-continued

No evidence for rs2942875-biased X inactivation in GEUVADIS RNA-seq data

| Sample | SNP | Read counts | | Total |
|---|---|---|---|---|
| NA12283 | rs2516023 T/C | 2 | 0 | |
| | rs1367830 C/T | 10 | 0 | |
| | rs2060113 C/T | 3 | 0 | |
| | Total maj/min | 15 | 0 | 1.00 |
| NA12341 | rs2516023 T/C | 7 | 1 | |
| | rs1367830 C/T | 9 | 0 | |
| | rs2060113 C/T | 6 | 0 | |
| | Total maj/min | 22 | 1 | 0.96 |
| NA12718 | rs2516023 T/C | 0 | 2 | |
| | rs1367830 C/T | 0 | 9 | |
| | rs2060113 C/T | 0 | 4 | |
| | Total maj/min | 0 | 15 | 0.00 |
| NA12815 | rs2516023 T/C | 0 | 3 | |
| | rs1367830 C/T | 1 | 7 | |
| | rs2060113 C/T | 0 | 3 | |
| | Total maj/min | 1 | 13 | 0.07 |
| NA20502 | rs2516023 T/C | 2 | 0 | |
| | rs1367830 C/T | 4 | 0 | |
| | rs2060113 C/T | 0 | 0 | |
| | Total maj/min | 6 | 0 | 1.00 |
| NA20503 | rs2516023 T/C | 0 | 0 | |
| | rs1367830 C/T | 1 | 0 | |
| | rs2060113 C/T | 1 | 0 | |
| | Total maj/min | 2 | 0 | 1.00 |
| NA20508 | rs2516023 T/C | 3 | 0 | |
| | rs1367830 C/T | 3 | 1 | |
| | rs2060113 C/T | 1 | 0 | |
| | Total maj/min | 7 | 1 | 0.88 |
| NA20514 | rs2516023 T/C | 2 | 2 | |
| | rs1367830 C/T | 3 | 3 | |
| | rs2060113 C/T | 2 | 1 | |
| | Total maj/min | 7 | 6 | 0.54 |
| NA20541 | rs2516023 T/C | 5 | 0 | |
| | rs1367830 C/T | 4 | 0 | |
| | rs2060113 C/T | 0 | 0 | |
| | Total maj/min | 9 | 0 | 1.00 |
| NA20582 | rs2516023 T/C | 4 | 2 | |
| | rs1367830 C/T | 12 | 4 | |
| | rs2060113 C/T | 4 | 2 | |
| | Total maj/min | 20 | 8 | 0.71 |
| NA20756 | rs2516023 T/C | 2 | 13 | |
| | rs1367830 C/T | 0 | 8 | |
| | rs2060113 C/T | 0 | 0 | |
| | Total maj/min | 2 | 21 | 0.09 |
| NA20761 | rs2516023 T/C | 1 | 6 | |
| | rs1367830 C/T | 3 | 8 | |
| | rs2060113 C/T | 1 | 1 | |
| | Total maj/min | 5 | 16 | 0.24 |
| NA20799 | rs2516023 T/C | 0 | 4 | |
| | rs1367830 C/T | 0 | 8 | |
| | rs2060113 C/C | — | — | |
| | Total maj/min | 0 | 12 | 0.00 |
| NA20800 | rs2516023 T/C | 0 | 1 | |
| | rs1367830 C/T | 0 | 11 | |
| | rs2060113 C/T | 0 | 4 | |
| | Total maj/min | 0 | 16 | 0.00 |
| NA20819 | rs2516023 T/C | 4 | 0 | |
| | rs1367830 C/T | 5 | 2 | |
| | rs2060113 C/T | 3 | 1 | |
| | Total maj/min | 12 | 3 | 0.80 |
| HG00133 | rs2516023 T/C | 2 | 2 | |
| | rs1367830 C/T | 6 | 8 | |
| | rs2060113 C/T | 2 | 1 | |
| | Total maj/min | 10 | 11 | 0.48 |
| HG00158 | rs2516023 T/C | 3 | 1 | |
| | rs1367830 C/T | 2 | 5 | |
| | rs2060113 C/T | 1 | 2 | |
| | Total maj/min | 6 | 8 | 0.43 |
| HG00239 | rs2516023 T/C | 3 | 2 | |
| | rs1367830 C/T | 4 | 3 | |
| | rs2060113 C/T | 1 | 2 | |
| | Total maj/min | 8 | 7 | 0.53 |
| HG00257 | rs2516023 T/C | 1 | 0 | |
| | rs1367830 C/T | 1 | 1 | |
| | rs2060113 C/T | 0 | 1 | |
| | Total maj/min | 2 | 2 | 0.50 |
| HG00315 | rs2516023 T/C | 2 | 3 | |
| | rs1367830 C/T | 6 | 2 | |
| | rs2060113 C/T | 1 | 1 | |
| | Total maj/min | 9 | 6 | 0.60 |
| HG00323 | rs2516023 T/C | 4 | 4 | |
| | rs1367830 C/T | 3 | 3 | |
| | rs2060113 C/T | 1 | 0 | |
| | Total maj/min | 8 | 7 | 0.53 |
| HG00334 | rs2516023 T/C | 0 | 4 | |
| | rs1367830 C/T | 0 | 8 | |
| | rs2060113 C/T | 0 | 3 | |
| | Total maj/min | 0 | 15 | 0.00 |
| HG00337 | rs2516023 T/C | 2 | 1 | |
| | rs1367830 C/T | 2 | 2 | |
| | rs2060113 C/T | 0 | 0 | |
| | Total maj/min | 4 | 3 | 0.57 |
| HG00364 | rs2516023 T/C | 8 | 2 | |
| | rs1367830 C/T | 7 | 6 | |
| | rs2060113 C/T | 3 | 3 | |
| | Total maj/min | 18 | 11 | 0.62 |
| HG00381 | rs2516023 T/C | 1 | 0 | |
| | rs1367830 C/T | 1 | 4 | |
| | rs2060113 C/T | 1 | 3 | |
| | Total maj/min | 3 | 7 | 0.30 |
| NA07037 | rs2516023 T/C | 7 | 0 | |
| | rs1367830 C/T | 13 | 0 | |
| | rs2060113 C/T | 7 | 0 | |
| | Total maj/min | 27 | 0 | 1.00 |
| NA07056 | rs2516023 T/C | 0 | 3 | |
| | rs1367830 C/T | 1 | 1 | |
| | rs2060113 C/T | 0 | 1 | |
| | Total maj/min | 1 | 5 | 0.17 |
| NA11892 | rs2516023 T/C | 3 | 0 | |
| | rs1367830 C/T | 4 | 0 | |
| | rs2060113 C/T | 2 | 0 | |
| | Total maj/min | 9 | 0 | 1.00 |
| NA11931 | rs2516023 T/C | 0 | 4 | |
| | rs1367830 C/T | 0 | 1 | |
| | rs2060113 C/T | 0 | 0 | |
| | Total maj/min | 0 | 5 | 0.00 |
| NA12234 | rs2516023 T/C | 1 | 0 | |
| | rs1367830 C/T | 5 | 1 | |
| | rs2060113 C/T | 1 | 0 | |
| | Total maj/min | 7 | 1 | 0.88 |
| NA12275 | rs2516023 T/C | 0 | 6 | |
| | rs1367830 C/T | 0 | 12 | |
| | rs2060113 C/T | 0 | 7 | |
| | Total maj/min | 0 | 25 | 0.00 |
| NA12383 | rs2516023 T/C | 2 | 0 | |
| | rs1367830 C/T | 10 | 1 | |
| | rs2060113 C/T | 4 | 0 | |
| | Total maj/min | 16 | 1 | 0.94 |
| NA12489 | rs2516023 T/C | 0 | 0 | |
| | rs1367830 C/T | 1 | 5 | |
| | rs2060113 C/T | 2 | 1 | |
| | Total maj/min | 3 | 6 | 0.33 |
| NA12843 | rs2516023 T/C | 1 | 6 | |
| | rs1367830 C/T | 1 | 5 | |
| | rs2060113 C/T | 1 | 4 | |
| | Total maj/min | 3 | 15 | 0.17 |
| NA12890 | rs2516023 T/C | 3 | 0 | |
| | rs1367830 C/T | 10 | 0 | |
| | rs2060113 C/T | 5 | 0 | |
| | Total maj/min | 18 | 0 | 1.00 |
| NA20505 | rs2516023 T/C | 4 | 1 | |
| | rs1367830 C/T | 7 | 0 | |
| | rs2060113 C/T | 3 | 0 | |
| | Total maj/min | 14 | 1 | 0.93 |
| NA20507 | rs2516023 T/C | 3 | 0 | |
| | rs1367830 C/T | 6 | 4 | |
| | rs2060113 C/T | 5 | 2 | |
| | Total maj/min | 14 | 6 | 0.70 |
| NA20529 | rs2516023 T/C | 5 | 0 | |
| | rs1367830 C/T | 11 | 1 | |
| | rs2060113 C/T | 3 | 0 | |
| | Total maj/min | 19 | 1 | 0.95 |
| NA20531 | rs2516023 T/C | 4 | 1 | |
| | rs1367830 C/T | 6 | 7 | |
| | rs2060113 C/T | 3 | 4 | |
| | Total maj/min | 13 | 12 | 0.52 |

TABLE 11-continued

No evidence for rs2942875-biased X inactivation in GEUVADIS RNA-seq data

| NA20585 | Read counts | | NA20589 | Read counts | | |
|---|---|---|---|---|---|---|
| rs2516023 T/C | 0 | 2 | rs2516023 T/C | 0 | 0 | |
| rs1367830 C/T | 0 | 5 | rs1367830 C/T | 6 | 0 | |
| rs2060113 C/T | 0 | 1 | rs2060113 C/T | 2 | 0 | |
| Total maj/min | 0 | 8 | 0.00 Total maj/min | 8 | 0 | 1.00 |

| NA20771 | Read counts | | NA20797 | Read counts | | |
|---|---|---|---|---|---|---|
| rs2516023 T/C | 4 | 2 | rs2516023 T/C | 11 | 0 | |
| rs1367830 C/T | 3 | 6 | rs1367830 C/T | 9 | 1 | |
| rs2060113 C/T | 2 | 0 | rs2060113 C/T | 4 | 0 | |
| Total maj/min | 9 | 8 | 0.53 Total maj/min | 24 | 1 | 0.96 |
| NA20807 | | | NA20813 | | | |
| rs2516023 T/C | 1 | 3 | rs2516023 T/C | 0 | 4 | |
| rs1367830 C/T | 3 | 8 | rs1367830 C/T | 1 | 7 | |
| rs2060113 C/T | 3 | 4 | rs2060113 C/T | 1 | 4 | |
| Total maj/min | 7 | 15 | 0.32 Total maj/min | 2 | 15 | 0.12 |

TABLE 12 trans association with classes of somatic SVs at SNPs previously reported to be associated with related phenotypes

| SNP | Location | Gene(s) reported | MAF | GWAS trait | Pany | Ploss |
|---|---|---|---|---|---|---|
| rs2736609 | 1:156202640 | PMF1, SEMA4A | 0.36 | mLOY | 0.5 | 0.69 |
| rs11125529 | 2:54475866 | ACYP2 | 0.14 | telo | 0.55 | 0.35 |
| rs13401811 | 2:111616104 | ACOXL, BCL2L11 | 0.18 | CLL | 0.57 | 0.67 |
| rs17483466 | 2:111797458 | ACOXL, BCL2L11 | 0.2 | CLL | 0.12 | 0.76 |
| rs58055674 | 2:111831793 | ACOXL | 0.18 | CLL | 0.2 | 0.45 |
| rs1439287 | 2:111871897 | ACOXL, BCL2L11 | 0.49 | CLL | 0.28 | 0.28 |
| rs9308731 | 2:111908262 | BCL2L11 | 0.45 | CLL | 0.37 | 0.55 |
| rs13015798 | 2:201909515 | FAM126B, CASP8 | 0.33 | CLL | 0.0067 | 0.59 |
| rs3769825 | 2:202111380 | CASP8, CASP10 | 0.43 | CLL | 0.14 | 0.032 |
| rs13397985 | 2:231091223 | SP140 | 0.19 | CLL | 0.028 | 0.00026 |
| rs9880772 | 3:27777779 | EOMES | 0.45 | CLL | 0.69 | 0.16 |
| rs115854006 | 3:48388170 | TREX1, PLXNB1 | 0.036 | mLOY | 0.4 | 0.55 |
| rs13088318 | 3:101242751 | SENP7 | 0.34 | mLOY | 0.75 | 0.55 |
| rs59633341 | 3:150018880 | TSC22D2 | 0.16 | mLOY | 0.47 | 0.44 |
| rs2201862 | 3:168648039 | EGFEM1P, MECOM | 0.5 | MPN | 0.13 | 0.38 |
| rs10936599 | 3:169492101 | MYNN | 0.25 | CLL, telo | 0.095 | 0.22 |
| rs9815073 | 3:188115682 | LPP | 0.34 | CLL | 0.26 | 0.49 |
| rs1548483 | 4:105749895 | TET2 | 0.034 | MPN | 0.67 | 0.19 |
| rs898518 | 4:109016824 | LEF1 | 0.42 | CLL | 0.95 | 0.95 |
| rs6858698 | 4:114683844 | CAMK2D | 0.16 | CLL | 0.63 | 0.57 |
| rs7675998 | 4:164007820 | NAF1 | 0.22 | telo | 0.48 | 0.6 |
| rs34002450 | 5:1280940 | TERT | 0.38 | CH | 0.0031 | 0.092 |
| rs7705526 | 5:1285974 | TERT | 0.33 | MPN | 0.00052 | 0.036 |
| rs2736100 | 5:1286516 | TERT | 0.5 | MPN, telo | 0.0014 | 0.069 |
| rs2853677 | 5:1287194 | TERT | 0.42 | MPN | 0.0043 | 0.44 |
| rs56084922 | 5:111061883 | NR | 0.078 | mLOY | 0.58 | 0.38 |
| rs9391997 | 6:409119 | IRF4 | 0.47 | CLL | 0.92 | 0.62 |
| rs872071 | 6:411064 | IRF4 | 0.47 | CLL | 0.99 | 0.7 |
| rs73718779 | 6:2969278 | SERPINB6 | 0.11 | CLL | 0.59 | 0.86 |
| rs926070 | 6:32257566 | HLA | 0.34 | CLL | 1 | 0.94 |
| rs674313 | 6:32578082 | HLA-DRB5 | 0.24 | CLL | 0.86 | 0.14 |
| rs9273363 | 6:32626272 | HLA | 0.3 | CLL | 0.46 | 1 |
| rs210142 | 6:33546837 | BAK1 | 0.3 | CLL | 0.63 | 0.44 |
| rs13191948 | 6:109634599 | SMPD2, CCDC162P | 0.46 | mLOY | 0.45 | 0.95 |
| rs2236256 | 6:154478440 | IPCEF1 | 0.46 | CLL | 0.72 | 0.099 |
| rs381500 | 6:164478388 | QKI | 0.45 | mLOY | 0.49 | 0.63 |
| rs4721217 | 7:1973579 | MAD1L1 | 0.4 | mLOY | 0.0055 | 0.69 |
| rs17246404 | 7:124462661 | POT1 | 0.28 | CLL | 0.99 | 0.3 |
| rs58270997 | 7:130729394 | PINT | 0.25 | MPN | 0.049 | 0.039 |
| rs35091702 | 8:30279470 | RBPMS | 0.26 | mLOY | 0.58 | 0.21 |
| rs2511714 | 8:103578874 | ODF1, KLF10 | 0.4 | CLL | 0.034 | 0.13 |
| rs2466035 | 8:128211229 | MYC | 0.33 | CLL | 0.59 | 0.55 |
| rs59384377 | 9:5005034 | JAK2 | 0.26 | MPN | 0.057 | 0.012 |
| rs12339666 | 9:5063296 | JAK2 | 0.26 | MPN | 0.11 | 0.027 |
| rs10974944 | 9:5070831 | JAK2 | 0.25 | MPN | 0.036 | 0.013 |
| rs1679013 | 9:22206987 | AS1, CDKN2B | 0.46 | CLL | 0.42 | 0.5 |
| rs1359742 | 9:22336996 | DMRTA1, CDKN2B-AS1 | 0.47 | CLL | 0.9 | 0.6 |
| rs621940 | 9:135870130 | GFI1B | 0.16 | MPN | 0.74 | 0.52 |
| rs1800682 | 10:90749963 | ACTA, FAS | 0.46 | CLL | 0.023 | 0.033 |
| rs4406737 | 10:90759724 | ACTA2, FAS | 0.44 | CLL | 0.45 | 0.51 |

TABLE 12-continued trans association with classes of somatic SVs at SNPs
previously reported to be associated with related phenotypes

| SNP | Location | Gene(s) reported | MAF | GWAS trait | Pany | Ploss |
|---|---|---|---|---|---|---|
| rs9420907 | 10:105676465 | OBFC1 | 0.13 | telo | 0.32 | 0.057 |
| rs7944004 | 11:2311152 | TSPAN32 | 0.49 | CLL | 0.69 | 0.5 |
| rs2521269 | 11:2321095 | C11orf21 | 0.46 | CLL | 0.095 | 0.27 |
| rs4754301 | 11:108048541 | NPAT, ATM, ACAT1 | 0.45 | mLOY | 0.95 | 0.9 |
| rs1800056 | 11:108138003 | ATM | 0.013 | MPN | 0.099 | 0.26 |
| rs35923643 | 11:123355391 | GRAMD1B | 0.2 | CLL | 0.027 | 0.045 |
| rs735665 | 11:123361397 | SCN3B, GRAMD1B | 0.19 | CLL | 0.055 | 0.049 |
| rs2953196 | 11:123368333 | NR | 0.25 | CLL | 0.049 | 0.1 |
| rs7310615 | 12:111865049 | SH2B3 | 0.48 | MPN | 0.39 | 0.47 |
| rs10687116 | 13:41678081 | WBP4 | 0.2 | mLOY | 0.76 | 0.59 |
| rs1122138 | 14:96180242 | TCL1A | 0.16 | mLOY | 0.33 | 0.37 |
| rs2887399 | 14:96180695 | TCL1A | 0.2 | mLOY | 0.31 | 0.79 |
| rs137952017 | 14:101176090 | DLK1 | 0.15 | mLOY | 0.018 | 0.15 |
| rs8024033 | 15:40403657 | BMF | 0.5 | CLL | 0.083 | 0.83 |
| rs11636802 | 15:56775597 | MNS1, RFXDC2 | 0.11 | CLL | 0.32 | 0.79 |
| rs72742684 | 15:56780767 | MNS1, RFX7 | 0.11 | CLL | 0.35 | 0.89 |
| rs2052702 | 15:69989505 | PCAT29 | 0.38 | CLL | 0.85 | 0.98 |
| rs7176508 | 15:70018990 | RPLP1 | 0.38 | CLL | 0.93 | 0.86 |
| rs12448368 | 16:81044947 | CENPN, ATMIN | 0.13 | mLOY | 0.034 | 0.26 |
| rs391023 | 16:85927814 | IRF8 | 0.36 | CLL | 0.077 | 0.37 |
| rs391855 | 16:85928621 | IRF8 | 0.42 | CLL | 0.0099 | 0.18 |
| rs391525 | 16:85944439 | IRF8 | 0.34 | CLL | 0.025 | 0.045 |
| rs1044873 | 16:85955671 | IRF8 | 0.39 | CLL | 0.034 | 0.13 |
| rs78378222 | 17:7571752 | TP53 | 0.013 | mLOY | 0.037 | $3.2 \times 10^{-5}$ |
| rs77522818 | 17:47817373 | FAM117A | 0.043 | mLOY | 0.011 | 0.077 |
| rs11082396 | 18:42080720 | SETBP1 | 0.13 | mLOY | 0.22 | 0.37 |
| rs4368253 | 18:57622287 | PMAIP1 | 0.32 | CLL | 0.59 | 0.87 |
| rs4987856 | 18:60793494 | BCL2 | 0.097 | CLL | 0.25 | 0.49 |
| rs4987855 | 18:60793549 | BCL2 | 0.097 | CLL | 0.34 | 0.52 |
| rs4987852 | 18:60793921 | BCL2 | 0.07 | CLL | 0.85 | 0.99 |
| rs17758695 | 18:60920854 | BCL2 | 0.03 | mLOY | 0.61 | 0.2 |
| rs8105767 | 19:22215441 | ZNF208 | 0.29 | telo | 0.62 | 0.98 |
| rs11083846 | 19:47207654 | PRKD2, STRN4 | 0.23 | CLL | 0.088 | 0.36 |
| rs60084722 | 20:30355738 | TPX2, BCL2L1, HM13 | 0.21 | mLOY | 0.018 | 0.0051 |
| rs755017 | 20:62421622 | RTEL1 | 0.13 | telo | 0.0047 | 0.0064 |
| rs555607708 | 22:29091856 | CHEK2 | 0.0019 | MPN | 0.0038 | 0.01 |

| SNP | PCNN-LOH | Pgain | Pauto | Pauto loss | PX loss |
|---|---|---|---|---|---|
| rs2736609 | 0.47 | 0.92 | 0.68 | 0.62 | 0.95 |
| rs11125529 | 0.082 | 1 | 0.21 | 0.95 | 0.25 |
| rs13401811 | 0.71 | 0.74 | 0.51 | 0.73 | 0.84 |
| rs17483466 | 0.11 | 0.92 | 0.15 | 0.72 | 0.5 |
| rs58055674 | 0.75 | 0.78 | 0.56 | 0.95 | 0.28 |
| rs1439287 | 0.71 | 0.59 | 0.92 | 0.21 | 0.36 |
| rs9308731 | 0.51 | 0.4 | 0.96 | 0.14 | 0.21 |
| rs13015798 | 0.11 | 0.061 | 0.015 | 0.87 | 0.16 |
| rs3769825 | 0.78 | 0.21 | 0.49 | 0.24 | 0.095 |
| rs13397985 | 0.91 | 0.25 | 0.13 | 0.0049 | 0.015 |
| rs9880772 | 0.59 | 0.14 | 0.97 | 0.6 | 0.87 |
| rs115854006 | 0.81 | 0.28 | 0.17 | 0.075 | 0.9 |
| rs13088318 | 0.24 | 0.15 | 0.24 | 0.29 | 0.68 |
| rs59633341 | 0.26 | 0.14 | 0.31 | 0.96 | 0.8 |
| rs2201862 | 0.75 | 0.0091 | 0.35 | 0.34 | 0.36 |
| rs10936599 | 0.4 | 0.6 | 0.16 | 0.28 | 0.62 |
| rs9815073 | 0.041 | 0.066 | 0.054 | 0.53 | 0.54 |
| rs1548483 | 0.3 | 0.34 | 0.71 | 0.13 | 0.48 |
| rs898518 | 0.58 | 0.58 | 0.39 | 0.59 | 0.76 |
| rs6858698 | 0.24 | 0.54 | 0.76 | 0.052 | 0.69 |
| rs7675998 | 0.69 | 0.62 | 0.42 | 0.085 | 0.67 |
| rs34002450 | 0.0012 | 0.026 | $7.8 \times 10^{-5}$ | 0.0019 | 0.75 |
| rs7705526 | $8.6 \times 10^{-5}$ | 0.16 | $4.8 \times 10^{-5}$ | 0.0092 | 0.2 |
| rs2736100 | 0.00095 | 0.12 | 0.00098 | 0.062 | 0.24 |
| rs2853677 | 0.00036 | 0.44 | 0.0014 | 0.38 | 0.92 |
| rs56084922 | 0.73 | 0.19 | 0.64 | 0.36 | 0.78 |
| rs9391997 | 0.38 | 0.93 | 0.66 | 0.73 | 0.68 |
| rs872071 | 0.35 | 0.97 | 0.69 | 0.73 | 0.75 |
| rs73718779 | 0.85 | 0.57 | 0.57 | 0.73 | 0.02 |
| rs926070 | 0.16 | 0.12 | 0.87 | 0.29 | 0.52 |
| rs674313 | 0.19 | 0.95 | 0.37 | 0.58 | 0.082 |
| rs9273363 | 0.59 | 0.07 | 0.053 | 0.014 | 0.19 |
| rs210142 | 0.99 | 0.9 | 0.92 | 0.58 | 0.4 |
| rs13191948 | 0.87 | 0.67 | 0.85 | 0.47 | 0.18 |
| rs2236256 | 0.41 | 0.39 | 0.82 | 0.2 | 0.53 |
| rs381500 | 0.17 | 0.43 | 0.083 | 0.068 | 0.56 |

TABLE 12-continued trans association with classes of somatic SVs at SNPs
previously reported to be associated with related phenotypes

| SNP | Location | Gene(s) reported | MAF | GWAS trait | Pany | Ploss |
|---|---|---|---|---|---|---|
| | rs4721217 | 0.28 | 0.01 | 0.009 | 0.57 | 0.45 |
| | rs17246404 | 0.78 | 0.029 | 0.53 | 0.29 | 0.58 |
| | rs58270997 | 0.039 | 0.45 | 0.29 | 0.94 | 0.34 |
| | rs35091702 | 0.88 | 0.85 | 0.52 | 0.97 | 0.055 |
| | rs2511714 | 0.34 | 0.46 | 0.6 | 0.32 | 0.011 |
| | rs2466035 | 0.25 | 0.65 | 0.89 | 0.25 | 0.34 |
| | rs59384377 | 0.97 | 0.74 | 0.37 | 0.024 | 0.18 |
| | rs12339666 | 0.98 | 0.87 | 0.4 | 0.032 | 0.35 |
| | rs10974944 | 0.66 | 0.99 | 0.17 | 0.0097 | 0.46 |
| | rs1679013 | 0.56 | 0.33 | 0.47 | 0.2 | 0.7 |
| | rs1359742 | 0.26 | 0.64 | 0.54 | 0.042 | 0.3 |
| | rs621940 | 0.073 | 0.25 | 0.44 | 0.18 | 0.52 |
| | rs1800682 | 0.12 | 0.29 | 0.037 | 0.39 | 0.92 |
| | rs4406737 | 0.3 | 0.15 | 0.15 | 0.35 | 0.59 |
| | rs9420907 | 0.99 | 0.87 | 0.45 | 0.059 | 0.13 |
| | rs7944004 | 0.66 | 0.27 | 0.29 | 0.021 | 0.37 |
| | rs2521269 | 0.76 | 0.18 | 0.099 | 0.18 | 0.3 |
| | rs4754301 | 0.44 | 0.19 | 0.51 | 0.46 | 0.74 |
| | rs1800056 | 0.25 | 0.54 | 0.093 | 0.77 | 0.77 |
| | rs35923643 | 0.11 | 0.049 | 0.0091 | 0.071 | 0.31 |
| | rs735665 | 0.17 | 0.034 | 0.016 | 0.08 | 0.34 |
| | rs2953196 | 0.81 | 0.22 | 0.06 | 0.31 | 0.87 |
| | rs7310615 | 0.85 | 0.86 | 0.86 | 0.33 | 0.25 |
| | rs10687116 | 0.72 | 0.6 | 0.8 | 0.99 | 0.73 |
| | rs1122138 | 0.23 | 0.54 | 0.07 | 0.051 | 0.48 |
| | rs2887399 | 0.088 | 0.61 | 0.064 | 0.095 | 0.49 |
| | rs137952017 | 0.25 | 0.0031 | 0.071 | 0.68 | 0.36 |
| | rs8024033 | 0.029 | 0.45 | 0.011 | 0.068 | 0.4 |
| | rs11636802 | 0.65 | 0.37 | 0.36 | 0.8 | 0.84 |
| | rs72742684 | 0.6 | 0.34 | 0.35 | 0.92 | 0.7 |
| | rs2052702 | 0.75 | 0.96 | 0.7 | 0.46 | 0.47 |
| | rs7176508 | 0.62 | 0.89 | 0.54 | 0.42 | 0.37 |
| | rs12448368 | 0.24 | 0.34 | 0.075 | 0.37 | 0.24 |
| | rs391023 | 0.0067 | 0.31 | 0.064 | 0.84 | 0.012 |
| | rs391855 | 0.0013 | 0.37 | 0.015 | 0.85 | 0.016 |
| | rs391525 | 0.0073 | 0.92 | 0.023 | 0.076 | 0.24 |
| | rs1044873 | 0.0055 | 0.97 | 0.024 | 0.15 | 0.4 |
| | rs78378222 | 0.99 | 0.29 | 0.42 | 0.0044 | 0.0059 |
| | rs77522818 | 0.08 | 0.53 | 0.013 | 0.091 | 0.36 |
| | rs11082396 | 0.5 | 0.42 | 0.44 | 0.99 | 0.78 |
| | rs4368253 | 0.89 | 0.086 | 0.54 | 0.55 | 0.83 |
| | rs4987856 | 0.083 | 0.29 | 0.19 | 0.15 | 0.44 |
| | rs4987855 | 0.14 | 0.37 | 0.28 | 0.14 | 0.44 |
| | rs4987852 | 0.7 | 0.68 | 0.8 | 0.91 | 0.4 |
| | rs17758695 | 0.45 | 0.036 | 0.83 | 0.32 | 0.23 |
| | rs8105767 | 0.18 | 0.12 | 0.22 | 0.72 | 0.81 |
| | rs11083846 | 0.025 | 0.51 | 0.14 | 0.4 | 0.36 |
| | rs60084722 | 0.049 | 0.77 | 0.17 | 0.51 | 0.16 |
| | rs755017 | 0.16 | 0.61 | 0.023 | 0.15 | 0.14 |
| | rs555607708 | 0.0001 | 0.3 | $7.7 \times 10^{-5}$ | $1.8 \times 10^{-6}$ | 0.76 |

TABLE 13

Risk increase for incident cancers conferred by somatic SVs

| | CLL | | MPN | | Any blood cancer | | Any non-blood cancer | |
|---|---|---|---|---|---|---|---|---|
| SV | P | OR (95% CI) | P | OR (95% CI) | P | OR (95% CI) | P | OR (95% CI) |
| 1p= | 1 | 0 (0-40) | 0.046 | 22.1 (0.54-133) | 0.4 | 1.96 (0.05-11.3) | 0.72 | 0.79 (0.31-1.69) |
| 1q= | 1 | 0 (0-51.9) | 1 | 0 (0-110) | 0.34 | 2.44 (0.06-14.1) | 0.43 | 1.31 (0.58-2.61) |
| 2p− | 0.027 | 38.1 (0.91-241) | 1 | 0 (0-436) | 0.13 | 7.55 (0.18-46.6) | 0.0044 | 3.57 (1.4-8.12) |
| 3+ | $7.8 \times 10^{-5}$ | 190 (19.6-936) | 1 | 0 (0-749) | $8.5 \times 10^{-5}$ | 43.2 (7.76-161) | 0.1 | 3.06 (0.55-11.3) |
| 3q= | 1 | 0 (0-423) | 1 | 0 (0-780) | 1 | 0 (0-74.3) | 0.0026 | 5.37 (1.69-14.8) |
| 4q− | 1 | 0 (0-133) | 1 | 0 (0-316) | 0.15 | 6.34 (0.15-38.8) | 0.73 | 0.41 (0.01-2.49) |
| 4q= | 1 | 0 (0-159) | 1 | 0 (0-328) | 0.011 | 13.4 (1.53-54.7) | 0.72 | 0.41 (0.01-2.5) |
| 5q− | 1 | 0 (0-167) | 0.011 | 93.4 (2.21-614) | 0.0082 | 16 (1.81-65.8) | 0.26 | 0 (0-1.86) |
| 5q= | 1 | 0 (0-230) | 1 | 0 (0-417) | 1 | 0 (0-40.9) | 0.43 | 1.7 (0.33-5.7) |
| 6p= | 1 | 0 (0-165) | 1 | 0 (0-286) | 1 | 0 (0-26.5) | 1 | 0.78 (0.09-3.04) |
| 7q− | 1 | 0 (0-137) | 1 | 0 (0-323) | 0.15 | 6.25 (0.15-38.5) | 1 | 0.79 (0.09-3.18) |

TABLE 13-continued

Risk increase for incident cancers conferred by somatic SVs

| | CLL | | MPN | | Any blood cancer | | Any non-blood cancer | |
|---|---|---|---|---|---|---|---|---|
| SV | P | OR (95% CI) | P | OR (95% CI) | P | OR (95% CI) | P | OR (95% CI) |
| 8+ | 0.018 | 60.8 (1.41-410) | 1 | 0 (0-606) | $6.8 \times 10^{-8}$ | 62.6 (17.5-186) | 0.65 | 1.48 (0.16-6.42) |
| 8q= | 1 | 0 (0-257) | 1 | 0 (0-460) | 1 | 0 (0-44.9) | 1 | 0.64 (0.02-3.98) |
| 9+ | 1 | 0 (0-324) | 1 | 0 (0-665) | 1 | 0 (0-54.3) | 0.067 | 3.02 (0.71-9.8) |
| 9p= | 1 | 0 (0-89.4) | $1.6 \times 10^{-21}$ | 560 (225-1.26e+03) | $1.1 \times 10^{-11}$ | 39.5 (16.8-83.1) | 0.42 | 1.37 (0.42-3.46) |
| 9q= | 1 | 0 (0-69.3) | 1 | 0 (0-155) | 1 | 0 (0-12.9) | 1 | 1 (0.31-2.46) |
| 10q− | 1 | 0 (0-205) | 1 | 0 (0-310) | 1 | 0 (0-34.7) | 0.32 | 1.63 (0.42-4.54) |
| 11q− | 0.0006 | 61.2 (6.93-251) | 1 | 0 (0-271) | 0.00099 | 16.9 (3.29-54.8) | 0.12 | 2.11 (0.72-5.15) |
| 11p= | 1 | 0 (0-52.5) | 1 | 0 (0-96.5) | 1 | 0 (0-8.84) | 0.08 | 1.74 (0.86-3.21) |
| 11q= | 1 | 0 (0-53.6) | 0.032 | 32.6 (0.79-202) | 0.0076 | 7.88 (1.57-24.3) | 1 | 0.84 (0.26-2.07) |
| 12+ | $1.2 \times 10^{-20}$ | 173 (78.1-355) | 1 | 0 (0-131) | $2 \times 10^{-15}$ | 33.9 (17-62.7) | 0.52 | 0.64 (0.17-1.73) |
| 12q= | 1 | 0 (0-126) | 1 | 0 (0-296) | 1 | 0 (0-24.2) | 0.76 | 1.07 (0.21-3.43) |
| 13q− | $3.4 \times 10^{-19}$ | 185 (80.2-392) | 1 | 0 (0-134) | $1.1 \times 10^{-11}$ | 29.5 (13.3-58.9) | 0.49 | 0.55 (0.11-1.68) |
| 13q= | $3.3 \times 10^{-7}$ | 81.5 (20.7-233) | 1 | 0 (0-149) | 0.00026 | 14 (3.67-38.4) | 1 | 0.88 (0.23-2.38) |
| 14+ | 1 | 0 (0-118) | 1 | 0 (0-291) | 1 | 0 (0-22.7) | 0.51 | 0.37 (0.01-2.23) |
| 14q− | 0.00017 | 123 (13.3-540) | 1 | 0 (0-488) | 0.00023 | 29.4 (5.48-102) | 1 | 0.68 (0.02-4.36) |
| 14q= | 1 | 0 (0-34.7) | 0.0014 | 38.4 (4.45-151) | 0.0035 | 6.74 (1.8-17.9) | 0.039 | 1.73 (0.99-2.86) |
| 15+ | 1 | 0 (0-65.7) | 1 | 0 (0-160) | 0.28 | 3.13 (0.08-18.6) | 0.81 | 1.03 (0.32-2.6) |
| 15q= | 1 | 0 (0-57) | 1 | 0 (0-116) | 0.32 | 2.65 (0.07-15.4) | 0.53 | 1.27 (0.53-2.63) |
| 16p= | 1 | 0 (0-84.4) | 1 | 0 (0-190) | 0.0022 | 12.4 (2.45-39.1) | 0.59 | 1.31 (0.41-3.29) |
| 16q= | 1 | 0 (0-112) | 1 | 0 (0-228) | 1 | 0 (0-19.6) | 0.57 | 1.25 (0.32-3.47) |
| 17+ | 1 | 0 (0-181) | 1 | 0 (0-487) | 0.11 | 9.2 (0.22-58.1) | 0.7 | 1.1 (0.13-4.53) |
| 17+ | 1 | 0 (0-140) | 1 | 0 (0-389) | 0.01 | 14.1 (1.61-57.3) | 0.73 | 1.26 (0.24-4.1) |
| 17p− | 1 | 0 (0-83) | 1 | 0 (0-169) | 1 | 0 (0-14.4) | 1 | 0.92 (0.24-2.51) |
| 17q= | 0.031 | 33.6 (0.8-214) | 1 | 0 (0-389) | 0.00075 | 19 (3.63-63.5) | 0.34 | 1.58 (0.04-4.64) |
| 18+ | 1 | 0 (0-159) | 1 | 0 (0-306) | 1 | 0 (0-30.2) | 0.26 | 0 (0-1.83) |
| 19p= | 1 | 0 (0-133) | 1 | 0 (0-419) | 1 | 0 (0-24.9) | 0.51 | 0.39 (0.01-2.35) |
| 19q= | 1 | 0 (0-47.3) | 1 | 0 (0-314) | 0.0013 | 9.1 (2.4-24.6) | 0.33 | 1.43 (0.66-2.79) |
| 20q− | 1 | 0 (0-187) | 1 | 0 (0-108) | 1 | 0 (0-34.1) | 0.26 | 0 (0-1.91) |
| 20q= | 1 | 0 (0-225) | 1 | 0 (0-360) | 0.1 | 9.59 (0.23-61.3) | 1 | 0.61 (0.01-3.85) |
| 21+ | 1 | 0 (0-236) | 1 | 0 (0-437) | 1 | 0 (0-41.9) | 0.42 | 1.77 (0.33-6.06) |
| 21q= | 0.042 | 24.4 (0.59-151) | 1 | 0 (0-462) | 0.2 | 4.5 (0.11-26.9) | 0.58 | 0.56 (0.07-2.18) |
| 22+ | $1.2 \times 10^{-8}$ | 207 (49-654) | 1 | 0 (0-218) | $8.7 \times 10^{-6}$ | 37.4 (9.1-115) | 1 | 0.65 (0.02-4.23) |
| 22q− | 1 | 0 (0-80.7) | 1 | 0 (0-494) | 1 | 0 (0-14.6) | 0.47 | 1.31 (0.46-3.05) |
| 22q= | 1 | 0.82 (0.02-4.99) | 1 | 0 (0-172) | 0.38 | 0.54 (0.11-1.63) | 0.45 | 1.08 (0.88-1.33) |
| −X | | | 1 | 0 (0-13) | | | | |

TABLE 14

Risk increase for mortality during ~7-year follow-up conferred by somatic SVs.

| SV type | Cancer status at assessment | P | HR (95% CI) |
|---|---|---|---|
| (a) All-cause mortality risk increase conferred by somatic SVs | | | |
| Loss | No previous Dx | $1.3 \times 10^{-7}$ | 2.08 (1.58-2.73) |
| Loss | Previous Dx | $5.4 \times 10^{-10}$ | 2.76 (2.00-3.80) |
| CNN-LOH | No previous Dx | 0.01 | 1.36 (1.07-1.71) |
| CNN-LOH | Previous Dx | $6.2 \times 10^{-5}$ | 1.81 (1.35-2.42) |
| Gain | No previous Dx | 0.00021 | 1.92 (1.36-2.70) |
| Gain | Previous Dx | 0.0055 | 1.97 (1.22-3.19) |
| (b) Non-cancer mortality risk increase conferred by somatic SVs | | | |
| Loss | No previous Dx | 0.0017 | 1.93 (1.28-2.92) |
| Loss | Previous Dx | 0.00015 | 3.22 (1.76-5.89) |
| CNN-LOH | No previous Dx | 0.19 | 1.26 (0.89-1.79) |
| CNN-LOH | Previous Dx | 0.04 | 1.84 (1.03-3.28) |
| Gain | No previous Dx | 0.096 | 1.59 (0.92-2.75) |
| Gain | Previous Dx | 0.31 | 1.67 (0.62-4.50) |

Various modifications and variations of the described methods, computer program products, systems and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

REFERENCES CITED

1 Jacobs, K. B. et al. Detectable clonal mosaicism and its relationship to aging and cancer. Nature Genetics 44, 651-658 (2012).
2. Laurie, C. C. et al. Detectable clonal mosaicism from birth to old age and its relationship to cancer. Nature Genetics 44, 642-650 (2012).
3 Genovese, G. et al. Clonal hematopoiesis and blood-cancer risk inferred from blood DNA sequence. New England Journal of Medicine 371, 2477-2487 (2014).
4. Jaiswal, S. et al. Age-related clonal hematopoiesis associated with adverse outcomes. New England Journal of Medicine 371, 2488-2498 (2014).
5. Xie, M. et al. Age-related mutations associated with clonal hematopoietic expansion and malignancies. Nature Medicine 20, 1472-1478 (2014).

6. McKerrell, T. et al. Leukemia-associated somatic mutations drive distinct patterns of age-related clonal hemopoiesis. Cell Reports 10, 1239-1245 (2015).
7. Machiela, M. J. et al. Characterization of large structural genetic mosaicism in human autosomes. American Journal of Human Genetics 96, 487-497 (2015).
8. Vattathil, S. & Scheet, P. Extensive hidden genomic mosaicism revealed in normal tissue. American Journal of Human Genetics 98, 571-578 (2016).
9. Young, A. L., Challen, G. A., Birmann, B. M. & Druley, T. E. Clonal haematopoiesis harbouring AML-associated mutations is ubiquitous in healthy adults. Nature Communications 7 (2016).
10. Forsberg, L. A., Gisselsson, D. & Dumanski, J. P. Mosaicism in health and disease clones picking up speed. Nature Reviews Genetics (2016).
11. Zink, F. et al. Clonal hematopoiesis, with and without candidate driver mutations, is com-mon in the elderly. Blood blood-2017 (2017).
12. Jaiswal, S. et al. Clonal hematopoiesis and risk of atherosclerotic cardiovascular disease. New England Journal of Medicine (2017).
13. Jones, A. V. et al. JAK2 haplotype is a major risk factor for the development of myeloproliferative neoplasms. Nature Genetics 41, 446-449 (2009).
14. Kilpivaara, O. et al. A germline JAK2 SNP is associated with predisposition to the develop-ment of JAK2V617F-positive myeloproliferative neoplasms. Nature Genetics 41, 455-459 (2009).
15. Olcaydu, D. et al. A common JAK2 haplotype confers susceptibility to myeloproliferative neoplasms. Nature Genetics 41, 450-454 (2009).
16. Koren, A. et al. Genetic variation in human DNA replication timing. Cell 159, 1015-1026 (2014).
17. Zhou, W. et al. Mosaic loss of chromosome Y is associated with common variation near TCL1A. Nature Genetics 48, 563-568 (2016).
18. Hinds, D. A. et al. Germ line variants predispose to both JAK2 V617F clonal hematopoiesis and myeloproliferative neoplasms. Blood 128, 1121-1128 (2016).
19. Wright, D. J. et al. Genetic variants associated with mosaic Y chromosome loss highlight cell cycle genes and overlap with cancer susceptibility. Nature Genetics (2017).
20. Forsberg, L. A. et al. Mosaic loss of chromosome Y in peripheral blood is associated with shorter survival and higher risk of cancer. Nature Genetics 46, 624-628 (2014).
21. Dumanski, J. P. et al. Smoking is associated with mosaic loss of chromosome Y. Science 347, 81-83 (2015).
22. Dumanski, J. P. et al. Mosaic loss of chromosome Y in blood is associated with Alzheimer disease. American Journal of Human Genetics 98, 1208-1219 (2016).
23. Sudlow, C. et al. U K Biobank: an open access resource for identifying the causes of a wide range of complex diseases of middle and old age. PLOS Medicine 12, 1-10 (2015).
24. Loh, P.-R., Palamara, P. F. & Price, A. L. Fast and accurate long-range phasing in a uk biobank cohort. Nature Genetics 48 (2016).
25. O'Connell, J. et al. Haplotype estimation for biobank-scale data sets. Nature Genetics (2016).
26. Loh, P.-R. et al. Reference-based phasing using the Haplotype Reference Consortium panel. Nature Genetics 48, 1443-1448 (2016).
27. Fischbach, G. D. & Lord, C. The Simons Simplex Collection: a resource for identification of autism genetic risk factors. Neuron 68, 192-195 (2010).
28. Davoli, T. et al. Cumulative haploinsufficiency and triplosensitivity drive aneuploidy patterns and shape the cancer genome. Cell 155, 948-962 (2013).
29. Beroukhim, R. et al. The landscape of somatic copy-number alteration across human cancers. Nature 463, 899-905 (2010).
30. Landau, D. A. et al. Mutations driving CLL and their evolution in progression and relapse. Nature 526, 525-530 (2015).
31. Puente, X. S. et al. Non-coding recurrent mutations in chronic lymphocytic leukaemia. Nature 526, 519-524 (2015).
32. Machiela, M. J. et al. Female chromosome X mosaicism is age-related and preferentially affects the inactivated X chromosome. Nature Communications 7 (2016).
33. Sinclair, E. J., Potter, A. M., Watmore, A. E., Fitchett, M. & Ross, F. Trisomy 15 associated with loss of the Y chromosome in bone marrow: a possible new aging effect. Cancer Genetics and Cytogenetics 105, 20-23 (1998).
34. Sutherland, G., Baker, E. & Seshadri, R. Heritable fragile sites on human chromosomes. V. A new class of fragile site requiring BrdU for expression. American Journal of Human Genetics 32, 542 (1980).
35. Hewett, D. R. et al. FRA10B structure reveals common elements in repeat expansion and chromosomal fragile site genesis. Molecular Cell 1, 773-781 (1998).
36. Richards, R. I. & Sutherland, G. R. Dynamic mutations: a new class of mutations causing human disease. Cell 70, 709-712 (1992).
37. Gurney, A. L., Carver-Moore, K., de Sauvage, F. J. & Moore, M. W. Thrombocytopenia in c-mpl-deficient mice. Science 265, 1445-1448 (1994).
38. Tefferi, A. Novel mutations and their functional and clinical relevance in myeloproliferative neoplasms: JAK2, MPL, TET2, ASXL1, CBL, IDH and IKZF1. Leukemia 24, 1128-1138 (2010).
39. Tukiainen, T. et al. Landscape of X chromosome inactivation across human tissues. bioRxiv 073957 (2016).
40. Loh, P.-R. et al. Contrasting genetic architectures of schizophrenia and other complex diseases using fast variance components analysis. Nature Genetics 47, 1385-1392 (2015).
41. Oddsson, A. et al. The germline sequence variant rs2736100 c in TERT associates with myeloproliferative neoplasms. Leukemia 28, 1371-1374 (2014).
42. Stacey, S. N. et al. A germline variant in the TP53 polyadenylation signal confers cancer susceptibility. Nature Genetics 43, 1098-1103 (2011).
43. Rawstron, A. C. et al. Monoclonal B-cell lymphocytosis and chronic lymphocytic leukemia. New England Journal of Medicine 359, 575-583 (2008).
44. Landgren, O. et al. B-cell clones as early markers for chronic lymphocytic leukemia. New England Journal of Medicine 360, 659-667 (2009).
45. Landau, D. A. et al. Evolution and impact of subclonal mutations in chronic lymphocytic leukemia. Cell 152, 714-726 (2013).
46. Ojha, J. et al. Monoclonal B-cell lymphocytosis is characterized by mutations in CLL putative driver genes and clonal heterogeneity many years before disease progression. Leukemia 28, 2395-2398 (2014).
47. Roulland, S. et al. t(14; 18) translocation: A predictive blood biomarker for follicular lymphoma. Journal of Clinical Oncology 32, 1347-1355 (2014).

48. Berndt, S. I. et al. Meta-analysis of genome-wide association studies discovers multiple loci for chronic lymphocytic leukemia. Nature Communications 7 (2016).
49. O'Keefe, C., McDevitt, M. A. & Maciejewski, J. P. Copy neutral loss of heterozygosity: a novel chromosomal lesion in myeloid malignancies. Blood 115, 2731-2739 (2010).
50. Chase, A. et al. Profound parental bias associated with chromosome 14 acquired uniparental disomy indicates targeting of an imprinted locus. Leukemia 29, 2069-2074 (2015).
51. Peiffer, D. A. et al. High-resolution genomic profiling of chromosomal aberrations using Infinium whole-genome genotyping. Genome Research 16, 1136-1148 (2006).
52. Diskin, S. J. et al. Adjustment of genomic waves in signal intensities from whole-genome SNP genotyping platforms. Nucleic Acids Research 36, e126-e126 (2008).
53. Nik-Zainal, S. et al. The life history of 21 breast cancers. Cell 149, 994-1007 (2012).
54. Vattathil, S. & Scheet, P. Haplotype-based profiling of subtle allelic imbalance with SNP arrays. Genome Research 23, 152-158 (2013).
55. Genovese, G., Leibon, G., Pollak, M. R. & Rockmore, D. N. Improved IBD detection using incomplete haplotype information. BMC Genetics 11, 58 (2010).
56. Huang, J. et al. Improved imputation of low-frequency and rare variants using the UK10K haplotype reference panel. Nature Communications 6 (2015).
57. Chang, C. C. et al. Second-generation PLINK: rising to the challenge of larger and richer datasets. GigaScience 4, 1-16 (2015).
58. Gusev, A. et al. Whole population, genome-wide mapping of hidden relatedness. Genome Research 19, 318-326 (2009).
59. Werling, D. M. et al. Limited contribution of rare, noncoding variation to autism spectrum disorder from sequencing of 2,076 genomes in quartet families. bioRxiv 127043 (2017).
60. Das, S. et al. Next-generation genotype imputation service and methods. Nature Genetics 48, 1284-1287 (2016).
61. Loh, P.-R. et al. Efficient Bayesian mixed model analysis increases association power in large cohorts. Nature Genetics 47, 284-290 (2015).
62. Lee, S. H., Wray, N. R., Goddard, M. E. & Visscher, P. M. Estimating missing heritability for disease from genome-wide association studies. American Journal of Human Genetics 88, 294-305 (2011).
63. Lappalainen, T. et al. Transcriptome and genome sequencing uncovers functional variation in humans. Nature 501, 506-511 (2013).
64. McKenna, A. et al. The genome analysis toolkit: a mapreduce framework for analyzing next-generation dna sequencing data. Genome Research 20, 1297-1303 (2010).
65. Turner, J. J. et al. InterLymph hierarchical classification of lymphoid neoplasms for epi-demiologic research based on the WHO classification (2008): update and future directions. Blood blood-2010 (2010).
66. Arber, D. A. et al. The 2016 revision to the World Health Organization (WHO) classification of myeloid neoplasms and acute leukemia. Blood blood-2016 (2016).
67. Affymetrix, Inc. Axoim® genotyping solution data analysis guide (2016). URL media.affymetrix.com/support/downloads/manuals/axiom_genotyping_solution_analysis_guide.pdf.
68. Quinlan, A. R. & Hall, I. M. BEDTools: a flexible suite of utilities for comparing genomic features. Bioinformatics 26, 841-842 (2010).
69. Bock, C., Walter, J., Paulsen, M. & Lengauer, T. CpG island mapping by epigenome prediction. PLOS Computational Biology 3, e110 (2007).
70. Price, A. L. et al. Long-range LD can confound genome scans in admixed populations. American Journal of Human Genetics 83, 132 (2008).
71. Lee, D.-H. et al. A PP4 phosphatase complex dephosphorylates RPA2 to facilitate DNA repair via homologous recombination. Nature Structural & Molecular Biology 17, 365-372 (2010).
72. Chen, D. et al. RYBP stabilizes p53 by modulating MDM2. EMBO Reports 10, 166-172 (2009).
73. Rao, S. S. et al. A 3D map of the human genome at kilobase resolution reveals principles of chromatin looping. Cell 159, 1665-1680 (2014).
74. Di Bernardo, M. C. et al. A genome-wide association study identifies six susceptibility loci for chronic lymphocytic leukemia. Nature Genetics 40, 1204-1210 (2008).
75. Slager, S. L. et al. Genome-wide association study identifies a novel susceptibility locus at 6p21.3 among familial CLL. Blood 117, 1911-1916 (2011).
76. Slager, S. L. et al. Common variation at 6p21.31 (BAK1) influences the risk of chronic lymphocytic leukemia. Blood 120, 843-846 (2012).
77. Berndt, S. I. et al. Genome-wide association study identifies multiple risk loci for chronic lymphocytic leukemia. Nature Genetics 45, 868-876 (2013).
78. Speedy, H. E. et al. A genome-wide association study identifies multiple susceptibility loci for chronic lymphocytic leukemia. Nature Genetics 46, 56-60 (2014).
79. Tapper, W. et al. Genetic variation at MECOM, TERT, JAK2 and HBSIL-MYB predisposes to myeloproliferative neoplasms. Nature Communications 6 (2015).
80. Codd, V. et al. Identification of seven loci affecting mean telomere length and their association with disease. Nature Genetics 45, 422-427 (2013).
81. Machiela, M. J. & Chanock, S. J. LD link: a web-based application for exploring population-specific haplotype structure and linking correlated alleles of possible functional variants. Bioinformatics 31, 3555-3557 (2015).

What is claimed is:

1. A computer-implemented method to detect somatic structural variants (SV), comprising;
determining, using one or more computing devices, total and relative allelic intensities for one or more samples, wherein determining the total and relative allelic intensities comprises converting genotype intensity data into log R2 ratio (LRR) and B allele frequency (BAF) values;
masking, using the one or more computing devices, constitutional segmental duplications in each sample of the one or more samples, wherein masking the constitutional segmental duplications comprises modeling, using the one or more computing devices, observed phased BAF deviations (pBAF) and wherein modeling the observed pBAFs is performed by modeling across individual chromosomes using a 25-state hidden Markov model (HMM) with states corresponding to pBAF values;
selecting regions to mask, which comprises computing a Viterbi path through the 25-state HMM and examining contiguous regions of nonzero states;
identifying, using the one or more computing devices, a putative set of somatic SV events for each sample in the one or more samples, wherein identifying the putative set of somatic SV events comprises use of a 3-state HMM and wherein the 3-state HMM is parameterized by a single parameter representing mean absolute BAF deviation (|ΔBAF|) within a given somatic SV event; and defining, using the one or more computing devices, one or more somatic SV events for each sample of the one or more samples, based at least in part on application of a likelihood ratio test to the putative set of somatic SV events.

2. The method of claim 1, further comprising locating, using the one or more computing devices, a chromosomal location of each identified somatic SV event for each sample in the one or more samples.

3. The method of claim 2, further comprising determining, using the one or more computing devices, a copy number of each identified somatic SV event for each sample in the one or more samples.

4. The method of claim 3, wherein determining the copy number of each identified somatic SV event comprises determining a relative probability that the event was a loss, copy-number neutral loss of heterozygosity (CNN-LOH), or gain based at least in part on the LRR and |ΔBAF| deviation.

5. The method of claim 2, wherein locating the chromosomal location of each identified somatic SV event comprises taking 5 samples from a posterior of the 3-state HMM and determining boundaries of each SV event based on a consensus of the 5 samples.

6. The method of claim 1, further comprising detecting, using the one or more computing devices, multiple sub-clonal events for each identified somatic SV event.

7. The method of claim 6, wherein detecting multiple sub-clonal events comprises re-analyzing each identified somatic SV using Viterbi decoding on a 51-state HMM with |ΔBAF| levels ranging from 0.01 to 0.25 in multiplicative increments.

8. The method of claim 1, further comprising detecting a disease or susceptibility to a disease based on detection of the one or more somatic SV events.

9. The method of claim 8, wherein the disease is cancer.

10. The method of claim 9, wherein the cancer comprises a hematological cancer.

11. The method of claim 10, wherein the hematological cancer is a leukemia.

12. The method of claim 11, wherein the leukemia is chronic lymphocytic leukemia (CLL).

13. The method of claim 8, where the detected one or more SV events comprise one or more SV events selected from 1p=, 1q=, 2p−, 3+, 3q=, 4q−, 4q−, 5q−, 5q=, 6p=, 7q−, 8+, 8q=, 9+, 9p=, 9q=, 10q−, 11q−, 11p=, 11q−, 12+, 12q−, 13q−, 13q−, 14+, 14q−, 14q=, 15+, 15q=, 16p=, 16q=, 17+, 17p−, 17q=, 18+, 19p=, 19q=, 20q−, 20q=, 21+, 21q=, 22+, 22q−, 22q=, and −X, wherein = refers to copy-number neutral loss-of-heterozygosity (CNN-LOH).

14. A method for detecting presence or susceptibility of a condition in subject, the method comprising detecting one or more somatic structural variants according to claim 1 in nucleic acids in a sample from the subject, wherein presence or absence of the one or more somatic structural variants indicates the presence or susceptibility of the condition.

15. The method of claim 14, wherein the nucleic acids are cell-free nucleic acids.

16. The method of claim 15, wherein the sample is maternal blood and the cell-free nucleic acids are fetal cell-free nucleic acids.

17. The method of claim 15, wherein the cell-free nucleic acids are circulating tumor DNA.

18. The method of claim 14, wherein the condition is fetal aneuploidy or cancer.

19. The method of claim 14, further comprising performing a medical procedure based on the detected presence or susceptibility of the condition.

20. A computer program product, comprising:

a non-transitory computer-executable storage device having computer-readable program instructions embodied thereon that when executed by a computer cause the computer to detect somatic structural variants (SVs) from genotyping data, the computer-executable program instructions comprising:

computer-executable program instruction to determine total and relative allelic intensities for one or more samples, wherein to determine the total and relative allelic frequencies comprises of to convert genotype intensity data into log R2 ratio (LRR) and B allele frequency (BAF) values;

computer-executable program instructions to mask constitutional segmental duplications, wherein to mask the constitutional segmental duplications comprises of to model observed phased BAF deviations (pBAF) and wherein to model the observed pBAFs is performed by to model across individual chromosomes using a 25-state hidden Markov model (HMM) with states corresponding to pBAF values;

computer-executable program instructions to select regions to mask, which comprises computing a Viterbi path through the 25-state HMM and examine contiguous regions of nonzero states;

computer-executable program instructions to identify a putative set of somatic SV events for each sample in the one or more samples, wherein to identify the putative set of somatic SV events comprises of use of a 3-state HMM and wherein the 3-state HMM is parameterized by a single parameter representing mean absolute BAF deviation (|ΔBAF|) within a given somatic SV event; and computer-executable program instructions to define one or more somatic SV events for each sample of the one or more samples.

21. The computer program product of claim 20 further comprising computer-executable program instruction to locate a chromosomal location of each identified somatic SV event for each sample in the one or more samples.

22. The computer program product of claim 21, further comprising computer-executable program instructions to determine a copy number of each identified somatic SV event.

23. The computer program product of claim 20, further comprising computer-executable program instruction to detect multiple sub-clonal events for each identified somatic SV.

24. The computer program product of claim 23, wherein the 3-state HMM is parameterized by a single parameter representing mean |ΔBAF| within a given somatic SV event.

25. The computer program product of claim 24, further comprising detecting a disease or susceptibility to a disease based on detection of the one or more somatic SV events.

26. The computer program product of claim 25, wherein the disease is cancer.

27. The computer program product of claim 26, wherein the cancer is a hematological cancer.

28. The computer program product of claim 27, wherein the hematological cancer is a leukemia.

29. The computer program product of claim 28, wherein the leukemia is chronic lymphocytic leukemia.

30. A kit comprising genotyping reagents and the computer program product of claim 20, wherein the genotyping reagents comprise of whole-genome amplification primers.

31. A system to detect one or somatic SV events, the system comprising:
- a storage device; and
- a processor communicatively coupled to the storage device, wherein the processor executes application code instructions that are stored in the storage device and that cause the system to:
- determine total and relative allelic intensities for one or more samples, wherein to determine the total and relative allelic frequencies comprises of to convert genotype intensity data into log R2 ratio (LRR) and B allele frequency (BAF) values;
- mask constitutional segmental duplications, wherein to mask the constitutional segmental duplications comprises of to model observed phased BAF deviations (pBAF) and wherein to model the observed pBAFs is performed by to model across individual chromosomes using a 25-state hidden Markov model (HMM) with states corresponding to pBAF values;
- select regions to mask, which comprises computing a Viterbi path through the 25-state HMM and examine contiguous regions of nonzero states;
- identify a putative set of somatic SV events for each sample in the one or more samples, wherein to identify the putative set of somatic SV events comprises of use of a 3-state HMM and wherein the 3-state HMM is parameterized by a single parameter representing mean expected absolute BAF deviation ($|\Delta BAF|$) within a given somatic SV event; and
- define one or more somatic SV events for each sample of the one or more samples.

* * * * *

UNITED STATES PATENT AND TRADEMARK OFFICE
CERTIFICATE OF CORRECTION

| | | |
|---|---|---|
| PATENT NO. | : 12,131,803 B2 | Page 1 of 1 |
| APPLICATION NO. | : 16/757329 | |
| DATED | : October 29, 2024 | |
| INVENTOR(S) | : Genovese et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1231 days.

Signed and Sealed this
Fourth Day of February, 2025

Coke Morgan Stewart
*Acting Director of the United States Patent and Trademark Office*